United States Patent
Langer et al.

(10) Patent No.: US 11,771,829 B2
(45) Date of Patent: Oct. 3, 2023

(54) SYSTEMS AND METHODS FOR LIQUID INJECTION

(71) Applicants: Massachusetts Institute of Technology, Cambridge, MA (US); The Brigham and Women's Hospital, Inc., Boston, MA (US); Novo Nordisk A/S, Bagsværd (DK)

(72) Inventors: Robert S. Langer, Newton, MA (US); Carlo Giovanni Traverso, Newton, MA (US); Alex G. Abramson, St. Louis, MO (US); Morten Revsgaard Frederiksen, Copenhagen (DK); Mikkel Oliver Jespersen, Bagsværd (DK); Brian Mouridsen, Bagsbærd (DK); Jesper Windum, Hilleroed (DK); Mette Poulsen, Bagsværd (DK); Brian Jensen, Brønshøj (DK); Jorrit Jeroen Water, Frederiksberg (DK); Mikkel Wennemoes Hvitfeld Ley, Bagsværd (DK); Xiaoya Lu, Toronto (CA); Andreas Vegge, Frederiksberg (DK)

(73) Assignees: Massachusetts Institute of Technology, Cambridge, MA (US); Novo Nordisk A/S, Bagsvaerd (DK); The Brigham and Women's Hospital, Inc., Boston, MA (US)

(*) Notice: Subject to any disclaimer, the term of this patent is extended or adjusted under 35 U.S.C. 154(b) by 910 days.

(21) Appl. No.: 16/778,152

(22) Filed: Jan. 31, 2020

(65) Prior Publication Data

US 2020/0246545 A1 Aug. 6, 2020

Related U.S. Application Data

(60) Provisional application No. 62/799,882, filed on Feb. 1, 2019.

(51) Int. Cl.
| | | |
|---|---|---|
| A61M 5/20 | (2006.01) | |
| A61K 9/00 | (2006.01) | |
| A61M 5/30 | (2006.01) | |

(52) U.S. Cl.
CPC ......... *A61M 5/2033* (2013.01); *A61K 9/0024* (2013.01); *A61M 5/30* (2013.01);
(Continued)

(58) Field of Classification Search
CPC .............. A61M 5/2033; A61M 5/30; A61M 2005/202; A61M 2202/0007;
(Continued)

(56) References Cited

U.S. PATENT DOCUMENTS

| 2,601,767 A | 7/1952 | Wall |
| 3,386,409 A | 6/1968 | Dawson |

(Continued)

FOREIGN PATENT DOCUMENTS

| CL | 199700115 | 1/1999 |
| CL | 2007003300 A1 | 11/2007 |

(Continued)

OTHER PUBLICATIONS

Thomas, "Gut motility, sphincters and reflex control." Anaesth Intensive Care Med., Feb. 2006, vol. 7, No. 2, pp. 57-58.
(Continued)

*Primary Examiner* — Jason E Flick
(74) *Attorney, Agent, or Firm* — Finnegan, Henderson, Farabow, Garrett & Dunner LLP

(57) ABSTRACT

Self-righting articles, such as self-righting capsules for administration to a subject, are generally provided. In some embodiments, the self-righting article may be configured such that the article may orient itself relative to a surface (e.g., a surface of a tissue of a subject). The self-righting articles described herein may comprise one or more tissue
(Continued)

engaging surfaces configured to engage (e.g., interface with, inject into, anchor) with a surface (e.g., a surface of a tissue of a subject). In some embodiments, the self-righting article may have a particular shape and/or distribution of density (or mass) which, for example, enables the self-righting behavior of the article. In some embodiments, the self-righting article may comprise a tissue interfacing component and/or a pharmaceutical agent (e.g., for delivery of the active pharmaceutical agent to a location internal of the subject) such as a liquid pharmaceutical agent. In some cases, upon contact of the tissue with the tissue engaging surface of the article, the self-righting article may be configured to release one or more tissue interfacing components. In some cases, the tissue interfacing component is associated with a self-actuating component. For example, the self-righting article may comprise a self-actuating component configured, upon exposure to a fluid, to release the tissue interfacing component from the self-righting article.

32 Claims, 52 Drawing Sheets

(52) U.S. Cl.
 CPC ............... *A61M 2005/202* (2013.01); *A61M 2202/0007* (2013.01); *A61M 2202/30* (2013.01); *A61M 2210/1042* (2013.01)

(58) Field of Classification Search
 CPC ...... A61M 2202/30; A61M 2210/1042; A61M 31/002; A61M 2005/206; A61M 5/3202; A61M 31/00; A61M 5/286; A61K 9/0024
 See application file for complete search history.

(56) References Cited

U.S. PATENT DOCUMENTS

| | | | |
|---|---|---|---|
| 3,442,045 A | 5/1969 | Green | |
| 3,797,492 A | 3/1974 | Place | |
| 3,826,220 A | 7/1974 | Jacobson | |
| 4,236,525 A | 12/1980 | Sluetz et al. | |
| 4,239,040 A | 12/1980 | Hosoya et al. | |
| 4,407,283 A | 10/1983 | Reynolds | |
| 4,425,117 A | 1/1984 | Hugemann et al. | |
| 5,017,187 A | 5/1991 | Sullivan | |
| 5,217,449 A * | 6/1993 | Yuda | A61B 1/041 604/890.1 |
| 5,279,607 A | 1/1994 | Schentag et al. | |
| 5,318,557 A | 6/1994 | Gross | |
| 5,443,843 A | 8/1995 | Curatolo et al. | |
| 5,474,785 A | 12/1995 | Wright et al. | |
| 5,690,691 A | 11/1997 | Chen et al. | |
| 6,030,641 A | 2/2000 | Yamashita et al. | |
| 6,041,258 A | 3/2000 | Cigaina et al. | |
| 6,099,504 A | 8/2000 | Gross et al. | |
| 6,120,803 A | 9/2000 | Wong et al. | |
| 6,334,856 B1 | 1/2002 | Allen et al. | |
| 6,346,519 B1 | 2/2002 | Petrus | |
| 6,449,511 B1 | 9/2002 | Mintchev et al. | |
| 6,472,423 B1 | 10/2002 | Ross et al. | |
| 6,488,962 B1 | 12/2002 | Berner et al. | |
| 6,503,231 B1 | 1/2003 | Prausnitz et al. | |
| 6,615,084 B1 | 9/2003 | Cigaina | |
| 6,660,197 B1 | 12/2003 | Buch-Rasmussen et al. | |
| 6,684,104 B2 | 1/2004 | Gordon et al. | |
| 6,945,952 B2 | 9/2005 | Kwon | |
| 7,076,305 B2 | 7/2006 | Imran et al. | |
| 7,076,307 B2 | 7/2006 | Boveja | |
| 7,177,693 B2 | 2/2007 | Starkebaum | |
| 7,211,062 B2 | 5/2007 | Kwon | |
| 7,569,032 B2 | 8/2009 | Naimark et al. | |
| 7,620,454 B2 | 11/2009 | Dinsmoor et al. | |
| 7,666,844 B2 | 2/2010 | Buch-Rasmussen et al. | |
| 7,678,135 B2 | 3/2010 | Maahs et al. | |
| 7,704,264 B2 | 4/2010 | Ewers et al. | |
| 7,742,818 B2 | 6/2010 | Dinsmoor et al. | |
| 8,084,053 B2 | 12/2011 | Buch-Rasmussen et al. | |
| 8,241,308 B2 | 8/2012 | Kortenbach et al. | |
| 8,252,329 B2 | 8/2012 | Tzannis et al. | |
| 8,454,997 B2 | 6/2013 | Hansen et al. | |
| 8,518,308 B2 | 8/2013 | Khoshnevis | |
| 8,518,430 B2 | 8/2013 | Buch-Rasmussen et al. | |
| 8,562,589 B2 | 10/2013 | Imran | |
| 8,682,440 B2 | 3/2014 | Imran et al. | |
| 8,721,620 B2 | 5/2014 | Imran | |
| 8,734,429 B2 | 5/2014 | Imran et al. | |
| 8,759,284 B2 | 6/2014 | Imran | |
| 8,764,733 B2 | 7/2014 | Imran | |
| 8,781,591 B2 | 7/2014 | Imran et al. | |
| 8,809,269 B2 | 8/2014 | Imran | |
| 8,809,271 B2 | 8/2014 | Imran | |
| 8,846,040 B2 | 9/2014 | Imran | |
| 8,852,083 B2 | 10/2014 | Mintchev et al. | |
| 8,852,151 B2 | 10/2014 | Imran | |
| 8,958,879 B2 | 2/2015 | Imran et al. | |
| 8,969,293 B2 | 3/2015 | Imran | |
| 8,980,822 B2 | 3/2015 | Imran | |
| 9,149,617 B2 | 10/2015 | Imran | |
| 9,186,233 B2 | 11/2015 | Gobel et al. | |
| 9,205,127 B2 | 12/2015 | Imran | |
| 9,259,386 B2 | 2/2016 | Imran | |
| 9,283,179 B2 | 3/2016 | Imran | |
| 9,284,367 B2 | 3/2016 | Imran | |
| 9,314,228 B2 | 4/2016 | Miller | |
| 9,402,806 B2 | 8/2016 | Imran | |
| 9,402,807 B2 | 8/2016 | Imran | |
| 9,403,002 B2 | 8/2016 | Imran et al. | |
| 9,415,004 B2 | 8/2016 | Imran | |
| 9,456,988 B2 | 10/2016 | Imran | |
| 9,457,065 B2 | 10/2016 | Imran | |
| 9,486,414 B2 | 11/2016 | Imran | |
| 9,492,378 B2 | 11/2016 | Imran | |
| 9,511,121 B2 | 12/2016 | Imran | |
| 9,539,207 B2 | 1/2017 | Imran | |
| 9,629,799 B2 | 4/2017 | Imran | |
| 9,643,005 B2 | 5/2017 | Imran et al. | |
| 9,757,514 B2 | 9/2017 | Imran et al. | |
| 9,757,548 B2 | 9/2017 | Imran | |
| 9,808,510 B2 | 11/2017 | Imran | |
| 9,814,763 B2 | 11/2017 | Imran | |
| 9,844,505 B2 | 12/2017 | Imran | |
| 9,844,655 B2 | 12/2017 | Imran | |
| 9,861,683 B2 | 1/2018 | Imran | |
| 9,907,747 B2 | 3/2018 | Imran | |
| 10,300,259 B2 | 5/2019 | Ziaie et al. | |
| 10,632,251 B2 | 4/2020 | Imran et al. | |
| 10,667,936 B2 | 6/2020 | Gobel | |
| 2001/0026636 A1 | 10/2001 | Mainguet | |
| 2002/0055734 A1 | 5/2002 | Houzego et al. | |
| 2002/0082543 A1 | 6/2002 | Park et al. | |
| 2002/0138049 A1 | 9/2002 | Allen et al. | |
| 2002/0198470 A1 | 12/2002 | Imran et al. | |
| 2003/0060734 A1 | 3/2003 | Yokoi et al. | |
| 2003/0161881 A1 | 8/2003 | Hansen et al. | |
| 2003/0181788 A1 | 9/2003 | Yokoi et al. | |
| 2004/0025330 A1 | 2/2004 | Sylvia et al. | |
| 2004/0044308 A1 | 3/2004 | Naimark et al. | |
| 2004/0044364 A1 | 3/2004 | DeVries et al. | |
| 2004/0087893 A1 | 5/2004 | Kwon | |
| 2004/0111011 A1 | 6/2004 | Uchiyama et al. | |
| 2004/0122315 A1 | 6/2004 | Krill | |
| 2004/0193229 A1 | 9/2004 | Starkebaum et al. | |
| 2004/0215171 A1 | 10/2004 | Houzego et al. | |
| 2004/0253304 A1 | 12/2004 | Gross et al. | |
| 2005/0055014 A1 | 3/2005 | Coppeta et al. | |
| 2005/0055039 A1 | 3/2005 | Burnett et al. | |
| 2005/0065463 A1 | 3/2005 | Tobinaga et al. | |
| 2005/0065571 A1 | 3/2005 | Imran | |
| 2005/0075654 A1 | 4/2005 | Kelleher | |
| 2005/0124875 A1 | 6/2005 | Kawano et al. | |
| 2005/0131345 A1 | 6/2005 | Miller | |

(56) References Cited

U.S. PATENT DOCUMENTS

| | | |
|---|---|---|
| 2005/0147559 A1 | 7/2005 | von Alten |
| 2005/0148847 A1 | 7/2005 | Uchiyama et al. |
| 2005/0149142 A1 | 7/2005 | Starkebaum |
| 2005/0171398 A1 | 8/2005 | Khait et al. |
| 2005/0183733 A1 | 8/2005 | Kawano et al. |
| 2005/0240239 A1 | 10/2005 | Boveja et al. |
| 2005/0245986 A1 | 11/2005 | Starkebaum |
| 2005/0250988 A1 | 11/2005 | Ewers et al. |
| 2005/0267414 A1 | 12/2005 | Abraham-Fuchs et al. |
| 2006/0004255 A1 | 1/2006 | Iddan et al. |
| 2006/0030752 A1 | 2/2006 | Orihara |
| 2006/0047309 A1 | 3/2006 | Cichocki |
| 2006/0058829 A1 | 3/2006 | Sampson et al. |
| 2006/0167339 A1 | 7/2006 | Gilad et al. |
| 2006/0259074 A1 | 11/2006 | Kelleher et al. |
| 2006/0271073 A1 | 11/2006 | Lam et al. |
| 2007/0021760 A1 | 1/2007 | Kelleher |
| 2007/0033682 A1 | 2/2007 | Sretavan et al. |
| 2007/0038181 A1 | 2/2007 | Melamud et al. |
| 2007/0106175 A1 | 5/2007 | Uchiyama et al. |
| 2007/0123809 A1 | 5/2007 | Weiss et al. |
| 2007/0135825 A1 | 6/2007 | Binmoeller |
| 2007/0156211 A1 | 7/2007 | Ferren et al. |
| 2007/0156248 A1 | 7/2007 | Marco et al. |
| 2007/0213659 A1 | 9/2007 | Trovato et al. |
| 2007/0292525 A1 | 12/2007 | Barbe et al. |
| 2008/0065168 A1 | 3/2008 | Bitton et al. |
| 2008/0121825 A1 | 5/2008 | Trovato |
| 2008/0188837 A1 | 8/2008 | Belsky et al. |
| 2008/0214894 A1 | 9/2008 | Wedel |
| 2008/0255543 A1 | 10/2008 | Tanaka et al. |
| 2008/0262478 A1 | 10/2008 | Krijnsen et al. |
| 2008/0269664 A1 | 10/2008 | Trovato et al. |
| 2008/0294101 A1 | 11/2008 | Kawano |
| 2008/0294143 A1 | 11/2008 | Tanaka et al. |
| 2009/0005639 A1 | 1/2009 | Kawano et al. |
| 2009/0030473 A1 | 1/2009 | Khawaled et al. |
| 2009/0043278 A1 | 2/2009 | Tanaka et al. |
| 2009/0104250 A1 | 4/2009 | Boyden et al. |
| 2009/0112191 A1 | 4/2009 | Boyden et al. |
| 2009/0137866 A1 | 5/2009 | Boyden et al. |
| 2009/0234331 A1 | 9/2009 | Langereis et al. |
| 2009/0253954 A1 | 10/2009 | Katayama |
| 2009/0253999 A1 | 10/2009 | Aoki et al. |
| 2009/0275923 A1 | 11/2009 | Shimizu et al. |
| 2009/0281557 A1 | 11/2009 | Sander et al. |
| 2009/0299144 A1 | 12/2009 | Shigemori et al. |
| 2009/0306473 A1 | 12/2009 | Tanaka et al. |
| 2009/0306632 A1 | 12/2009 | Trovato et al. |
| 2009/0306633 A1 | 12/2009 | Trovato et al. |
| 2010/0021536 A1 | 1/2010 | Gross |
| 2010/0033324 A1 | 2/2010 | Shimizu et al. |
| 2010/0049120 A1 | 2/2010 | Dijksman et al. |
| 2010/0056874 A1 | 3/2010 | Dijksman et al. |
| 2010/0063486 A1 | 3/2010 | Dijksman et al. |
| 2010/0094206 A1 | 4/2010 | Boyd et al. |
| 2010/0094207 A1 | 4/2010 | Boyd et al. |
| 2010/0179381 A1 | 7/2010 | Kawano et al. |
| 2010/0204678 A1 | 8/2010 | Imran |
| 2010/0228313 A1 | 9/2010 | Starkebaum et al. |
| 2010/0247453 A1 | 9/2010 | Jones |
| 2010/0286628 A1 | 11/2010 | Gross |
| 2010/0286668 A1 | 11/2010 | Tanaka et al. |
| 2010/0305656 A1 | 12/2010 | Imran et al. |
| 2010/0331827 A1 | 12/2010 | Shimizu |
| 2011/0017612 A1 | 1/2011 | Dijksman et al. |
| 2011/0034766 A1 | 2/2011 | Tanaka |
| 2011/0071589 A1 | 3/2011 | Starkebaum et al. |
| 2011/0087195 A1 | 4/2011 | Uhland et al. |
| 2011/0098651 A1 | 4/2011 | Falo, Jr. et al. |
| 2011/0106063 A1 | 5/2011 | Dijksman et al. |
| 2011/0106064 A1 | 5/2011 | Zou et al. |
| 2011/0152792 A1 | 6/2011 | Takada |
| 2011/0160129 A1 | 6/2011 | Imran |
| 2011/0160699 A1 | 6/2011 | Imran |
| 2011/0207998 A1 | 8/2011 | Katayama |
| 2011/0208270 A1 | 8/2011 | Imran et al. |
| 2012/0010590 A1 | 1/2012 | Imran |
| 2012/0095290 A1* | 4/2012 | Kawano ............ A61B 1/00158 600/117 |
| 2012/0116358 A1 | 5/2012 | Dijksman et al. |
| 2012/0143171 A1 | 6/2012 | Shimizu et al. |
| 2012/0305573 A1 | 12/2012 | Shi et al. |
| 2012/0305574 A1 | 12/2012 | Shi et al. |
| 2013/0108695 A1 | 5/2013 | Grenier et al. |
| 2013/0164371 A1 | 6/2013 | Imran |
| 2013/0164372 A1 | 6/2013 | Imran |
| 2013/0164373 A1 | 6/2013 | Imran |
| 2013/0165372 A1 | 6/2013 | Imran |
| 2013/0165373 A1 | 6/2013 | Imran |
| 2013/0165772 A1 | 6/2013 | Traverso et al. |
| 2013/0165859 A1 | 6/2013 | Imran |
| 2013/0171244 A1 | 7/2013 | Imran |
| 2013/0171245 A1 | 7/2013 | Imran |
| 2013/0171246 A1 | 7/2013 | Imran |
| 2013/0171247 A1 | 7/2013 | Imran |
| 2013/0172257 A1 | 7/2013 | Imran |
| 2013/0172672 A1 | 7/2013 | Iddan et al. |
| 2013/0172694 A1 | 7/2013 | Zou et al. |
| 2013/0177527 A1 | 7/2013 | Imran |
| 2013/0177550 A1* | 7/2013 | Imran .................... A61M 5/00 530/387.3 |
| 2013/0189353 A1 | 7/2013 | Imran |
| 2013/0195970 A1 | 8/2013 | Imran |
| 2013/0197440 A1 | 8/2013 | Zou et al. |
| 2013/0204233 A1 | 8/2013 | Zou et al. |
| 2013/0274659 A1 | 10/2013 | Imran et al. |
| 2013/0338583 A1 | 12/2013 | Imran |
| 2014/0135698 A1 | 5/2014 | Zou et al. |
| 2014/0142380 A1 | 5/2014 | Takahashi |
| 2014/0163637 A1 | 6/2014 | Imran et al. |
| 2014/0221912 A1 | 8/2014 | Imran |
| 2014/0221927 A1 | 8/2014 | Imran et al. |
| 2014/0234418 A1 | 8/2014 | Coulter et al. |
| 2014/0243921 A1 | 8/2014 | Imran et al. |
| 2014/0256631 A1 | 9/2014 | Imran |
| 2014/0257238 A1 | 9/2014 | Imran |
| 2014/0276595 A1 | 9/2014 | Imran |
| 2014/0335168 A1 | 11/2014 | Imran |
| 2014/0336112 A1 | 11/2014 | Imran |
| 2014/0378764 A1 | 12/2014 | Mintchev et al. |
| 2015/0011874 A1 | 1/2015 | Amoako-Tuffour et al. |
| 2015/0023962 A1 | 1/2015 | Imran |
| 2015/0025496 A1 | 1/2015 | Imran |
| 2015/0051589 A1 | 2/2015 | Sako et al. |
| 2015/0064241 A1 | 3/2015 | Conrad |
| 2015/0141967 A1 | 5/2015 | Pardoel et al. |
| 2015/0147390 A1 | 5/2015 | Imran |
| 2015/0174076 A1 | 6/2015 | Harris et al. |
| 2015/0174400 A1 | 6/2015 | Imran et al. |
| 2015/0238571 A1 | 8/2015 | Imran |
| 2015/0328287 A1 | 11/2015 | Morales et al. |
| 2015/0329630 A1 | 11/2015 | Morales et al. |
| 2015/0329631 A1 | 11/2015 | Morales et al. |
| 2015/0329633 A1 | 11/2015 | Morales et al. |
| 2016/0015648 A1 | 1/2016 | Gross et al. |
| 2016/0015816 A1 | 1/2016 | Benjamin et al. |
| 2016/0022873 A1 | 1/2016 | Besner et al. |
| 2016/0144000 A1 | 5/2016 | Imran |
| 2016/0158516 A1 | 6/2016 | Imran |
| 2016/0166650 A1 | 6/2016 | Imran |
| 2016/0220759 A1 | 8/2016 | Enggaard et al. |
| 2016/0235663 A1 | 8/2016 | Zou et al. |
| 2016/0263045 A1 | 9/2016 | Grenier et al. |
| 2016/0278899 A1 | 9/2016 | Heller et al. |
| 2017/0027520 A1 | 2/2017 | Terry et al. |
| 2017/0027862 A1 | 2/2017 | Imran |
| 2017/0028195 A1 | 2/2017 | Imran et al. |
| 2017/0043144 A1 | 2/2017 | Imran |
| 2017/0049708 A1 | 2/2017 | Imran |
| 2017/0050005 A1 | 2/2017 | Imran |
| 2017/0051051 A1 | 2/2017 | Imran et al. |
| 2017/0066824 A1 | 3/2017 | Imran et al. |
| 2017/0066841 A1 | 3/2017 | Imran et al. |

(56) References Cited

U.S. PATENT DOCUMENTS

| | | |
|---|---|---|
| 2017/0081399 A1 | 3/2017 | Imran |
| 2017/0087299 A1 | 3/2017 | Anderson |
| 2017/0100459 A1 | 4/2017 | Imran |
| 2017/0106099 A1 | 4/2017 | Bellinger et al. |
| 2017/0174758 A1 | 6/2017 | Imran |
| 2017/0189269 A1 | 7/2017 | Fischer et al. |
| 2017/0189659 A1 | 7/2017 | Imran |
| 2017/0216589 A1 | 8/2017 | Imran et al. |
| 2017/0231902 A1 | 8/2017 | Imran |
| 2017/0258732 A1 | 9/2017 | Imran et al. |
| 2017/0258833 A1 | 9/2017 | Imran et al. |
| 2017/0296092 A1 | 10/2017 | Jones et al. |
| 2018/0008771 A1 | 1/2018 | Imran et al. |
| 2018/0015146 A1 | 1/2018 | Imran |
| 2018/0037643 A9 | 2/2018 | Imran et al. |
| 2018/0049725 A1 | 2/2018 | Jones et al. |
| 2018/0064366 A1 | 3/2018 | Sweeney et al. |
| 2018/0070857 A1 | 3/2018 | Jones et al. |
| 2018/0168488 A1 | 6/2018 | Jones et al. |
| 2018/0193621 A1 | 7/2018 | Bonner et al. |
| 2018/0296814 A1 | 10/2018 | Shimizu |
| 2018/0311154 A1 | 11/2018 | Kanasty et al. |
| 2019/0046721 A1 | 2/2019 | Iordanov et al. |
| 2019/0133937 A1 | 5/2019 | Imran et al. |
| 2019/0223846 A1 | 7/2019 | Kerkhof et al. |
| 2019/0254966 A1 | 8/2019 | Bellinger et al. |
| 2019/0262265 A1 | 8/2019 | Bellinger et al. |
| 2019/0282791 A1 | 9/2019 | Jones et al. |
| 2019/0321613 A1 | 10/2019 | Jones et al. |
| 2020/0009371 A1 | 1/2020 | Langer et al. |
| 2020/0129441 A1 | 4/2020 | Abramson et al. |
| 2020/0147298 A1 | 5/2020 | Traverso et al. |
| 2020/0205729 A1 | 7/2020 | Jones et al. |
| 2020/0246545 A1 | 8/2020 | Langer et al. |
| 2020/0306515 A1 | 10/2020 | Traverso et al. |
| 2020/0324095 A1 | 10/2020 | Traverso et al. |
| 2020/0376192 A1 | 12/2020 | Langer et al. |

FOREIGN PATENT DOCUMENTS

| | | |
|---|---|---|
| CL | 2007003301 A1 | 11/2007 |
| CN | 1820798 A | 8/2006 |
| CN | 1887373 A | 1/2007 |
| CN | 100998904 A | 7/2007 |
| CN | 100376299 C | 3/2008 |
| CN | 103025319 | 4/2013 |
| CN | 104983385 A | 10/2015 |
| CN | 106137099 A | 11/2016 |
| CN | 106730284 A | 5/2017 |
| CN | 108836237 | 11/2018 |
| DE | 102005032290 A1 | 1/2007 |
| DE | 102014015919 A1 | 12/2015 |
| EP | 0197697 A2 | 10/1986 |
| EP | 0415671 A2 | 3/1991 |
| EP | 1784140 A1 | 5/2007 |
| EP | 2201938 A1 | 6/2010 |
| EP | 2661983 A1 | 11/2013 |
| FR | 2794654 A1 | 12/2000 |
| JP | 55166142 | 12/1980 |
| JP | 58019232 | 2/1983 |
| JP | 2003093332 A | 4/2003 |
| JP | 2003325438 A | 11/2003 |
| JP | 2004222998 A | 8/2004 |
| JP | 2013022291 A | 2/2013 |
| JP | 2013-515576 A | 5/2013 |
| JP | 2016-529066 A | 9/2016 |
| KR | 20180053852 A | 5/2018 |
| WO | 2000/062759 A1 | 10/2000 |
| WO | WO 2001/026602 A1 | 4/2001 |
| WO | 2001/058424 A1 | 8/2001 |
| WO | 2006/020929 A2 | 2/2006 |
| WO | 2006/084164 A2 | 8/2006 |
| WO | 2006/125074 A1 | 11/2006 |
| WO | 2006/131522 A1 | 12/2006 |
| WO | 2007/093806 A1 | 8/2007 |
| WO | 2007/127976 A2 | 11/2007 |
| WO | WO 2007/136735 A2 | 11/2007 |
| WO | 2008/111078 A2 | 9/2008 |
| WO | 2009/063375 A1 | 5/2009 |
| WO | 2009/063376 A1 | 5/2009 |
| WO | 2009/063377 A1 | 5/2009 |
| WO | 2010/140401 A1 | 12/2010 |
| WO | WO 2011/079302 A2 | 6/2011 |
| WO | WO 2011/112229 A2 | 9/2011 |
| WO | 2011/141372 A1 | 11/2011 |
| WO | 2013/101908 A1 | 7/2013 |
| WO | WO 2013/183624 A1 | 12/2013 |
| WO | 2014/007824 A1 | 1/2014 |
| WO | WO 2015/035111 A1 | 3/2015 |
| WO | 2016/067087 A2 | 5/2016 |
| WO | 2016/102526 A1 | 6/2016 |
| WO | 2016/155671 A1 | 10/2016 |
| WO | WO 2016/179120 A1 | 11/2016 |
| WO | 2016/193375 A1 | 12/2016 |
| WO | 2017/004623 A1 | 1/2017 |
| WO | 2017/044665 A1 | 3/2017 |
| WO | 2018/112235 A1 | 6/2018 |
| WO | 2018/112245 A1 | 6/2018 |
| WO | 2018/182612 A1 | 10/2018 |
| WO | 2018/182623 A1 | 10/2018 |
| WO | 2018/182641 A1 | 10/2018 |
| WO | 2018/183932 A1 | 10/2018 |
| WO | 2018/183934 A1 | 10/2018 |
| WO | 2018/183941 A2 | 10/2018 |
| WO | 2018/213576 A1 | 11/2018 |
| WO | 2018/213579 A1 | 11/2018 |
| WO | 2018/213582 A1 | 11/2018 |
| WO | 2018/213588 A1 | 11/2018 |
| WO | 2018/213593 A1 | 11/2018 |
| WO | 2018/213600 A1 | 11/2018 |
| WO | 2019/036363 A1 | 2/2019 |
| WO | 2019/036382 A1 | 2/2019 |
| WO | 2019/121686 A1 | 6/2019 |
| WO | 2019/147824 A1 | 8/2019 |
| WO | 2020/157324 A1 | 8/2020 |
| WO | 2020/160399 A1 | 8/2020 |

OTHER PUBLICATIONS

Traverso et al., "Microneedles for drug delivery via the gastrointestinal tract." J. Pharm. Sci., Feb. 2015, vol. 104, No. 2, pp. 362-367. Published online Sep. 22, 2014.

Várkonyi et al., "Mono-monostatic Bodies: The Answer to Arnold's Question," Math. Intell., Sep. 2006, vol. 28, No. 4, p. 34-38.

Várkonyi et al., "Static Equilibria of Rigid Bodies: Dice, Pebbles, and the Poincare-Hopf Theorem. J." Nonlinear Sci., Jun. 2006, vol. 16, pp. 255-281. Online publication May 22, 2006.

Vassallo et al., "Measurement of axial forces during emptying from the human stomach." Am J Physiol. Aug. 1992, vol. 263, No. 2, Pt 1, pp. G230-G239.

Vazharov, "Perforation as a complication of the diagnostic upper and lower endoscopy of the gastrointestinal tract." J. Imab—Annual Proceeding (Scientific Papers), Aug. 2012, vol. 18, No. 3, p. 273-275.

Vinther et al., "Insulin analog with additional disulfide bond has increased stability and preserved activity." Protein Sci., Mar. 2013, vol. 22, No. 3, pp. 296-305. Published online Dec. 26, 2012.

Wallace et al., "The cellular and molecular basis of gastric mucosal defense." FASEB J, May 1996, vol. 10, No. 7, pp. 731-740.

Wang et al., "Recent advances in the design of polymeric microneedles for transdermal drug delivery and biosensing." Lab Chip, Apr. 2017, vol. 17, No. 8, pp. 1373-1387.

Wiesner et al., "Normal colonic wall thickness at CT and its relation to colonic distension." J Comput Assist Tomogr, Jan.-Feb. 2002, vol. 26, No. 1, pp. 102-106.

Yoshida et al., "Complexation hydrogels as potential carriers in oral vaccine delivery systems." Eur J Pharm Biopharm., Mar. 2017, vol. 112, pp. 138-142. Available online Nov. 27, 2016.

Zhang et al., Systematic review: applications and future of gastric electrical stimulation. Aliment Pharmacol Ther., Oct. 2006, vol. 24, No. 7, pp. 991-1002.

(56) References Cited

OTHER PUBLICATIONS

Kim et al., "Microneedles for drug and vaccine delivery" Adv. Drug Deliv. Rev., Nov. 2012, vol. 64, No. 14, pp. 1547-1568. Available online May 1, 2012.

Koetting et al., "pH-responsive and enzymatically-responsive hydrogel microparticles for the oral delivery of therapeutic proteins: Effects of protein size, crosslinking density, and hydrogel degradation on protein delivery". J. Control. Release, Jan. 2016, vol. 221, pp. 18-25. Available online Dec. 2, 2015.

Lee et al., "Bioadhesive-Based Dosage Forms: The Next Generation". J Pharm Sci. Jul. 2000, vol. 89, No. 7, pp. 850-866.

Miller et al., "The cost of unsafe injections." Bull World Health Organ., 1999, vol. 77, No. 10, pp. 808-811.

Rao, "Rheology of Fluid and Semisolid Foods Principles and Applications." Second Edition, Springer US., 2007, book, 491 pages.

Steffe, "Rheological Methods in Food Process Engineering." Second Edition, Freeman Press, 1996, book, 428 pages.

Goffredo et al., "A smart pill fordrug delivery with sensing capabilities," 2015 37th Annual International Conference of the IEEE Engineering in Medicine and Biology Society (EMBC), Milan, Aug. 2015, pp. 1361-1364.

Banerjee et al., "Intestinal mucoadhesive devices for oral delivery of insulin." Bioeng Transl Med., Sep. 2016, vol. 1, No. 3, pp. 338-346. Published online Aug. 19, 2016.

International Search Report and Written Opinoin dated Jul. 30, 2018 for Application No. PCT/US2018/033210 (16 pages).

International Search Report and Written Opinion dated Jul. 30, 2018 for Application No. PCT/US2018/033183 (17 pages).

International Search Report and Written Opinion dated Sep. 21, 2018 for Application No. PCT/US2018/033187 (15 pages).

International Search Report and Written Opinion dated Aug. 10, 2018 for Application No. PCT/US2018/033204 (16 pages).

International Search Report and Written Opinion dated Oct. 15, 2018 for Application No. PCT/US2018/033193 (19 pages).

International Search Report and Written Opinion dated Jul. 30, 2018 for Application No. PCT/US2018/033217 (13 pages).

International Search Report and Written Opinion dated Apr. 8, 2020 for Application No. PCT/EP2020/052521 (10 pages).

International Search Report and Written Opinion dated May 12, 2020 for Application No. PCT/US2020/016807 (11 pages).

U.S. Appl. No. 16/614,083, filed Nov. 15, 2019, by Traverso et al.
U.S. Appl. No. 16/614,177, filed Nov. 15, 2019, by Traverso et al.
U.S. Appl. No. 16/614,229, filed Nov. 15, 2019, by Traverso et al.
U.S. Appl. No. 16/691,514, filed Nov. 21, 2019, by Traverso, et al.

Diabetes Control and Complications Trial Research Group. "The effect of intensive diabetes treatment on the development and progression of long-term complications in insulin-dependent diabetes mellitus." Sep. 1993, N. Engl. J. Med., vol. 329, No. 14, pp. 977-986.

Cision PR Newswire. "Non-Insulin Therapies for Diabetes: GLP-1 Agonists, DPP4 Inhibitors and SGLT2 Inhibitors, 2016-2026." Retrieved from www.prnewswire.com/news-releases/non-insulin-therapies-for-diabetes-glp-1-agonists-dpp4-inhibitors-and-sglt2-inhibitors-2016-2026-300317435.html. Aug. 23, 2016, 11 pages.

FDA Guidance for Industry, "Food-effect bioavailability and Fed Bioequialence Studies." Dec. 2002, U.S. Department of Health and Human Services, Food and Drug Administration, Center for Drug Evaluation and Research (CDER), 12 pages.

Abell et al., "Gastric Electrical Stimulation for Medically Refractory Gastroparesis." Aug. 2003, Gastroenterology, vol. 125, No. 2, pp. 421-428.

Abrahamsson et al., "A novel in vitro and numerical analysis of shear-induced drug release from extended-release tablets in the fed stomach." Aug. 2005, Pharm Res., vol. 22, No. 8, pp. 1215-1226.

Aguirre et al., "Current status of selected oral peptide technologies in advanced preclinical development and in clinical trials" Nov. 2016, Adv Drug Deliv Rev., vol. 106, Pt B, pp. 223-241 Epub Feb. 24, 2016.

Ahmad et al., "Enhancement of oral insulin bioavailability: in vitro and in vivo assessment of nanoporous stimuli-responsive hydrogel microparticles." Mar. 2016, Expert Opin Drug Deliv., vol. 13, No. 5, pp. 621-632.

Alcock et al., "Long-term thermostabilization of live poxviral and adenoviral vaccine vectors at supraphysiological temperatures in carbohydrate glass." Sci Transl Med., Feb. 2010, vol. 2, No. 19, pp. 1-9.

Anderloni et al., "Advances, problems, and complications of polypectomy." Clin Exp Gastroenterol., Aug. 2014, vol. 30, No. 7, pp. 285-296.

Andrews et al., "Mucoadhesive polymeric platforms for controlled drug delivery." Eur J Pharm Biopharm, Mar. 2009, vol. 71, No. 3, pp. 505-518.

Aran et al., "An oral microjet vaccination system elicits antibody production in rabbits." Sci Transl Med, Mar. 2017, vol. 9, No. 380, pp. 1-10.

Banerjee et al., "Intestinal micropatches for oral insulin delivery." J. Drug Target. Mar. 2017, vol. 25, No. 7, pp. 608-615.

Bass et al., "Gastrointestinal safety of an extended-release, nondefomnable, oral dosage form (OROS: a retrospective study." Drug Saf., Dec. 2002, vol. 25, No. 14, pp. 1021-1033.

Becker et al., "Novel orally swallowable IntelliCap(®) device to quantify regional drug absorption in human GI tract using diltiazem as model drug." AAPS PharmSciTech., Dec. 2014, vol. 15, No. 6, pp. 1490-1497.

Boddupalli et al., "Mucoadhesive drug delivery system: An overview." J Adv Pharm Technol Res., Oct. 2010, vol. 1, No. 4, pp. 381-387.

Bolondi et al., "Measurement of gastric emptying time by real-time ultrasonography." Gastroenterology, Oct. 1985, vol. 89, No. 4, pp. 752-759.

Brayden et al., "Oral delivery of peptides: opportunities and issues for translation." Adv Drug Deliv Rev., Nov. 2016, vol. 106, No. Pt B, pp. 193-195.

Brunton, "GLP-1 receptor agonists vs. DPP-4 inhibitors for type 2 diabetes: is one approach more successful or preferable than the other?" Int J Clin Pract., May 2014, vol. 68, No. 5, pp. 557-567.

Bui et al., "Prediction of viscosity of glucose and calcium chloride solutions." J. Food Eng., May 2004, vol. 62, No. 4, pp. 345-349.

Buse et al., "Liraglutide once a day versus exenatide twice a day for type 2 diabetes: a 26-week randomised, parallel-group, multinational, open-label trial (LEAD-6)." Lancet Jul. 2009, vol. 374, No. 9683, pp. 39-47.

Caffarel-Salvador et al., "Oral delivery of biologies using drug-device combinations." Curr Opin Pharmacol., Oct. 2017, vol. 36, pp. 8-13.

Calvert et al., "Management of type 2 diabetes with multiple oral hypoglycaemic agents or insulin in primary care retrospective cohort study" Br J. Gen. Pract., Jun. 2007, vol. 57, No. 539, 6 pages.

Camilleri et al., "Axial forces during gastric emptying in health and models of disease." Dig. Dis. Sci., Dec. 1994; vol. 39, No. 12, pp. 14S-17S.

Carino et al., "Oral insulin delivery." Adv Drug Deliv Rev., Feb. 1999, vol. 35, No. 2-3, pp. 249-257.

Carlson, "Ousting the "ouch factor" in drug delivery." Biotechnol Healthc., Dec. 2007, vol. 4, No. 6, pp. 15-16.

Chaddock et al., "Novel MRI tests of orocecal transit time and whole gut transit time: studies in normal subjects." Neurogastroenterol Motil., Feb. 2014, vol. 26, No. 2, pp. 205-214.

Cui et al., "The study of a remote-controlled gastrointestinal drug delivery and sampling system." Telemed J E Health., Sep. 2008, vol. 14, No. 7, pp. 715-719.

Dallel et al., "Gestion des seringues a insuline utilisées par les diabétiqués insulino-traités a domicile. A propos de 100 patients [Disposal of insulin syringes by diabetic patients. Report of 100 patients]." Tunis Med., Jul. 2005, vol. 83, No. 7, pp. 390-392. French.

Degen et al., "Variability of gastrointestinal transit in healthy women and men." Gut., Aug. 1996, vol. 39, No. 2, pp. 299-305.

Delvaux et al., "Clinical evaluation of the use of the M2A patency capsule system before a capsule endoscopy procedure, in patients

(56) References Cited

OTHER PUBLICATIONS with known or suspected intestinal stenosis." Endoscopy., Sep. 2005, vol. 37, No. 9, pp. 801-807.
DeFronzo et al., "Effects of exenatide versus sitagliptin on postprandial glucose, insulin and glucagon secretion, gastric emptying, and caloric intake: a randomized, cross-over study.", Curr Med Res Opin., Oct. 2008, vol. 24, No. 10, pp. 2943-2952.
Des Rieux et al., "Nanoparticles as potential oral delivery systems of proteins and vaccines: a mechanistic approach." J Control Release. Nov. 2006, vol. 116, No. 1, pp. 1-27.
Diamond et al., "Experience with a pill-swallowing enhancement aid." Clin Pediatr (Phila). Apr. 2010, vol. 49, No. 4, pp. 391-393.
Domokos et al., "Geometry and self-righting of turtles." Proc Biol Sci. Jan. 2008, vol. 275, No. 1630, pp. 11-17.
Eisen et al., "Complications of upper GI endoscopy." Gastrointest Endosc. Jun. 2002, vol. 55, No. 7, pp. 784-793.
Eldor et al., "Glucose-reducing effect of the ORMD-0801 oral insulin preparation in patients with uncontrolled type 1 diabetes: a pilot study" PLoS One., Apr. 2013, vol. 8, No. 4, p. e59524.
Ensign et al., "Oral drug delivery with polymeric nanoparticles: the gastrointestinal mucus barriers." Adv Drug Deliv Rev., May 2012, vol. 64, No. 6, pp. 557-570.
Fallowfield et al., "Patients' preference for administration of endocrine treatments by injection or tablets: results from a study of women with breast cancer." Ann Oncol., Feb. 2006, vol. 17, No. 2, pp. 205-210.
Ferrua et al., "Modeling the fluid dynamics in a human stomach to gain insight of food digestion." J Food Sci., Sep. 2010, vol. 75, No. 7, pp. R151-R162.
Finkelstone et al., "Etiology of small bowel thickening on computed tomography." Can J Gastroenterol, Dec. 2012, vol. 26, No. 12, pp. 897-901.
Foster et al., "Effect of Texture of Plastic and Elastic Model Foods on the Parameters of Mastication." J Neurophysiol, Jun. 2006, vol. 95, No. 6, pp. 3469-3479.
Fox et al., "Fabrication of Sealed Nanostraw Microdevices for Oral Drug Delivery." ACS Nano., Jun. 2016, vol. 10, No. 6 5873-81.
Fox et al., "Micro/nanofabricated Platforms for Oral Drug Delivery." J Control Release., Dec. 2015, vol. 219, No. 34, pp. 431-444.
Gao et al., "Biodegradable, pH-responsive carboxymethyl cellulose/poly(acrylic acid) hydrogels for oral insulin delivery." Macromol Biosci., Apr. 2014, vol. 14, No. 4, pp. 565-575.
Gilroy et al., "Controlled release of biologies for the treatment of type 2 diabetes." J Control Release, Oct. 2016, vol. 240, No. 14, pp. 151-164. Available online Dec. 2, 2015.
Giudice et al., "Needle-free vaccine delivery." Adv Drug Deliv Rev., Apr. 2006, vol. 58, No. 1, pp. 68-89. Available online Mar. 24, 2006.
Glendorf et al., "Importance of the Solvent-Exposed Residues of the Insulin B Chain alpha-Helix for Receptor Binding." Biochemistry Apr. 2008, vol. 4 7, No. 16, pp. 4743-4751.
Gregory et al., "Pattern of gastric emptying the pig: relation to feeding." Br J Nutr. Jan. 1990, vol. 64, No. 1, pp. 45-58.
Guilloteau et al., "Nutritional programming of gastrointestinal tract development. Is the pig a good model for man?" Nutr Res Rev., Jun. 2010, vol. 23, No. 1, pp. 4-22.
Gupta et al., "A permeation enhancer for increasing transport of therapeutic macromolecules across the intestine." J Control Release, Dec. 2013, vol. 172, No. 2, pp. 541-549. Available online May 14, 2013.
Harding et al., "The crystal structure of insulin. II. An investigation of rhombohedral zinc insulin crystals and a report of other crystalline forms." J Mol Biol. Mar. 1966, vol. 16, No. 1, pp. 212-226.
Harrison, "Insulin in Alcoholic Solution By the Mouth." Br Med J. Dec. 1923, vol. 2, No. 3286, pp. 1204-1205.
Hay, "Can 'Robotic' Pills Replace Injections?" The Wall Street Journal Feb. 17, 2014, 4 pages. Retrieved from www.wsj.com/articles/can-8216robotic8217-pills-replace-injections-1392681501?tesla=y.

He et al., "Scalable fabrication of size-controlled chitosan nanoparticles for oral delivery of insulin", Biomaterials, Jun. 2017, vol. 130, No. 7, pp. 28-41.
Hoebler et al., "Particle size of solid food after human mastication and in vitro simulation of oral breakdown." Int J Food Sci Nutr, Jan. 2000, vol. 51, No. 5, pp. 353-366.
Höög et al., "Capsule retentions and incomplete capsule endoscopy examinations: an analysis of 2300 examinations." Gastroenterol Res Pract., Sep. 2011, vol. 2012, Article ID 518718, pp. 1-7.
Hvid et al., "In situ phosphorylation of Akt and ERK1/2 in rat mammary gland, colon, and liver following treatment with human insulin and IGF-1." Toxicol Pathol., Jun. 2011, vol. 39, No. 4, pp. 623-640.
Ingersoll et al., "The impact of medication regimen factors on adherence to chronic treatment: a review of literature." J Behav Med., Jun. 2008, vol. 31, No. 3, pp. 213-224.
Jalabert-Malbos et al., "Particle size distribution in the food bolus after mastication of natural foods." Food Qual Prefer., Jul. 2007, vol. 18, No. 5 , pp. 803-812.
Kalantzi et al., "Characterization of the human upper gastrointestinal contents under conditions simulating bioavailability/bioequivalence studies." Pharm Res., Jan. 2006, vol. 23, No. 1, pp. 165-176.
Kim et al., "Droplet-born air blowing: Novel dissolving microneedle fabrication", J. Control. Release, Jun. 2013, vol. 170, No. 3, pp. 430-436.
Kong et al., "Disintegration of solid foods in human stomach." J Food Sci., Jun. 2008, vol. 73, No. 5, pp. R67-R80.
Lahiji et al., "A patchless dissolving microneedle delivery system enabling rapid and efficient transdermal drug delivery." Sci Rep., Jan. 2015, vol. 21, No. 5, p. 7914.
Lee et al., "Formulation of two-layer dissolving polymeric microneedle patches for insulin transdermal delivery in diabetic mice." J Biomed Mater Res. Part A., Jan. 2017, vol. 105, No. 1, pp. 84-93. Available online Aug. 29, 2016.
Ling et al., "Dissolving polymer microneedle patches for rapid and efficient transdermal delivery of insulin to diabetic rats." Acta Biomater., Nov. 2013, vol. 9, No. 11, pp. 8952-8961 Available online Jun. 29, 2013.
Marasini et al., "Oral delivery of nanoparticle-based vaccines." Expert Rev Vaccines, Nov. 2014, vol. 13, No. 11, pp. 1361-1376. Published online Aug. 26, 2014.
Mathiowitz et al., "Biologically erodable microspheres as potential oral drug delivery systems." Nature, Mar. 1997, vol. 386, No. 6623, pp. 410-414.
Metcalf et al., "Simplified assessment of segmental colonic transit." Gastroenterology, Jan. 1987, vol. 92, No. 1, pp. 40-47.
Mikiewicz et al., "Soluble insulin analogs combining rapid- and long-acting hypoglycemic properties—From an efficient E. coli expression system to a pharmaceutical formulation." PLoS One, Mar. 2017, vol. 12, No. 3, p. e0172600.
More, "Bluetooth low energy: wireless connectivity for medical monitoring." J Diabetes Sci Technol., Mar. 2010, vol. 4, No. 2, pp. 457-463.
Morishita et al., "Novel oral insulin delivery systems based on complexation polymer hydrogels: single and multiple administration studies in type 1 and 2 diabetic rats." J Control Release, Feb. 2006, vol. No 3, pp. 587-594. Available online Dec. 2, 2005.
Moroz et al., "Oral delivery of macromolecular drugs: Where we are after almost 100 years of attempts." Adv Drug Deliv Rev., Jun. 2016, vol. 101, pp. 108-121. Available online Jan. 27, 2016.
Nahata et al., "Extemporaneous drug formulations." Clin Ther., Nov. 2008, vol. 30, No. 11, pp. 2112-2119.
Nakamura et al., "Oral insulin delivery using P(MAA-g-EG) hydrogels: effects of network morphology on insulin delivery characteristics." J Control Release, Mar. 2004, vol. 95, No. 3, pp. 589-599.
Nordquist et al., "Novel microneedle patches for active insulin delivery are efficient in maintaining glycaemic control: an initial comparison with subcutaneous administration." Pharm Res., Jul. 2007, vol. 24, No. 7, pp. 1381-1388.
Omre, "Bluetooth low energy: wireless connectivity for medical monitoring." J Diabetes Sci Technol., Mar. 2010, vol. 4, No. 2, pp. 457-463.

(56) References Cited

OTHER PUBLICATIONS

Ortiz et al., "Metallic ions released from stainless steel, nickel-free, and titanium orthodontic alloys: toxicity and DNA damage." Am J Orthod Dentofacial Orthop., Sep. 2011, vol. 140, No. 3, pp. e115-e122.
Ortiz et al., "Identification of insulin variants using Raman spectroscopy." Anal Biochem, Sep. 2004, vol. 332, No. 2, pp. 245-252. Available online Jul. 24, 2004.
Osterberg et al., "Adherence to medication." N Engl J Med., Aug. 2005, vol. 353, No. 5, pp. 487-497.
Outlander Anatomy, Anatomy Lesson #44: "Terrific Tunnel—GI System, Part 1". Oct. 18, 2016. 43 pages. Retrieved from www.outlanderanatomy.com/anatomy-lesson-44-terrific-tunnel-gi-system-part-1/.
Pawar et al., "Targeting of gastrointestinal tract for amended delivery of protein/peptide therapeutics: strategies and industrial perspectives." J Control Release, Dec. 2014, vol. 196, No. 28, pp. 168-183. Available online Oct. 14, 2014.
Podolsky, "Healing the epithelium: Solving the problem from two sides," J Gastroenterol., Jan. 1997, vol. 32, pp. 122-126.
Pratley et al.,"Liraglutide versus sitagliptin for patients with type 2 diabetes who did not have adequate glycaemic control with metformin: a 26-week, randomised, parallel-group, open-label trial." Lancet, Apr. 2010, vol. 375, No. 9724, pp. 1447-1456.
Prego et al., "The potential of chitosan for the oral administration of peptides." Expert Opin Drug Deliv., Sep. 2005, vol. 2, No. 5, pp. 843-854.
Rapaccini et al., "Gastric wall thickness in normal and neoplastic subjects: a prospective study performed by abdominal ultrasound." Gastrointest Radiol., Jul. 1988, vol. 13, No. 3, pp. 197-199.
Ravi et al., "Needle free injection technology: A complete insight." Int J Pharm Investig., Oct. 2015, vol. 5, No. 4, pp. 192-199.
Römgens et al., "Monitoring the penetration process of single microneedles with varying tip diameters." J Mech Behav Biomed Mater., Dec. 2014, vol. 40, pp. 397-405. Available online Oct. 8, 2014.
Saniocki, "New insights into tablet sticking: characterization and quantification of sticking to punch surfaces during tablet manufacter by direct compaction. PhD Thesis." University Hamburg., 2014, 159 pages.
Santonen et al., "Review on toxicity of stainless steel." Finnish Institute of Occupational Health, Helsinki, Nov. 2010. 87 pages. Retrieved from: www.bssa.org.uk/cms/File/Review on Toxicity of Stainless Steel Finnish Health Institute.pdf.
Schmidt et al., "Viscosity and electrolyte concentrations in gastric juice from cystic fibrosis children compared to healthy children." Eur J Pediatr., May 1981, vol. 136, No. 2, pp. 193-197.
Schoellhammer et al., "Of microneedles and ultrasound: Physical modes of gastrointestinal macromolecule delivery." Tissue Barriers, Feb. 2016, vol. 4, No. 2, e1150235, 5 pages.
Schoellhammer et al., "Ultrasound-Mediated Delivery of RNA to Colonic Mucosa of Live Mice." Gastroenterology, Apr. 2017, vol. 152, No. 5, pp. 1151-1160.
Schoellhammer et al., "Ultrasound-mediated gastrointestinal drug delivery." Sci Transl Med., Oct. 2015, vol. 7, No. 310, p. 1-11.
Schwartz et al., "Electrical stimulation of the isolated rat intestine in the presence of nutrient stimulus enhances glucagon-like peptide-1 release." Physiol Meas., Sep. 2010, vol. 31, No. 9, pp. 1147-1159.
Sharma et al., "Development of enteric submicron particle formulation of papain for oral delivery." Int J Nanomedicine, 2011, vol. 6, pp. 2097-2111.
Sher et al., "Simulation of peristaltic flow of chyme in small intestine for couple stress fluid." Meccanica, Feb. 2014, vol. 49, pp. 325-334. Published online Aug. 29, 2013.
Sokolowski et al., "Needle phobia: etiology, adverse consequences, and patient management." Dent Clin North Am., Oct. 2010, vol. 54, No. 4, pp. 731-744.
Stewart et al., "In vitro and ex vivo strategies for intracellular delivery." Nature, Oct. 2016, vol. 538, No. 7624, pp. 183-192.
Tang et al., "Biodegradable polymer nanoparticles that rapidly penetrate the human mucus barrier." Proc Natl Acad Sci U S A., Nov. 2009, vol. 106, No. 46, p. 19268-19273.
Taverner et al., "Enhanced paracellular transport of insulin can be achieved via transient induction of myosin light chain phosphorylation." J Control Release, Jul. 2015, vol. 28, No. 210, pp. 189-197. Available online May 14, 2015.
International Search Report and Written Opinion for International Application No. PCT/EP2020/082967 dated Feb. 24, 2021 (15 pages).
U.S. Appl. No. 16/691,579, filed Nov. 21, 2019, Abramson et al., US 20200129441 A1.
U.S. Appl. No. 16/614,172, filed Nov. 15, 2019, Traverso et al., US 20200324095 A1.
U.S. Appl. No. 16/614,299, filed Nov. 15, 2019, Traverso et al., US 20200306515 A1.
U.S. Appl. No. 16/613,766, filed Nov. 14, 2019, Traverso et al., US 20200147298 A1.
U.S. Appl. No. 16/614,083, filed Nov. 15, 2019, Traverso et al.
U.S. Appl. No. 16/614,177, filed Nov. 15, 2019, Traverso et al.
U.S. Appl. No. 16/691,514, filed Nov. 21, 2019, Traverso et al.
U.S. Appl. No. 16/614,229, filed Nov. 15, 2019, Traverso et al.
Extended European Search Report for EP Application No. 18802890.6 dated Feb. 2, 2021 (7 pages).
Ferreira D.C. et al. A Nanocommunication System for Endocrine Diseases. Cluster Comput. (2017) vol. 20, pp. 689-706.
International Search Report for International Application No. PCT/EP2021/072199 dated Nov. 24, 2021 (14 pages).

\* cited by examiner

0 Deg    45 Deg    90 Deg

Control
With Washer

SYSTEMS AND METHODS FOR LIQUID INJECTION

RELATED APPLICATIONS

This application claims priority under 35 U.S.C. § 119(e) to U.S. Provisional Application Ser. No. 62/799,882, filed Feb. 1, 2019, and entitled "SYSTEMS AND METHODS FOR LIQUID INJECTION," which is hereby incorporated herein by reference in its entirety for all purposes.

FIELD

The present invention generally relates to self-righting systems and related components such as self-righting articles, self-actuating articles including, for example, self-actuating needles and/or self-actuating biopsy punches, as well as components with relatively high loading of active pharmaceutical ingredients (API).

BACKGROUND

The GI tract offers an incredible opportunity for diagnosing and treating patients. The development of smart dosage systems and articles to enable this has witnessed significant growth over the preceding decade. One of the most significant challenges in maximizing delivery and interaction with the mucosa is ensuring juxtaposition between an article and/or dosing system and the GI mucosa. Prior attempts at doing this have included the introduction of mucoadhesives as well as texturing of one side of a 2 sided system. Orally ingested drugs generally diffuse through the GI tract tissue walls in order to enter the blood stream. Typical ingested pills or articles release their cargo into the GI tract randomly and allow it move via convection and diffusion to the tissue wall. However, many biologic drugs such as insulin cannot move through the liquid in the GI tract because they will be, for example, degraded by enzymes, even if housed in a solid formulation.

Additionally, many pharmaceutical drug formulations on the market require administration via in injection, including numerous vaccines, RNA, and peptides. Injections traditionally involve the use of a liquid formulation passing through a hollow needle and entering into the body intravenously or intramuscularly.

Accordingly, improved systems, articles and methods are needed.

SUMMARY

The present invention generally relates to self-righting articles, such as self-righting capsules.

In one aspect, self-righting articles are provided. In some embodiments, the self-righting article comprises a first portion, a second portion adjacent the first portion having a different average density than the first portion, and a hollow portion, wherein the self-righting article is configured and arranged to be encapsulated in a 000 capsule, or smaller.

In some embodiments, although the self-righting article is configured for potential encapsulation in a 000 capsule, or smaller, the self-righting article does not necessarily need to be encapsulated in such capsule. In embodiments wherein the self-righting article is to be administered, such as by ingesting the self-righting article, the self-righting article may thus be administered without encapsulation.

In some embodiments, the self-righting article comprises a first portion, a second portion adjacent the first portion having a different average density than the first portion, and a tissue-interfacing component associated with the self-righting article, wherein a ratio of an average density of the first material to an average density of the second material is greater than or equal to 2.5:1. In some embodiments, the ratio of an average density of the second material to an average density of the first material is greater than or equal to 2.5:1.

In some embodiments, the self-righting article is configured to anchor at a location internal to a subject and comprises at least a first portion having an average density greater than 1 g/cm$^3$ wherein a longitudinal axis perpendicular to a tissue-engaging surface of the article is configured to maintain an orientation of 20 degrees or less from vertical when acted on by $0.09*10^{-4}$ Nm or less externally applied torque and at least one anchoring mechanism associated with the self-righting article.

In some embodiments, the self-righting article is configured for administration to a location internal to a subject and comprises at least a first portion having an average density greater than 1 g/cm$^3$, the self-righting article has a self-righting time from 90 degrees in water of less than or equal to 0.05 second, at least two tissue interfacing components comprising a tissue-contacting portion configured for contacting tissue, each tissue-contacting portion comprising an electrically-conductive portion configured for electrical communication with tissue and an insulative portion configured to not be in electrical communication with tissue, and a power source in electric communication with the at least two tissue interfacing components.

In another aspect, self-actuating articles are provided. In some embodiments, the article comprises an outer shell, a spring at least partially encapsulated within the outer shell, a support material associated with the spring such that the support material maintains at least a portion of the spring under at least 5% compressive strain under ambient conditions and a tissue interfacing component associated with the spring.

In some embodiments, the article is configured to anchor at a location internal to a subject and comprises an outer shell, a spring at least partially encapsulated with the outer shell, the spring maintained in an at least partially compressed state by a support material under at least 5% compressive strain, and at least one anchoring mechanism operably linked to the spring.

In some embodiments, the article is configured for administration to at a location internal to a subject and comprises an outer shell, a spring at least partially encapsulated with the outer shell, the spring maintained in an at least partially compressed state by a support material under at least 5% compressive strain, at least two tissue interfacing components comprising a tissue-contacting portion configured for contacting tissue, each tissue-contacting portion comprising an electrically-conductive portion configured for electrical communication with tissue and an insulative portion configured to not be in electrical communication with tissue, and a power source in electric communication with the at least two tissue interfacing components.

In another aspect, self-righting articles are provided. In some embodiments, the article comprises a first portion having a mass, a second portion having a mass different than the mass of the first portion; a self-actuating component comprising a spring and a support material adapted to maintain the spring in at least a partially compressed state, wherein the support material is configured for at least partial degradation in a biological fluid; a tissue interfacing component associated with an active pharmaceutical agent and operably linked to the self-actuating component; and a tissue engaging surface configured to contact a surface of a tissue internal to a subject; wherein the self-righting article is configured as a monostatic body due to the center of mass of the self-righting article and the shape of the self-righting article; wherein when the self-righting article is at least partially supported by the tissue of the subject, the self-righting article orients in a direction to allow the tissue interfacing component to release at least a portion of the active pharmaceutical agent into the tissue. In some embodiments the article is so configured that upon said at least partial degradation of the support material, the spring expands to release said portion of the active pharmaceutical agent into the tissue. In some embodiments, the expansion of the spring forces the pharmaceutical agent into the tissue.

In some embodiments, the first portion comprises a first material and the second portion comprises a second material, wherein the first material and the second material are different. In some embodiments, the first portion comprises a first material and the second portion comprises a second material, wherein the first material and the second material are the same.

In some embodiments, the self-righting article has an average density greater than 1 g/cm$^3$.

In some embodiments, the first material and/or second material is selected from the group consisting of a polymer, a ceramic, a metal, a metal alloy, and combinations thereof.

In some embodiments, the metal is selected from the group consisting of stainless steel, iron-carbon alloys, Field's metal, wolfram, molybdemum, gold, zinc, iron, and titanium. In some embodiments, the ceramic is selected from the group consisting of hydroxyapatite, aluminum oxide, calcium oxide, tricalcium phosphate, zirconium oxide, silicates, and silicon dioxide. In some embodiments, the polymer is selected from the group consisting of polycaprolactone, polylactic acid, polyethylene glycol, polypropylene, polyethylene, polycarbonate, polystyrene, polyether ether ketone, akrylonitril-butadien-styren, amorphous polyetherimide, and polyvinyl alcohol.

In some embodiments, the spring comprises a spring constant in the range of 100 N/m to 1500 N/m.

In some embodiments the support material is configured as a plug, wherein the plug is operably linked to the tissue interfacing component, and wherein the plug is exposed to the exterior of the self-righting article via a hole in the tissue engaging surface.

In some embodiments the self-righting article is provided, wherein the spring is positioned in a space surrounded by the first portion, wherein the tissue interfacing component is configured as a projectile that extends substantially along the major axis of the self-righting article; wherein the tissue interfacing component is operably linked to the spring at one end and operably linked to the plug at the other end, and wherein the plug is located in a space surrounded by the second portion and configured such that the second portion prevents the spring in at least a partially compressed state from pushing the plug out of the hole in the tissue engaging surface via the tissue interfacing component.

In some embodiments, the tissue interfacing component is configured to pierce the plug upon activation of the spring.

In some embodiments, the support material is configured in the shape of a flat structure with a major plane and operably linked to the spring, and wherein the major plane of the flat structure is perpendicular to the major axis of the spring. In some embodiments the support material comprises a first surface along the major plane and having a first total surface area, wherein the support material comprises a second surface parallel to the first surface along the major plane and having a second total surface area different from the first total surface area, wherein the first surface comprises one or more cavities, and wherein the first total surface area is greater than the second total surface area.

In some embodiments, the support material is configured within the self-righting article such that the biological fluid entering the self-righting article contacts the first surface to initiate the at least partial degradation of the support material; and wherein the one or more cavities is configured for controlled failure of the support material after the at least partial degradation of the support material.

In some embodiments, the spring is positioned in a space surrounded by the first portion; wherein the support material is positioned between the first portion and the second portion; wherein the support material comprises a hole through which the tissue interfacing component extends substantially along the major axis of the self-righting article; wherein the tissue interfacing component is configured in the shape of a projectile such that one end of the projectile is operably linked to the spring and the other end of the projectile is located proximate to a hole in the tissue engaging surface such that a distance exists between the projectile and the hole; and wherein the tissue engaging surface is on the second portion. In some embodiments, the one or more cavities surround the hole in the support material. In some embodiments, the support material is configured in the shape of a disk.

In some embodiments, the support material is selected from the group consisting of a sugar, a derivative of a sugar, starch, sugar alcohol, maltose, isomalt, calcium carbonate, zinc, sodium chloride, polymers, and combinations thereof.

In some embodiments, the self-righting article comprises one or more vents configured such that the self-actuating component is in fluidic communication with an external environment. In some embodiments, the one or more vents are located in the first portion. In some embodiments, the one or more vents are covered by a coating. In some embodiments, the biological fluid is gastric fluid.

In some embodiments, the self-righting article comprises a self-actuating component comprising a spring and a support material adapted to maintain the spring in at least a partially compressed state, wherein the support material is configured for at least partial degradation in a biological fluid, a chamber comprising a liquid active pharmaceutical agent, and a tissue interfacing component operably linked to the self-actuating component, the tissue interfacing component comprising an inlet, an outlet, and a channel fluidically connected to the inlet and the outlet.

In some embodiments, the chamber is configured to be in fluidic communication with the inlet upon activation of the self-actuating component.

In some embodiments, the self-righting article is at least partially supported by the tissue of the subject, the self-righting article orients in a direction to allow the tissue interfacing component to release at least a portion of the active pharmaceutical agent into the tissue.

In some embodiments, the self-righting article comprises a plug associated with the tissue interfacing component, wherein the tissue interfacing component is configured to pierce the plug upon activation of the self-actuating component.

Those of ordinary skill in the art would understand based upon the teachings of this specification that, in some embodiments, the self-actuating component may be triggered at a desired time to actuate (e.g., upon exposure to a fluid, after a particular length of time, and/or a particular set of physiological conditions).

In some embodiments, the tissue interfacing component is dissolvable or retractable.

In some embodiments, the self-righting article has an average density greater than 1 g/cm$^3$.

In some embodiments, the support material is configured as a plug and wherein the plug is operably linked to the tissue interfacing component.

In some embodiments, the tissue interfacing component is configured as a projectile that extends substantially along the major axis of the self-righting article.

In some embodiments, the support material is configured within the self-righting article such that the biological fluid entering the self-righting article contacts a first surface to initiate the at least partial degradation of the support material. In some embodiments, the support material is selected from the group consisting of a sugar, a derivative of a sugar, starch, sugar alcohol, maltose, isomalt, calcium carbonate, zinc, sodium chloride, polymers, and combinations thereof.

In some embodiments, the self-righting article comprises one or more vents configured such that the self-actuating component is in fluidic communication with an external environment.

In some embodiments, the one or more vents are covered by a coating.

In some embodiments, the article comprises a component configured to retract the tissue interfacing component.

In some embodiments, the article comprises a tissue interfacing component capable of piercing tissue where such components are multi-layered with an inner layer of an aqueous sensitive material.

In some embodiments, the aqueous sensitive material comprises gelatin.

In some embodiments, the tissue interfacing component comprises an outer layer impervious to aqueous fluid such that following triggering an inner layer of the tissue interfacing component is exposed to the fluid in the chamber, mechanically weakening at least a portion of the tissue interfacing component after passage of the fluid through the needle.

In some embodiments, the article comprises a tissue interfacing component configured to retract upon contact with a plug of the self-righting element thereby revealing an aqueous inner layer on both sides upon piercing tissue.

In some embodiments the article comprises an outer shell having an exterior shape comprising a round cross-section, the outer shell defining a first axis, an actuation mechanism comprising a self-actuating component comprising a first spring component and a support material adapted to maintain the first spring component in at least a partially compressed state, wherein the support material is configured for at least partial degradation in a biological fluid, a chamber disposed within the outer shell, the chamber comprising a liquid active pharmaceutical agent, and a tissue interfacing component disposed relative to the outer shell and configured for transfer of liquid from the chamber to a portion of tissue of the lumen wall at a location internal to the subject, wherein the article is self-righting having a geometric center and a center of mass, the center of mass being offset from the geometric center in a first direction along the first axis.

In some embodiments, when the article is supported by tissue of the lumen wall while being oriented such that the center of mass is offset laterally from the geometric center, the article experiences an externally applied torque due to gravity acting to orient the article with the first axis oriented along the direction of gravity such that the tissue interfacing component interacts with the tissue at the location internal to the subject, and upon at least partial degradation of the support material, the actuation mechanism acts on the liquid active pharmaceutical agent such that the tissue interfacing components releases at least a portion of the liquid active pharmaceutical agent into the tissue at the location internal to the subject.

In some embodiments, the liquid active pharmaceutical agent and the chamber are constructed and arranged such that, when the article is oriented with the first axis oriented along the direction of gravity and the tissue interfacing component is interacting with the tissue, the center of mass of the liquid is disposed below said geometric center relative to the surface of the tissue.

In some embodiments, the liquid active pharmaceutical agent and the chamber are constructed and arranged such that, when the article is oriented with the first axis oriented along the direction of gravity and the tissue interfacing component is interacting with the tissue, the center of mass of the liquid is disposed closer to the surface of the tissue than the geometric center of the article.

In some embodiments, the chamber comprises a movable wall, wherein the movable wall is configured to expel liquid active pharmaceutical agent from the chamber.

In some embodiments, the chamber comprises a cylindrical wall, and wherein the movable wall of the chamber comprises a plunger in slideable engagement with the cylindrical wall.

In some embodiments, the tissue interfacing component is operably linked to the self-actuating component, the tissue interfacing component comprising an inlet, an outlet, and a channel fluidically connected to the inlet and the outlet.

In some embodiments, the channel is configured to be in fluidic communication with the chamber comprising the liquid active pharmaceutical ingredient upon activation of the activation mechanism.

In some embodiments, the tissue interfacing component forms or comprises an injection needle operably linked to the first spring component, wherein the first spring component is operable from a first configuration to a second configuration upon at least partial degradation of the support material, wherein the injection needle is retained within the article when the first spring component is in the first configuration, and wherein the injection needle is configured to be advanced from the article and into the lumen wall by movement of the first spring component from the first configuration to the second configuration.

In some embodiments, the injection needle extends through the chamber when the first spring assumes the first configuration and/or when the first spring assumes the second configuration.

In some embodiments, the injection needle comprises a tissue penetration end, a second end portion opposite the tissue penetrating end, and a side wall extending between the tissue penetrating end and the second end portion, the side wall comprising a side hole disposed such that, when the first spring component is in the second configuration, fluid communication is established between the chamber and the tissue penetration end of the injection needle.

In some embodiments, when the first spring component is in the first configuration, the side hole is positioned outside the chamber comprising the liquid active pharmaceutical agent.

In some embodiments, the chamber further comprises an end wall arranged opposite the movable wall, wherein the end wall comprises a penetrable seal, and wherein, when the first spring component assumes the first configuration, the tissue penetrating end of the injection needle is embedded in the penetrable seal, and wherein, when the first spring component assumes the second configuration, the injection needle pierces the penetrable seal.

In some embodiments, the actuation mechanism comprises a second spring component held releasably in a compressed state, the second spring component being configured to release from the compressed state, upon the first spring component moving from the first configuration into the second configuration, to drive the movable wall to expel liquid active pharmaceutical agent from the chamber.

In some embodiments, the first spring component is arranged coaxially with the second spring component, such as radially within the second spring component, with at least partial axial overlap between the first spring component and the second spring component.

In some embodiments, the actuation assembly comprises a third spring component held releasably in a compressed state, the third spring component being configured to release when all or a predefined portion of expellable liquid active pharmaceutical agent from the chamber has been expelled, the release of the third spring component causing the injection needle to retract relative to the article housing.

In some embodiments, the third spring component is arranged coaxially with the first spring component, such as radially within the first spring component, with at least partial axial overlap between the third spring component and the first spring component.

In some embodiments, the tissue interfacing component is at least partly dissolvable or becomes soft after actuation/penetration.

In some embodiments, the tissue interfacing component comprises a jet injection component and wherein the first spring component is configured to expel liquid active pharmaceutical agent through the jet injection component at a penetration velocity allowing the liquid active pharmaceutical agent to penetrate gastric submucosa of the lumen wall.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

(FIGS. 45A-45C) Histology of ex vivo swine stomach after an LSOMA insulin injection using (FIG. 45A) a hematoxylin and eosin stain, (FIG. 45B) an immunohistochemistry stain against smooth muscle actin, or (FIG. 45D) an immunohistochemistry stain against insulin. (FIGS. 45D-45E) Histology of in vivo swine stomach after an L-SOMA administration of green dye using (FIG. 45D) a hematoxylin and eosin stain or (FIG. 45E) an immunohistochemistry stain against smooth muscle actin. (FIGS. 45F-45J) Zoomed histology images respectively corresponding to the boxed section of the images FIGS. 45A-45E (A-E: Scale Bar=1 mm. F-J: Scale bar=250 µm);

DETAILED DESCRIPTION

Overview

Figure 1:
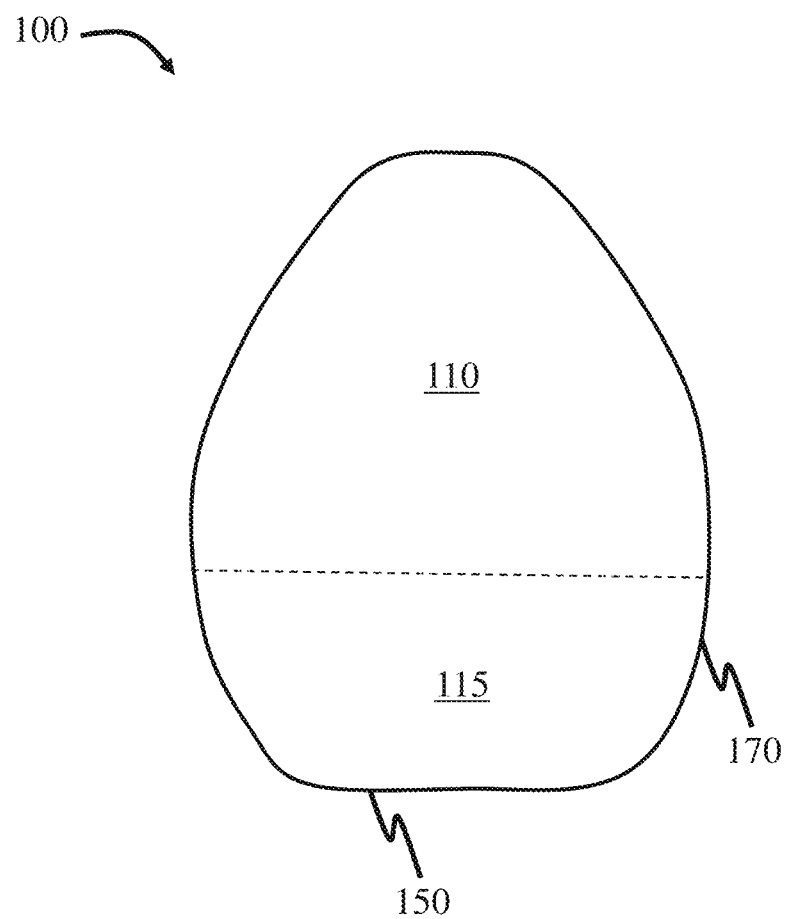
FIG. 1 is a schematic diagram of a self-righting system, according to one set of embodiments.

Self-righting articles, such as self-righting capsules for administration to a subject, are generally provided. In some embodiments, the self-righting article may be configured such that the article may orient itself relative to a surface (e.g., a surface of a tissue of a subject). The self-righting articles described herein may comprise one or more tissue engaging surfaces configured to engage (e.g., interface with, inject into, anchor) with a surface (e.g., a surface of a tissue of a subject). For example, the self-righting article may be placed at any orientation proximate a surface and the self-righting article will (re)-orient itself such that the tissue engaging surface is in contact (e.g., direct contact) with the surface. In some embodiments, the self-righting article may have a particular shape and/or distribution of density (or mass) which, for example, enables the self-righting behavior of the article. In some such embodiments, the capsule containing the self-righting article may be administered to a subject (e.g., for delivery of the self-righting article to a location internal of the subject such as the gastrointestinal tract). In some embodiments, the self-righting may comprise a tissue interfacing component and/or a pharmaceutical agent (e.g., for delivery of the active pharmaceutical agent to a location internal of the subject). In some cases, upon contact of the tissue with the tissue engaging surface of the article, the self-righting article may be configured to release one or more tissue interfacing components. In some cases, the tissue interfacing component is associated with a self-actuating component. For example, the self-righting article may comprise a self-actuating component configured, upon exposure to a fluid, to release the tissue interfacing component from the self-righting article. In some cases, the tissue interfacing component may comprise and/or be associated with the pharmaceutical agent (e.g., for delivery to a location internal to a subject).

The self-righting articles described herein may be useful, for example, as a general platform for delivery of a wide variety of pharmaceutical agents that otherwise are generally delivered via injection directly into tissue due to degradation in the GI tract. In some cases, the self-righting article may be configured to deliver pharmaceutical agents at a desired location and/or at a desired time and/or over a desired duration to a subject. In some embodiments, the self-righting articles described herein may be used to deliver sensors and/or take biopsies, for example, without the need for an endoscopy. In certain embodiments, the self-righting articles described herein may be used to anchor one or more articles to a surface of tissue e.g., in the GI tract. In some cases, the self-righting articles described herein may be used to provide electrical stimulation directly into tissue.

Advantageously, in some embodiments, the self-righting articles and/or self-actuating components described herein may be useful as a general platform for delivery of a wide variety of pharmaceutical agents (e.g., APIs) that are typically delivered via injection directly into tissue due to degradation in the GI tract. For example, the self-righting article may be capable of localizing itself to the tissue wall in a specified direction (e.g., allowing loaded drugs to avoid long passages through the GI tract fluid before diffusing into the blood stream). This article, in some cases, may serve as a platform to allow drugs that are currently degraded by the enzymes in the GI tract to be absorbed with higher bioavailability. Additionally, the article may enable mechanical and electrical mechanisms such as needle plungers, anchors, sensors, etc., to actuate directly at and/or into the tissue wall. In this way, in certain embodiments, the article may serve as a vehicle to deliver electronics or other articles into the GI tract.

In some embodiments, the tissue interfacing component (e.g., associated with a self-actuating component) may comprise a relatively high loading of active pharmaceutical ingredients (e.g., drugs). For example, in certain embodiments, the tissue interfacing component comprises a solid therapeutic agent (e.g., a solid API) and, optionally, a support material (e.g., a binder such as a polymer) such that the solid therapeutic agent is present in the component in a relatively high amount (e.g., greater than or equal to 80 wt %) versus the total weight of the tissue interfacing component. Such tissue-interfacing components may be useful for delivery of API doses (e.g., to a subject). Advantageously, in some embodiments, the reduction of volume required to deliver the required API dose as compared to a liquid formulation permits the creation of solid needle delivery systems for a wide variety of drugs in a variety of places/tissues (e.g., tongue, GI mucosal tissue, skin) and/or reduces and/or eliminates the application of an external force in order to inject a drug solution through the small opening in the needle.

In some embodiments, the article does not comprise a solid therapeutic agent (e.g., the article comprises a liquid therapeutic agent). In some cases, a physiologically relevant dose may be present in a single tissue interfacing component (e.g., having a relatively high API loading).

In an exemplary embodiment, the self-righting article may comprise a tissue interfacing component and a self-actuating component (e.g., comprising a spring and/or a support material) associated with the tissue interfacing component.

As illustrated in FIG. 1, in some embodiments, system 100 (e.g., a self-righting article) comprises a tissue-engaging surface 150. While embodiments described herein refer to a single tissue interfacing surface, in some embodiments, two or more tissue interfacing surfaces may be present. In certain embodiments, the self-righting article may be designed and configured such that the tissue-engaging surface contacts a surface (e.g., a surface of a tissue at a location internal to a subject such as a surface of a stomach of the subject). In some embodiments, system 100 will self-right (e.g., will orient without the need or use of external forces applied to the self-righting article) such that tissue-engaging surface 150 contacts the surface. In certain embodiments, the self-righting article is configured such that an axis essentially perpendicular to the tissue-engaging surface preferentially aligns parallel to the direction of gravity. As described in more detail herein, the self-righting article may be configured such that the axis essentially perpendicular to the tissue-engaging surface is able to maintain an orientation of 20 degrees or less from vertical under externally applied torque. In some embodiments, the self-righting article is configured such that the tissue interfacing component has a longest longitudinal axis oriented within 15 degrees of vertical upon self-righting.

Without wishing to be bound by theory, the self-righting article may be designed to self-right as a result of a distribution of densities (and/or masses) within the self-righting article. For example, in some embodiments, system 100 (e.g., a self-righting article) comprises a first portion 110 and a second portion 115, the first portion and the second portion having different densities and/or different masses. Different densities/masses of the self-righting article are described in more detail herein. In certain embodiments, the self-righting article may have a particular shape which enables the self-righting behavior. For example, as illustrated in FIG. 1, system 100 comprises a monostatic shape (e.g., a mono-monostatic shape, a gomboc-type shape) as indicated by external surface 170 of system 100. The term "monostatic" as used herein is given its ordinary meaning in the art and generally refers to a three-dimensional shape which has a single stable resting position (e.g., a point of balance). The term "mono-monostatic" as used herein is given its ordinary meaning in the art and generally refers to a three-dimensional shape having a single stable resting position and a single unstable resting position. By way of example, and without wishing to be bound by theory, a sphere with a center of mass shifted from the geometrical center is general considered a mono-monostatic shape. The term "gomboc" as used herein is given its ordinary meaning in the art and generally refers to a convex three-dimensional shape which, when placed on a flat surface, has a single stable point of equilibrium (or orientation) and a single unstable point of equilibrium (or orientation). For example, and without wishing to be bound by theory, a gomboc-type shape when placed on a surface at any orientation other than the single stable orientation of the shape, then the shape will tend to re-orient to its single stable orientation. Such shapes are described in more detail below.

Figure 2:
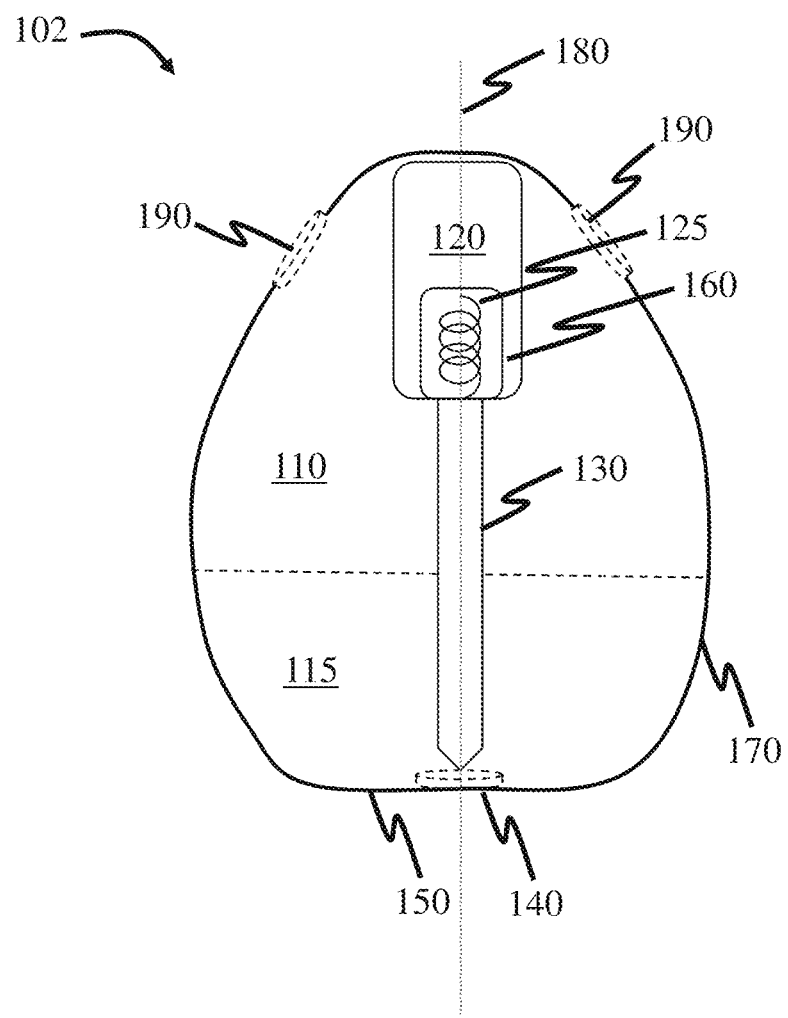
FIG. 2 is a cross-sectional schematic diagram of an exemplary self-righting system, according to one set of embodiments.

FIG. 2 shows a cross-sectional illustration of exemplary system 102. In some embodiments, system 102 comprises a self-actuating component 120. Self-actuating component 120 may be configured, e.g., upon exposure to a particular fluid, to release tissue interfacing component 130 associated with self-actuating component 120, from system 102. For example, in some cases, self-actuating component 120 comprises a spring 125 such that, upon actuation of the self-actuating component, spring 125 expands pushing tissue interfacing component 130 out of system 102 through hole 140 (associated with tissue engaging surface 150). In some cases, spring 125 comprises a support material 160 which maintains spring 125 under compression (e.g., under at least 5% compressive strain). In some cases, upon exposure of support material 160 and/or spring 125 to a fluid, the spring may be configured to release at least 10% (e.g., at least 20%, at least 30%, at least 40%, at least 50%, at least 60%, at least 70%, at least 80%, at least 90%, including any percentage therein) of a stored compressive energy of the spring (e.g., such that tissue interfacing component 130 is released). In some embodiments, the spring is associated with the support material (e.g., at least partially encapsulated by the support material, in direct contact with the support material).

In some embodiments, the hole (e.g., hole 140 of FIG. 2) may comprise a fluidic gate (e.g., a plug, a coating, a barrier). In some cases, the fluidic gate may prevent a fluid (e.g., a fluid external to the system) from entering the system at the hole until a desired time. In certain embodiments, the fluidic gate comprises a barrier material. Non-limiting examples of suitable barrier materials include foils of polycaprolactone, thermoplastic elastomers, cellulose, and silicone. The barrier material may comprise one or more hydrophobic materials. In certain embodiments the barrier material may comprise one or more hydrophilic materials (e.g., sugar, PEG). Possible fabrication methods for these coatings include spray coating, dip coating, wrapping, deposition or other manufacturing methods. Those of ordinary skill in the art would be capable of selecting suitable hydrophobic and hydrophilic materials as a barrier material based upon the teachings of this specification.

In certain embodiments, tissue interfacing component 130 comprises an active pharmaceutical agent. In some embodiments, the active pharmaceutical agent may be present in the tissue interfacing component at relatively high amounts (e.g., greater than or equal to 10 wt %, greater than or equal to 80 wt %, or greater than or equal to 90 wt % API versus the total weight of the tissue interfacing component). The self-righting articles described herein may, in some cases, be administered to a subject e.g., such that the pharmaceutical agent is delivered to the subject. For example, in some cases, the article may be administered to the subject and a pharmaceutical agent is released from the article at a location internal to the subject. Administration of the articles and release of pharmaceutical agents are described in more detail herein.

Figure 38:
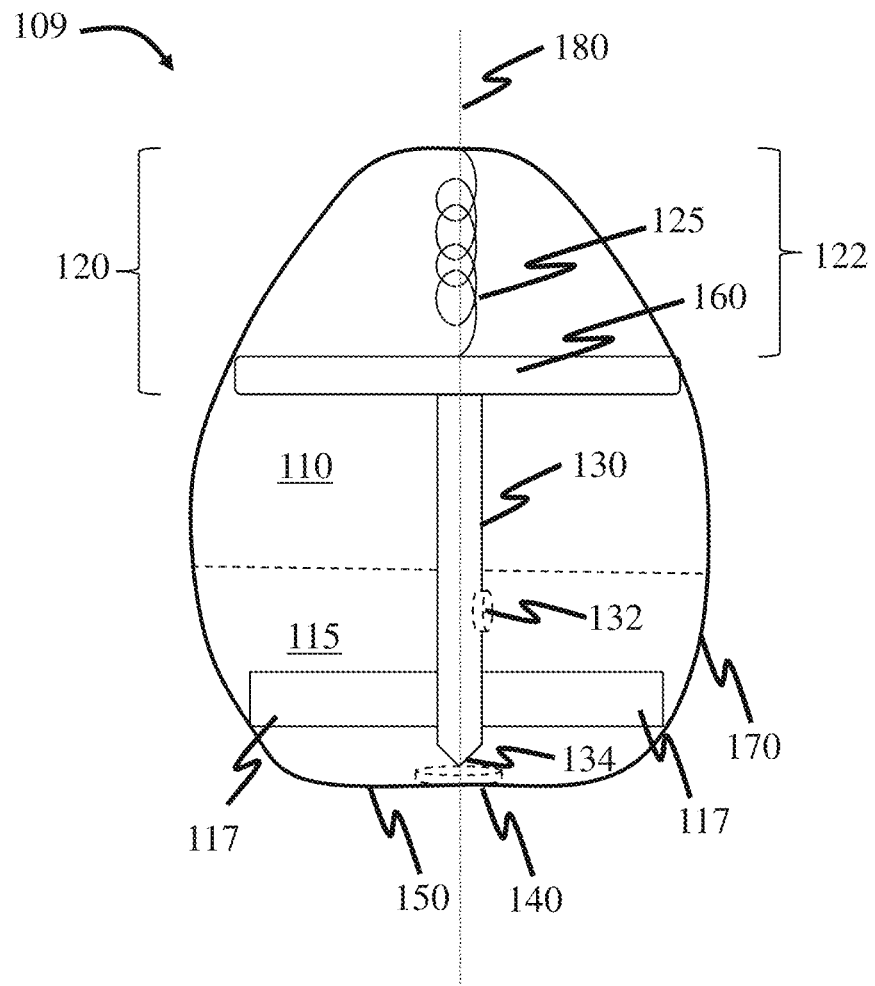
FIG. 38 is a cross-sectional schematic diagram of an exemplary self-righting system, according to one set of embodiments.
Figures 39A, 39B, 39C, 39D:
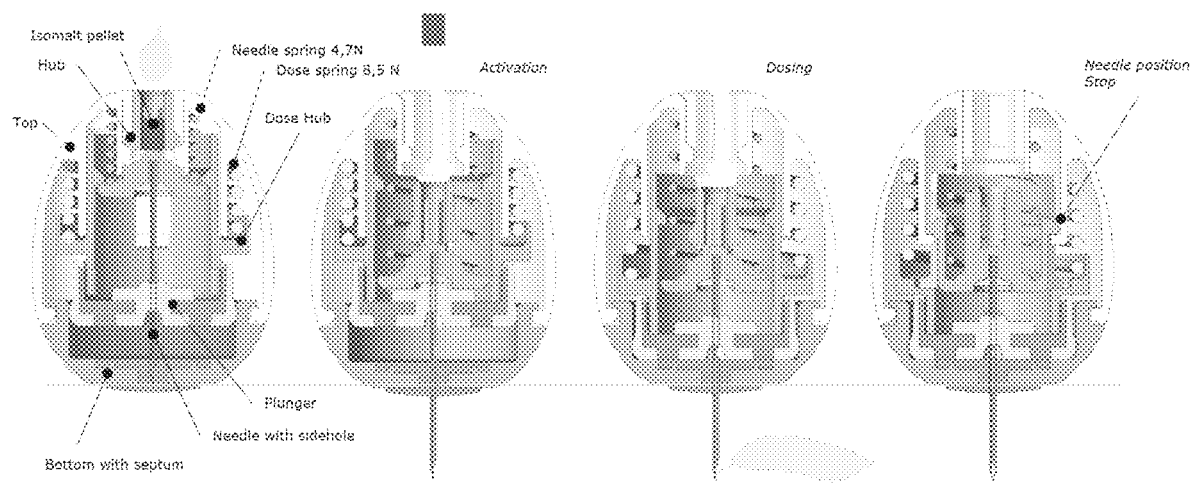
FIG. 39A is a cross-sectional schematic illustration of an exemplary system, according to one set of embodiments.
FIG. 39B is a cross-sectional schematic illustration of an exemplary system, according to one set of embodiments.
FIG. 39C is a cross-sectional schematic illustration of an exemplary system, according to one set of embodiments.
FIG. 39D is a cross-sectional schematic illustration of an exemplary system, according to one set of embodiments.
Figure 39E:
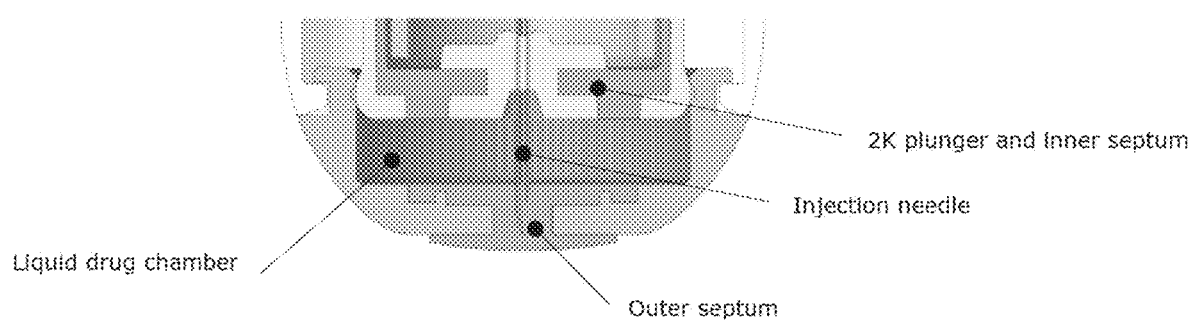
FIG. 39E is a close up view of a portion of the schematic illustrated in FIG. 39A, according to one set of embodiments.
Figures 40A, 40B, 40C, 40D, 40E:
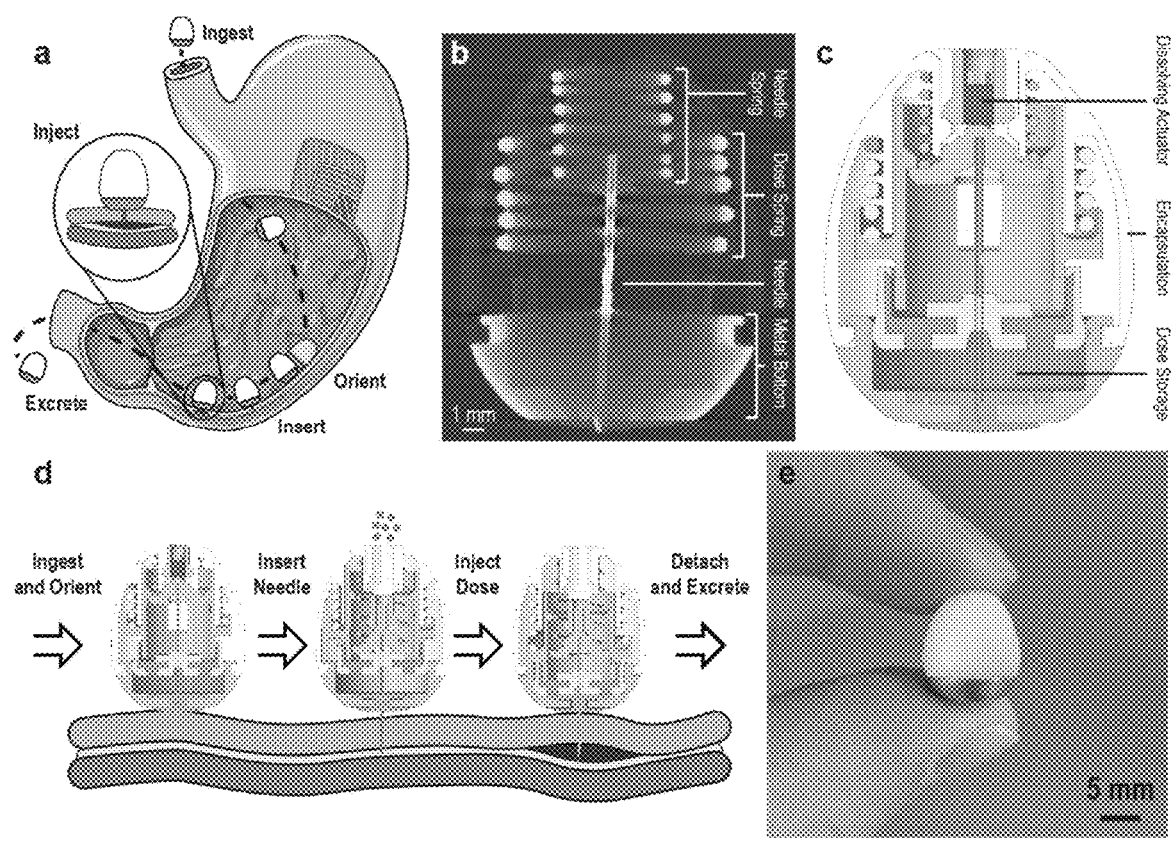
FIGS. 40A-40E show, according to one set of embodiments, A) an orally dosed Liquid injecting Self-Orienting Millimeter-scale Actuator (L-SOMA) delivers a formulation of active pharmaceutical ingredient into the stomach submucosa. The system first orients towards the tissue wall. Next, a hydration based actuator is activated and a compressed spring propels a 32 G needle into the stomach submucosa. After needle insertion, a second spring injects the drug payload. Finally, the encapsulation detaches and is excreted. (B) Micro-CT scan of the L-SOMA system before actuation. (C) CAD design of the L-SOMA. (D) Timeline of the L-SOMA after ingestion. After the hydration based actuator dissolves, the needle spring expands and inserts the needle. The needle plunger then triggers the dose spring to expand and deliver the liquid formulation. (E) L-SOMA capsule prototype.

In some embodiments, the tissue interfacing component may be configured to facilitate transfer of an active pharmaceutical agent (e.g., a liquid active pharmaceutical agent) from a chamber of the self-righting article into a tissue of a subject (e.g., at a location internal to the subject). For example, as illustrated in FIG. 38, system 109 comprises a self-actuating component 120 comprising a spring 125 such that, upon actuation of the self-actuating component, spring 125 expands pushing a tissue interfacing component 130 out of system 109 through hole 140 (associated with tissue engaging surface 150). In some cases, spring 125 comprises a support material 160 which maintains spring 125 under compression (e.g., under at least 5% compressive strain). In some embodiments, system 109 comprises tissue interfacing component 130 associated spring 125 and chamber 117. In some embodiments, chamber 117 comprises an active pharmaceutical agent (e.g., a liquid active pharmaceutical agent). In some embodiments, upon activation of self-actuating component 120, tissue interfacing component facilitates fluidic communication between chamber 117 and the environment external to system 109 and/or to a tissue in contact with tissue engaging surface 150.

In some embodiments, the tissue interfacing component comprises an inlet in fluidic communication with an outlet of the tissue interfacing component. For example, in some embodiments, the tissue interfacing component (e.g., a needle such as a hollow needle) comprises an inlet, an outlet, and a fluidic channel in fluidic communication with the inlet and the outlet. For example, as illustrated in FIG. 38, system 109 comprises tissue interfacing component 130 comprising inlet 132 and outlet 134 in fluidic communication with inlet 132. Upon activation of self-actuating component 120, inlet 132 may be brought into fluidic communication with fluidic chamber 117 (e.g., comprising an active pharmaceutical agent and/or a liquid). In some embodiments, fluidic communication between inlet 132 and fluidic chamber 117 facilitates the flow of a fluid from fluidic chamber 117 through tissue interfacing component 130 such that it exits outlet 134. In some embodiments, outlet 134 may interface with a surface of tissue of a subject such that the liquid is injected into the tissue. In some embodiments, hole 140 may comprise a plug (e.g., a septum) such that, upon activation of self-actuating component 120, tissue interfacing component 130 pierces the plug in hole 140.

The channel of the tissue interfacing component need not be present within the body of tissue interfacing component, but may, in some embodiments, be a channel disposed on a surface of the tissue interfacing component (e.g., configured to facilitate flow of the fluid in the fluidic chamber to the tissue of a subject upon activation of the self-activating component). In some embodiments, the fluidic channel is disposed within the tissue interfacing component.

In some embodiments, the tissue interfacing component may comprises a first end portion configured to penetrate tissue (e.g., a tissue penetration end) and a second end portion opposite the first end portion. In some embodiments, the tissue interfacing component comprises a side wall extending between the first end portion and the second end portion.

In some embodiments, the side wall comprises a hole. For example, referring again to FIG. 38, tissue interfacing component 130 has a first end portion comprising outlet 134 and a hole 32 in the side wall of tissue interfacing component 130. Hole 132 may be configured in some cases such that, when in fluidic communication with chamber 117, a fluid disposed in chamber 117 enters hole 132 and becomes in fluidic communication with outlet 134.

In some cases, when the first spring component is in the first configuration, the side hole may be positioned outside the chamber comprising the liquid active pharmaceutical agent. In some embodiments, the hole may be positioned adjacent the chamber when the spring is in the second configuration.

In some embodiments, tissue interfacing component 130 does not comprise hole 132. In some embodiments, the tissue interfacing component may comprise a channel in the side wall of the tissue interfacing component. The channel may have any suitable shape. For example, the shape may be any suitable cross-sectional shape including circular, oval, triangular, irregular, trapezoidal, square or rectangular, or the like. Those of ordinary skill in the art would be capable of selecting channel dimensions and/or shape based upon the teachings of this specification.

Shapes and considerations for tissue interfacing components are described in more detail, below.

In some embodiments, after a particular time period after activation of the self-actuating component, the tissue interfacing component may be configured to mechanically weaken, degrade, and/or dissolve. For example, at least a portion of the tissue interfacing component may, in the presence of a biological fluid, comprise a material (e.g., gelatin) that mechanically weakens, degrades, and/or dissolves.

In some embodiments, the tissue interfacing component is configured to be retracted after a particular period of time after activation of the self-actuating component. In some embodiments, the first spring component is operable from a first configuration to a second configuration up-on at least partial degradation of the support material, wherein the injection needle is retained within the article when the first spring component is in the first configuration. In some embodiments, the tissue interfacing component is configured to be advanced from the article and into tissue of the subject (e.g., such as a lumen wall). For example, movement of the spring from the first configuration to the second configuration such that the tissue interfacing component contacts and/or penetrates a tissue adjacent the article.

In some embodiments, the tissue interfacing component extends through the chamber when the first spring assumes the first configuration and/or when the first spring assumes the second configuration.

In some embodiments, the tissue interfacing component may be retracted by actuation of the spring from the second configuration to a third configuration, such that the tissue interfacing component no longer interfaces with the tissue adjacent the article.

The distance the tissue interfacing component travels, the shape of the tissue interfacing component, the length of the tissue interfacing component, and/or the angle of a surface of the outlet of the tissue interfacing component may be adjusted to facilitate the flow of a fluid comprising an active pharmaceutical agent in accordance with the description herein.

In some embodiments, the self-actuating component may comprise a second support material configured, for example, to activate a second stage of the self-actuating component configured to interface with the fluidic chamber. In some embodiments, the self-actuating component may facilitate the exit of the fluid (e.g., by applying pressure to the fluidic chamber) from the fluidic chamber into the inlet of the tissue interfacing component.

In some embodiments, the fluidic chamber (e.g., chamber 117 of FIG. 38) may be fluidically isolated until, for example, activation of the self-actuating component. In some embodiments, upon activation of the self-actuating component, the fluidic chamber may be in fluidic communication with at least a portion of a tissue interfacing component (e.g., an inlet of the tissue interfacing component).

In some embodiments, the chamber comprises a movable wall. For example, in some embodiments, the moveable wall may be configured to expel liquid active pharmaceutical agent from the chamber. In some embodiments, the chamber comprises a chamber wall (e.g., having a cross-sectional shape such as a cylindrical shape, a square shape, or the like). In some embodiments, the movable wall of the chamber comprises a plunger in slideable engagement with the chamber wall. In some embodiments, the chamber comprises an end wall portion arranged opposite the movable wall. In some embodiments, the end wall comprises a penetrable seal. In some embodiments, when the first spring component assumes the first configuration, the tissue penetrating end of the tissue interfacing component is embedded in the penetrable seal. In some embodiments, when the first spring component assumes the second configuration, the tissue interfacing component pierces the penetrable seal.

In some embodiments, the tissue interfacing component comprises an injection needle.

In some embodiments, the actuation mechanism (e.g., a self-actuating component as described herein) comprises a second spring component held releasably in a compressed state. In some embodiments, the second spring component is configured to release from the compressed state, upon the first spring component moving from the first configuration into the second configuration. For example, the first spring component moving from the first configuration into the second configuration may, in some cases, drive the movable wall to expel liquid active pharmaceutical agent from the chamber.

Figure 52:
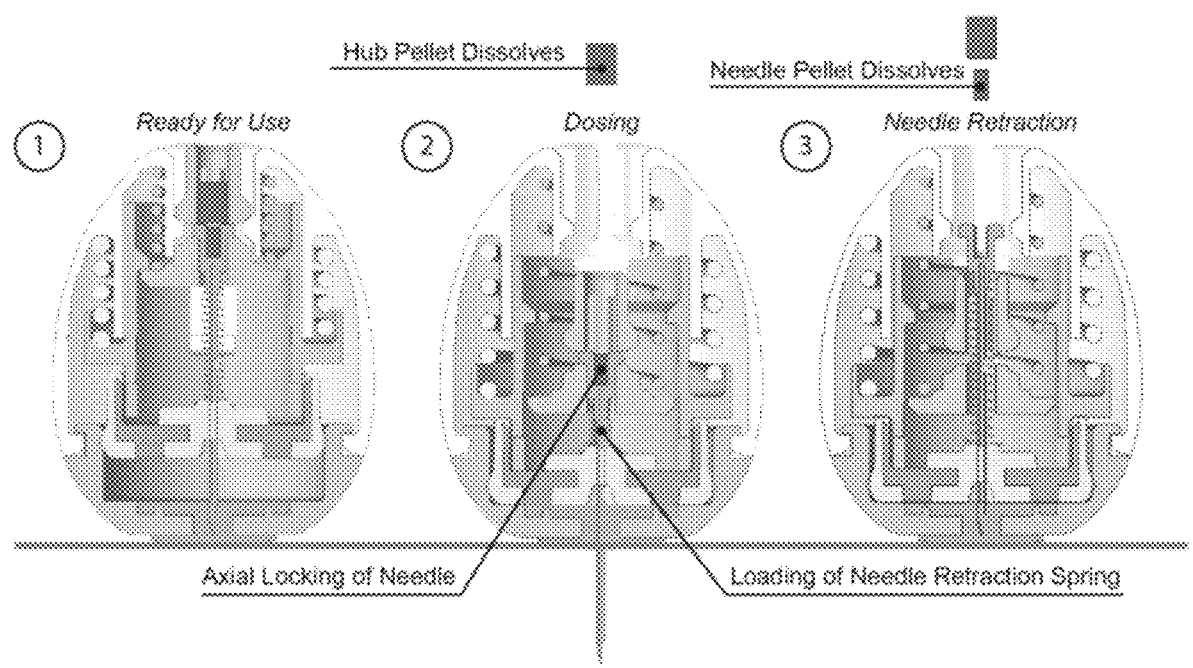
FIG. 52 shows L-SOMA needle retraction, according to one set of embodiments. Device designed to retract needle after injection.

In some embodiments, the first spring component is arranged coaxially with the second spring component, such as radially within the second spring component (see FIG. 52). In some embodiments, the first spring component is arranged coaxially with the second spring component with at least partial axial overlap between the first spring component and the second spring component.

In some embodiments, the actuation mechanism comprises a third spring component held releasably in a compressed state. In some embodiments, the third spring component is configured to release when all or a predefined portion of expellable liquid active pharmaceutical agent from the chamber has been expelled. In some embodiments, the release of the third spring component causes the tissue interfacing component to retract relative to the article outer shell (e.g., such that the tissue interfacing component is contained within the article).

In some embodiments, the third spring component is arranged coaxially with the first spring component, such as radially within the first spring component. In some embodiments, the third spring component is arranged coaxially with the first spring component with at least partial axial overlap between the third spring component and the first spring component.

In some embodiments, as described in more detail below, the tissue interfacing component is at least partly dissolvable and/or becomes mechanically soft after actuation/penetration.

In certain embodiments, the tissue interfacing component comprises a jet injection component (e.g., for liquid jet injection using high velocity stream into a tissue of a subject). In an exemplary embodiment, the jet injection component comprises a chamber comprising a polymeric portion. In certain embodiments, the polymeric portion may comprise an acid (e.g., a weak acid) and/or a base. In some cases, a fluid (e.g., a gastric fluid) may enter the chamber such that it reacts with the acid and/or base to form a gas. In some cases, the chamber may comprise a coating (e.g., such that the fluid does not contact the polymeric portion under the coating dissolves). In another exemplary embodiments, the jet injection component comprises a plunger/piston (e.g., activated by a spring associated with the plunger/piston) such that a material is expelled rapidly from the system.

In some embodiments, the first spring component is configured to expel liquid active pharmaceutical agent through the jet injection component at a penetration velocity such that the liquid active pharmaceutical agent penetrates at least a portion of tissue of a location internal to a subject (e.g., a gastric submucosa of a lumen wall).

In some embodiments, the articles/systems described herein are administered to a subject (e.g., orally). In certain embodiments, the system may be administered orally, rectally, vaginally, nasally, or uretherally. In certain embodiments, upon reaching a location internal to the subject (e.g., the gastrointestinal tract), at least a portion of a support material degrades such that a spring extends and/or a tissue interfacing component interfaces (e.g., contacts, penetrates) with a tissue located internal to the subject. In some embodiments, the location internally of the subject is the colon, the duodenum, the ileum, the jejunum, the stomach, or the esophagus. In some embodiments, the location internal to the subject comprises a lumen (e.g., having a lumen wall). As described above and herein, in some embodiments, an active pharmaceutical ingredient may be released during and/or after penetrate of the tissue located internal to the subject. For example, the articles and/or systems described herein may be suitable for ingestion into a lumen of a subject (e.g., for the delivery of an active pharmaceutical agent at the lumen). Such a lumen may have, in some cases, a lumen wall associated with the lumen (e.g., such that the active pharmaceutical agent is injected/delivered to the lumen wall).

Figure 3:
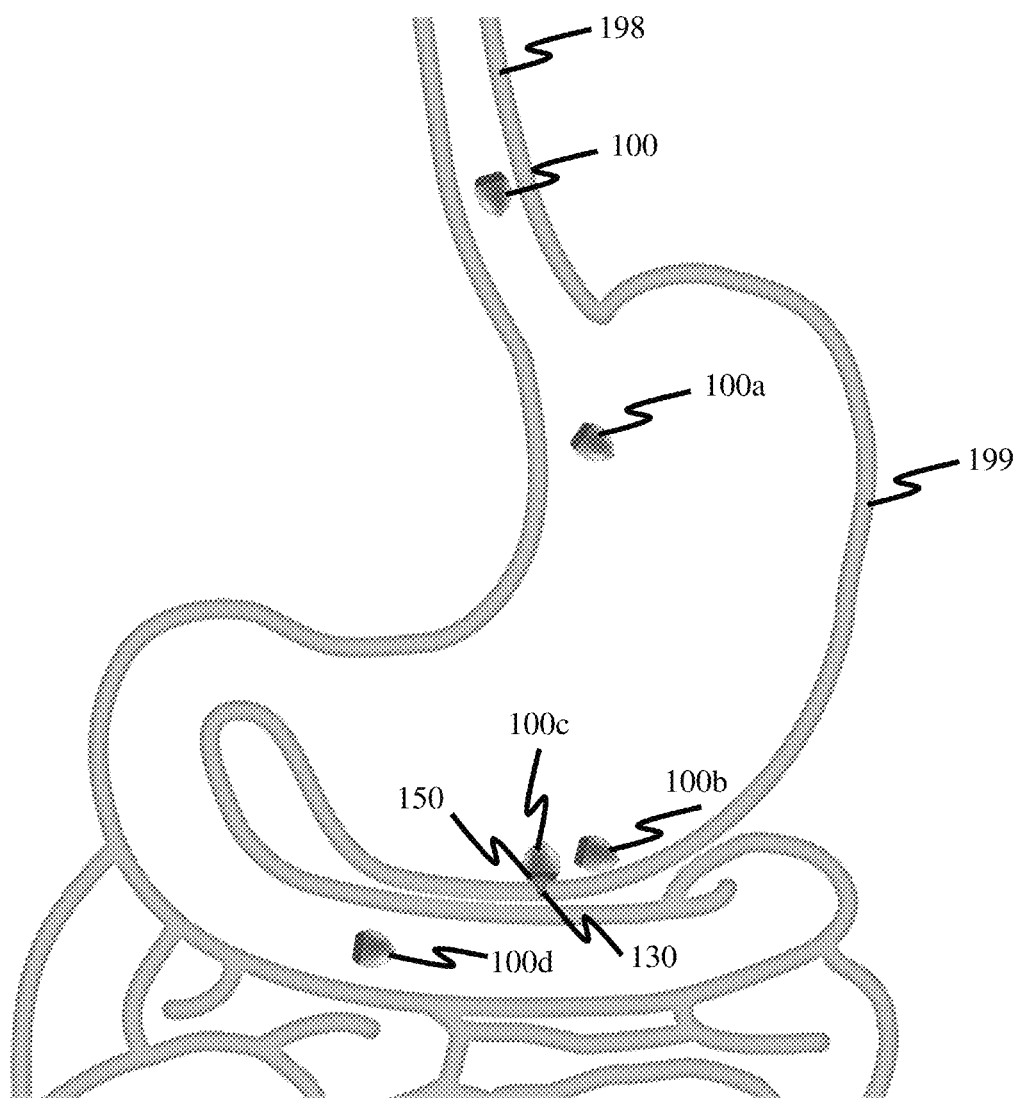
FIG. 3 is a schematic illustration of administration of a self-righting system, according to one set of embodiments.

By way of example, and without wishing to be limited by such an exemplary set of embodiments, the system may be administered to a subject orally where it, in some cases, travels to the stomach of the subject, sinks to the bottom of the subject's stomach, and the system self-rights such that a tissue-engaging surface of the system contacts the stomach tissue (e.g., the system is at least partly supported by the stomach tissue). For example, as illustrated schematically in FIG. 3, exemplary system 100 may be administered to a subject (e.g., orally) such that system 100 enters gastrointestinal system 198 of the subject. System 100 may travel through gastrointestinal system 198 until reaching stomach 199 of the subject (system 100a). In some embodiments, system 100 may sink to the bottom of stomach 199 (system 100b) such that it contacts a surface of stomach 199. In certain embodiments, system 100 self-rights (system 100c) such that tissue engaging surface 150 of system 100 contacts the surface of stomach 199 and system 100 self-actuates such that tissue interfacing component 130 interfaces with a tissue at a location internal to a subject (e.g., the surface of stomach 199). While FIG. 3 illustrates interfacing of the tissue interfacing component with surface of the stomach 199, those of ordinary skill in the art would understand, based upon the teachings of this specification, that the tissue interfacing component may contact one or more layers underlying the surface of the stomach (or other location internal to the subject) including e.g., mucosal, sub-mucosal, and/or muscular tissue layer(s).

In some cases, as described herein, self-righting of system 100 may be driven by gravitational forces (e.g., acting on a center of mass of system 100). After a desired period of time, in some embodiments, system 100 disengages (e.g., tissue interfacing component 130 dissolves and/or is released) and exits stomach 199 (system 100*d*). The description above is not meant to be limiting and those of ordinary skill in the art would understand that other interactions between the system and the gastrointestinal system of a subject are also possible, as described herein. In some embodiments, system 100 is a monostatic body, as described in more detail below.

In an exemplary embodiment, the self-righting article (or system) as described herein comprises an outer shell having an exterior shape comprising a round cross-section, the outer shell defining a first axis, an actuation mechanism comprising a self-actuating component comprising a first spring component and a support material adapted to maintain the first spring component in at least a partially compressed state, wherein the support material is configured for at least partial degradation in a biological fluid, and a chamber disposed within the outer shell, the chamber comprising a liquid active pharmaceutical agent. In some embodiments, a tissue interfacing component is disposed relative to the outer shell and configured for transfer of liquid from the chamber to a portion of tissue of the lumen wall at a location internal to the subject, wherein the article is self-righting having a geometric center and a center of mass, the center of mass being offset from the geometric center in a first direction along the first axis.

The following description provides various embodiments for the self-righting, self-actuating, and relatively high API loaded components of the systems described herein.

Self-Righting

As described above, in some embodiments, the self-righting article may comprise two or more portions having different average densities such that, for example, the self-righting article may orient itself substantially perpendicular to the surface (e.g., a surface substantially orthogonal to the force of gravity, a surface of a tissue such as the wall of the gastrointestinal tract). In some cases, the self-righting article may have a particular shape which, for example, enables the self-righting behavior of the article. In some embodiments, the self-righting article may be disposed (e.g., encapsulated) in a capsule. In certain embodiments, the self-righting article is not provided in a capsule. In some embodiments, the capsule containing the self-righting article may be administered to a subject (e.g., for delivery of the self-righting article to a location internal of the subject such as the gastrointestinal tract). In some embodiments, the self-righting article and/or the capsule may comprise a pharmaceutical agent (e.g., for delivery of the active pharmaceutical agent to a location internal of the subject).

The self-righting articles described herein may be useful, for example, as a general platform for delivery of a wide variety of pharmaceutical ingredients that otherwise are generally delivered via injection directly into tissue due to degradation in the GI tract. In some embodiments, the self-righting articles described herein may be used to deliver sensors and/or take biopsies, for example, without the need for an endoscopy.

Advantageously, the self-righting article may be capable of localizing itself to the tissue wall in a specified direction (e.g., allowing loaded drugs to avoid long passages through the GI tract fluid before diffusing into the blood stream). As described herein, this article, in some cases, may serve as a platform to allow drugs that are currently degraded by the enzymes in the GI tract to be absorbed with higher bioavailability. Additionally, the article may enable mechanical and electrical mechanisms such as needle plungers, anchors, sensors, etc., to actuate directly at and/or into the tissue wall. In this way, in certain embodiments, the article may serve as a vehicle to deliver electronics or other articles into the GI tract.

In some embodiments, the self-righting article may have a particular cross-sectional shape. In certain embodiments, the shape may be any suitable cross-sectional shape including circular, oval, triangular, irregular, trapezoidal, square or rectangular, or the like. In certain embodiments, the self-righting article may be non-spherical. In some embodiments, the self-righting article may be a monostatic body and/or has only one stable point (e.g., the self-righting article may stably maintain a particular orientation in only one given orientation). In an exemplary embodiment, the self-righting article has a gomboc shape and/or comprises a gomboc shaped component. Self-righting articles having a gomboc shape may self-right to a particular orientation upon displacement from that orientation, without additional forces. In some cases, the self-righting article may self-right in a fluid (e.g., a liquid having a relatively low viscosity, a liquid having a relatively high viscosity). Advantageously, the shape is such that the self-righting article orients the self-righting article predictably and quickly while minimizing the motion caused from forces inside of the GI tract is described. In some cases, at least a surface of the self-righting article comprises a flat surface. For example, as illustrated in FIG. 1 and FIG. 2, in some embodiments, tissue engaging surface 150 may be flat.

Referring again to FIG. 1, in some embodiments, self-righting article comprises a first portion 110 and a second portion 115 adjacent first portion 110, having a different average density than the first portion and/or a different mass than the first portion. For example, in some embodiments, the self-righting article comprises a first portion and a second portion adjacent the first portion having a different average density in the first portion. For example, the first portion may have a first average density and a second portion may have a second average density, different than the first average density. In some embodiments, a ratio of an average density of the first portion to an average density of the second portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than equal to 8:1, greater than or equal to 9:1, or greater than or equal to 10:1. In certain embodiments, a ratio of an average density of the first portion to an average density of the second portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible. Without wishing to be bound by theory, the self-righting article having a first portion and a second portion having different average densities may result in the self-righting article substantially maintaining a particular orientation(s) relative to the surface (e.g. a wall of the gastrointestinal track).

In some embodiments, a ratio of an average density of the second portion to an average density of the first portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than equal to 8:1, greater than or equal to 9:1, or greater than or equal to 10:1. In certain embodiments, a ratio of an average density of the second portion to an average density of the first portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible.

In certain embodiments, the self-righting article comprises a first portion and a second portion adjacent the first portion having a different mass than the first portion. For example, the first portion may have a first mass and a second portion may have a second mass, different than the first mass. In some embodiments, a ratio of a mass of the first portion to a mass of the second portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than or equal to 8:1, greater than or equal to 9:1, or greater than or equal to 10:1. In certain embodiments, a ratio of a mass of the first portion to a mass of the second portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible. Without wishing to be bound by theory, the self-righting article having a first portion and a second portion having different masses may result in the self-righting article substantially maintaining a particular orientation(s) relative to the surface (e.g. a wall of the gastrointestinal track).

In some embodiments, a ratio of a mass of the second portion to a mass of the first portion may be greater than 1:1, greater than equal to 2:1, greater than equal to 2.5:1, greater than equal to 3:1, greater than equal to 3.5:1, greater than equal to 4:1, greater than or equal to 4.5:1, greater than or equal to 5:1, greater than equal to 5.5:1, greater than equal to 5.5:1, greater than equal to 6:1, greater than or equal to 6.5:1, greater than or equal to 7:1, greater than or equal to 8:1, greater than or equal to 9:1, or greater than or equal to 10:1. In certain embodiments, a ratio of a mass of the second portion to a mass of the first portion may be less than or equal to 15:1, less than or equal to 10:1, less than or equal to 9:1, less than or equal to 8:1, less than or equal to 7:1, less than or equal to 6.5:1, less than or equal to 6:1, less than or equal to 5.5:1, less than or equal to 5:1, less than or equal to 4.5:1, less than or equal to 4:1, less than or equal to 3.5:1, less than or equal to 3:1, less than or equal to 2.5:1, less than or equal to 2:1, or less than or equal to 1.5:1. Combinations of the above referenced ranges are possible (e.g., greater than or equal to 1:1 and less than or equal to 15:1). Other ranges are also possible.

Figure 4:
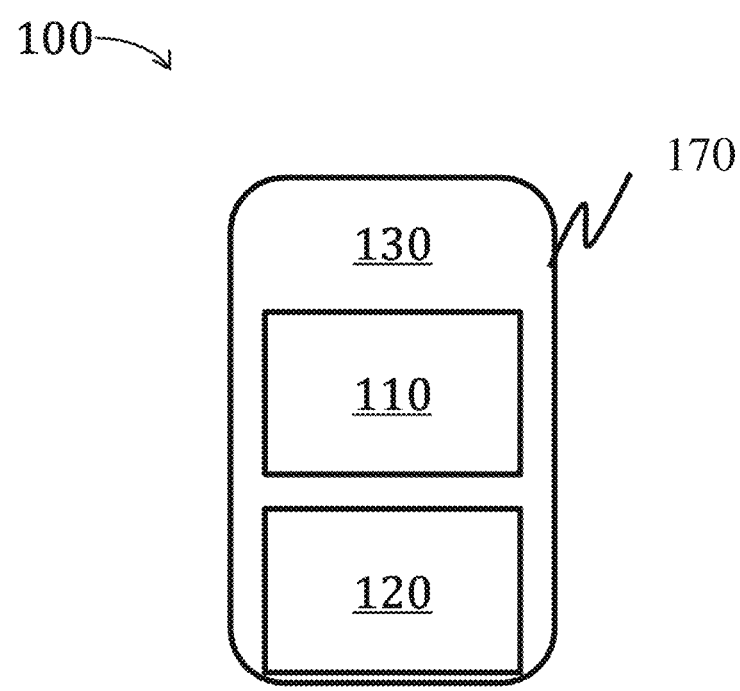
FIG. 4 is a schematic diagram of an exemplary self-righting article, according to one set of embodiments.

As illustrated in FIG. 4, system 100 may comprise a first portion 110 and a second portion 120 adjacent first portion 110. As used herein, when a portion is referred to as being "adjacent" another portion, it can be directly adjacent to (e.g., in contact with) the portion, or one or more intervening components (e.g., a liquid, a hollow portion) also may be present. A portion that is "directly adjacent" another portion means that no intervening component(s) is present.

For example, referring again to FIG. 1, first portion 110 may occupy a first volume of the self-righting article having a first average density and/or mass and second portion 115 may occupy a remaining volume of the self-righting article having a second average density and/or mass. In certain embodiments, referring back to FIG. 4, first portion 110 may occupy a first volume of the self-righting article, second portion 115 may occupy a second volume of the self-righting article, and a third portion 130 may be hollow and/or may contain one or more (additional) components.

In some embodiments, the first portion occupies greater than or equal to 1 vol %, greater than or equal to 5 vol %, greater than or equal to 10 vol %, greater than or equal to 20 vol %, greater than or equal to 25 vol %, greater than or equal to 30 vol %, greater than or equal to 40 vol %, greater than or equal to 45 vol %, greater than or equal to 50 vol %, greater than or equal to 55 vol %, greater than or equal to 60 vol %, greater than or equal to 65 vol %, greater than or equal to 70 vol %, greater than or equal to 75 vol %, greater than or equal to 80 vol %, greater than or equal to 90 vol %, or greater than or equal to 95 vol %, versus the total volume of the self-righting article. In certain embodiments, the first portion occupies less than or equal to 99 vol %, less than or equal to 95 vol %, less than or equal to 90 vol %, less than or equal to 80 vol %, less than or equal to 75 vol %, less than or equal to 70 vol %, less than or equal to 60 vol %, less than or equal to 55 vol %, less than or equal to 50 vol %, less than or equal to 45 vol %, less than or equal to 40 vol %, less than or equal to 30 vol %, less than or equal to 25 vol %, less than or equal to 20 vol %, less than or equal to 10 vol %, or less than or equal to 5 vol %, versus the total volume of the self-righting article. Combinations of the above-referenced ranges are also possible (e.g., greater than or equal to 1 vol % and less than or equal to 99 vol %, greater than or equal to 40 vol % and less than or equal to 60 vol %. Other ranges are also possible.

In certain embodiments, the second portion occupies greater than or equal to 1 vol %, greater than or equal to 5 vol %, greater than or equal to 10 vol %, greater than or equal to 20 vol %, greater than or equal to 25 vol %, greater than or equal to 30 vol %, greater than or equal to 40 vol %, greater than or equal to 45 vol %, greater than or equal to 50 vol %, greater than or equal to 55 vol %, greater than or equal to 60 vol %, greater than or equal to 65 vol %, greater than or equal to 70 vol %, greater than or equal to 75 vol %, greater than or equal to 80 vol %, greater than or equal to 90 vol %, or greater than or equal to 95 vol %, versus the total volume of the self-righting article. In some embodiments, the second portion occupies less than or equal to 99 vol %, less than or equal to 95 vol %, less than or equal to 90 vol %, less than or equal to 80 vol %, less than or equal to 75 vol %, less than or equal to 70 vol %, less than or equal to 60 vol %, less than or equal to 55 vol %, less than or equal to 50 vol %, less than or equal to 45 vol %, less than or equal to 40 vol %, less than or equal to 30 vol %, less than or equal to 25 vol %, less than or equal to 20 vol %, less than or equal to 10 vol %, or less than or equal to 5 vol %, versus the total volume of the self-righting article. Combinations of the above-referenced ranges are also possible (e.g., greater than or equal to 1 vol % and less than or equal to 99 vol %, greater than or equal to 40 vol % and less than or equal to 60 vol %. Other ranges are also possible.

In some embodiments, the third portion (e.g., the hollow portion) occupies greater than or equal to 1 vol %, greater than or equal to 5 vol %, greater than or equal to 10 vol %, greater than or equal to 20 vol %, greater than or equal to 25 vol %, greater than or equal to 30 vol %, greater than or equal to 40 vol %, greater than or equal to 45 vol %, greater than or equal to 50 vol %, greater than or equal to 55 vol %, greater than or equal to 60 vol %, greater than or equal to 65 vol %, greater than or equal to 70 vol %, greater than or equal to 75 vol %, greater than or equal to 80 vol %, greater than or equal to 90 vol %, or greater than or equal to 95 vol %, versus the total volume of the self-righting article. In certain embodiments, the third portion occupies less than or equal to 99 vol %, less than or equal to 95 vol %, less than or equal to 90 vol %, less than or equal to 80 vol %, less than or equal to 75 vol %, less than or equal to 70 vol %, less than or equal to 60 vol %, less than or equal to 55 vol %, less than or equal to 50 vol %, less than or equal to 45 vol %, less than or equal to 40 vol %, less than or equal to 30 vol %, less than or equal to 25 vol %, less than or equal to 20 vol %, less than or equal to 10 vol %, or less than or equal to 5 vol %, versus the total volume of the self-righting article. Combinations of the above-referenced ranges are also possible (e.g., greater than or equal to 1 vol % and less than or equal to 99 vol %, greater than or equal to 40 vol % and less than or equal to 60 vol %. Other ranges are also possible.

In some embodiments, the self-righting article may comprise any suitable ratio of a first volume occupied by the first portion versus a second volume occupied by the second portion. In certain embodiments, the ratio of the first volume to the second volume is greater than or equal to 1:100, greater than or equal to 1:50, greater than or equal to 1:25, greater than or equal to 1:10, greater than or equal to 1:8, greater than or equal to 1:6, greater than or equal to 1:4, greater than or equal to 1:3, greater than or equal to 1:2, greater than or equal to 1:1.5, greater than or equal to 1:1.1, greater than or equal to 1:1, greater than or equal to 1.1:1, greater than or equal to 1.5:1, greater than or equal to 2:1, greater than or equal to 3:1, greater than or equal to 4:1, greater than or equal to 6:1, greater than or equal to 8:1, greater than or equal to 10:1, greater than or equal to 25:1, or greater than or equal to 50:1. In certain embodiments, the ratio of the first volume to the second volume is less than or equal to 100:1, less than or equal to 50:1, less than or equal to 25:1, less than or equal to 10:1, less than or equal to 8:1, less than or equal to 6:1, less than or equal to 4:1, less than or equal to 2:1, less than or equal to 1.5:1, less than or equal to 1.1:1, less than or equal to 1:1, less than or equal to 1:1.1, less than or equal to 1:1.5, less than or equal to 1:2, less than or equal to 1:4, less than or equal to 1:6, less than or equal to 1:8, less than or equal to 1:10, less than or equal to 1:25, or less than or equal to 1:50. Combinations of the above-referenced ranges are also possible (e.g., greater than or equal to 1:100 and less than or equal to 100:1, greater than or equal to 1:10 and less than or equal to 10:1, greater than or equal to 1:2 and less than or equal to 2:1). Other ranges are also possible. Other volume ratios are also possible.

Without wishing to be bound by theory, in some embodiments, the ratio of the first volume occupied by the first portion versus the second volume occupied by the second portion may be selected such that the center of mass of the self-righting article has one local minimum.

In some embodiments, the self-righting article is configured to be administered directly to a subject (e.g., without encapsulation in a capsule). In certain embodiments, the self-righting article is configured and arranged to be encapsulated in a capsule having a shell (e.g., outer surface 170 of FIG. 4 comprises a shell). In some such embodiments, referring now to FIG. 4, the self-righting article may comprise a third portion 130 (e.g., a hollow portion). In certain embodiments, a tissue interfacing component and/or an active pharmaceutical ingredient may be disposed within the hollow portion.

In some embodiments, the capsule is a 000 capsule or smaller (e.g., the capsule has a shape or size as described in the USP including, but not limited to, 000 capsule, 00 capsule, 0 capsule, 1 capsule, 2 capsule, 3 capsule, 4 capsule, or 5 capsule.) In certain embodiments, the capsule at least partially encapsulates the first portion and the second portion of the self-righting article. In some embodiments, multiple devices can be placed inside of a capsule. In some embodiments, although the self-righting article may be configured for potential encapsulation in a 000 capsule, or smaller, the self-righting article does not necessarily need to be encapsulated in such capsule. In embodiments wherein the self-righting article is to be administered, such as by ingesting the self-righting article, the self-righting article may thus be administered without encapsulation.

In certain embodiments, the self-righting article may comprise a coating on at least a portion of an outer surface of the self-righting article. In certain embodiments, the system (e.g., the system comprising the self-righting article) comprises a coating (e.g., a film disposed on a least a surface of the system). In some embodiments, the coating may be applied as an aqueous or organic solvent-based polymer system, fats and/or wax. In certain embodiments, the coating comprises one or more of a polymer, a plasticizer, a colorant, a solvent, a fat, and a wax. Non-limiting examples of suitable fats and/or waxes include beeswax, carnauba wax, cetyl alcohol, and cetostearyl alcohol.

Non-limiting examples of suitable polymers for the coating include of cellulosic (e.g. hydroxypropylmethylcellulose, hydroxypropylcellulose, hydroxyethylcellulose, hydroxyethylcellulose phthalate, ethylcellulose, cellulose acetate phthalate, cellulose acetate trimellitate), vinyl (e.g. poly(vinyl pyrrolidone), poly(vinyl alcohol), poly(vinyl pyrrolidone)-poly(vinyl acetate)copolymers, poly(vinyl alcohol)-poly(ethylene glycol) co-polymers, poly(vinyl acetate phthalate), glycols (e.g. poly(ethylene glycol)), acrylics (e.g. amino alkyl methacrylate copolymers), other carbohydrates (e.g. maltodextrin, polydextrose), and combinations thereof.

Non-limiting examples of suitable colorants include natural pigments (e.g. riboflavin, beta-carotene, carmine lake), inorganic pigments (e.g. titanium dioxide, iron oxides), water-soluble dyes (FD&C Yellow #5, FD&C blue #2), FD&C lakes (FD&C Yellow #5 Lake, FD&C Blue #2 Lake), and D&C lakes (D&C Yellow #10 Lake, D&C Red #30 Lake). Non-limiting examples of suitable plasticizers include polyhydric alcohols (e.g. propylene glycol, glycerol, polyethylene glycols), acetate esters (e.g. triacetin, triethyl citrate, acetyl triethyl citrate), phthalate esters (e.g. diethyl phthalate), glycerides (e.g. acylated monoglycerides) and oils (e.g. castor oils, mineral oils).

Polymers, plasticizers, colorants, solvents, fats, and/or waxes may be combined in any suitable amount to form the coating. The coating may be applied in any suitable method including, for example, dip coating and/or spray atomization. Other methods of depositing the coating are also possible.

In some embodiments, a tissue interfacing component is associated with the self-righting article. Non-limiting examples of tissue interfacing components include needles (e.g., stainless steel needles, needles comprising an API), biopsy punches, microneedles (e.g., microneedles comprising an API), projectiles, or the like.

In some embodiments, the tissue-interfacing component comprises a spring-actuated component. Such tissue interfacing components are generally described in a co-owned International Patent Application No. WO 2018/213600, entitled "SELF-RIGHTING SYSTEMS AND RELATED COMPONENTS AND METHODS" filed on May 17, 2018 which is incorporated herein by reference in its entirety. For example, a self-righting article comprising a tissue interfacing component (e.g., a needle) may be administered to a subject such that, he self-righting article orients at a location internal of the subject such that the tissue interfacing opponent punctures a tissue proximate the location internal of the subject. In some such amendments, and active pharmaceutical ingredient associated with the self-righting article may be released into and or proximate the tissue. In some embodiments, the tissue-interfacing component may penetrate the tissue. In some embodiments, the tissue is penetrated with a force of greater than or equal to 1 mN and less than or equal to 20,000 mN (e.g., greater than or equal to 10 mN and less than or equal to 20 mN, greater than or equal to 10 mN and less than or equal to 100 mN, greater than or equal to 100 mN and less than or equal to 20,000 mN, greater than or equal to 5,000 mN and less than or equal to 20,000 mN).

In certain embodiments, the tissue interfacing component may be oriented within the self-righting article such that, upon administration to a subject, the tissue interfacing component is aligned substantially orthogonally (e.g., within 15° of orthogonal) with a tissue internal to the subject (e.g., GI mucosal tissue). In some embodiments, the tissue interfacing component may be disposed within a hollow portion of the self-righting device such that the tissue interfacing component releases from the self-righting device along a longitudinal axis of the hollow portion. For example, referring again to FIG. 2, self-righting article may have a longest longitudinal axis 180 aligned within 15 degrees of orthogonal of tissue engaging surface 150. In certain embodiments, longest longitudinal axis 180 is parallel to a major axis of tissue interfacing component 130. In some embodiments, tissue interfacing component 130 is released (e.g., upon activation of self-actuating component 120 and/or spring 125) such that spring 125 expands along longitudinal axis 180 and/or tissue interfacing component travels parallel to the direction of longitudinal axis 180. In some such embodiments, tissue interfacing component may exit hole 140 and enter a tissue of the subject in a direction substantially parallel to longitudinal axis 180. In other embodiments, however, the tissue interfacing component is not aligned substantially orthogonally with a tissue internal to a subject.

In some embodiments, the self-righting article has a longest longitudinal axis oriented within less than or equal to 15 degrees, less than or equal to 10 degrees, less than or equal to 5 degrees, less than or equal to 2 degrees, or less than or equal to 1 degree of vertical upon self-righting. In certain embodiments, the self-righting article has a longest longitudinal axis oriented within greater than or equal to 0.1 degrees, greater than or equal to 1 degree, greater than or equal to 2 degrees, greater than or equal to 5 degrees, or greater than or equal to 10 degrees. Combinations of the above-referenced ranges are also possible (e.g., greater than or equal to 0.1 degrees and less than or equal to 15 degrees). Other ranges are also possible.

In certain embodiments, the tissue-interfacing component has a longest longitudinal axis oriented within less than or equal to 15 degrees, less than or equal to 10 degrees, less than or equal to 5 degrees, less than or equal to 2 degrees, or less than or equal to 1 degree of vertical upon self-righting. In some embodiments, the tissue-interfacing component has a longest longitudinal axis oriented within greater than or equal to 0.1 degrees, greater than or equal to 1 degree, greater than or equal to 2 degrees, greater than or equal to 5 degrees, or greater than or equal to 10 degrees. Combinations of the above-referenced ranges are also possible (e.g., greater than or equal to 0.1 degrees and less than or equal to 15 degrees). Other ranges are also possible.

In some embodiments, the hollow portion may be cylindrical in shape. Other shapes are also possible.

In an exemplary embodiment, the tissue-interfacing component comprises a plurality of microneedles. In another exemplary embodiment, the tissue interfacing component comprises a single needle. In yet another exemplary embodiment, the tissue interfacing component comprises a biopsy component (e.g., a biopsy jaw). In some cases, the tissue interfacing component may comprise an anchoring mechanism (e.g., a hook, a mucoadhesive). Tissue interfacing components are described in more detail, below.

As described above, in some embodiments, the first portion comprises a first material having a first average density. In some embodiments, the first material and/or the second material may be selected to impart a particular mass and/or density to the first portion and/or the second portion.

In some embodiments the average density of the first portion is less than or equal to 2 g/mL, less than or equal to 1.8 g/mL, less than equal to 1.6 g/mL, less than or equal to 1.4 g/mL, less than or equal to 1.2 g/mL, less than or equal to 1 g/mL, less than or equal to 0.8 g/mL, less than or equal to 0.6 g/mL, less than or equal to 0.4 g/mL, less than or equal to 0.2 g/mL, less than or equal to 0.1 g/mL, less than or equal to 0.05 g/mL, or less than or equal to 0.02 g/mL. In certain monuments, the first portion has an average density of greater than or equal to 0.01 g/mL, greater than or equal to 0.02 g/mL, greater than or equal to 0.05 g/mL, greater than or equal to 0.1 g/mL, greater than or equal to 0.2 g/mL, greater than or equal to 0.4 g/mL, greater than or equal to 0.6 g/mL, greater than or equal to 0.8 g/mL, greater than or equal to 1 g/mL, greater than or equal to 1.2 g/mL, greater than or equal to 1.4 g/mL, greater than or equal to 1.6 g/mL, or greater than or equal to 1.8 g/mL. Combinations of the above referenced ranges are also possible (e.g., greater than or equal to 0.01 g/mL and less than or equal to 2 g/mL, greater than or equal to 0.6 g/mL and less than or equal to 2 g/mL). Other ranges are also possible.

In certain embodiments, the second portion comprises a second material having a second average density (e.g., different than the first average density). In some embodiments, the average density of the second portion (e.g. and/or second material) is less than or equal to 20 g/mL, less than or equal to 18 g/mL, less than or equal to 16 g/mL, less than or equal to 14 g/mL, less than or equal to 12 g/mL, less than or equal to 10 g/mL, less than or equal to 8 g/mL, less than or equal to 6 g/mL, less than or equal to 4 g/mL, or less than or equal to 3 g/L. In certain embodiments, the average density of the second portion is greater than or equal to 2 g/mL, greater than or equal to 3 g/mL, greater than or equal to 4 g/mL, greater than or equal to 6 g/mL, greater than or equal to 8 g/mL, greater than equal to 10 g/mL, greater than equal to 12 g/mL, greater than or equal to 14 g/mL, greater than or equal to 16 g/mL, or greater than or equal to 18 g/mL. Combinations of the above referenced ranges are also possible (e.g., greater than or equal to 2 g/mL and less than or equal to 20 g/mL). Other ranges are also possible. In some embodiments, the second portion may have an average density in one or more ranges described above in the context of the first portion (e.g., greater than or equal to 0.6 g/mL and less than or equal to 2 g/mL) and is different than the average density of the first portion.

The first portion and the second portion may be selected to have any suitable mass. In some embodiments, the first portion may have a total mass (e.g., including all components within the first portion) of greater than or equal to 20 mg, greater than or equal to 50 mg, greater than or equal to 75 mg, greater than or equal to 100 mg, greater than or equal to 200 mg, greater than or equal to 300 mg, greater than or equal to 400 mg, greater than or equal to 500 mg, greater than or equal to 750 mg, greater than or equal to 1 g, greater than or equal to 1.5 g, greater than or equal to 2 g, greater than or equal to 3 g. greater than or equal to 4 g, greater than or equal to 5 g, greater than or equal to 7 g, greater than or equal to 10 g, greater than or equal to 15 g, including any mass in between 20 mg and 15 g. In certain embodiments, the first portion may have a total mass of less than or equal to 15 g, less than or equal to 10 g, less than or equal to 7 g, less than or equal to 5 g, less than or equal to 4 g, less than or equal to 3 g, less than or equal to 2 g, less than or equal to 1.5 g, less than or equal to 1 g, less than or equal to 750 mg, less than or equal to 500 mg, less than or equal to 400 mg, less than or equal to 300 mg, less than or equal to 200 mg, less than or equal to 100 mg, less than or equal to 75 mg, less than or equal to 50 mg, or less than or equal to 20 mg, including any mass in between 15 g and 20 mg. Combinations of the above-referenced ranges are also possible (e.g., greater than or equal to 50 mg and less than or equal to 4 g, greater than or equal to 50 mg and less than or equal to 15 g). In some embodiments, the first portion or second portion has a mass in a range of greater than equal to 20 mg and less than or equal to 15 g. In some embodiments, the first portion or second portion has a mass in a range of greater than equal to 20 mg and less than or equal to 1 g. In some embodiments, the first portion or second portion has a mass in a range of greater than equal to 300 mg and less than or equal to 12 g. In some embodiments, the first portion or second portion has a mass in a range of greater than equal to 100 mg and less than or equal to 250 mg. In some embodiments, the first portion or second portion has a mass in a range of greater than equal to 20 mg and less than or equal to 15 g. In some embodiments, the first portion or second portion has a mass in a range of greater than equal to 1.5 and less than or equal to 6.5 g. Other ranges are also possible.

In certain embodiments, the second portion may have a total mass (e.g., including all components within the second portion) of greater than or equal to 50 mg, greater than or equal to 75 mg, greater than or equal to 100 mg, greater than or equal to 200 mg, greater than or equal to 400 mg, greater than or equal to 500 mg, greater than or equal to 750 mg, greater than or equal to 1 g, greater than or equal to 1.5 g, greater than or equal to 2 g, greater than or equal to 3 g. greater than or equal to 4 g, greater than or equal to 5 g, greater than or equal to 7 g, or greater than or equal to 10 g In certain embodiments, the second portion may have a total mass of less than or equal to 15 g, less than or equal to 10 g, less than or equal to 7 g, less than or equal to 5 g, less than or equal to 4 g, less than or equal to 3 g, less than or equal to 2 g, less than or equal to 1.5 g, less than or equal to 1 g, less than or equal to 750 mg, less than or equal to 500 mg, less than or equal to 400 mg, less than or equal to 200 mg, less than or equal to 100 mg, or less than or equal to 75 mg. Combinations of the above-referenced ranges are also possible (e.g., greater than or equal to 50 mg and less than or equal to 4 g, greater than or equal to 50 mg and less than or equal to 15 g). Other ranges are also possible.

In some embodiments the first material and/or second material is selected from the group consisting of polymers, ceramics, metals, and combinations thereof (e.g., metal filled polymer). In some cases, the first material and/or the second material may be biocompatible. In some cases, the metal may be selected from the group consisting of stainless steel, iron-carbon alloys, Field's metal, wolfram, molybdemum, gold, zinc, iron, and titanium.

In some embodiments, the ceramic may be selected from the group consisting of hydroxyapatite, aluminum oxide, calcium oxide, tricalcium phosphate, silicates, silicon dioxide, and zirconium oxide.

In certain embodiments, the polymer may be selected from the group consisting of polycaprolactone, polylactic acid, polyethylene glycol, polypropylene, polyethylene, polycarbonate, polystyrene, and polyether ether ketone, akrylonitril-butadien-styren, amorphous polyetherimide, and polyvinyl alcohol.

In an exemplary embodiment, the first material comprises a metal and the second material comprises a polymer.

The self-righting article generally has a geometric center (e.g., center of the geometric volume). In some embodiments, the self-righting article has a geometric center and a center of mass, the center of mass being offset from the geometric center in a first direction along the first axis. In some embodiments, when the article is supported by tissue of a subject (e.g., a lumen wall) while being oriented such that the center of mass is offset laterally from the geometric center, the article experiences an externally applied torque due to gravity acting to orient the article with the first axis oriented along the direction of gravity. In some such embodiments, the tissue engaging surface interacts with the tissue at the location internal to the subject (e.g., such that a tissue interfacing component may interface with the tissue).

In certain embodiments, the density, mass, and/or volume of the first portion and/or the second portion may be selected such that the self-righting article exhibit self-righting behavior. For example, in some embodiments, a center of mass of the self-righting article may be offset from the geometric center such that the article, suspended via an axis passing through the geometric center, with the center of mass offset laterally from the geometric center, is configured to maintain an orientation of 20 degrees or less from vertical when acted on by $0.09*10^{-4}$ Nm or less externally applied torque.

In some embodiments, the self-righting article maintains an orientation of 20° or less from vertical when acted on by $0.09*10^{-4}$ Nm or less of externally applied torque. In certain embodiments, the self-righting article maintains an orientation of 15° or less, 12° or less, 10° or less, 8° or less, 6° or less, 4° or less, or 2° or less from vertical when acted on by $0.09*10^{-4}$ Nm or less of externally applied torque. In some embodiments, the self-righting article maintains an orientation of greater than or equal to 1°, greater than or equal to 2°, greater than or equal to 4°, greater than or equal to 6°, greater than or equal to 8°, greater than or equal to 10°, greater than or equal to 12°, or greater than or equal to 15° from vertical when acted on by 0.09*10^−4 Nm or less of externally applied torque. Combinations of the above referenced ranges are also possible (e.g., 20° or less and greater than or equal to 1°). Other ranges are also possible.

In some embodiments the self-righting article may be characterized as having a particular self-righting time from 90° in a particular fluid. The self-righting time may be determined by placing the self-righting article in the particular fluid at 90°, and allowing the self-righting article to return to a particular orientation otherwise maintained by the self-righting article in the absence of the fluid (e.g., an orientation corresponding to a stable point of equilibrium (or orientation) of the article).

In certain embodiments, the fluid is oil. In some such embodiments, the self-righting article has a self-righting time from 90° in oil of less than or equal to 0.15 seconds, less than or equal to 0.1 seconds, less than or equal to 0.05 seconds, or less than or equal to 0.02 seconds. In certain embodiments, the self-righting article has a self-righting time from 90° in oil of greater than or equal to 0.01 seconds, greater than or equal to 0.02 seconds, greater than or equal to 0.05 seconds, greater than or equal to 0.1 seconds, or greater than or equal to 0.12 seconds. Combinations of the above referenced ranges are also possible (e.g., less than or equal to 0.15 seconds and greater than or equal to 0.01 seconds). Other ranges are also possible. Self-righting time in oil is determined with the system/article fully submerged.

In some embodiments, the fluid is gastric fluid. In some such embodiments the self-righting article has a self-righting time from 90° in gastric fluid of less than or equal to 0.06 seconds, less than or equal to 0.05 seconds, less than or equal to 0.04 seconds, less than or equal to 0.03 seconds, or less than or equal to 0.02 seconds. In certain embodiments, the self-righting article has a self-righting time from 90° in gastric fluid of greater than or equal to 0.005 seconds greater than or equal to 0.01 seconds, greater than or equal to 0.02 seconds, greater than or equal to 0.03 seconds, greater than or equal to 0.04 seconds, or greater than or equal to 0.05 seconds. Combinations of the above referenced ranges are also possible (e.g., less than or equal to 0.06 seconds and greater than or equal to 0.005 seconds). Other ranges are also possible. Self-righting time in gastric fluid is determined with the system/article fully submerged.

In certain embodiments, the fluid is mucus. In some such embodiments the self-righting article has a self-righting time from 90° in mucus of less than or equal to 0.05 seconds, less than or equal to 0.04 seconds, less than or equal to 0.03 seconds, or less than or equal to 0.02 seconds. In certain embodiments, the self-righting article has a self-righting time from 90° in mucus of greater than or equal to 0.005 seconds greater than or equal to 0.01 seconds, greater than or equal to 0.02 seconds, greater than or equal to 0.03 seconds, greater than or equal to 0.04 seconds, or greater than or equal to 0.045 seconds. Combinations of the above referenced ranges are also possible (e.g., less than or equal to 0.05 seconds and greater than or equal to 0.005 seconds). Other ranges are also possible. Self-righting time in mucus is determined with the system/article fully submerged.

In some embodiments, the fluid is water. In some such embodiments the self-righting article has a self-righting time from 90° in water of less than or equal to 0.05 seconds, less than or equal to 0.04 seconds, less than or equal to 0.03 seconds, or less than or equal to 0.02 seconds. In certain embodiments, the self-righting article has a self-righting time from 90° in water of greater than or equal to 0.005 seconds greater than or equal to 0.01 seconds, greater than or equal to 0.02 seconds, greater than or equal to 0.03 seconds, greater than or equal to 0.04 seconds, or greater than or equal to 0.045 seconds. Combinations of the above referenced ranges are also possible (e.g., less than or equal to 0.05 seconds and greater than or equal to 0.005 seconds). Other ranges are also possible. Self-righting time in water is determined with the system/article fully submerged.

In some embodiments, the self-righting article comprises one or more vents (e.g., to permit the flow of air and/or fluid through the self-righting article). In some embodiments, the self-righting article comprises one or more (e.g., two or more, three or more, four or more) vents associated with at least a portion (e.g., the first portion, the second portion) of the self-righting article. In some such embodiments, the vent may permit a fluid (e.g., gastric fluid) to enter at least a portion of the self-righting article such that e.g., the self-actuating component and/or the spring are exposed to the fluid (e.g., such that the self-actuating component and/or the spring actuate). For example, referring again to FIG. 2, system 102 comprises vents 190 associated with at least a portion of the self-righting article (e.g., first portion 110). In some cases, vent(s) 190 may be in fluidic communication with self-actuating component 120, support material 160, and/or spring 125. While vents are depicted herein as being associated with the first portion of the self-righting article, in some embodiments, one of ordinary skill in the art based upon the teachings of this specification would understand that one or more vents may be associated with the second portion of the self-righting article.

In some embodiments, one or more vents (e.g., vent 190 of FIG. 2) may comprise a fluidic gate (e.g., a plug, a coating, a barrier). In some cases, the fluidic gate may prevent a fluid (e.g., a fluid external to the system) from entering the system at the vent until a desired time. In certain embodiments, the fluidic gate comprises a barrier material. Non-limiting examples of suitable barrier materials include foils of polycaprolactone, thermoplastic elastomers, silicone, cellulosic (e.g. hydroxypropylmethylcellulose, hydroxypropylcellulose, hydroxyethylcellulose, hydroxyethylcellulose phthalate, ethylcellulose, cellulose acetate phthalate, cellulose acetate trimellitate), vinyl (e.g. poly (vinyl pyrrolidone), poly(vinyl alcohol), poly(vinyl pyrrolidone)-poly(vinyl acetate)copolymers, poly(vinyl alcohol)-poly(ethylene glycol) co-polymers, poly(vinyl acetate phthalate), glycols (e.g. poly(ethylene glycol)), acrylics (e.g. amino alkyl methacrylate copolymers), other carbohydrates (e.g. maltodextrin, polydextrose), and combinations thereof. The barrier material may comprise one or more hydrophilic materials. The barrier material may comprise one or more hydrophobic materials. Those of ordinary skill in the art would be capable of selecting suitable hydrophilic or hydrophobic materials as a barrier material based upon the teachings of this specification. In certain embodiments, at least one of the one or more vents (e.g., at least one, at least two, all of the vents) does not comprise a fluidic gate (e.g., the vent is open).

In certain embodiments, the self-righting article does not comprise vents.

In some embodiments, the self-righting article may have a particular larges cross-sectional dimension. In some embodiments, the largest cross-sectional dimension of the self-righting article is less than or equal to 2.0 cm, less than or equal to 1.8 cm, less than or equal to 1.6 cm, less than or equal to 1.4 cm, less than or equal to 1.2 cm, less than or equal to 1.1 cm, less than or equal to 1 cm, less than equal to 0.8 cm, less than or equal to 0.6 cm, less than or equal to 0.4 cm, or less than or equal to 0.2 cm, including any dimension less than 2.0 cm (e.g., 0.1 cm, 0.3 cm, 0.5 cm ... 1.7 cm, etc.). In certain embodiments, the largest cross-sectional dimension of the self-righting article is greater than or equal to 0.1 cm, greater than or equal to 0.2 cm, greater than or equal to 0.4 cm, greater than or equal to 0.6 cm, greater than or equal to 0.8 cm, greater than or equal to 1 cm, greater than or equal to 1.2 cm, greater than or equal to 1.4 cm, greater than or equal to 1.6 cm, greater than or equal to 1.8 cm, including any dimension greater than 0.1 cm and less than or equal to 2.0 cm (e.g., 0.3 cm, 0.5 cm ... 1.7 cm, 1.9 cm, etc.). Combinations of the above referenced ranges are also possible (e.g., less than or equal to 2 cm and greater than or equal to 0.1 cm, less than or equal to 1.1 cm and greater than or equal to 0.1 cm). Other ranges are also possible.

In some embodiments, the self-righting article may be administered (e.g., orally) to a subject. In some such embodiments, the self-righting article may comprise one or more active pharmaceutical ingredients. In certain embodiments, the active pharmaceutical ingredient is released at a location internal of the subject (e.g. within the G.I. tract).

In certain embodiments, one or more sensors may be associated with the self-righting article. For example, in some cases, one or more sensors may be used to determine the location of the self-righting article (e.g., a location internal to a subject) and/or to trigger actuation of one or more tissue interfacing components associated with the self-righting article. Non-limiting examples of suitable sensors include pH, gas, light, GPS, Bluetooth, orientation, proximity, thermal, fluid, and others.

In some cases, one or more of the first portion and/or second portion may be magnetic.

In an exemplary embodiment, the self-righting article is ingestible. According to certain embodiments, the ingestible self-righting article comprises a first portion having an average density, a second portion having an average density different from the average density of the first portion, and a payload portion for carrying an agent for release internally of a subject that ingests the article. In certain embodiments, the self-righting article comprises at least a first portion having an average density greater than 1 g/cm$^3$. According to certain embodiments, the ratio of the average density of the first portion to the average density of the second portion is greater than or equal to 2.5:1. In certain exemplary embodiments, the self-righting article comprises a first portion comprising a first material having a first average density, and a second portion comprising a second material having a second average density different from the first average density. In certain embodiments, the self-righting article comprises a first material and a second material different than the first material, and an active pharmaceutical agent associated with the self-righting article. According to some embodiments, the ratio of an average density of the first material to an average density of the second material is greater than or equal to 2.5:1. In some embodiments, the self-righting article has a largest cross-sectional dimension of less than or equal to 1.1 cm.

In certain embodiments, the article has a geometric center, and a center of mass offset from the geometric center such that the article, suspended via an axis passing through the geometric center, with the center of mass offset laterally from the geometric center, experiences an externally applied torque of 0.09*10^–4 Nm or less due to gravity about the axis. According to some embodiments, the self-righting article is configured to be encapsulated in a 000 or smaller capsule. In other embodiments, the self-righting article is not encapsulated. In certain embodiments, the self-righting article comprises a tissue interfacing component associated with the self-righting article. Some exemplary embodiments are related to an axis essentially perpendicular to the tissue-engaging surface of the self-righting article configured to maintain an orientation of 20 degrees or less from vertical when acted on by 0.09*10^–4 Nm or less externally applied torque. According to some embodiments, the self-righting article has a most stable, lowest-potential-energy physical configuration, and a self-righting time, from 90 degrees offset in any orientation from the most stable configuration, in water of less than or equal to 0.05 seconds. According to certain embodiments, the self-righting article has a rate of obstruction of less than or equal to 1% (e.g., less than or equal to 0.5%, less than or equal to 0.1%).

Certain exemplary embodiments are related to a method of delivering a pharmaceutical agent to a location internal of a subject. According to some embodiments, the method comprises administering, to the subject, a capsule comprising an outer shell and a self-righting article, and orienting the self-righting article at the location internal of a subject such that the tissue interfacing component punctures a tissue proximate the location internal of the subject.

Tissue Anchoring

In some embodiments, the article (e.g., the self-righting article) may be configured to anchor to a location internal to a subject (e.g., a tissue at a location internal to a subject). As described above, in some embodiments, the self-righting article may comprise one or more tissue interfacing components comprising one or more anchoring mechanisms (e.g., a hook, a mucoadhesive). Hooks are described in more detail below. Mucoadhesives are described in more detail below. In an exemplary embodiment, the self-righting article may, in some cases, have a longitudinal axis perpendicular to a tissue-engaging surface of the article configured to maintain an orientation of 20 degrees or less from vertical when acted on by 0.09*10^–4 Nm or less externally applied torque and at least one anchoring mechanism associated with the self-righting article. In another exemplary embodiment, the article may comprise a spring associated with (e.g., at least partially encapsulated with, in direct contact with) a support material (e.g., such that the spring is maintained in an at least partially compressed state by a support material under at least 5% compressive strain) and at least one anchoring mechanism operably linked to the spring. Springs and support materials are described in more detail, below. Other embodiments are also possible comprising at least one anchoring mechanism associated with a self-righting article and/or a self-actuating component.

Figure 5:
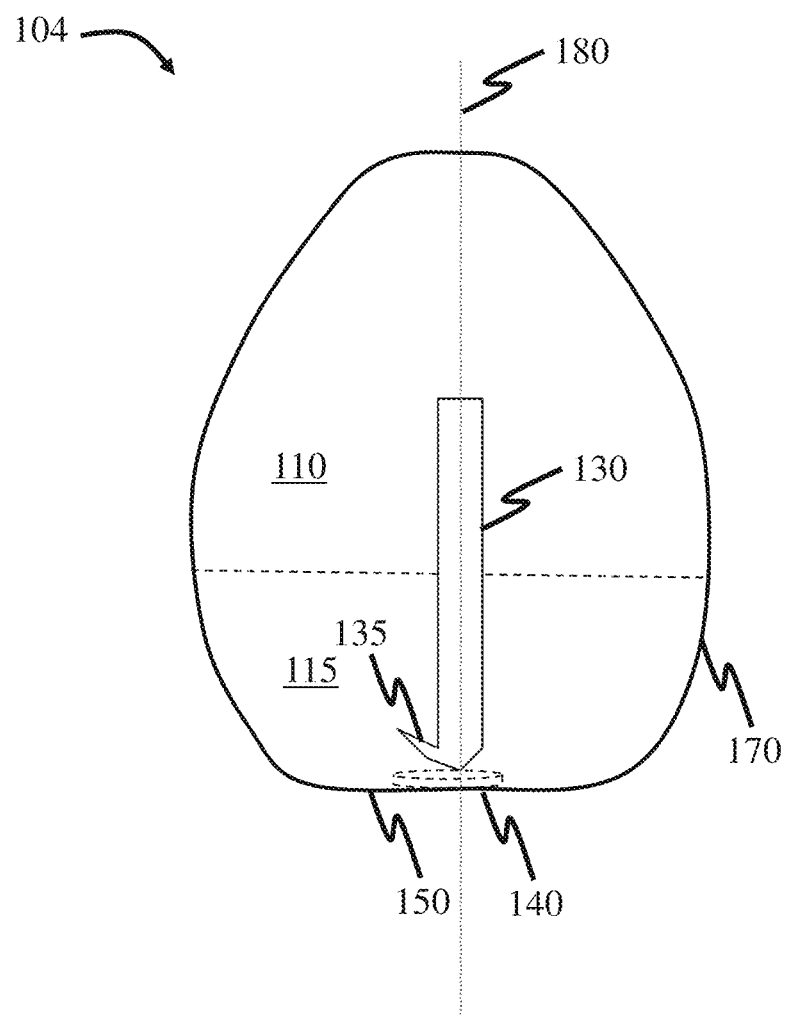
FIG. 5 is a cross-sectional schematic diagram of an exemplary self-righting system, according to one set of embodiments.

In some embodiments, the anchoring mechanism comprises a hook (e.g., a hooked needle). For example, as illustrated in FIG. 5, system 104 comprises a first portion 110 and a second portion 115. In certain embodiments, a tissue-engaging surface 150 is associated with second portion 115. In some cases, system 104 may comprises a tissue interfacing component 130 comprising an anchoring mechanism 135. In some embodiments, anchoring mechanism 135 may be a hook. In certain embodiments, anchoring mechanism 135 may be disposed internally within system 104 and released (e.g., via hole 140) under a desired set of conditions (e.g., at a particular location internal to a subject). In certain embodiments, not depicted in FIG. 5, hook 135 may disposed on an external surface of system 104.

Figure 6:
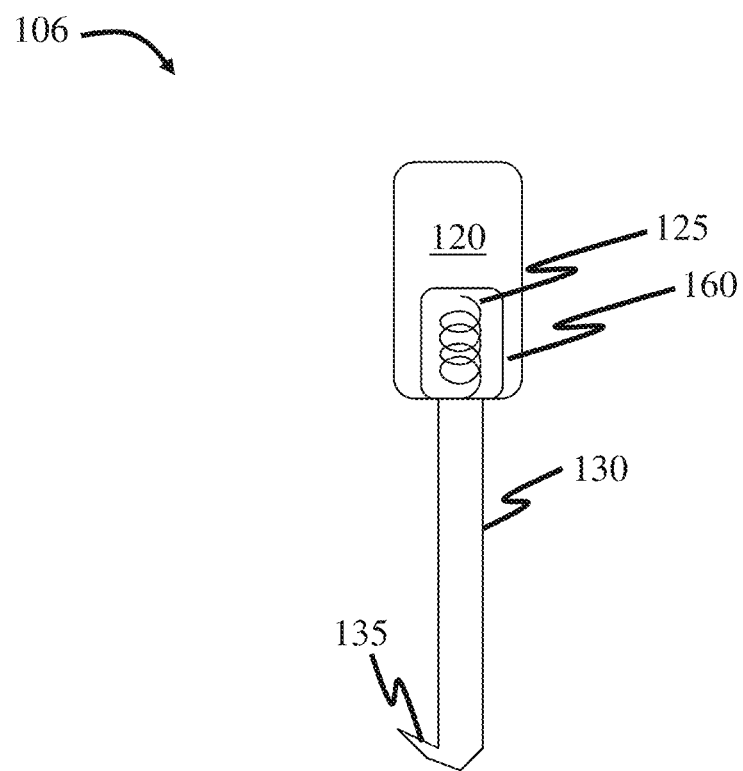
FIG. 6 is a cross-sectional schematic diagram of an exemplary self-actuating component, according to one set of embodiments.

Referring now to FIG. 6, in certain embodiments, system 106 comprises anchoring mechanism 135 associated with self-actuating component 120 (e.g., comprising spring 125 and/or support material 160). In certain embodiments, upon exposure to a fluid (e.g., gastric fluid) and/or under a particular set of conditions (e.g., physiological conditions of the gastrointestinal tract such as in the stomach), the self-actuating component actuates inserting the anchoring mechanism into a tissue located internal to a subject.

In some embodiments, the anchoring mechanism (and/or the article comprising the anchoring mechanism) is configured to be retained at a location internal to a subject. For example, in some embodiments, the anchoring mechanism engages with a surface (e.g., a surface of a tissue) at the location internal to the subject such that it is retained at that location.

Advantageously, the systems comprising one or more anchoring mechanisms described herein may be inserted into a surface of tissue at a location internal to a subject, and may maintain contact with the tissue under relatively high applied forces and/or relatively high change in orientation (e.g., by compressive forces exerted by the gastrointestinal tract and/or under high flow rates within the gastrointestinal tract). In some embodiments, the systems described herein do not substantially block orifices within the gastrointestinal tract (e.g., in the pylorus) e.g., restricting flow and enabling longer contact times. In certain embodiments, natural replenishment of the walls of the gastrointestinal tract may permit desirable detachment and/or expulsion of the systems described herein, without the need for surgical and/or endoscopic retrieval.

For example, in some embodiments, the anchoring mechanism may be inserted into a surface of a tissue at a location internal to a subject and maintains contact with the tissue (e.g., the system remains anchored) under a change of orientation of the system of greater than or equal to 1 degree, greater than or equal to 2 degrees, greater than or equal to 5 degrees, greater than or equal to 10 degrees, greater than or equal to 15 degrees, greater than or equal to 20 degrees, greater than or equal to 25 degrees, greater than or equal to 30 degrees, greater than or equal to 45 degrees, greater than or equal to 60 degrees, greater than or equal to 75 degrees, or greater than or equal to 85 degrees. In certain embodiments, the system may remain anchored under a change of orientation of the system of less than or equal to 90 degrees, less than or equal to 85 degrees, less than or equal to 75 degrees, less than or equal to 60 degrees, less than or equal to 45 degrees, less than or equal to 30 degrees, less than or equal to 25 degrees, less than or equal to 20 degrees, less than or equal to 15 degrees, less than or equal to 10 degrees, less than or equal to 5 degrees, or less than or equal to 2 degrees. Combinations of the above-referenced ranges are also possible (e.g., greater than or equal to 1 degree and less than or equal to 90 degrees, greater than or equal to 1 degree and less than or equal to 45 degrees, greater than or equal to 2 degrees and less than or equal to 30 degrees). Other ranges are also possible.

In certain embodiments, the system (e.g., comprising the anchoring mechanism) is configured to be retained at the location internal to the subject under a normal retention force of greater than or equal to 0.002 N, greater than or equal to 0.004 N, greater than or equal to 0.006 N, greater than or equal to 0.008 N, greater than or equal to 0.01 N, greater than or equal to 0.012 N, greater than or equal to 0.014 N, greater than or equal to 0.016 N, greater than or equal to 0.018 N, greater than or equal to 0.02 N, greater than or equal to 0.025 N, greater than or equal to 0.03 N, greater than or equal to 0.04 N, greater than or equal to 0.05 N, greater than or equal to 0.1 N, greater than or equal to 0.15 N, greater than or equal to 0.2 N, greater than or equal to 0.25 N, greater than or equal to 0.3 N, greater than or equal to 0.35 N, greater than or equal to 0.4 N, greater than or equal to 0.5 N, greater than or equal to 0.6 N, greater than or equal to 0.7 N, greater than or equal to 0.8 N, or greater than or equal to 0.9 N of normally applied force per anchoring mechanism. In some embodiments, the system has a normal retention force of less than or equal to 1 N, less than or equal to 0.9 N, less than or equal to 0.8 N, less than or equal to 0.7 N, less than or equal to 0.6 N, less than or equal to 0.5 N, less than or equal to 0.4 N, less than or equal to 0.35 N, less than or equal to 0.3 N, less than or equal to 0.25 N, less than or equal to 0.2 N, less than or equal to 0.15 N, less than or equal to 0.1 N, less than or equal to 0.05 N, less than or equal to 0.04 N, less than or equal to 0.03 N, less than or equal to 0.025 N, less than or equal to 0.02 N, less than or equal to 0.018 N, less than or equal to 0.016 N, less than or equal to 0.014 N, less than or equal to 0.012 N, less than or equal to 0.01 N, less than or equal to 0.008 N, less than or equal to 0.006, or less than or equal to 0.004 N of normally applied force per anchoring mechanism. Combinations of the above referenced ranges are also possible (e.g., greater than or equal to 0.002 N and less than or equal to 1 N, greater than or equal to 0.02 N and less than or equal to 0.08 N, greater than or equal to 0.1 N and less than or equal to 1 N). Other ranges are also possible. The normal retention force as described herein may be determined by inserting the anchoring mechanism of the system into a surface of tissue (e.g., ex vivo swine stomach) to a penetration depth of at least 0.9 mm and then pulling the system, in a direction orthogonal to the surface of the tissue until the system dislodges from the tissue. The maximum force before dislodging the system is the normal retention force.

In some embodiments, the system (e.g., comprising the anchoring mechanism) is configured to be retained at the location internal to the subject under an orthogonal retention force of greater than or equal to 0.002 N, greater than or equal to 0.004 N, greater than or equal to 0.006 N, greater than or equal to 0.008 N, greater than or equal to 0.01 N, greater than or equal to 0.012 N, greater than or equal to 0.014 N, greater than or equal to 0.016 N, greater than or equal to 0.018 N, greater than or equal to 0.02 N, greater than or equal to 0.025 N, greater than or equal to 0.03 N, greater than or equal to 0.04 N, greater than or equal to 0.05 N, greater than or equal to 0.1 N, greater than or equal to 0.15 N, greater than or equal to 0.2 N, greater than or equal to 0.25 N, greater than or equal to 0.3 N, greater than or equal to 0.35 N, greater than or equal to 0.4 N, greater than or equal to 0.5 N, greater than or equal to 0.6 N, greater than or equal to 0.7 N, greater than or equal to 0.8 N, or greater than or equal to 0.9 N of normally applied force per anchoring mechanism. In some embodiments, the system has an orthogonal retention force of less than or equal to 1 N, less than or equal to 0.9 N, less than or equal to 0.8 N, less than or equal to 0.7 N, less than or equal to 0.6 N, less than or equal to 0.5 N, less than or equal to 0.4 N, less than or equal to 0.35 N, less than or equal to 0.3 N, less than or equal to 0.25 N, less than or equal to 0.2 N, less than or equal to 0.15 N, less than or equal to 0.1 N, less than or equal to 0.05 N, less than or equal to 0.04 N, less than or equal to 0.03 N, less than or equal to 0.025 N, less than or equal to 0.02 N, less than or equal to 0.018 N, less than or equal to 0.016 N, less than or equal to 0.014 N, less than or equal to 0.012 N, less than or equal to 0.01 N, less than or equal to 0.008 N, less than or equal to 0.006, or less than or equal to 0.004 N of normally applied force per anchoring mechanism. Combinations of the above referenced ranges are also possible (e.g., greater than or equal to 0.002 N and less than or equal to 1 N, greater than or equal to 0.02 N and less than or equal to 0.08 N, greater than or equal to 0.1 N and less than or equal to 1 N). Other ranges are also possible. The orthogonal retention force as described herein may be determined by inserting the anchoring mechanism of the system into a surface of tissue (e.g., ex vivo swine stomach) to a penetration depth of at least 0.9 mm and then applying a force to the system (see e.g., FIG. 64), in a direction parallel to the surface of the tissue, until the system dislodges from the tissue. The maximum force before dislodging the system is the orthogonal retention force.

In some embodiments, the system is configured to remain anchored to the surface of the tissue located internal to the subject under less than or equal to 30 degrees change in orientation and less than or equal to 1 N of applied (e.g., normal, orthogonal) force.

In some embodiments, the system comprises two or more anchoring mechanisms. In some cases, the system may comprise a single self-righting article comprising two or more anchoring mechanisms. In certain embodiments, the system comprises two or more self-righting articles each comprising one or more anchoring mechanisms. In certain embodiments, the force required to dislodge the anchoring mechanism (e.g., the normal retention force, the orthogonal retention force) may be increased by increasing the number of anchoring mechanisms associated with the system. Without wishing to be bound by theory, the spacing between anchoring mechanisms may be related to the retention force (e.g., the normal retention force, the orthogonal retention force) of the system.

In some embodiments, the system may have an average spacing between anchoring mechanisms of greater than or equal to 0.1 mm, greater than or equal to 0.2 mm, greater than or equal to 0.3 mm, greater than or equal to 0.4 mm, greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.2 mm, greater than or equal to 1.4 mm, greater than or equal to 1.5 mm, greater than or equal to 1.6 mm, greater than or equal to 1.8 mm, or greater than or equal to 2 mm. In certain embodiments, the system may have an average spacing between anchoring mechanisms of less than or equal to 2.5 mm, less than or equal to 2 mm, less than or equal to 1.8 mm, less than or equal to 1.6 mm, less than or equal to 1.4 mm, less than or equal to 1.2 mm, less than or equal to 1 mm, less than or equal to 0.9 mm, less than or equal to 0.8 mm, less than or equal to 0.7 mm, less than or equal to 0.6 mm, less than or equal to 0.5 mm, less than or equal to 0.4 mm, less than or equal to 0.3 mm, or less than or equal to 0.2 mm. Combinations of the above-referenced ranges are also possible (e.g., greater than or equal to 0.1 mm and less than or equal to 2.5 mm, greater than or equal to 1 mm and less than or equal to 1.5 mm). Other ranges are also possible.

The anchoring mechanism may have any suitable dimension and/or shape. For example, in some embodiments, the largest dimension (e.g., the length) of the tissue interfacing component comprising the anchoring mechanism may be less than or equal to 1 cm, less than or equal to 0.8 cm, less than or equal to 0.6 cm, less than or equal to 0.5 cm, less than or equal to 0.4 cm, less than or equal to 0.3 cm, less than or equal to 0.25 cm, less than or equal to 0.23 cm, or less than or equal to 0.2 cm. In certain embodiments, the largest dimension (e.g., the length) of the tissue interfacing component comprising the anchoring mechanism may be greater than or equal to 0.15 cm, greater than or equal to 0.2 cm, greater than or equal to 0.23 cm, greater than or equal to 0.25 cm, greater than or equal to 0.3 cm, greater than or equal to 0.4 cm, greater than or equal to 0.5 cm, greater than or equal to 0.6 cm, or greater than or equal to 0.8 cm. Combinations of the above-referenced ranges are also possible (e.g., greater than or equal to 0.2 cm and less than or equal to 1 cm, greater than or equal to 0.15 cm and less than or equal to 1 cm). Other ranges are also possible.

In some embodiments, the anchoring mechanism has a particular anchor length. By way of example, for an anchoring mechanism comprising a hook, the anchor length corresponds to the largest cross-sectional dimension of a bent length of the hook (e.g., a diameter of the hook, not including any unbent portion). In certain embodiments, the anchor length is greater than or equal to 10 microns, greater than or equal to 20 microns, greater than or equal to 23 microns, greater than or equal to 25 microns, greater than or equal to 30 microns, greater than or equal to 34 microns, greater than or equal to 35 microns, greater than or equal to 40 microns, greater than or equal to 50 microns, greater than or equal to 60 microns, greater than or equal to 70 microns, greater than or equal to 80 microns, greater than or equal to 90 microns, greater than or equal to 100 microns, greater than or equal to 120 microns, greater than or equal to 140 microns, greater than or equal to 160 microns, greater than or equal to 180 microns, greater than or equal to 200 microns, or greater than or equal to 225 microns. In certain embodiments, the anchor length is less than or equal to 250 microns, less than or equal to 225 microns, less than or equal to 200 microns, less than or equal to 180 microns, less than or equal to 160 microns, less than or equal to 140 microns, less than or equal to 120 microns, less than or equal to 100 microns, less than or equal to 90 microns, less than or equal to 80 microns, less than or equal to 70 microns, less than or equal to 60 microns, less than or equal to 50 microns, less than or equal to 40 microns, less than or equal to 30 microns, or less than or equal to 20 microns. Combinations of the above-referenced ranges are also possible (e.g., greater than or equal to 10 microns and less than or equal to 250 microns). Other ranges are also possible.

In some cases, the anchoring mechanism may be configured to have an optimal penetration depth (e.g., the depth at which the anchoring mechanism is disposed beneath the surface of a tissue located internal to a subject). In some embodiments, the anchoring mechanism has a penetration depth of greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.2 mm, greater than or equal to 1.4 mm, greater than or equal to 1.5 mm, greater than or equal to 1.7 mm, greater than or equal to 1.9 mm, greater than or equal to 2 mm, greater than or equal to 2.2 mm, greater than or equal to 2.4 mm, greater than or equal to 2.5 mm, greater than or equal to 3 mm, greater than or equal to 3.5 mm, greater than or equal to 4 mm, greater than or equal to 4.5 mm, or greater than or equal to 5 mm. In certain embodiments, the anchoring mechanism has a penetration depth of less than or equal to 6 mm, less than or equal to 5 mm, less than or equal to 4.5 mm, less than or equal to 4 mm, less than or equal to 3.5 mm, less than or equal to 3 mm, less than or equal to 2.5 mm, less than or equal to 2.4 mm, less than or equal to 2.2 mm, less than or equal to 2 mm, less than or equal to 1.9 mm, less than or equal to 1.7 mm, less than or equal to 1.5 mm, less than or equal to 1.4 mm, less than or equal to 1.2 mm, less than or equal to 1 mm, less than or equal to 0.9 mm, less than or equal to 0.8 mm, less than or equal to 0.7 mm, or less than or equal to 0.6 mm. Combinations of the above-referenced ranges are also possible (e.g., greater than or equal to 0.5 mm and less than or equal to 6 mm, greater than or equal to 0.9 mm and less than or equal to 2.5 mm). Other ranges are also possible. Without wishing to be bound by theory, the displacement of the tissue may be greater than or equal to the penetration depth of the anchoring mechanism. By way of example only, and in a particular set of embodiments, the anchoring mechanism may displace tissue up to 14 mm to achieve a penetration depth of e.g., up to 4 mm.

Advantageously, the systems comprising an anchoring mechanism described herein may be retained for a relatively long period of time under physiological conditions and fluid flows (e.g., exposed to a fluid flowing at approximately 0.1 m/s). For example, in some embodiments, the system comprising an anchoring mechanism is retained at a surface of tissue located internal to a subject for greater than or equal to 1 hour, greater than or equal to 2 hours, greater than or equal to 4 hours, greater than or equal to 8 hours, greater than or equal to 12 hours, greater than or equal to 24 hours, greater than or equal to 2 days, greater than or equal to 3 days, greater than or equal to 5 days, greater than or equal to 7 days, or greater than or equal to 10 days. In certain embodiments, the system is retained for less than or equal to 14 days, less than or equal to 10 days, less than or equal to 7 days, less than or equal to 5 days, less than or equal to 3 days, less than or equal to 2 days, less than or equal to 24 hours, less than or equal to 12 hours, less than or equal to 8 hours, less than or equal to 4 hours, or less than or equal to 2 hours. Combinations of the above referenced ranges are also possible (e.g., greater than or equal to 1 hour and less than or equal to 14 days). Other ranges are also possible. In some cases, the anchoring mechanism may be configured to be retained for relative very long periods of time under physiological conditions and fluid flows. For example, in certain embodiments, the anchoring mechanism may be retained at a surface of tissue location internal to a subject for greater than or equal to 1 month, greater than or equal to 2 months, greater than or equal to 3 months, greater than or equal to 6 months, or greater than or equal to 1 year. In some embodiments, the anchoring mechanism may be retained at a surface of tissue location internal to a subject for less than or equal to 2 years, less than or equal to 1 year, less than or equal to 6 months, less than or equal to 3 months, or less than or equal to 2 months. Combinations of the above-referenced ranges are also possible (e.g., greater than or equal to 1 hour and less than or equal to 2 years, greater than or equal to 1 month and less than or equal to 2 years). Other ranges are also possible.

The anchoring mechanisms described herein may comprise any suitable material. In some embodiments, the anchoring mechanism material is relatively non-degradable. In certain embodiments, the anchoring mechanism may be configured to degrade within a certain period of time. In some embodiments, the anchoring mechanism is configured to degrade within one or more ranges of time described above in the context of being retained. For example, in some embodiments, the anchoring mechanism is configured to degrade (e.g., such that the system is no longer retained at the location internal to the subject) in greater than or equal to 1 hour, greater than or equal to 2 hours, greater than or equal to 4 hours, greater than or equal to 8 hours, greater than or equal to 12 hours, greater than or equal to 24 hours, greater than or equal to 2 days, greater than or equal to 3 days, greater than or equal to 5 days, greater than or equal to 7 days, or greater than or equal to 10 days. In certain embodiments, the anchoring mechanism is configured to degrade in less than or equal to 14 days, less than or equal to 10 days, less than or equal to 7 days, less than or equal to 5 days, less than or equal to 3 days, less than or equal to 2 days, less than or equal to 24 hours, less than or equal to 12 hours, less than or equal to 8 hours, less than or equal to 4 hours, or less than or equal to 2 hours. Combinations of the above referenced ranges are also possible (e.g., greater than or equal to 1 hour and less than or equal to 14 days). Other ranges are also possible. In some cases, the anchoring mechanism may be configured to degrade (e.g., such that the system is no longer retained at the location internal to the subject) in greater than or equal to 1 month, greater than or equal to 2 months, greater than or equal to 3 months, greater than or equal to 6 months, or greater than or equal to 1 year. In some embodiments, the anchoring mechanism may degrade in less than or equal to 2 years, less than or equal to 1 year, less than or equal to 6 months, less than or equal to 3 months, or less than or equal to 2 months. Combinations of the above-referenced ranges are also possible (e.g., greater than or equal to 1 hour and less than or equal to 2 years, greater than or equal to 1 month and less than or equal to 2 years). Other ranges are also possible.

In some cases, the anchoring mechanism may comprise a conductive material, as described below.

Electrical Stimulation

In some embodiments, the systems, articles, and methods described herein may be useful for providing electrical stimulation at a location internal to a subject. Advantageously, the systems described herein may be administered orally (e.g., in a capsule) to provide temporary electrical stimulation to the gastrointestinal tract, as compared to traditional methods including e.g., endoscopic placement and/or electrical device installation. In some embodiments, the system comprises one or more anchoring mechanisms, wherein at least one anchoring mechanism comprises a conductive portion (e.g., for electrical communication with the tissue at the location internal to the subject). Such systems may be useful for, for example, iontophoresis (e.g., introducing an API into a tissue internal to a subject during application of a local electric current). In certain embodiments in which the systems described herein are configured for iontophoresis, the system may comprise a first tissue interfacing component (e.g., contained within a first self-righting article) comprising a conductive tip and a second tissue interfacing component (e.g., contained within a second self-righting article) configured to contact but not penetrate tissue (e.g., a blunt cylinder). In some embodiments, one or more electrodes may be in electrical communication with the first and/or second tissue interfacing components.

In some embodiments, the system (e.g., a self-righting system) comprises two or more tissue interfacing components. In certain embodiments, each of the tissue interfacing components comprises a tissue-contacting portion configured to contact tissue. In some cases, the tissue-contacting portion may be electrically conductive. In certain embodiments, the tissue-contacting portion may be electrically insulative.

In some embodiments, the tissue-contacting portion comprises a first electrically-conductive portion and a second insulative portion. In some such embodiments, the electrically conductive portion may be configured for electrical communication with tissue and the insulative portion may be configured to not be in electrical communication with tissue.

Without wishing to be bound by theory, in some embodiments, the length of the insulative portion may be configured to prevent electrical communication with certain layers of tissue (e.g., for muscle stimulation of the stomach the length may correspond to the outer muscular layer (e.g., 2-4 mm), for SI mucosa the length may be e.g., 0.1-1 mm. In some cases, the insulative portion may be configured such that gastrointestinal fluid and/or a mucus coating of the tissue does not contact the electrically conductive portion (e.g., without wishing to be bound by theory, the gastrointestinal fluid and mucus coating are generally electrically conductive, and thus may prevent, in some cases, electrical stimulation from reaching the underlying tissue). The tissue contacting portion may comprise any suitable ratio of the electrically conductive portion to the insulative portion. For example, in some embodiments, the electrically conductive portion is present in the tissue contacting portion in the amount greater than or equal to 0.1%, greater than or equal to 0.5%, greater than or equal to 1%, greater than or equal to 2%, greater than or equal to 5%, greater than or equal to 10%, greater than equal to 20%, greater than equal to 30%, greater than equal to 40%, greater than equal to 50%, greater than equal to 60%, greater or equal to 70%, greater or equal to 80%, or greater or equal to 90%, of the total surface area of the tissue contacting portion of the tissue interfacing component. In certain embodiments, the electrically conductive portion is present in the tissue contacting portion in an amount less than or equal to 100%, less than equal to 90%, less than or equal to 80%, less than or equal to 70%, less than or equal to 60%, less than or equal to 50%, less than or equal to 40%, less than or equal to 30%, less than or equal to 20%, less than or equal to 10%, less than or equal to 5%, less than or equal to 2%, less than or equal to 1%, or less than or equal to 0.5% of the total surface area of the tissue contacting portion of the tissue interfacing component. Combinations of the above referenced ranges are also possible (e.g., greater than or equal to 0.1% and less than or equal to 100%, greater than or equal to 10% and less than or equal to 100%, greater than or equal to 30% and less than or equal to 90%). Other ranges are also possible. In some embodiments, the tip of the tissue contacting portion is conductive and the remainder of the tissue contacting portion is insulative.

In certain embodiments, the insulative portion is present in the tissue contacting portion in the amount greater than or equal to 10%, greater than equal to 20%, greater than equal to 30%, greater than equal to 40%, greater than equal to 50%, greater than equal to 60%, greater or equal to 70%, greater or equal to 80%, or greater or equal to 90%, of the total surface area of the tissue contacting portion of the tissue interfacing component. In certain embodiments, the insulative portion is present in the tissue contacting portion in an amount less than or equal to 100%, less than equal to 90%, less than or equal to 80%, less than or equal to 70%, less than or equal to 60%, less than or equal to 50%, less than or equal to 40%, less than or equal to 30%, or less than or equal to 20% of the total surface area of the tissue contacting portion of the tissue interfacing component. Combinations of the above referenced ranges are also possible (e.g., greater than or equal to 10% less than or equal to 100%, greater than or equal to 30% and less than or equal to 90%). Other ranges are also possible.

In some embodiments, the system comprises a self-righting article as described herein and at least one tissue interfacing component each comprising a tissue contacting portion configured for contacting tissue associated with each tissue interfacing opponent. In certain embodiments, the system comprises two or more self-righting articles described herein, each self-righting article comprising at least one tissue interfacing component, each tissue interfacing component comprising a tissue contacting portion configured for contacting tissue. For example, in an exemplary set of embodiments, a single self-righting article may be administered to a subject, the self-righting article comprising two or more tissue interfacing components, where a power source may be placed in electrical communication with the two or more tissue interfacing components, such that a current may be applied to the tissue in direct contact with a tissue contacting portion of the tissue interfacing components. In another exemplary set of embodiments, two (or more) self-righting articles may be administered to the subject, each self-righting article comprising at least one tissue interfacing component, where a power source may be placed electrical communication with the to self-righting articles, such an economy be applied to the tissue in direct contact with the tissue contacting portion of each tissue interfacing component from each self-righting article. Other combinations are also possible. One of ordinary skill in the art would understand how to select combinations of self-righting articles, tissue interfacing components, and tissue contacting portions based upon the teachings of this specification.

As described herein, in some embodiments, a system comprising a self-righting article and/or a self-actuating article may be administered to a subject, where the system comprises at least one tissue interfacing component disposed within the article (e.g., the self-writing article and/or the self-actuating article). The system may be administered such that, at least one interfacing component is released from the article and/or inserted into the tissue at a location internal to the subject. In certain embodiments, a current may be applied (e.g., generated by a power source knowledgeable communication with the tissue interfacing component) such that the current travels across two or more tissue interfacing components. In some such embodiments, the tissue interfacing components are not electrical communication with the tissue.

The electrically conductive portion may comprise any suitably electrically conductive material. Non-limiting examples of suitable electronic conductive materials include electrically conductive polymers, silver, copper, gold, stainless steel, platinum, zinc, and steel. Other conductive materials are also possible.

The insulative portion may comprise any suitably electrically insulating material. Non-limiting examples of suitable to insulative materials include polymers such as parylene, polycaprolactone, and polyethylene. Other insulative materials are also possible.

The electrically conductive material and/or the insulative material may, in some cases, be provided as a coating on the tissue interfacing component. In certain embodiments, the tissue contacting portion may comprise a bulk material comprising the electrically conductive and/or the insulative material.

In some embodiments, the current applied (e.g., across the tissue contacting portions, for electrically stimulating the tissue) may be greater than or equal to 0.001 milliamps, greater than or equal to 0.01 milliamps, greater than or equal to 0.1 milliamps, greater than or equal to 0.5 milliamps, greater than or equal to 1 milliamp, greater than or equal to 5 milliamps, greater than or equal to 10 milliamps, greater than or equal to 50 milliamps, greater than or equal to 100 milliamps, or greater than or equal to 250 milliamps. In certain embodiments, the current applied may be less than or equal to 500 milliamps, less than or equal to 250 milliamps, less than or equal to 100 milliamps, less than or equal to 50 milliamps, less than or equal to 10 milliamps, less than or equal to 5 milliamps, less than or equal to 1 milliamp, less than or equal to 0.5 milliamps, less than or equal to 0.1 milliamps, or less than or equal to 0.01 milliamps. Combinations of the above-referenced ranges are also possible (e.g., greater than or equal to 0.001 milliamps and less than or equal to 500 milliamps, greater than or equal to 0.1 milliamps and less than or equal to 10 milliamps). Other ranges are also possible. Current may be applied using any suitable means including, for example, an external power source (e.g., a battery).

In certain embodiments, the system is configured to be retained at the location internal to subject under greater than or equal to 0.1 N (e.g., greater than or equal to 0.6 N) of force and/or a change in orientation of greater than or equal to 30 degrees, as described above.

Self-Actuating

Self-actuating articles including, for example, self-actuating tissue interfacing components such as self-actuating needles, self-actuating anchoring mechanisms, and/or self-actuating biopsy punches, are generally provided. Advantageously, in some embodiments, the self-actuating articles described herein may be useful as a general platform for delivery of a wide variety of pharmaceutical drugs that are typically delivered via injection directly into tissue due to degradation in the GI tract. The self-actuating articles described herein may also be used to deliver sensors, electrical stimulation, anchor systems described herein to tissue, and/or take biopsies without the need for an endoscopy. In some embodiments, the article comprises a spring (e.g., a coil spring, wave springs, Belleville washers, a beam, a membrane, a material having particular mechanical recovery characteristics). Those of ordinary skill in the art would understand that the term spring is not intended to be limited to coil springs, but generally encompass any reversibly compressive material and/or component which, after releasing an applied compressive force on the material/component, the material/component substantially returns to an uncompressed length of the material/component under ambient conditions (e.g., within 40%, within 50%, within 60%, within 70%, within 80%, within 90%, within 95%, or any percentage in between, of the length of the material/component prior to compression).

In certain embodiments, the term spring of the self-actuating article may be provided as, or further comprise, an expanding component. Those of ordinary skill in the art would understand the term extending component comprises reversibly and irreversibly compressive materials and are components which, upon stimulating and/or releasing a restraint on the expanding component, the expanding component extends in at least one direction (e.g., along its length). In some embodiments, the expanding component comprises a gaseous composition(s) for expanding the gaseous volume expanding component (e.g., a mixture of baking soda and vinegar).

In some embodiments, the spring and/or expanding component may extend in at least one direction via thermal expansion, swelling (e.g., due to fluid absorption), a gas driven process, a pneumatic process, a hydraulic process, an electrical motor, a magnetic mechanism, a torsional spring mechanism, a chemical gas generator, and/or an self-catalyzing reaction. In an exemplary set of embodiments, the spring and/or expanding component may extend in at least one direction upon exposure of the spring and/or expanding component to a fluid (e.g., gastrointestinal fluid).

In some cases, the spring and/or the expanding component may be activated (e.g., extended in at least one direction, returns to an uncompressed length of the component) by any suitable activation mechanism. Non-limiting examples of suitable activation mechanisms include release of a pressure difference, electrical timer, light sensor, color sensor, enzymatic sensor, capacitance, magnetism, activation by applied stress (e.g., shape memory materials), external activation (e.g., applied magnetic field, applied light, reaction with gastrointestinal fluid such as stomach acid), and combinations thereof. In an exemplary set of embodiments, the spring and/or expanding component are activated by interaction (e.g., reaction) with a gastrointestinal fluid.

In some cases, the activation mechanism displaces the tissue interfacing component by a particular distance (e.g., less than or equal to 10 mm, less than or equal to 8 mm, less than or equal to 6 mm, less than or equal to 4 mm, less than or equal to 2 mm) and/or with a particular force (e.g., greater than or equal to 0.1 N, greater than or equal to 0.3 N, greater than or equal to 0.5 N, greater than or equal to 1 N, greater than or equal to 1.5 N).

Figure 26:
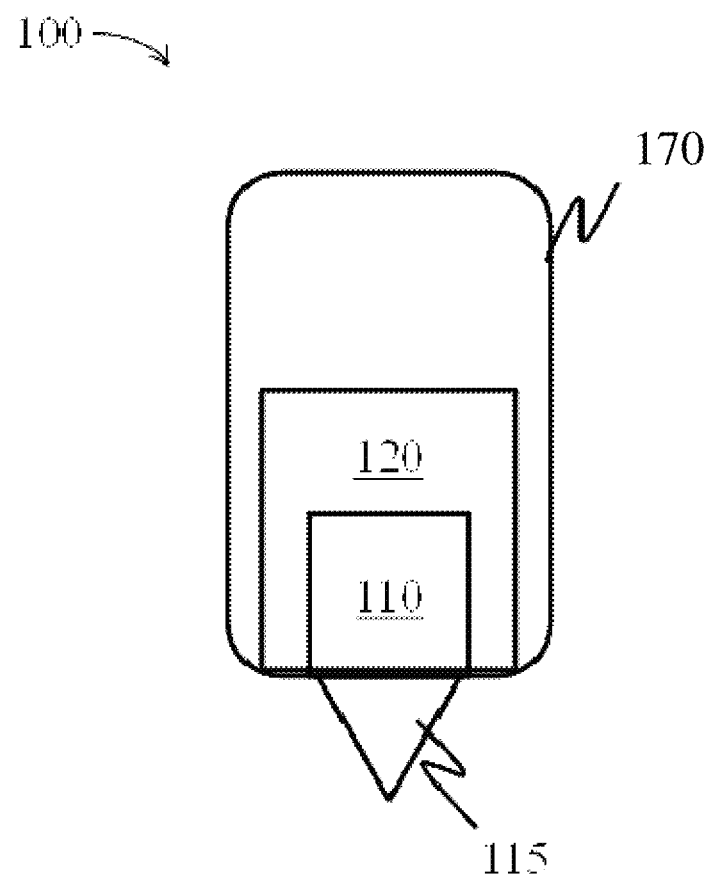
FIG. 26 is a schematic illustration of a self-actuating article, according to one set of embodiments.

As illustrated in FIG. 26, in some embodiments, article 100 comprises a spring 110 and a support material 120 associated with (e.g., operably linked with) spring 110. Support material 120, in certain embodiments, maintains the spring under compressive strain under a first set of conditions (e.g., under ambient conditions (e.g., room temperature, atmospheric pressure and relative humidity)). In some embodiments, the support material at least partially releases (e.g., at least a portion of the support material degrades) the spring from compressive strain under a second set of conditions different than the first set of conditions. For example, in some embodiments, the second set of conditions comprises physiological conditions (e.g., at or about 37° C., in physiologic fluids such as gastric fluid).

In some cases, spring 110 may be adjacent (e.g., directly adjacent) support material 120. As used herein, when a component is referred to as being "adjacent" another component, it can be directly adjacent to (e.g., in contact with) the component, or one or more intervening components also may be present. A component that is "directly adjacent" another component means that no intervening component(s) is present. In some cases, the spring may be at least partially embedded within the support material. In certain embodiments, the spring is coated with the support material.

In certain embodiments, referring again to FIG. 26, article 100 comprises an outer shell 170 (e.g., such that spring 110 is at least partially encapsulated within outer shell 170).

In some cases, the support material may be a coating. In some embodiments, the support material is a biodegradable coating. In certain embodiments, the coating may have any suitable thickness. For example, the thickness of the coating may be greater than or equal to 3 mm, greater than or equal to 4 mm, or greater than or equal to 5 mm. In certain embodiments, the thickness of the coating may be less than or equal to 6 mm, less than or equal to 5 mm, or less than or equal to 4 mm. Combinations of the above-referenced ranges are also possible (e.g., greater than or equal to 3 mm and less than or equal to 6 mm). In certain embodiments, the biodegradable coating at least partially degrades under physiological conditions. In some cases, the support material may be a brittle material. Non-limiting examples of suitable support materials include sugars and/or polymers (e.g., polyethylene glycol, polyvinylpyrrolidinone, polyvinylalcohol).

The support material may have any suitable cross-sectional dimension. In some embodiments, the average cross-sectional dimension of the support material is greater than or equal to 0.1 mm, greater than or equal to 0.5 mm, greater than or equal to 1 mm, greater than or equal to 2 mm, greater than or equal to 3 mm, greater than or equal to 4 mm, or greater than or equal to 5 mm. In certain embodiments, the average cross-sectional dimension of the support material is less than or equal to 10 mm, less than or equal to 6 mm, less than or equal to 5 mm, less than or equal to 4 mm, less than or equal to 3 mm, less than or equal to 2 mm, less than or equal to 1 mm, or less than or equal to 0.5 mm. Combinations of the above-referenced ranges are also possible (e.g., greater than or equal to 0.1 mm and less than or equal to 10 mm). Other ranges are also possible.

In some embodiments, the support material, the spring, and/or the expanding component comprise one or more materials configured to dissolve (e.g., in an acidic environment in a pH neutral environment, in water, in a basic environment), melt at physiological temperature (e.g., 37° C.), change in stiffness (e.g., in response to a change in temperature, in response to fluid absorption), thermally expand, and/or change in shape (e.g., in response to fluid absorption, by deflation, by leakage).

Support Material

In some embodiments, the support material is positioned at a distal end of a spring (e.g., at an opposing end from the end of the spring associated with the tissue interfacing component).

Figure 7:
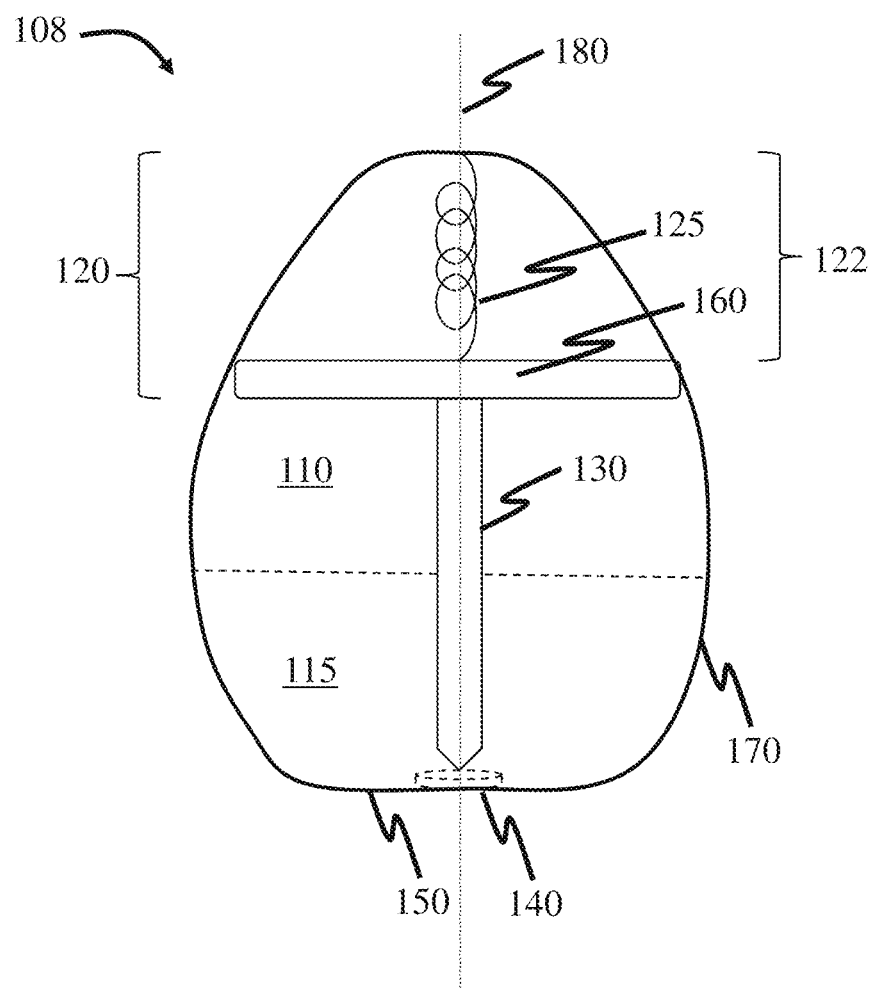
FIG. 7 is a cross-sectional schematic diagram of an exemplary self-righting system, according to one set of embodiments.

For example, as illustrated in FIG. 7, system 108 comprises spring 125 associated with support material 160 which maintains spring 125 under compression (e.g., under at least 5% compressive strain). In some embodiments, support material 160 may be in the form of a disk positioned at a distal end of spring 125. In certain embodiments, spring 125 may be in direct contact with support material 160 (e.g., a disk). In some cases, one or more additional layers and/or components may be positioned between spring 125 and disk 160. In some embodiments, spring 125 may be at least partially embedded in support material 160 (e.g., disk).

In certain embodiments, the support material comprises a plug configured to maintain the spring under compression e.g., until the support material dissolves. The term "plug", as used herein, is given its ordinary meaning in the art and generally refers to a component configured to obstruct. In an exemplary set of embodiments, the article comprises an outer shell and a support material associated with at a least a portion of the outer shell. In certain embodiments, upon exposure of the outer shell and the support material to a fluid (e.g., gastrointestinal fluid), the support material disassociates and a spring directly adjacent the support material releases at least a portion of its stored energy (e.g., such that a tissue interfacing component is released from the article).

In some cases, the support material may be in the form of a disk (e.g., comprising a sugar). For example, the support material may be a disk having an axis orthogonal to the major plane, where the axis orthogonal to the major plane of the disk is perpendicular to a major axis of the spring, such that the support material maintains the spring in a state of compression. The disk may be disposed within the article such that e.g., a fluid may interact with the support material such that it may dissolve, releasing the spring.

Other configurations for the support material are also possible.

Advantageously, the configuration and/or material used for the support material may permit tuning of the dissolution of the support material. In some cases, the dissolution of the support material may be tuned such that the tissue interfacing component is released from the article at a desired location and/or at a desired time. In certain embodiments, the geometry of the support material (e.g., the shape, the ratio of a first surface area to a second surface area) may be design and configured such that the holding force/strength (e.g., against a spring) may be tuned.

The support material (e.g., the disk) may comprise any suitable material. Non-limiting examples of suitable materials include sugars and derivatives thereof (e.g., sugar alcohols such as isomalt, sugar mixtures such as toffee), starch, calcium carbonate, zinc, sodium chloride, and/or polymers (e.g., polyethylene glycol, polyvinylpyrrolidinone, polyvinylalcohol, polyethylene oxide, diethyl pyrocarbonate, hydrogels). Other materials are also possible. Without wishing to be bound by theory, the support material may be selected to be relatively brittle (e.g., such that the spring is released upon dissolution of the support material).

The support material may comprise any suitable shape. In some embodiments, the support material has a cylindrical shape, an ellipsoidal shape, a spherical shape, a section of a sphere, a conical shape, a tapered shape (e.g., a tapered disk such as a section of a cone), triangular shape, rectangular shape, prismatic shape, star shape, and combinations thereof. In certain embodiments, the support material has a disk shape (e.g., a tapered disk shape). Other shapes are also possible.

In certain embodiments, the support material may be configured to have a particular architecture which provides desirable dissolution profiles. For example, in some embodiments, the support material may be configured to enhance dissolution profiles, have controlled failure modes (e.g., breakage into small pieces at relatively predictable locations) and/or provide structural integrity of the support material.

Figure 8:
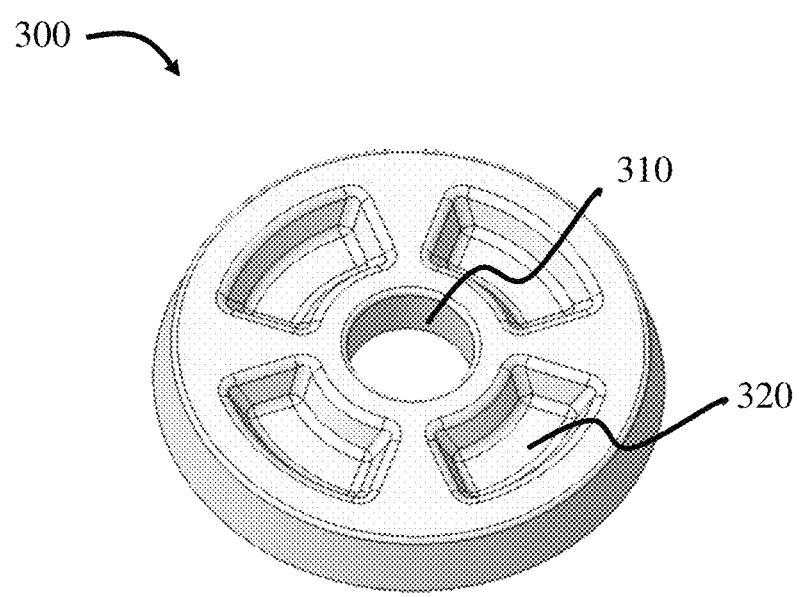
FIG. 8 is a schematic illustration of a support material, according to one set of embodiments.

In an exemplary embodiment illustrated in FIG. 8, support material 300 comprises a hole 310 and one or more cavities 320. Without wishing to be bound by theory, the cavities of the support material may be useful for controlling surface area (e.g., exposed to a fluid prior to dissolution) and/or provide locations of controlled mechanical failure after at least partial dissolution of the support material (e.g., after exposure to the fluid). The support material may comprise any suitable number of holes (e.g., one or more, two or more, three or more, four or more, five or more holes) and/or any suitable numbers of cavities (e.g., one or more, two or more, three or more, four or more, five or more, six or more, seven or move, eight or more, nine or more, ten or more cavities) such that e.g., mechanical failure of the support material (e.g., upon exposure to a fluid such as gastrointestinal fluid) may be controlled (e.g., to occur within a certain amount of time, such as in less than 10 minutes after exposure to the fluid).

While FIG. 8 depicts a plurality of cavities, other structures are also possible. In some embodiments, the support material comprises one or more cavities, one or more rings, and/or one or more holes. The cavities, rings, and/or holes may have any suitable shape.

Figure 9:
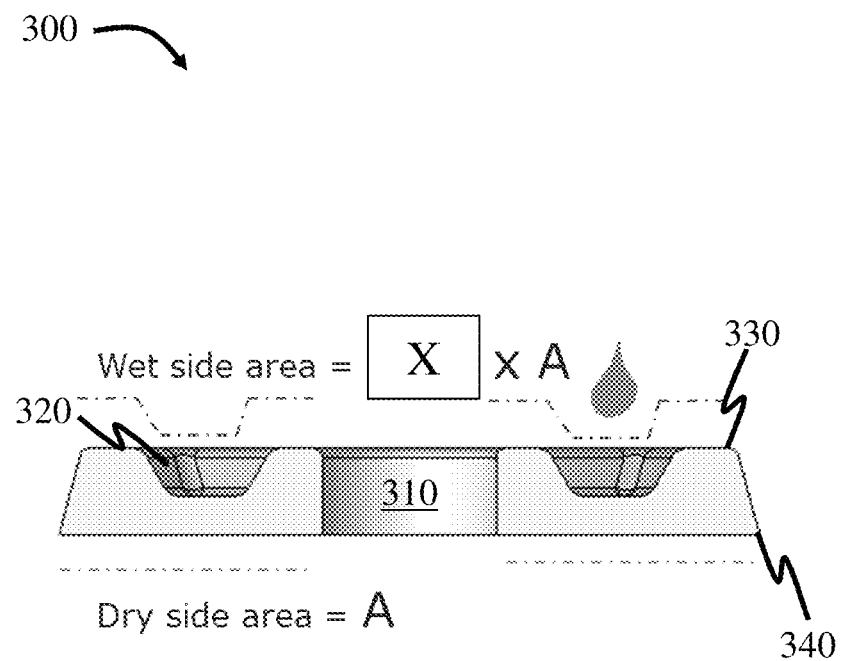
FIG. 9 is a schematic illustration of a support material, according to one set of embodiments.

In some embodiments, the support material may have a first surface having a first total surface area and a second surface, having a second total surface area different than the first total surface area. For example, as illustrated in FIG. 9, support material 300 comprises a first side 330 having a first surface, and second side 340 (e.g., opposite first side 330), having a second surface. In some embodiments, the first surface has a total surface area greater than or equal to a total surface area of the second surface.

Figure 10:
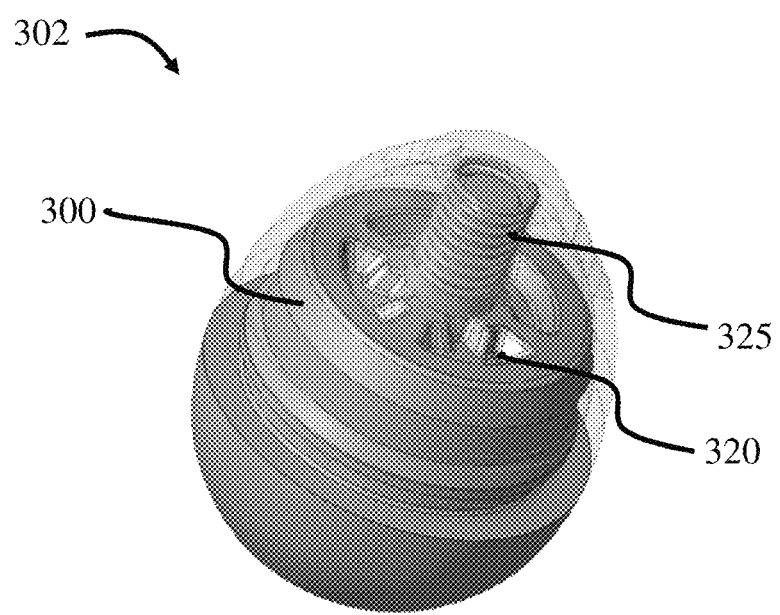
FIG. 10 is a schematic diagram of a self-righting system, according to one set of embodiments.

FIG. 10 shows an exemplary system 302 comprising support material 300 comprising a plurality of cavities 320 and associated with spring 325.

In some embodiments, the first surface has a first total surface area that is greater than or equal to 0.1, greater than or equal to 0.2, greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1, greater than or equal to 1.1, greater than or equal to 1.2, greater than or equal to 1.25, greater than or equal to 1.3, greater than or equal to 1.35, greater than or equal to 1.4, greater than or equal to 1.45, greater than or equal to 1.5, greater than or equal to 1.55, greater than or equal to 1.6, greater than or equal to 1.65, greater than or equal to 1.7, greater than or equal to 1.75, greater than or equal to 1.8, greater than or equal to 1.9, or greater than or equal to 2 times a second total surface area of the second surface. In certain embodiments, the first total surface area is less than or equal to 2.5, less than or equal to 2, less than or equal to 1.9, less than or equal to 1.8, less than or equal to 1.75, less than or equal to 1.7, less than or equal to 1.65, less than or equal to 1.6, less than or equal to 1.55, less than or equal to 1.5, less than or equal to 1.45, less than or equal to 1.4, less than or equal to 1.35, less than or equal to 1.3, less than or equal to 1.25, less than or equal to 1.2, less than or equal to 1.1, less than or equal to 1, less than or equal to 0.9, less than or equal to 0.8, less than or equal to 0.7, less than or equal to 0.6, less than or equal to 0.5, less than or equal to 0.4, less than or equal to 0.3, or less than or equal to 0.2 times the second total surface area. Combinations of the above-referenced ranges are also possible (e.g., greater than or equal to 0.1 and less than or equal to 2.5, greater than or equal to 1 and less than or equal to 2.5, greater than or equal to 1.4 and less than or equal to 1.6). Other ranges are also possible. Those of ordinary skill in the art would understand that total surface area described herein generally refers to the geometric surface area of an equivalent smooth surface, irrespective of local micro- and nano-scale roughness. Advantageously, such ratios of total surface area of the first surface to the total surface area second surface may increase the strength of resistance to mechanical failure by forces exerted by an adjacent spring and/or controlling the dissolution/failure time of the support material upon exposure to a fluid such as gastrointestinal fluid (e.g., exposure of the surface having the greater surface area as compared to the other surface).

In some embodiments, the roughness (e.g., microscale roughness, nanoscale roughness) and/or texture of one or more surfaces (e.g., the first surface, the second surface) of the support material may be increased or decreased (e.g., to alter dissolution time of the support material).

In some embodiments, the support material has desirable mechanical properties (e.g., such that the spring recovers at least a portion of its uncompressed length relatively quickly). For example, in certain embodiments, the support material may have a critical stress of greater than or equal to 0.01 N, greater than or equal to 0.1 N, greater than or equal to 0.5 N, greater than or equal to 1 N, greater than or equal to 2 N, greater than or equal to 3 N, greater than or equal to 5 N, greater than or equal to 7 N, greater than or equal to 10 N, greater than or equal to 15 N, greater than or equal to 20 N, greater than or equal to 25 N, greater than or equal to 30 N, greater than or equal to 35 N, greater than or equal to 40 N, greater than or equal to 45 N, greater than or equal to 50 N, or greater than or equal to 60 N, including any critical stress value in between. In certain embodiments, the support material may have a critical stress of less than or equal to 70 N, less than or equal to 60 N, less than or equal to 50 N, less than or equal to 45 N, less than or equal to 40 N, less than or equal to 35 N, less than or equal to 30 N, less than or equal to 25 N, less than or equal to 20 N, less than or equal to 15 N, less than or equal to 10 N, less than or equal to 7 N, less than or equal to 5 N, less than or equal to 3 N, less than or equal to 2 N, less than or equal to 1 N, less than or equal to 0.5 N, or less than or equal to 0.1 N. including any critical stress value in between. Combinations of the above-referenced ranges are also possible (e.g., greater than or equal to 10 N and less than or equal to 70 N, greater than or equal to 30 N and less than or equal to 45 N). Other ranges are also possible. The critical stress is generally the maximum force the support material can hold (e.g., as applied by the adjacent spring) before cracking and may be determined by calculating the critical stress, where:

$$\sigma_c^2 = \frac{2\gamma E}{\pi a},$$

where $\sigma_c$ is the critical stress applied by the spring, $\gamma$ is the surface energy of the material, E is the Young's modulus of the material, and $\alpha$ is the surface area perpendicular to the applied stress. In some embodiments, the support material may have a characteristic dissolution time. In certain embodiments, the characteristic dissolution time of the support material is less than or equal to 10 minutes, less than or equal to 9 minutes, less than or equal to 8 minutes, less than or equal to 7 minutes, less than or equal to 6 minutes, less than or equal to 5 minutes, less than or equal to 4 minutes, less than or equal to 3 minutes, or less than or equal to 2 minutes. In some embodiments, the characteristic dissolution time of the support material is greater than or equal to 1 minute, greater than or equal to 2 minutes, greater than or equal to 3 minutes, greater than or equal to 4 minutes, greater than or equal to 5 minutes, greater than or equal to 6 minutes, greater than or equal to 7 minutes, greater than or equal to 8 minutes, or greater than or equal to 9 minutes. Combinations of the above-referenced ranges are also possible (e.g., greater than or equal to 1 minute and less than or equal to 10 minutes). Other ranges are also possible. The characteristic dissolution time is determined as the time in which a support material begins to propagate a crack after exposure to gastrointestinal fluid.

*Spring

In some embodiments, the support material maintains at least a portion of the spring under at least 5%, at least 10%, at least 15%, at least 20%, at least 25%, at least 30%, at least 40%, at least 50%, at least 60%, at least 70%, or at least 80% compressive strain under the first set of conditions. In certain embodiments, the support material maintains at least a portion of the spring under less than or equal to 90%, less than or equal to 80%, less than or equal to 70%, less than or equal to 60%, less than or equal to 50%, less than or equal to 40%, less than or equal to 30%, less than or equal to 25%, less than or equal to 20%, less than or equal to 15%, or less than or equal to 10% compressive strain under the first set of conditions.

In certain embodiments, the spring recovers (e.g., within less than 10 minutes, less than 5 minutes, less than 1 minute, less than 30 seconds, less than 10 seconds, less than 5 seconds, less than 1 second, less than 0.1 seconds, less than 0.01 seconds) to a length of greater than or equal to 10%, greater than or equal to 20%, greater than or equal to 30%, greater than or equal to 40%, greater than or equal to 50%, greater than or equal to 60%, greater than or equal to 70%, greater than or equal to 80%, greater than or equal to 85%, greater than or equal to 90%, greater than or equal to 95%, greater than or equal to 98%, or greater than or equal to 99% of the length of the spring (e.g., an uncompressed spring length) prior to applying and/or in the absence of the compressive strain (e.g., by the support material), including any percentage in between 10% and 99%. In some embodiments, the spring recovers to a length of less than or equal to 100%, less than or equal to 99%, less than or equal to 98%, less than or equal to 95%, less than or equal to 90%, less than or equal to 85%, less than or equal to 80%, less than or equal to 75%, less than or equal to 70%, less than or equal to 60%, less than or equal to 50%, less than or equal to 40%, less than or equal to 30%, or less than or equal to 20% of the length of the spring prior to applying and/or in the absence of the compressive strain, including any percentage in between 20% and 100%. Advantageously, the use of springs and support materials as described herein may enable, for example, the release of a tissue interfacing component (e.g., a needle) associated with (e.g., operably linked with) the spring such that the tissue interfacing component contacts and/or penetrates tissue proximate the article. In an illustrative example, in some embodiments, a needle associated with the spring is administered to a subject such that, upon degradation of the support material, the spring recovers and the needle is pushed into tissue proximate the article such that the needle penetrates the tissue (e.g., a GI mucosal layer). In some such embodiments, an active pharmaceutical ingredient may be delivered into the tissue by the tissue interfacing components. For example, in some embodiments, the article comprises an active pharmaceutical ingredient such that, upon release of the spring at a location internal of a subject, the active pharmaceutical ingredient is released (e.g., into tissue proximate the location internal of the subject). In other embodiments, a biopsy may be conducted (e.g., by the tissue interfacing component such as a biopsy device) upon release of the spring by the support material. Referring again to FIG. 26, in some embodiments, article 100 comprises tissue interfacing component 115 associated with spring 110. Tissue interfacing components (e.g., needles, hooks, high API loaded components) are described in more detail, herein.

In certain embodiments, the tissue interfacing component comprises a needle, a patch or an array of needles (e.g., microneedles), a biopsy component, a hook, a mucoadhesive patch, or combinations thereof.

In some embodiments, the spring comprises an elastic material. In certain embodiments, the spring comprises a material selected from the group consisting of nitinol, metals, polymers, and combinations thereof.

In certain embodiments, the spring may have a particular spring constant. For example, in some embodiments, the spring constant of the spring may be greater than or equal to 100 N/m, greater than or equal to 150 N/m, greater than or equal to 200 N/m, greater than or equal to 250 N/m, greater than or equal to 300 N/m, greater than or equal to 350 N/m, greater than or equal to 400 N/m, greater than or equal to 450 N/m, greater than or equal to 500 N/m, greater than or equal to 600 N/m, greater than or equal to 700 N/m, greater than or equal to 800 N/m, greater than or equal to 900 N/m, greater than or equal to 1000 N/m, greater than or equal to 1100 N/m, greater than or equal to 1200 N/m, greater than or equal to 1300 N/m, or greater than or equal to 1400 N/m, less than or equal to 1500 N/m, less than or equal to 1800 N/m, or greater than or equal to 2000 N/m, and including any spring constant in between these values. In certain embodiments, the spring constant of the spring may be less than or equal to 2200 N/m, less than or equal to 2000 N/m, less than or equal to 1800 N/m, less than or equal to 1500 N/m, less than or equal to 1400 N/m, less than or equal to 1300 N/m, less than or equal to 1200 N/m, less than or equal to 1100 N/m, less than or equal to 1000 N/m, less than or equal to 900 N/m, less than or equal to 800 N/m, less than or equal to 700 N/m, less than or equal to 600 N/m, less than or equal to 500 N/m, less than or equal to 450 N/m, less than or equal to 400 N/m, less than or equal to 350 N/m, less than or equal to 300 N/m, less than or equal to 250 N/m, less than or equal to 200 N/m, or less than or equal to 150 N/m, including any spring constant in between these values. Combinations of the above-referenced ranges are also possible (e.g., greater than or equal to 100 N/m and less than or equal to 500 N/m, greater than or equal to 100 N/m and less than or equal to 1500 N/m). Other ranges are also possible.

In some embodiments, the spring is compressed (e.g., by the support material) by greater than or equal to 1 mm, greater than or equal to 2 mm, greater than or equal to 3 mm, greater than or equal to 4 mm, greater than or equal to 5 mm, greater than or equal to 6 mm, greater than or equal to 7 mm, greater than or equal to 8 mm, greater than or equal to 9 mm, greater than or equal to 10 mm, greater than or equal to 12 mm, or greater than or equal to 15 mm along a longitudinal axis of the spring as compared to the uncompressed length of the spring. In certain embodiments, the spring is compress by less than or equal to 20 mm, less than or equal to 15 mm, less than or equal to 12 mm, less than or equal to 10 mm, less than or equal to 9 mm, less than or equal to 8 mm, less than or equal to 7 mm, less than or equal to 6 mm, less than or equal to 5 mm, less than or equal to 4 mm, less than or equal to 3 mm, or less than or equal to 2 mm along a longitudinal axis of the spring as compared to the uncompressed length of the spring. Combinations of the above-referenced ranges are also possible (e.g., greater than or equal to 1 mm and less than or equal to 5 mm, greater than or equal to 5 mm and less than or equal to 10 mm). Other ranges are also possible.

In certain embodiments, the spring is configured to release a desirable amount of a stored compressive energy of the spring (e.g., upon exposure of the support material to a fluid such as gastrointestinal fluid). For example, the spring and/or the support material may be exposed to a fluid and, upon at least partial dissolution of the support material, the spring at least partially releases stored compressive energy e.g., to displace the tissue interfacing component operably linked to the spring (e.g., to release it into a tissue located internal to a subject). For example, in some embodiments, the spring is configured to release at least 10%, at least 20%, at least 30%, at least 40%, at least 50%, at least 60%, at least 70%, or at least 80% of the stored compressive energy of the spring, including any percentage in between these values. In certain embodiments, the spring is configured to release at least 90% of the stored compressive energy of the spring, at least 92% of the stored compressive energy of the spring, at least 94% of the stored compressive energy of the spring, at least 96% of the stored compressive energy of the spring, at least 98% of the stored compressive energy of the spring, or at least 99% of the stored compressive energy of the spring (e.g., upon exposure of the support material to a fluid such as gastrointestinal fluid), including any percentage in between these values. In certain embodiments, the spring is configured to release less than or equal to 100% of the stored compressive energy of the spring, less than 99% of the stored compressive energy of the spring, less than 98% of the stored compressive energy of the spring, less than 96% of the stored compressive energy of the spring, less than 94% of the stored compressive energy of the spring, less than 92% of the stored compressive energy of the spring, or less than 91% of the stored compressive energy of the spring. In some embodiments, the spring is configured to release less than or equal to 90%, less than or equal to 80%, less than or equal to 70%, less than or equal to 60%, less than or equal to 50%, less than or equal to 40%, less than or equal to 30%, or less than or equal to 20% of the stored compressive energy of the spring (e.g., upon exposure of the support material to a fluid such as gastrointestinal fluid), including any percentage in between these values. Combinations of the above-referenced ranges are also possible (e.g., at least 92% and less than 98% of the stored compressive energy of the spring, at least 94% and less than 96% of the stored compressive energy of the spring, at least 10% and less than or equal to 99%). Other ranges are also possible.

In some embodiments, the spring is configured to release the stored compressive energy of the spring within any suitable time of exposing the support material to a fluid and/or mechanical failure (e.g., cracking, fracture) of the support material. For example, in some embodiments, the spring is configured to release the stored compressive energy (e.g., at least 10% of the stored compressive energy) of the spring within less than 5 ms, less than 4 ms, less than 3 ms, less than 2 ms, less than 1 ms, less than 0.5 ms, or less than 0.2 ms of mechanical failure of the support material. In certain embodiments, the spring is configured to release the stored compressive energy of the spring within in greater than 0.1 ms, greater than 0.2 ms, greater than 0.5 ms, greater than 1 ms, greater than 2 ms, greater than 3 ms, or greater than 4 ms of mechanical failure of the support material. Combinations of the above-referenced ranges are also possible (e.g., within less than 5 ms and greater than 1 ms, within less than 2 ms and greater than 0.1 ms). Other ranges are also possible.

In certain embodiments, the spring is configured to release the stored compressive energy of the spring (e.g., at least 10% of the stored compressive energy) as described herein within less than 10 min, less than 9 min, less than 7 min, less than 5 min, less than 3 min, or less than 1 min of exposing the support material to a fluid, including any time in between these values. In some embodiments, the spring is configured to release the stored compressive energy of the spring within greater than 30 seconds, greater than 1 min, greater than 3 min, greater than 5 min, greater than 7 min, or greater than 9 min, including any time in between these values. Combinations of the above-referenced ranges (e.g., within less than 10 min and greater than 30 seconds, within less than 7 min and greater than 5 min). Other ranges are also possible.

Any combination of the above-referenced ranges are also possible. For example, in certain embodiments, the spring is configured to release at least 10% (e.g., at least 90%) of the stored compressive energy of the spring within 10 min of exposing the support material to a fluid. In certain embodiments, the spring is configured to release at least 10% (e.g., at least 90%) of a stored compressive energy of the spring within 30 seconds of exposing the support material to a fluid. In some embodiments, the spring is configured to release less than or equal to 100% of a stored compressive energy of the spring within 10 min of exposing the support material to a fluid. In certain embodiments, the spring is configured to release less than or equal to 100% of the stored compressive energy of the spring within 30 seconds of exposing the support material to a fluid.

In certain embodiments, the spring is configured to release at least 10% (e.g., at least 90%) of the stored compressive energy of the spring within 5 ms of mechanical failure of the support material. In certain embodiments, the spring is configured to release at least 10% (e.g., at least 90%) of a stored compressive energy of the spring within 0.1 ms of mechanical failure of the support material. In some embodiments, the spring is configured to release less than or equal to 100% of a stored compressive energy of the spring within 5 ms of mechanical failure of the support material. In certain embodiments, the spring is configured to release less than or equal to 100% of the stored compressive energy of the spring within 0.1 ms of mechanical failure of the support material.

The spring may have any suitable cross-sectional dimension. In some embodiments, the largest cross-sectional dimension of the (uncompressed) spring is greater than or equal to 1 mm, greater than or equal to 2 mm, greater than or equal to 3 mm, greater than or equal to 4 mm, or greater than or equal to 5 mm. In certain embodiments, the largest cross-sectional dimension of the (uncompressed) spring is less than or equal to 10 mm, less than or equal to 6 mm, less than or equal to 5 mm, less than or equal to 4 mm, less than or equal to 3 mm, or less than or equal to 2 mm. Combinations of the above-referenced ranges are also possible (e.g., greater than or equal to 1 mm and less than or equal to 10 mm). Other ranges are also possible.

In some embodiments, the article is administered to a subject (e.g., orally). In certain embodiments, the article may be administered orally, rectally, vaginally, nasally, or uretherally. In certain embodiments, upon reaching a location internal to the subject (e.g., the gastrointestinal tract), at least a portion of the support material degrades such that the spring extends and/or the tissue interfacing component interfaces (e.g., contacts, penetrates) with a tissue located internal to the subject. In some embodiments, the location internally of the subject is the colon, the duodenum, the ileum, the jejunum, the stomach, or the esophagus. In certain embodiments, the location internally of the subject is in the buccal space, in the venous system (e.g., an artery), in the respiratory system (e.g., lung), in the renal system, in the urinary system, or in the gastrointestinal system. As described above and herein, in some embodiments, an active pharmaceutical ingredient is released during and/or after penetrate of the tissue located internal to the subject.

In some embodiments, the tissue interfacing component comprises a needle and the tissue is penetrated with a force of greater than or equal to 1 mN and less than or equal to 100 mN (e.g., greater than or equal to 10 mN and less than or equal to 20 mN). In certain embodiments, the tissue interfacing component comprises a plurality of microneedles and the tissue is penetrated with a force of greater than or equal to 100 mN and less than or equal to 10 N (e.g., greater than or equal to 1 N and less than or equal to 2 N, greater than or equal to 100 mN and less than or equal to 6 N).

In some cases, and as described herein, the article may be oriented such that a longitudinal axis of the tissue interfacing component is orthogonal (e.g., within less than or equal to 10%, less than or equal to 5%, or less than or equal to 1% of 90°) to the tissue located proximate the article. In some embodiments, the self-actuating articles (e.g., comprising a tissue-interfacing component) described herein may be associated with one or more self-righting articles. Non-limiting examples of suitable self-righting articles are generally described in a co-owned International Patent Application No. WO 2018/213600, entitled "SELF-RIGHTING SYSTEMS AND RELATED COMPONENTS AND METHODS" filed on May 17, 2018, which is incorporated herein by reference in its entirety.

In an exemplary embodiment, the article comprises an outer shell, a spring at least partially encapsulated within the outer shell, a support material associated with the spring such that the support material maintains at least a portion of the spring under at least 5% compressive strain under ambient conditions, and a tissue interfacing component operably linked to the spring. In certain embodiments, the article comprises a tissue interfacing component and a spring associated with the tissue interfacing component, the spring maintained in an at least partially compressed state by a support material under at least 5% compressive strain. According to certain embodiments, the spring is configured to release at least 10% (e.g., at least 90%) of a stored compressive energy of the spring within 0.1 ms of mechanical failure of the support material. According to certain embodiments, the article compresses a pharmaceutical agent associated with the tissue interfacing component. In some embodiments, the article comprises a self-righting article associated with the tissue interfacing component.

Needle Distance and Velocity

Figure 11:
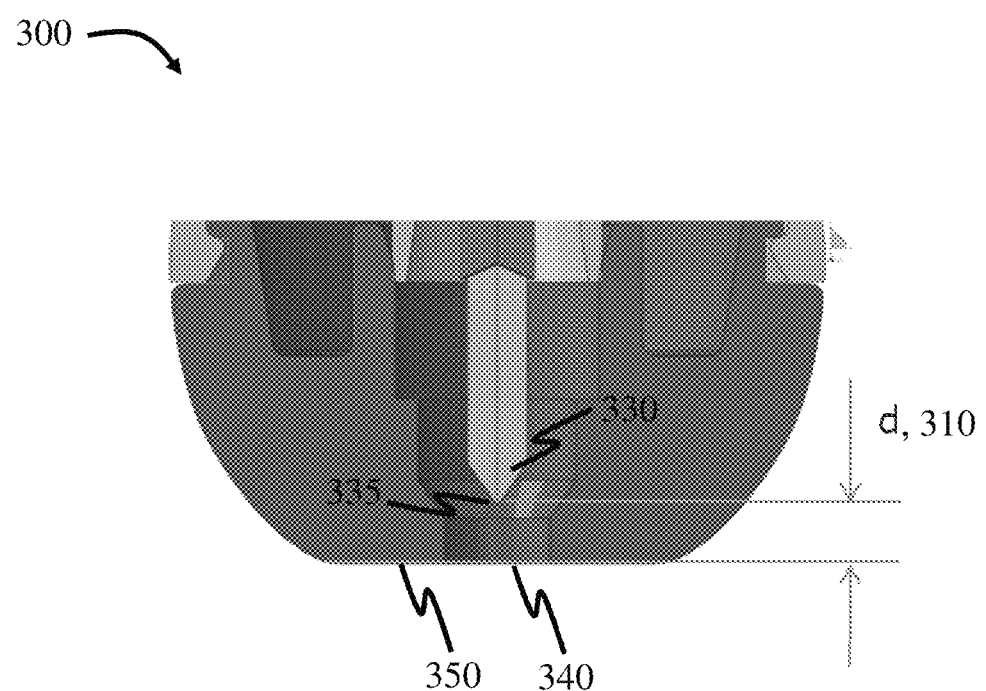
FIG. 11 is a cross-sectional schematic diagram of an exemplary self-righting system, according to one set of embodiments.

In some embodiments, as illustrated in FIG. 11, a self-righting system such as exemplary system 300 comprises a tissue interfacing component 330 proximate a hole 340 in tissue engaging surface 350. For example, referring again to FIG. 2, a self-actuating component 120 comprises a spring 125 such that, upon actuation of the self-actuating component, spring 125 expands pushing tissue interfacing component 130 out of system 102 through hole 140 (associated with tissue engaging surface 150). Referring back to FIG. 11, in some embodiments, an end 335 of the tip of tissue interfacing component 330 may be positioned such that it has a particular distance 310, d, from the tissue engaging surface. Without wishing to be bound by theory, the greater the distance, d, between the end of the tip of the tissue interfacing component and the tissue engaging surface, the greater the velocity at which the tissue interfacing component passes through the tissue engaging surface (e.g., and into a tissue of a subject located internal to a subject). For example, the tissue interfacing component may accelerate over the distance, d, traveled. Advantageously, the distance, d, may be selected such that, for example, the system remains in contact with the tissue (e.g., does not bounce off of the tissue) upon activation of the self-actuating component and/or engagement of the tissue interfacing component with the surface of the tissue.

In some embodiments, the system is configured such that the tissue interfacing component has a velocity at impact with the tissue of a subject (e.g., the velocity of the tip of the tissue interfacing component as it passes through the tissue engaging surface) of greater than or equal to 0.1 m/s, greater than or equal to 0.2 m/s, greater than or equal to 0.5 m/s, greater than or equal to 1 m/s, greater than or equal to 1.5 m/s, greater than or equal to 2 m/s, greater than or equal to 5 m/s, greater than or equal to 10 m/s, greater than or equal to 12 m/s, greater than or equal to 15 m/s, greater than or equal to 20 m/s, greater than or equal to 25 m/s, greater than or equal to 50 m/s, greater than or equal to 60 m/s, greater than or equal to 70 m/s, greater than or equal to 75 m/s, greater than or equal to 80 m/s, greater than or equal to 90 m/s, greater than or equal to 100 m/s, greater than or equal to 120 m/s, or greater than or equal to 150 m/s, including any velocity in between these values. In certain embodiments, the tissue interfacing component has a velocity at impact with the tissue of the subject of less than or equal to 200 m/s, less than or equal to 150 m/s, less than or equal to 120 m/s, less than or equal to 100 m/s, less than or equal to 90 m/s, less than or equal to 80 m/s, less than or equal to 75 m/s, less than or equal to 70 m/s, less than or equal to 60 m/s, less than or equal to 50 m/s, less than or equal to 25 m/s, less than or equal to 20 m/s, less than or equal to 15 m/s, less than or equal to 12 m/s, less than or equal to 10 m/s, less than or equal to 5 m/s, less than or equal to 2 m/s, less than or equal to 1.5 m/s, less than or equal to 1 m/s, less than or equal to 0.5 m/s, or less than or equal to 0.2 m/s, including any velocity in between these values. Combinations of the above-referenced ranges are also possible (e.g., greater than or equal to 0.1 m/s and less than or equal to 80 m/s, greater than or equal to 0.1 m/s and less than or equal to 25 m/s, greater than or equal to 20 m/s and less than or equal to 80 m/s). Other ranges are also possible.

In some embodiments, the tip of tissue interfacing component (e.g., prior to engagement with the tissue of the subject) is positioned at a distance of greater than or equal to 0 mm, greater than or equal to 0.1 mm, greater than or equal to 0.2 mm, greater than or equal to 0.5 mm, greater than or equal to 1.0 mm, greater than or equal to 1.5 mm, greater than or equal to 2.0 mm, or greater than or equal to 2.5 mm from the tissue engaging surface, including any distance in between these values. In certain embodiments, the tip of the tissue interfacing component is positioned at a distance of less than or equal to 3.0 mm, less than or equal to 2.5 mm, less than or equal to 2.0 mm, less than or equal to 1.5 mm, less than or equal to 1.0 mm, less than or equal to 0.5 mm, less than or equal to 0.2 mm, or less than or equal to 0.1 mm from the tissue engaging surface, including any distance in between these values. Combinations of the above-referenced ranges are also possible (e.g., greater than or equal to 0 mm and less than or equal to 3 mm, greater than or equal to 0.1 mm and less than or equal to 3.0 mm). Other ranges are also possible.

Plugs and Vents

In some embodiments, the system may comprise one or more vents (e.g., such that at least a portion of the system is in fluidic communication with the external environment). For example, referring again to FIG. 2, system 102 comprises at least one vent 190, such that e.g., self-actuating component 120 is in fluidic communication with an external environment. In certain embodiments, a fluid external to system 102 enters through vent(s) 190 and contacts self-actuating component 102, support material 160, and/or spring 125 (e.g., such that the spring extends).

In certain embodiments, at least a portion of the system may be fluidically isolated from the external environment. For example, referring again to FIG. 2, in some cases, hole 140 and/or vent(s) 190 may comprise a fluidic gate, as described herein. The fluidic gate, in certain embodiments, prevents fluid from contacting one or more internal components of the system (e.g., the tissue interfacing component, the self-actuating component) until a desired time and/or location. In some embodiments, each fluidic gate may be the same or different. For example, the fluidic gate associated with hole 140 may dissolve under a first set of conditions and/or rate, and the fluidic gate associated with vent(s) 190 may dissolve under a second set of conditions and/or rate, different than the first set of conditions and/or rate. In an exemplary embodiment, the fluidic gate associated with hole 140 may comprise a hydrophobic material and the fluidic gate associated with vent 190 may comprise a dissolvable material. Other combinations are also possible.

In some cases, the fluidic gate may be a plug. In some cases, the fluidic gate may prevent a fluid (e.g., a fluid external to the system) from entering the system at the hole and/or vent(s) until a desired time. In certain embodiments, the fluidic gate comprises a barrier material. Non-limiting examples of suitable barrier materials include foils of polycaprolactone, thermoplastic elastomers, cellulose, and silicone. The barrier material may comprise one or more hydrophobic materials. Those of ordinary skill in the art would be capable of selecting suitable hydrophobic materials as a barrier material based upon the teachings of this specification.

In some embodiments, the fluidic gate may comprise a dissolvable material (e.g., the fluidic gate dissolves such that a fluid enters the system at a desired time and/or location internal to a subject). Non-limiting examples of suitable dissolvable materials include sugar and polyvinyl alcohol.

In certain embodiments, the fluidic gate may comprise a substantially non-dissolvable material (e.g., the material does not dissolve under physiological conditions in the gastrointestinal environment e.g., in less than 7 days, in less than 3 days, in less than 24 hours). In some such embodiments, the non-dissolvable material may have suitable mechanical properties such that the tissue interfacing component, upon release from the system, can penetrate through at least a portion of the non-dissolvable material.

Figure 35:
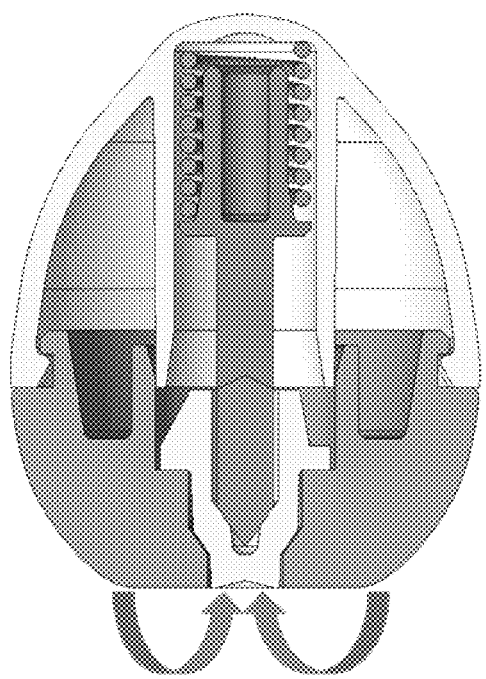
FIG. 35 is a schematic illustration of an exemplary system, according to one set of embodiments.

Referring now to FIG. 35, in some embodiments, the fluidic gate may be present in hole 140 such that the tissue interfacing component is not in fluidic communication with the external environment (e.g., until dissolution/removal of the plug).

Fluidicially Isolated Compartments

The systems described herein may, in some cases, comprise two or more fluidically isolated components. For example, in some embodiments, two or more portions of the system may not be in fluidic communication.

Referring again to FIG. 2, in some embodiments, first portion 110 and second portion 115 are not in fluidic communication. In certain embodiments, self-actuating component 120 may be fluidically isolated (e.g., not in fluidic communication) with tissue interfacing component 130. Advantageously, having two or more fluidically isolated components may, in some cases, permit the dissolution and/or actuation of one component without dissolution and/or activation of another component. By way of example, in an exemplary embodiment, tissue interfacing component 130 may be fluidically isolated from self-actuating component 120 such that, upon exposure of self-actuating component 120 to a fluid, self-actuating component 120 actuates (e.g., spring 125 expands) without exposing tissue interfacing component 130 to the fluid. For example, tissue interfacing component may comprise an API that, upon exposure to the fluid, would at least partially dissolve. Advantageously, preventing exposure of the tissue interfacing component to the fluid (e.g., protection of the tissue interfacing component) until a desired time (e.g., after release from the system) may prevent premature dissolution of the API prior to insertion into a tissue of a subject and/or may maintain the tissue interfacing component's mechanical integrity.

In some embodiments, the support material (e.g., the support material associated with the spring) is configured such that at least a portion of the self-actuating component (e.g., a first surface of the support material, a spring) is not in fluidic communication with the tissue interfacing component. That is to say, in some cases, the support material may act as a barrier (e.g., a fluidic barrier) between this self-actuating component and the tissue interfacing component. For example, referring again to FIG. 7, in some embodiments, a portion 122 of system 108 is not in fluidic communication with tissue interfacing component 130. In some such embodiments, portion 122 may be exposed to a fluid such that at least a portion of support material 160 dissolves without tissue interfacing component 130 being contacted by the fluid.

Assembly Process

In some embodiments, the system may be assembled such that a self-actuating component (e.g., comprising a spring and a support material) and a tissue interfacing component are associated with one another. For example, as illustrated in FIGS. 34A-34E a bottom portion and top portion of the system may be fixed along a 1-D axis. The bottom portion, in some embodiments, is held in place at its center hole, and the top is held in place by a hole e.g., which is drilled directly in the center of the top. The support material, in certain embodiments, is placed on top of the bottom portion, and the tissue interfacing component, already inside of the holder, may be placed on top of the support material. In some cases, the spring may then be placed on top of the support material. An alignment pin may be used, in some cases, which may be placed through the top portion and the spring. The top portion and bottom portion may be, in some cases, then moved together until they either snap together, are press fit, or are threaded together. In some embodiments, the alignment pin may then be removed. Other methods of assembling the components are also possible.

High API

In some embodiments, as described above and herein, the system comprises a component (e.g., a tissue interfacing component) comprising a solid therapeutic agent (e.g., a solid API) and a second material (e.g., a support(ing) material for the solid API such as a binder and/or a polymer) such that the solid therapeutic agent is present in the component in an amount of greater than or equal to 10 wt % versus the total weight of the tissue interfacing component. Such tissue-interfacing components may be useful for delivery of API doses (e.g., to a subject). Advantageously, in some embodiments, the reduction of volume required to deliver the required API dose as compared to a liquid formulation permits the creation of solid needle delivery systems for a wide variety of drugs in a variety of places/tissues (e.g., tongue, GI mucosal tissue, skin) and/or reduces and/or eliminates the application of an external force in order to inject a drug solution through the small opening in the needle. In some cases, a physiologically relevant dose may be present in a single tissue interfacing component (e.g., having a relatively high API loading).

In certain embodiments, the API is substantially solid (e.g., a powder, a compressed powder, a crystalline solid, an amorphous solid) i.e. a solid therapeutic agent. In some embodiments, the API may be in liquid form. In certain embodiments, the API may be In some embodiments, the tissue-interfacing component comprises a needle, a biopsy component, a projectile, a plurality of microneedles, a hook, a mucoadhesive patch, or combinations thereof. In certain embodiments, as described herein and above, the tissue interfacing component is configured to penetrate tissue (e.g., skin, tongue, tissue of the GI tract such as GI mucosal tissue). In some embodiments, the tissue in penetrated with a force of greater than or equal to 1 mN and less than or equal to 20 N (e.g., greater than or equal to 10 mN and less than or equal to 20 mN, greater than or equal to 1 mN and less than or equal to 100 mN, greater than or equal to 20 mN and less than or equal to 1 N, greater than or equal to 1 N and less than or equal to 20 N, greater than or equal to 10 N and less than or equal to 20 N).

Advantageously, a tissue-interfacing component comprising a needle and/or a plurality of microneedles comprising a relative high API loading (e.g., greater than or equal to 10 wt % versus the total weight of the component) may significantly reduce the number of needles and/or the overall size of the microneedle array required to deliver a particular API dose, as compared to traditional microneedles (e.g., generally comprising less than 10 wt % loading and/or requiring a plurality of microneedles on the order of thousands to tens of thousands of microneedles to deliver a similar dose).

In some embodiments, the tissue-interfacing component has a particular largest dimension (e.g., length). In certain embodiments, the largest dimension of the tissue interfacing component is greater than or equal to 1 mm, greater than or equal to 2 mm, greater than or equal to 3 mm, greater than or equal to 5 mm, greater than or equal to 7 mm, greater than or equal to 10 mm, greater than or equal to 12 mm, greater than or equal to 15 mm, greater than or equal to 20 mm, greater than or equal to 25 mm, greater than or equal to 30 mm, or greater than or equal to 50 mm. In some embodiments, the largest dimension of the tissue interfacing component is less than or equal to 100 mm, less than or equal to 50 mm, less than or equal to 30 mm, less than or equal to 25 mm, less than or equal to 20 mm, less than or equal to 15 mm, less than or equal to 12 mm, less than or equal to 10 mm, less than or equal to 7 mm, less than or equal to 5 mm, less than or equal to 3 mm, or less than or equal to 2 mm. Combinations of the above-referenced ranges are also possible.

In certain embodiments, the tissue-interfacing component has an average cross-sectional dimension (e.g., diameter) of greater than or equal to 0.25 mm, greater than or equal to 0.5 mm, greater than or equal to 0.6 mm, greater than or equal to 0.7 mm, greater than or equal to 0.8 mm, greater than or equal to 0.9 mm, greater than or equal to 1 mm, greater than or equal to 1.1 mm, greater than or equal to 1.2 mm, greater than or equal to 1.3 mm, greater than or equal to 1.4 mm, greater than or equal to 1.5 mm, greater than or equal to 1.7 mm, mm, greater than or equal to 1.9 mm, greater than or equal to 2.5 mm, greater than or equal to 3.0 mm, greater than or equal to 4.0 mm, or greater than or equal to 5.0 mm. In some embodiments, the tissue-interfacing component has an average cross-sectional dimension of less than or equal to 6.0 mm, less than or equal to 5.0 mm, less than or equal to 4.0 mm, less than or equal to 3.0 mm, less than or equal to 2.5 mm, less than or equal to 1.9 mm, less than or equal to 1.7 mm, less than or equal to 1.5 mm, less than or equal to 1.4 mm, less than or equal to 1.3 mm, less than or equal to 1.2 mm, less than or equal to 1.1 mm, less than or equal to 1 mm, less than or equal to 0.9 mm, less than or equal to 0.8 mm, less than or equal to 0.7 mm, or less than or equal to 0.6, or less than or equal to 0.5 mm. Combinations of the above-referenced ranges are also possible (e.g., greater than or equal to 0.5 mm and less than or equal to 2.0 mm). Other ranges are also possible.

In some embodiments, the tissue interfacing component may comprise a plurality of microneedles. In some such embodiments, the plurality of microneedles may have a particular base largest cross-sectional dimension (e.g., diameter of the base), a particular height, and/or a particular spacing.

In some embodiments, the average diameter of the base of the plurality of microneedles is greater than or equal to 100 microns, greater than or equal to 150 microns, greater than or equal to 200 microns, greater than or equal to 250 microns, greater than or equal to 300 microns, greater than or equal to 350 microns, greater than or equal to 400 microns, or greater than or equal to 450 microns. In certain embodiments, the average diameter of the base of the plurality of microneedles is less than or equal to 500 microns, less than or equal to 450 microns, less than or equal to 400 microns, less than or equal to 350 microns, less than or equal to 300 microns, less than or equal to 250 microns, less than or equal to 200 microns, or less than or equal to 150 microns. Combinations of the above-referenced ranges are also possible (e.g., greater than or equal to 100 microns and less than or equal to 500 microns). Other ranges are also possible.

In certain embodiments, the average height of the plurality of microneedles is greater than or equal to 0.1 mm, greater than or equal to 0.2 mm, greater than or equal to 0.5 mm, greater than or equal to 0.7 mm, greater than or equal to 1 mm, greater than or equal to 1.2 mm, greater than or equal to 1.5 mm, or greater than or equal to 2 mm. In some embodiments, the average height of the plurality of microneedles is less than or equal to 2.5 mm, less than or equal to 2 mm, less than or equal to 1.5 mm, less than or equal to 1.2 mm, less than or equal to 1 mm, less than or equal to 0.7 mm, less than or equal to 0.5 mm, or less than or equal to 0.2 mm. Combinations of the above-referenced ranges are also possible (e.g., greater than or equal to 0.1 mm and less than or equal to 2.5 mm). Other ranges are also possible.

In some cases, the average spacing (e.g., spacing between adjacent microneedles in the plurality of microneedles) of the plurality of microneedles may be greater than or equal to 100 microns, greater than or equal to 200 microns, greater than or equal to 300 microns, greater than or equal to 400 microns, greater than or equal to 500 microns, greater than or equal to 600 microns, greater than or equal to 700 microns, greater than or equal to 800 microns, greater than or equal to 900 microns, greater than or equal to 1000 microns, greater than or equal to 1100 microns, greater than or equal to 1200 microns, greater than or equal to 1300 microns, or greater than or equal to 1400 microns. In certain embodiments, the average spacing of the plurality of microneedles is less than or equal to 1500 microns, less than or equal to 1400 microns, less than or equal to 1300 microns, less than or equal to 1200 microns, less than or equal to 1100 microns, less than or equal to 1000 microns, less than or equal to 900 microns, less than or equal to 800 microns, less than or equal to 700 microns, less than or equal to 600 microns, less than or equal to 500 microns, less than or equal to 400 microns, less than or equal to 300 microns, or less than or equal to 200 microns. Combinations of the above-referenced ranges are also possible (e.g., greater than or equal to 100 microns and less than or equal to 1500 microns). Other ranges are also possible.

Figure 33:
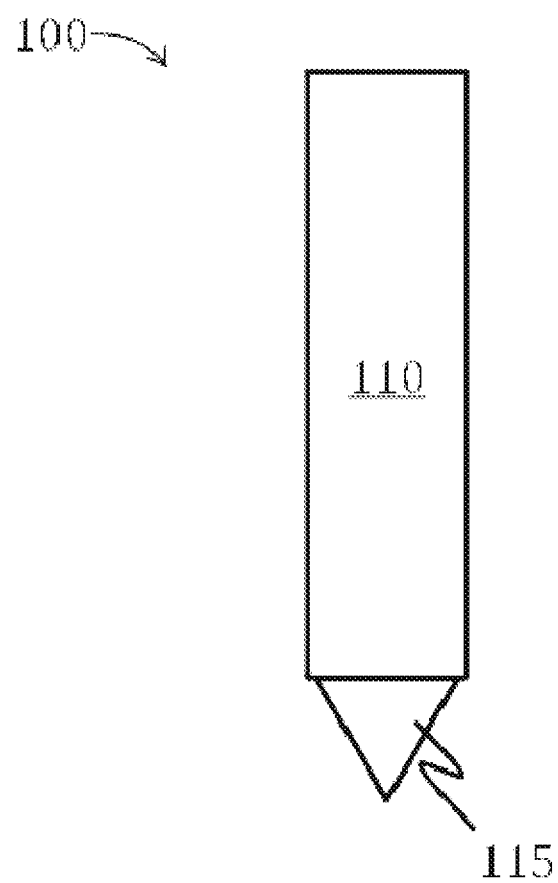
FIG. 33 is a schematic illustration of a tissue interfacing component, according to one set of embodiments.
Figures 34A, 34B, 34C, 34D, 34E:
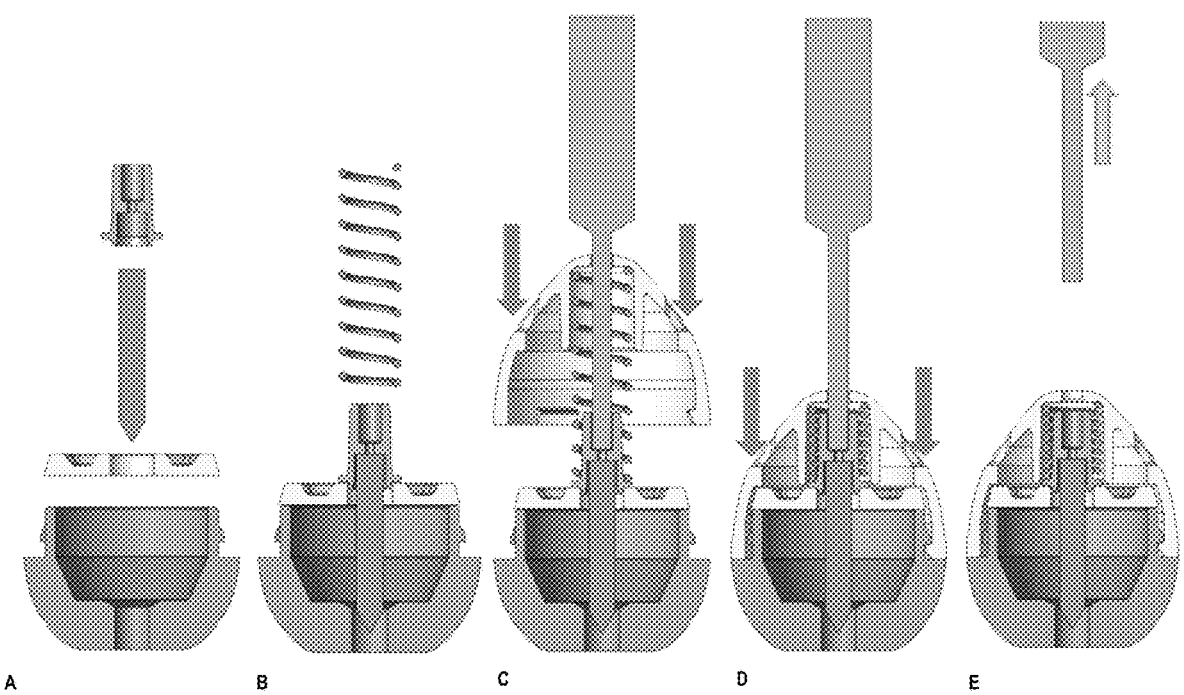
FIGS. 34A-34E are schematic illustrations of an exemplary assembly process for the system, according to one set of embodiments.

Advantageously, in some embodiments, the tissue-interfacing component (e.g., needle), dissolves relatively quickly, reducing and/or eliminating the risk of secondary penetration by the component in undesired locations. In some embodiments, the largest cross-sectional dimension (e.g., length) of the component is designed to be delivered to whichever organ it is targeting to prevent pain and/or undesired perforation of the GI tract. In some embodiments, the tissue interfacing component comprises a base portion and a tip. For example, as illustrated in FIG. 33, tissue interfacing component 100 comprises base portion 110 and tip 115. In some embodiments, the base portion and/or the tip portion comprises a mucoadhesive material. Non-limiting examples of suitable mucoadhesive materials include polymers such as poly(vinyl alcohol), hydroxylated methacrylate, and poly(methacrylic acid), polyacrylates (e.g., polyacrylic acid, thiolated poly(acrylic acid), Carbopol®), cyanoacrylates, sodium carboxymethylcellulose, hyaluronic acid, hydroxypropylcellulose, polycarbophil, chitosan, mucin, alginate, xanthan gum, gellan, poloxamer, celluloseacetophthalate, methyl cellulose, hydroxy ethyl cellulose, poly(amidoamine) dendrimers, poly(dimethyl siloxane), poly(vinyl pyrrolidone), polycarbophil, combinations thereof, and copolymers thereof.

In some embodiments, the base portion and/or the tip comprises a solid therapeutic agent (e.g., API) and a second material (if present), such that the solid therapeutic agent is present in the tissue interfacing component in an amount of greater than or equal to 10 wt % versus the total weight of the tissue interfacing component. In certain embodiments, the solid therapeutic agent is present in the tissue interfacing component in an amount of greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, or greater than or equal to 99.1 wt % versus the total weight of the tissue interfacing component. In some embodiments, the solid therapeutic agent is present in the tissue interfacing component in an amount of less than or equal to 100 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, or less than or equal to 20 wt % versus the total weight of the tissue interfacing component. Combinations of the above-referenced ranges are also possible (e.g., greater than or equal to 10 wt % and less than or equal to 100 wt %, greater than or equal to 80 wt % and less than or equal to 100 wt %). Other ranges are also possible. In an exemplary set of embodiments, the solid therapeutic agent is present in the tissue interfacing component in an amount greater than or equal to 80 wt % and less than or equal to 100 wt % versus the total weight of the tissue interfacing component.

In certain embodiments, the solid therapeutic agent is present in the base portion in an amount of greater than or equal to 0 wt %, greater than or equal to 5 wt %, greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, or greater than or equal to 99 wt % versus the total weight of the base portion. In some embodiments, the solid therapeutic agent is present in the base portion in an amount of less than or equal to 100 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, less than or equal to 20 wt %, less than or equal to 10 wt %, or less than or equal to 5 wt % versus the total weight of the base portion. Combinations of the above-referenced ranges are also possible (e.g., greater than or equal to 10 wt % and less than or equal to 100 wt %, greater than or equal to 80 wt % and less than or equal to 100 wt %). Other ranges are also possible. In an exemplary embodiment, the base portion substantially comprises only the solid therapeutic agent.

In certain embodiments, the solid therapeutic agent is present in the tip in an amount of greater than or equal to 0 wt %, greater than or equal to 5 wt %, greater than or equal to 10 wt %, greater than or equal to 20 wt %, greater than or equal to 30 wt %, greater than or equal to 40 wt %, greater than or equal to 50 wt %, greater than or equal to 60 wt %, greater than or equal to 70 wt %, greater than or equal to 80 wt %, greater than or equal to 90 wt %, greater than or equal to 95 wt %, greater than or equal to 98 wt %, or greater than or equal to 99 wt % versus the total weight of the tip. In some embodiments, the solid therapeutic agent is present in the tip in an amount of less than or equal to 100 wt %, less than or equal to 99 wt %, less than or equal to 98 wt %, less than or equal to 95 wt %, less than or equal to 90 wt %, less than or equal to 80 wt %, less than or equal to 70 wt %, less than or equal to 60 wt %, less than or equal to 50 wt %, less than or equal to 40 wt %, less than or equal to 30 wt %, less than or equal to 20 wt %, less than or equal to 10 wt %, or less than or equal to 5 wt % versus the total weight of the tip. Combinations of the above-referenced ranges are also possible (e.g., greater than or equal to 10 wt % and less than or equal to 100 wt %, greater than or equal to 80 wt % and less than or equal to 100 wt %). Other ranges are also possible. In an exemplary embodiment, the tip substantially comprises only the solid therapeutic agent. In another exemplary embodiment, the tip substantially comprises no solid therapeutic agent.

In certain embodiments, the tissue interfacing component comprises greater than or equal to 10 wt % (e.g., greater than or equal to 80 wt %) solid therapeutic agent, regardless of the makeup of the base portion and/or the tip, versus the total weight of the tissue interfacing component.

In some embodiments, the tissue interfacing component comprises greater than or equal to 0.1 mg, greater than or equal to 0.5 mg, greater than or equal to 0.8 mg, greater than or equal to 1 mg, greater than or equal to 1.5 mg, greater than or equal to 2 mg, greater than or equal to 2.5 mg, greater than or equal to 3 mg, greater than or equal to 4 mg, greater than or equal to 5 mg, greater than or equal to 7 mg, greater than or equal to 9 mg of therapeutic agent (e.g., solid therapeutic agent). In certain embodiments, the tissue interfacing component comprises less than or equal to 10 mg, less than or equal to 9 mg, less than or equal to 7 mg, less than or equal to 5 mg, less than or equal to 4 mg, less than or equal to 3 mg, less than or equal to 2.5 mg, less than or equal to 2 mg, less than or equal to 1.5 mg, less than or equal to 1 mg, less than or equal to 0.8 mg, less than or equal to 0.5 mg, or less than or equal to 0.2 mg of therapeutic agent. Combinations of the above-referenced ranges are also possible (e.g., greater than or equal to 0.1 mg and less than or equal to 10 mg). Other ranges are also possible.

In certain embodiments, at least a portion of the solid therapeutic agent (e.g., API) is associated with a base portion and/or one or more tips of the tissue interfacing component. For example, in some embodiments, the solid therapeutic agent and second material (if present) are distributed substantially homogeneously in the tissue interfacing component (e.g., in the base portion and/or in the tip). In some cases, the solid therapeutic agent may be a coating (e.g., disposed on at least a portion of the tip(s)) such that the tissue interfacing component comprises greater than or equal to 10 wt % solid therapeutic agent versus the total weight of the tissue interfacing component.

In some embodiments, the tissue interfacing component may comprise an additional coating. In some embodiments, the additional coating may comprise a material configured to e.g., slow the dissolution time relative to the dissolution of the tissue interfacing component without said additional coating. Non-limiting examples of suitable additional coating materials including Zn, Al, Mg, polymers (e.g., enteric polymers, polycaprolactone, parylene, hypromellose, polyethylene glycol), and combinations thereof. Other additional coating materials are also possible. In some embodiments, the additional coating may be configured such that the solid therapeutic agent is released over a particular amount of time. For example, in some embodiments, the additional coating is configured such that the solid therapeutic agent is released in less than or equal to 6 months, less than or equal to 3 months, less than or equal to 1 month, less than or equal to 2 weeks, less than or equal to 1 week, less than or equal to 4 days, less than or equal to 2 days, less than or equal to 1 day, less than or equal to 12 hours, less than or equal to 6 hours, less than or equal to 3 hours, less than or equal to 1 hour, less than or equal to 30 minutes, less than or equal to 15 minutes, less than or equal to 10 minutes, less than or equal to 5 minutes, or less than or equal to 2 minutes (e.g., upon exposure of the additional coating to a fluid such as gastric fluid). In certain embodiments, the additional coating is configured such that the solid therapeutic agent is released in greater than or equal to 1 minute, greater than or equal to 2 minutes, greater than or equal to 5 minutes, greater than or equal to 10 minutes, greater than or equal to 15 minutes, greater than or equal to 30 minutes, greater than or equal to 1 hour, greater than or equal to 3 hours, greater than or equal to 6 hours, greater than or equal to 12 hours, greater than or equal to 1 day, greater than or equal to 2 days, greater than or equal to 4 days, greater than or equal to 1 week, greater than or equal to 2 weeks, greater than or equal to 1 month, or greater than or equal to 3 months. Combinations of the above-referenced ranges are also possible (e.g., greater than or equal to 1 minute and less than or equal to 1 day, greater than or equal to 1 day and less than or equal to 2 weeks, greater than or equal to 1 week and less than or equal to 6 months). Other ranges are also possible.

In certain embodiments, the tissue interfacing component comprises a plurality of microneedles comprising the solid therapeutic agent and the second material (if present).

In some embodiments, at least a portion of the solid therapeutic agent is present on at least a surface of the tip. In certain embodiments, at least a portion of the second material is present on at least a surface of the tip.

The tissue-interfacing components described herein may be formed using any suitable method. In some embodiments, the tissue-interfacing component is formed by providing the solid therapeutic agent and the second material (if present) and centrifuging and/or compressing, using at least 1 MPa of pressure, the solid therapeutic agent and a second material together to form the tissue interfacing component. In some embodiments, the second material (if present) and the solid therapeutic agent is heated to form the tissue interfacing component.

In some embodiments, the tissue-interfacing component is formed using at least 1 MPa of pressure, at least 2 MPa of pressure, at least 3 MPa of pressure, at least 5 MPa of pressure, at least 7 MPa of pressure, at least 10 MPa of pressure, at least 12 MPa of pressure, at least 15 MPa of pressure, at least 20 MPa of pressure, at least 25 MPa of pressure, at least 30 MPa of pressure, at least 40 MPa of pressure, at least 50 MPa of pressure, at least 75 MPa of pressure, at least 150 MPa of pressure, at least 300 MPa of pressure, at least 600 MPa of pressure, at least 900 MPa of pressure, at least 1 GPa of pressure, or at least 1.2 GPa of pressure. In some embodiments, the tissue-interfacing component is formed using less than or equal to 1.4 GPa of pressure, less than or equal to 1.2 GPa of pressure, less than or equal to 1 GPa of pressure, less than or equal to 900 MPa of pressure, less than or equal to 600 MPa of pressure, less than or equal to 300 MPa of pressure, less than or equal to 150 MPa of pressure, less than or equal to 100 MPa of pressure, less than or equal to 75 MPa of pressure, less than or equal to 50 MPa of pressure, less than or equal to 40 MPa of pressure, less than or equal to 30 MPa of pressure, less than or equal to 25 MPa of pressure, less than or equal to 20 MPa of pressure, less than or equal to 15 MPa of pressure, less than or equal to 12 MPa of pressure, less than or equal to 10 MPa of pressure, less than or equal to 7 MPa of pressure, less than or equal to 5 MPa pressure, less than or equal to 3 MPa of pressure, or less than or equal to 2 MPa of pressure. Combinations of the above-referenced ranges are also possible (e.g., at least 1 MPa of pressure and less than or equal to 100 MPa of pressure, at least 20 MPa of pressure and less than or equal to 100 MPa of pressure, at least 100 MPa and less than or equal to 1.4 GPa of pressure). Other ranges are also possible.

In certain embodiments, the tissue interfacing component may be formed at a particular temperature. For example, the tissue interfacing component, in some embodiments, is formed at a temperature of greater than or equal to 50° C., greater than or equal to 60° C., greater than or equal to 70° C., greater than or equal to 80° C., greater than or equal to 90° C., greater than or equal to 100° C., or greater than or equal to 120° C. In some embodiments, the tissue interfacing component is formed at a temperature of less than or equal to 150° C., less than or equal to 130° C., less than or equal to 120° C., less than or equal to 110° C., less than or equal to 100° C., less than or equal to 90° C., less than or equal to 80° C., less than or equal to 70° C., or less than or equal to 60° C. Combinations of the above referenced ranges are also possible (e.g., greater than or equal to 50° C. and less than or equal to 130° C.). Other temperatures and ranges are also possible.

Advantageously, the tissue interfacing component may have desirable mechanical properties (e.g., Young's elastic modulus) e.g., such that the tissue interfacing component may suitably puncture tissue of the gastrointestinal tract. In some embodiments, the Young's elastic modulus of the tissue interfacing component is greater than or equal to 100 MPa (e.g., greater than or equal to 125 MPa, greater than or equal to 150 MPa, greater than or equal to 175 MPa, greater than or equal to 200 MPa, greater than or equal to 250 MPa, greater than or equal to 300 MPa, or greater than or equal to 350 MPa). In certain embodiments, the tissue interfacing component has a Young's elastic modulus of less than or equal to 400 MPa, less than or equal to 350 MPa, less than or equal to 300 MPa, less than or equal to 250 MPa, less than or equal to 200 MPa, less than or equal to 175 MPa, less than or equal to 150 MPa, or less than or equal to 125 MPa. Combinations of the above-referenced ranges are also possible (e.g., greater than or equal to 100 MPa and less than or equal to 250 MPa, greater than or equal to 100 MPa and less than or equal to 400 MPa). Other ranges are also possible.

In some cases, the tissue interfacing component may be configured to penetrate a particular depth into human gastrointestinal mucosal tissue at a particular force. For example, the tissue interfacing component may be configured to penetrate greater than or equal to 1 mm (e.g., greater than or equal to 2 mm, greater than or equal to 3 mm, or greater than or equal to 4 mm) with a force of less than or equal to 20 N (e.g., less than or equal to less than or equal to 10 N, less than or equal to 5 N, less than or equal to 1 N, less than or equal to 500 mN, less than or equal to 100 mN, less than or equal to 50 mN, less than or equal to 20 mN, less than or equal to 15 mN, less than or equal to 10 mN, less than or equal to 5 mN).

As described above and herein, the tissue interfacing component may be configured to have a particular velocity at penetration into e.g., human gastrointestinal mucosal tissue.

In some embodiments, the second material comprises a polymerizable monomer and/or a polymer. In certain embodiments, the second material is biodegradable. Non-limiting examples of suitable materials for the second material include polyethylene glycol, polyvinylpyrrolidone, polylactic acid, polysaccharides (e.g., maltose, lactose, starch, cellulose), acacia, methyl cellulose, gelatin, tragacanth, clays, HPMC, stearic acid, sodium stearate, magnesium stearate, talc, polyethylene glycol, mineral oil, preservatives (e.g., phenol, paraben, cetrimide), antioxidants (e.g., gallic acid, tocopherol), derivatives thereof, and combinations thereof.

In some embodiments, the tissue interfacing component comprises a coating having a yield strength of greater than or equal to 50 MPa (e.g., greater than or equal to 60 MPa, greater than or equal to 70 MPa, or greater than or equal to 80 MPa).

In some embodiments, the coating may be comprised of a thin film metal, a ceramic or a Diamond Like Coating (DLC). In some embodiments, the tissue interfacing component does not comprise a coating.

In some embodiments, the coating may be comprised of a corrodible material (e.g. iron, zinc, aluminum or alloys) such that when the coating comes in contact with the physiological environment it will disintegrate and present the therapeutic agent. In certain embodiments, the coating may comprise a polymer such as parylene, as described herein.

In some cases, the tissue interfacing component may be configured to deliver a particular amount of active pharmaceutical agent per square centimeter of tissue of a subject. For example, in some embodiments, the tissue interfacing component is configured to deliver greater than or equal to 0.01 µg, greater than or equal to 0.05 µg, greater than or equal to 0.1 µg, greater than or equal to 0.2 µg, greater than or equal to 0.5 µg, greater than or equal to 0.7 µg, greater than or equal to 1 µg, greater than or equal to 2 µg, greater than or equal to 5 µg, or greater than or equal to 10 µg of pharmaceutical agent per square centimeter of tissue of the subject proximate the penetration location of the tissue interfacing component. In certain embodiments, the tissue interfacing component is configured to deliver less than or equal to 20 µg, less than or equal to 5 µg, less than or equal to 2 µg, less than or equal to 1 µg, less than or equal to 0.7 µg, less than or equal to 0.5 µg, less than or equal to 0.2 µg, less than or equal to 0.1 µg, or less than or equal to 0.05 µg of pharmaceutical agent per square centimeter of tissue. Combinations of the above-referenced ranges are also possible (e.g., greater than or equal to 1 µg and less than or equal to 20 µg). In some embodiments, the tissue interfacing component is configured to deliver greater than or equal to 1 µg of pharmaceutical agent per square centimeter of tissue of the subject over any suitable time period (e.g., in greater than or equal to 0.1 seconds, in greater than or equal to 0.5 seconds, in greater than or equal to 1 second, in greater than or equal to 5 seconds, in greater than or equal to 30 seconds, greater than or equal to 1 minute, greater than or equal to 5 minutes, 10 minutes, greater than or equal to 30 minutes, greater than or equal to 1 hour, greater than or equal to 4 hours, greater than or equal to 24 hours, greater than or equal to 48 hours, greater than or equal to 72 hours, greater than or equal to 96 hours, greater than or equal to 120 hours, greater than or equal to 144 hours, greater than or equal to 168 hours).

In certain embodiments, the tissue interfacing component comprises a binder (e.g., in some cases, the second material is a binder). Non-limiting examples of suitable binders include sugar such as sorbitol and sucrose, gelatin, polymers such as polyvinyl alcohol (PVA), polyethylene glycol (PEG), polycaprolactone (PCL), and polyvinylpyrrolidone (PVP), and polymers comprising ethanol or other Class 3 organic solvents (e.g., acetic acid, heptane, acetone, formic acid, isobutyl acetate, etc.).

In an exemplary embodiment, the article comprises greater than or equal to 80 wt % solid active pharmaceutical agent versus the total article weight. In certain embodiments, the article comprises greater than or equal to 1 mg of active pharmaceutical agent. According to some embodiments, the pharmaceutical agent is selected from the group consisting of bacteriophage, DNA, mRNA, insulin, human growth hormone, monoclonal antibodies, adalimumab, epinephrine, and ondansetron. In certain exemplary embodiments, the active pharmaceutical agent is cast into a mold to form the article. In some embodiments, the mold is centrifuged. According to certain embodiments, the article further comprises a binder. In certain embodiments, the binder comprises sugar such as sorbitol or sucrose, gelatin, polymer such as PVA, PEG, PCL, PVA, or PVP, and/or ethanol. According to certain embodiments, the article has a Young's elastic modulus of greater than or equal to 100 MPa. In some embodiments, the article is configured to penetrate at least 1 mm into human gastrointestinal mucosal tissue with a force of less than or equal to 20 mN. According to certain embodiments, the article is configured to deliver at least 1 mg of pharmaceutical agent per square centimeter of a tissue of a subject, and/or the article comprises greater than or equal to 1 mg of active pharmaceutical agent per square centimeter.

Certain exemplary embodiments are related to a method of forming the article, wherein the method comprises introducing, into a mold, a composition comprising greater than 80 wt % solid pharmaceutical agent versus the total weight of the composition, applying greater than or equal to 1 MPa of pressure to the composition, and heating the composition to a temperature of at least 70° C. for at least 1 minute. As used herein, the term "active pharmaceutical ingredient" (also referred to as a "drug" or "therapeutic agent") refers to an agent that is administered to a subject to treat a disease, disorder, or other clinically recognized condition, or for prophylactic purposes, and has a clinically significant effect on the body of the subject to treat and/or prevent the disease, disorder, or condition.

Agents

According to some embodiments, the composition and methods described herein are compatible with one or more therapeutic, diagnostic, and/or enhancement agents, such as drugs, nutrients, microorganisms, in vivo sensors, and tracers. In some embodiments, the active substance, is a therapeutic, nutraceutical, prophylactic or diagnostic agent. While much of the specification describes the use of therapeutic agents, other agents listed herein are also possible.

In some embodiments, the agent may be in powder form. In some embodiments, the agent may be in solid form. In some embodiments, the agent may be in liquid form.

In some embodiments, the system comprises a chamber (e.g., a reservoir) configured to contain the active pharmaceutical agent (or a liquid comprising the active pharmaceutical agent).

Agents can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals, Certain such agents may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, non-steroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti(retro)viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements).

In certain embodiments, the active substance is one or more specific therapeutic agents. As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition. Listings of examples of known therapeutic agents can be found, for example, in the United States Pharmacopeia (USP), Goodman and Gilman's The Pharmacological Basis of Therapeutics, 10th Ed., McGraw Hill, 2001; Katzung, B. (ed.) Basic and Clinical Pharmacology, McGraw-Hill/Appleton & Lange; 8th edition (Sep. 21, 2000); Physician's Desk Reference (Thomson Publishing), and/or The Merck Manual of Diagnosis and Therapy, 17th ed. (1999), or the 18th ed (2006) following its publication, Mark H. Beers and Robert Berkow (eds.), Merck Publishing Group, or, in the case of animals, The Merck Veterinary Manual, 9th ed., Kahn, C. A. (ed.), Merck Publishing Group, 2005; and "Approved Drug Products with Therapeutic Equivalence and Evaluations," published by the United States Food and Drug Administration (F.D.A.) (the "Orange Book"). Examples of drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. In certain embodiments, the therapeutic agent is a small molecule. Exemplary classes of therapeutic agents include, but are not limited to, analgesics, anti-analgesics, anti-inflammatory drugs, antipyretics, antidepressants, antiepileptics, antipsychotic agents, neuroprotective agents, anti-proliferatives, such as anti-cancer agents, antihistamines, antimigraine drugs, hormones, prostaglandins, antimicrobials (including antibiotics, antifungals, antivirals, antiparasitics), antimuscarinics, anxioltyics, bacteriostatics, immunosuppres sant agents, sedatives, hypnotics, antipsychotics, bronchodilators, anti-asthma drugs, cardiovascular drugs, anesthetics, anti-coagulants, inhibitors of an enzyme, steroidal agents, steroidal or non-steroidal anti-inflammatory agents, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated into the drug delivery device. These may be vitamins, supplements such as calcium or biotin, or natural ingredients such as plant extracts or phytohormones.

In some embodiments, the therapeutic agent is one or more antimalarial drugs. Exemplary antimalarial drugs include quinine, lumefantrine, chloroquine, amodiaquine, pyrimethamine, proguanil, chlorproguanil-dapsone, sulfonamides such as sulfadoxine and sulfamethoxypyridazine, mefloquine, atovaquone, primaquine, halofantrine, doxycycline, clindamycin, artemisinin and artemisinin derivatives. In some embodiments, the antimalarial drug is artemisinin or a derivative thereof. Exemplary artemisinin derivatives include artemether, dihydroartemisinin, arteether and artesunate. In certain embodiments, the artemisinin derivative is artesunate.

In another embodiment, the therapeutic agent is an immunosuppressive agent. Exemplary immunosuppressive agents include glucocorticoids, cytostatics (such as alkylating agents, antimetabolites, and cytotoxic antibodies), antibodies (such as those directed against T-cell receptors or Il-2 receptors), drugs acting on immunophilins (such as cyclosporine, tacrolimus, and sirolimus) and other drugs (such as interferons, opioids, TNF binding proteins, mycophenolate, and other small molecules such as fingolimod).

In certain embodiments, the therapeutic agent is a hormone or derivative thereof. Non-limiting examples of hormones include insulin, growth hormone (e.g., human growth hormone), vasopres sin, melatonin, thyroxine, thyrotropin-releasing hormone, glycoprotein hormones (e.g., luteinzing hormone, follicle-stimulating hormone, thyroid-stimulating hormone), eicosanoids, estrogen, progestin, testosterone, estradiol, cortisol, adrenaline, and other steroids.

In some embodiments, the therapeutic agent is a small molecule drug having molecular weight less than about 2500 Daltons, less than about 2000 Daltons, less than about 1500 Daltons, less than about 1000 Daltons, less than about 750 Daltons, less than about 500 Daltons, less or than about 400 Daltons. In some cases, the therapeutic agent is a small molecule drug having molecular weight between 200 Daltons and 400 Daltons, between 400 Daltons and 1000 Daltons, or between 500 Daltons and 2500 Daltons.

In some embodiments, the therapeutic agent is selected from the group consisting of active pharmaceutical agents such as insulin, nucleic acids, peptides, bacteriophage, DNA, mRNA, human growth hormone, monoclonal antibodies, adalimumab, epinephrine, GLP-1 Receptor agoinists, semaglutide, liraglutide, dulaglitide, exenatide, factor VIII, small molecule drugs, progrstin, vaccines, subunit vaccines, recombinant vaccines, polysaccharide vaccines, and conjugate vaccines, toxoid vaccines, influenza vaccine, shingles vaccine, prevnar pneumonia vaccine, mmr vaccine, tetanus vaccine, hepatitis vaccine, HIV vaccine Ad4-env Clade C, HIV vaccine Ad4-mGag, dna vaccines, ma vaccines, etanercept, infliximab, filgastrim, glatiramer acetate, rituximab, bevacizumab, any molecule encapsulated in a nanoparticle, epinephrine, lysozyme, glucose-6-phosphate dehydrogenase, other enzymes, certolizumab pegol, ustekinumab, ixekizumab, golimumab, brodalumab, gusellu, ab, secikinumab, omalizumab, tnf-alpha inhibitors, interleukin inhibitors, vedolizumab, octreotide, teriperatide, crispr cas9, insulin glargine, insulin detemir, insulin lispro, insulin aspart, human insulin, antisense oligonucleotides, and ondansetron.

In an exemplary embodiment, the therapeutic agent is insulin.

In some embodiments, the tissue-interfacing component described herein comprises two or more types of therapeutic agents.

In certain embodiments, the therapeutic agent is present in the tissue interfacing component at a concentration such that, upon release from the tissue interfacing component, the therapeutic agent elicits a therapeutic response.

In some cases, the therapeutic agent may be present at a concentration below a minimal concentration generally associated with an active therapeutic agent (e.g., at a microdose concentration). For example, in some embodiments, the tissue interfacing component comprises a first therapeutic agent (e.g., a steroid) at a relatively low dose (e.g., without wishing to be bound by theory, low doses of therapeutic agents such as steroids may mediate a subject's foreign body response(s) (e.g., in response to contact by a tissue interfacing components) at a location internal to a subject). In some embodiments, the concentration of the therapeutic agent is a microdose less than or equal to 100 µg and/or 30 nMol. In other embodiments, however, the therapeutic agent is not provided in a microdose and is present in one or more amounts listed above.

In some embodiments, the tissue-interfacing component comprises a self-actuating component. Such self-actuating tissue interfacing components are generally described in a co-owned International Patent Application No. WO 2018/213600, entitled "SELF-RIGHTING SYSTEMS AND RELATED COMPONENTS AND METHODS" filed on May 17, 2018 which is incorporated herein by reference in its entirety.

In some embodiments, the tissue-interfacing component is administered to a subject (e.g., orally). In certain embodiments, the article may be administered orally, rectally, vaginally, nasally, or uretherally. In certain embodiments, the tissue-interfacing component (e.g., and/or the API contained therein) is administered by contacting the skin of a subject with the component. In an exemplary embodiment, the tissue-interfacing component (e.g., and/or the API contained therein) is administered by contacting the buccal tissue (e.g., lip, palatal area, cheek, sublingual, tongue) of a subject with the component. In yet another exemplary embodiment, the tissue-interfacing component is administered orally and, upon reaching a location internal the subject (e.g., the GI tract such as the colon, the duodenum, the ileum, the jejunum, the stomach, the buccal space, the esophagus, etc.), the tissue-interfacing component interfaces (e.g., contacts) with the tissue of the subject at the location internal the subject and at least partially penetrates the tissue. In certain embodiments, at least a portion of the tissue-interfacing component penetrates the tissue of the subject and at least a portion of the support material and/or the active pharmaceutical agent dissolves into the tissue of the subject.

Advantageously, administration of a tissue-interfacing component having a relatively high loading of API to the GI tract may permit more effective delivery of the API as compared to traditional methods. For example, without wishing to be bound by theory, delivering a drug via an injection to the GI tract has been shown to have a higher bioavailability compared to other methods.

In some embodiments, the system comprises a self-righting article (e.g., configured to localize to a location internal to a subject at a particular orientation), a self-actuating component (e.g., configured to activate under a particular set of conditions e.g., upon exposure to a fluid such as gastrointestinal fluid), a tissue-interfacing component associated with the self-actuating component, and an API associated with the tissue-interfacing component. In certain embodiments, the system comprises a self-righting article, a self-actuating component, and a tissue interfacing component associated with the self-actuating component. In some embodiments, the system comprises a self-actuating component and a tissue interfacing component associated with the self-actuating component. In certain embodiments, the system comprises a self-righting article and an API associated with the self-righting article. In some embodiments, the system comprises a tissue interfacing component and an API associated with the tissue interfacing component. In some embodiments, the system comprises a self-actuating component, a tissue interfacing component associated with the self-actuating component, and an API associated with the tissue interfacing component. Self-righting articles, self-actuating components, tissue interfacing components, and APIs and related configurations are described above and herein.

Definitions

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the self-righting article.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

EXAMPLES

The following examples are intended to illustrate certain embodiments described herein, including certain aspects of the present invention, but do not exemplify the full scope of the invention.

Example 1—Self-Righting Article

A self-righting article consisting of a specific shape and/or density distribution, optionally, with the capacity for encapsulation in standard '000,' '00,' or potentially smaller or larger capsules are provided. For example, the distribution of density and/or shape may be such that:

1. The design has only one stable point and one unstable point so that it will always right itself to a single configuration and orientation;

2. The design of the article has a relatively low righting time to its stable configuration from every possible orientation;

3. The design minimizes the destabilizing effects felt from forces in the GI tract such as fluid flow and muscle contractions; and/or 4. The design allows for the loading of articles of various shapes and weights into the system via hollow crevices created in specific locations on the article.

In some cases, the article shape originates from a smooth curve that is drawn within the two right quadrants of a Cartesian plane and rotated about the y axis. The shape has several noticeable characteristics. It possesses a flat bottom perpendicular to the y axis moving into a high curvature corner and then slowly lowers its curvature as the curve continues. The flat bottom section of the curve may help to satisfy the third specification for the article. Because the bottom is flat and is surrounded by steep corners, a larger force is required to push the article onto its side. This is similar to the way that an ellipsoid will wobble when pushed but a cube will not.

The rest of the curve may be is optimized in a way to satisfy the first and second specifications using the equations below. The righting times of the article are calculated from the angular kinematic equation:

$$\Delta\theta = \omega t + \tfrac{1}{2}\alpha t^2$$

where $\omega$ is the angular velocity, t is time and $\alpha$ is angular acceleration. The angular acceleration is calculated from the torques generated by the gravitational and buoyant forces acting on the article. $\alpha = \tau/I$ where $\tau$ is torque and I is moment of inertia. Torque is determined from the cross product between the force and distance vectors: $\tau = \|d \otimes F\| = d*F*\sin(\theta)$ where d is a distance vector from the center of mass (for gravity) or center of volume (for buoyancy) to the edge point of the curve touching the resting surface, F is the force vector in the direction of the force generated, and $\theta$ is the angle between those two vectors.

The article can be made, in some cases, of two different materials: one with a high density and another with a low density. The ratio of the densities is defined so that the center of mass of the shape is located at the origin of the coordinate system. The lower half of the plane consists of the high density material while the upper portion of the plane consists of the low density material. In order to keep the material densities realizable from currently available materials, certain holes and modifications can be made to the original shape which are explained in the examples. These holes and modification are also utilized to house articles within the system, which are then taken into account when determining the densities of the other materials.

Once a 3D shape has been designed, it is possible to test the righting times from a given orientation by using the equations above. The weight and volume of the article determine the acting forces that determine the torque and are set by the densities of the materials as well as the generated curve. The distance and angle measurements used to determine the torque are determined solely by the generated curve. A curve is generated by drawing a smooth curve through a set of points in radial coordinates with the angle coordinate set. The code then varies the distance coordinates of the points until the minimum set of righting times is reached.

Example 2

Figure 12:
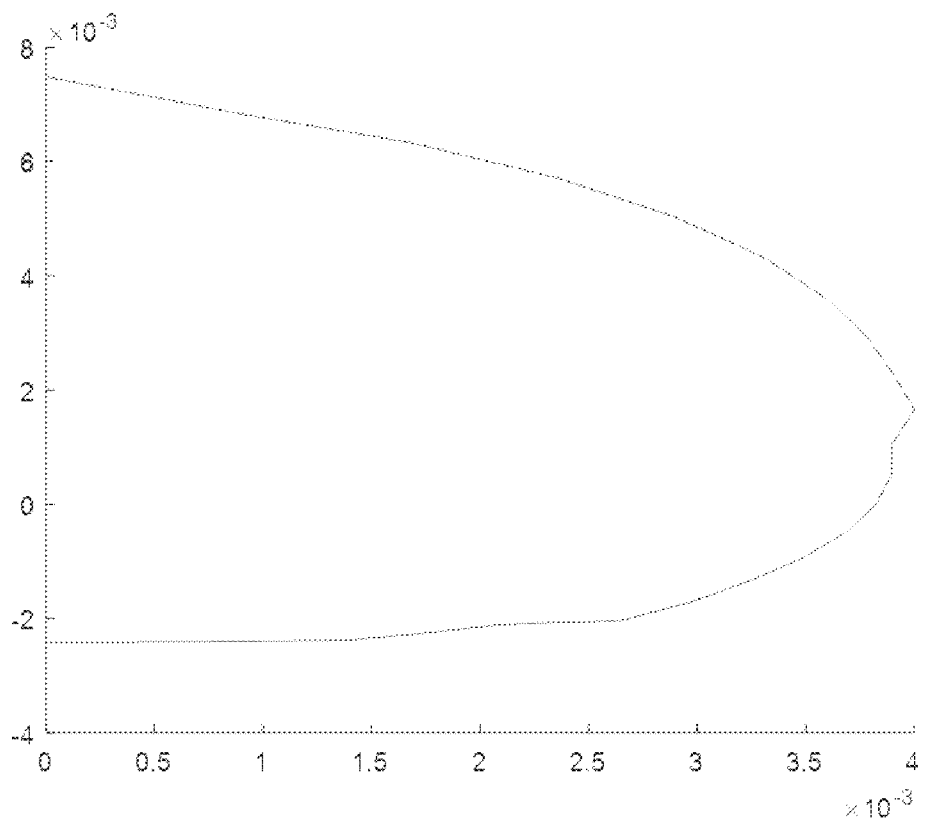
FIG. 12 is a plot of an exemplary self-righting shape graph, according to one set of embodiments.
Figure 13:
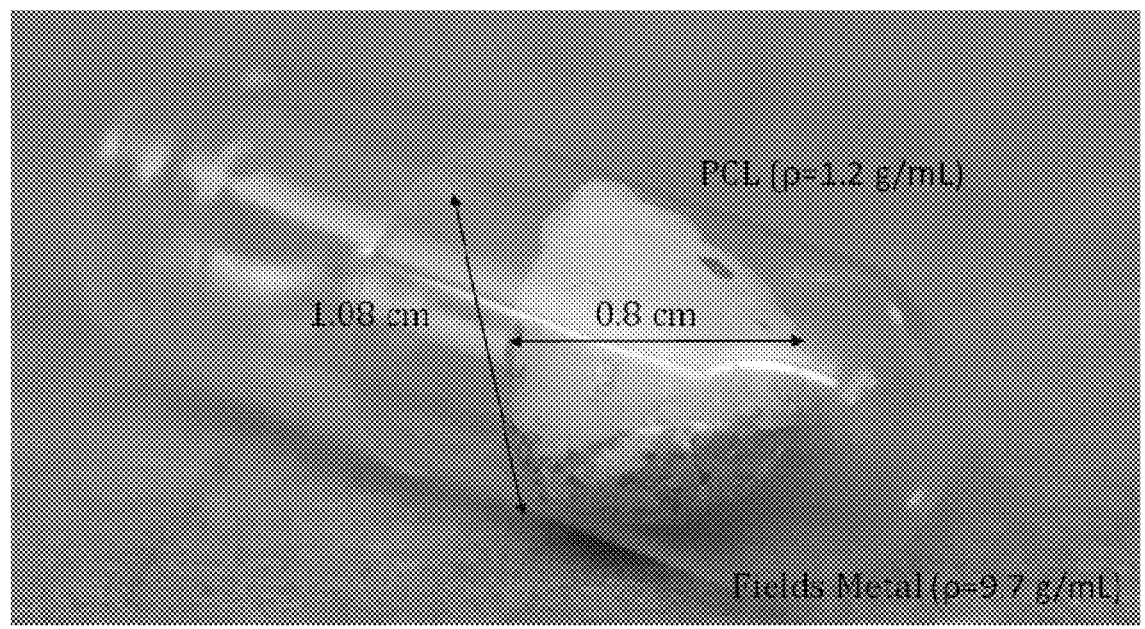
FIG. 13 is a photograph of an exemplary self-righting article inside a 000 capsule, according to one set of embodiments.
Figure 14:
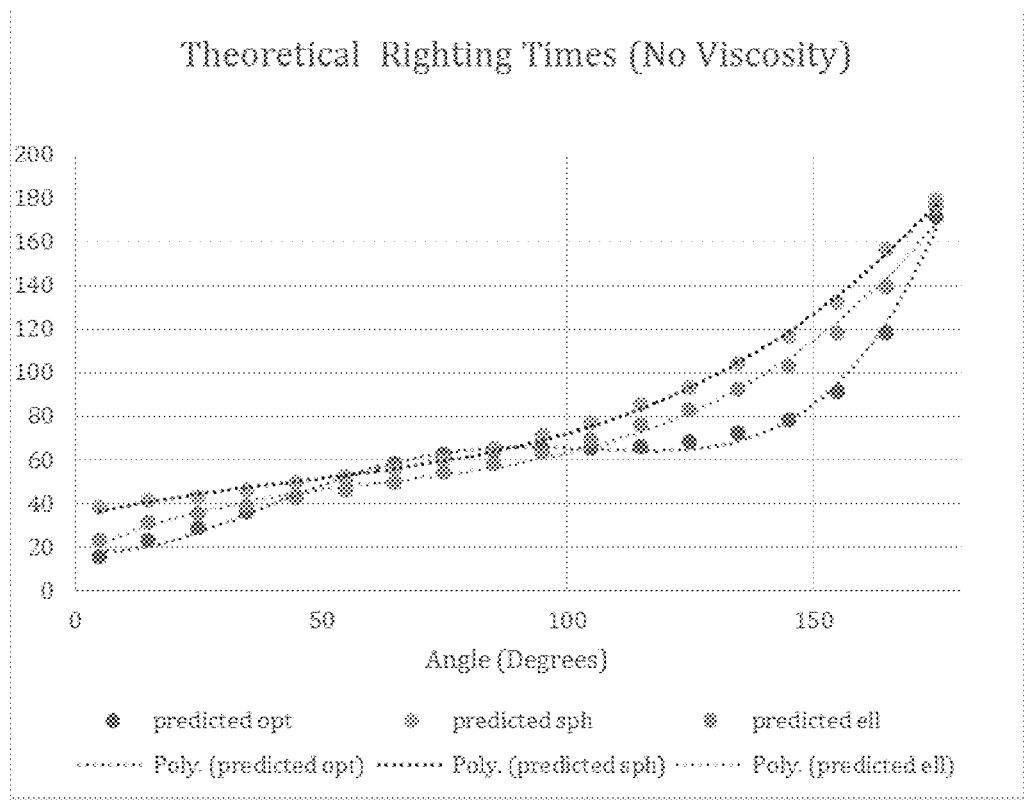
FIG. 14 is a plot of self-righting article speed of righting testing via computer models (predicted), according to one set of embodiments.
Figure 15:
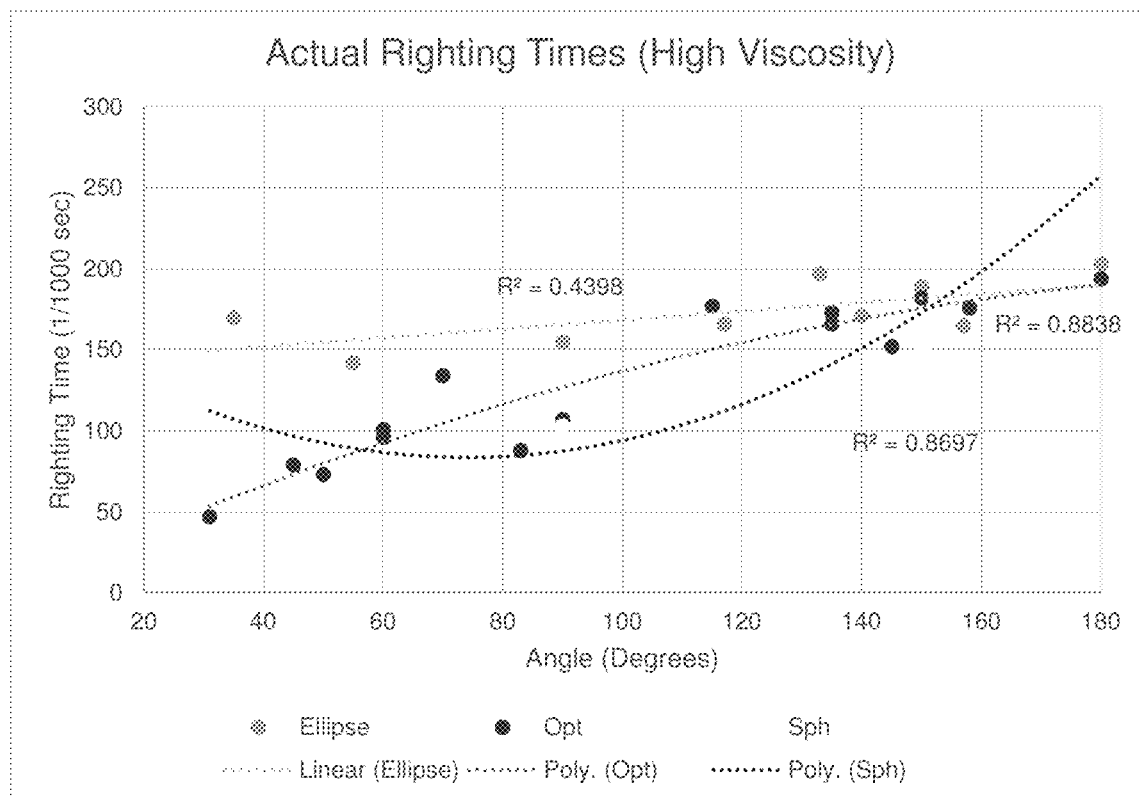
FIG. 15 is a plot of self-righting article speed of righting via high speed camera analysis (poly), according to one set of embodiments.
Figure 16:
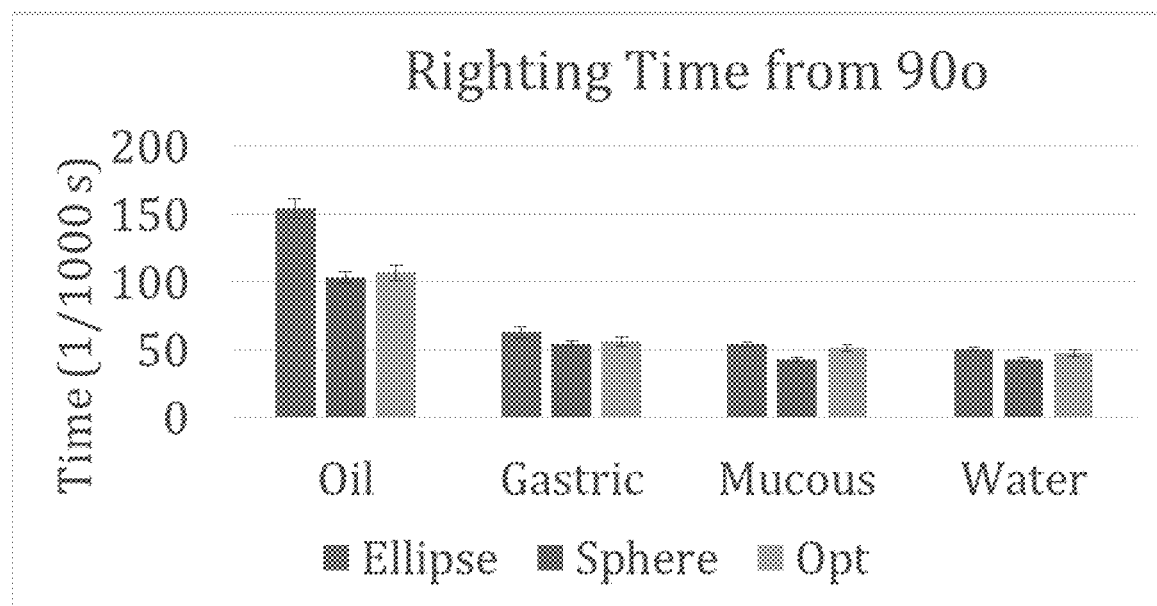
FIG. 16 is a plot of self-righting article speed of righting via high speed camera analysis (poly), according to one set of embodiments.
Figure 17:
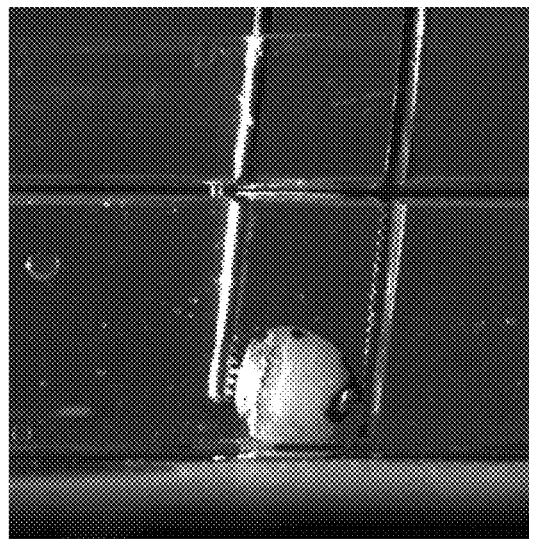
FIG. 17 is a photograph of an exemplary self-righting article, according to one set of embodiments.
Figure 18:
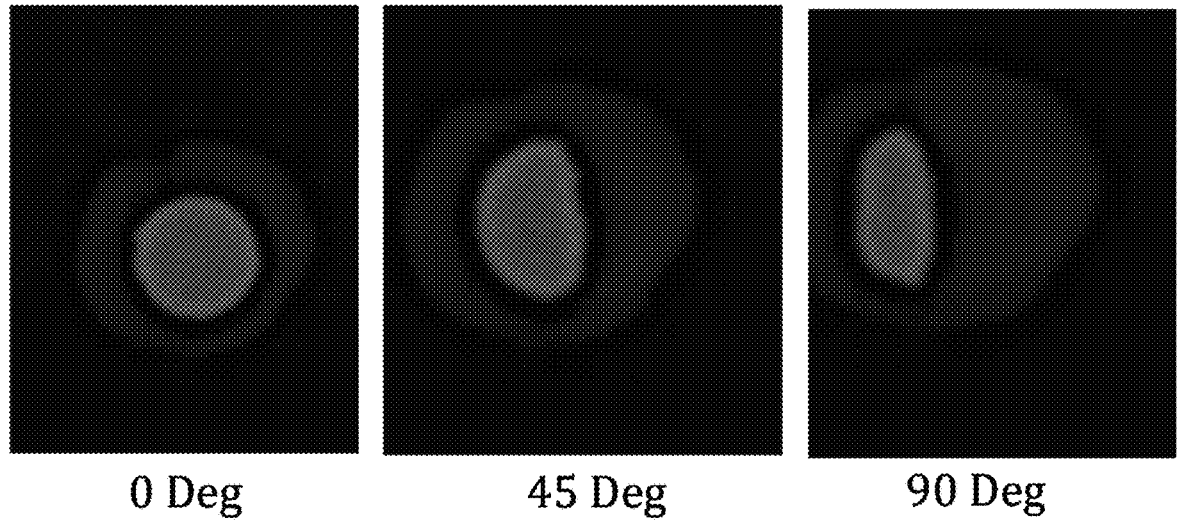
FIG. 18 is a series of x-ray images of an exemplary self-righting article at 0, 45, and 90 degrees of orientation compared to a control (washer), according to one set of embodiments.
Figure 18:
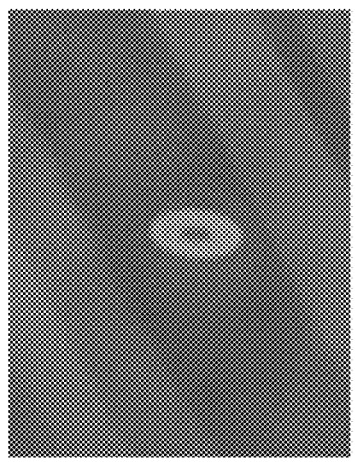
Figure 19:
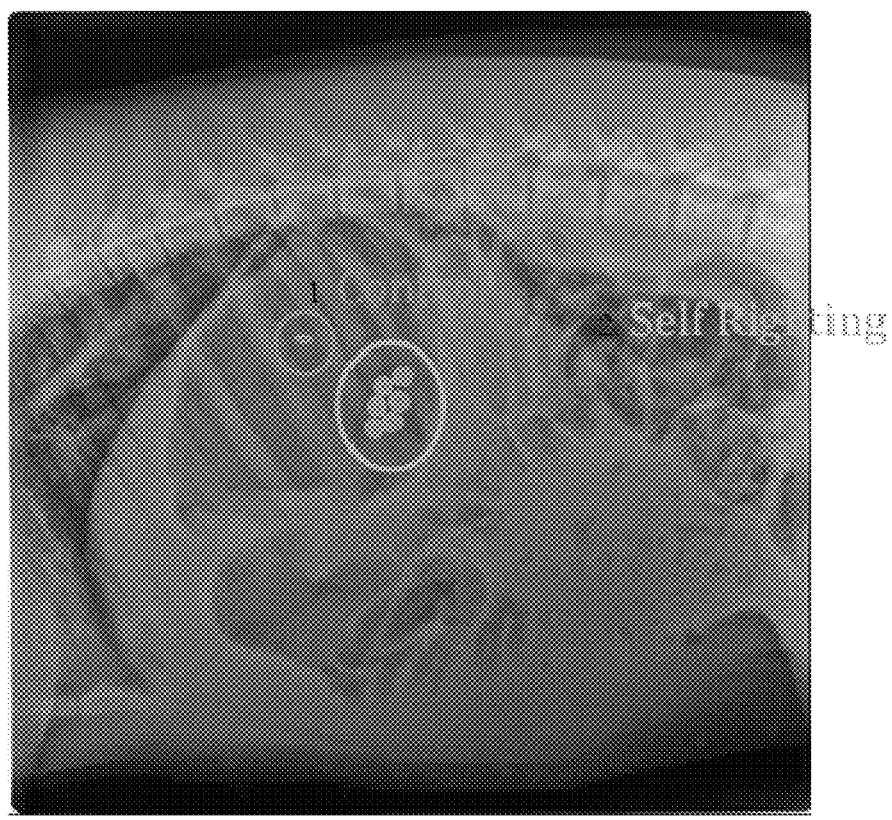
FIG. 19 is an x-ray photograph of an exemplary series of self-righting articles in the GI of a pig, according to one set of embodiments
Figure 20:
FIG. 20 is an endoscopy of an exemplary self-righting article in the GI of a pig, according to one set of embodiments.
Figure 21:
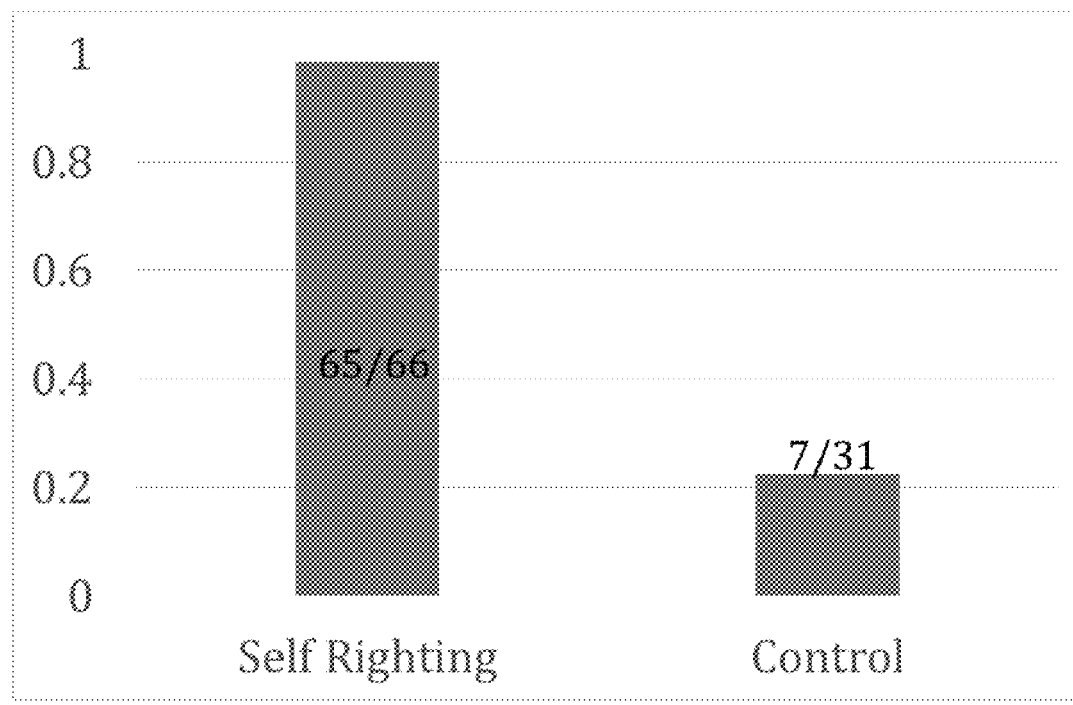
FIG. 21 is a plot of the fraction of articles righted, according to one set of embodiments.

A solid shape that is created by rotating a smooth curve defined by the around the y axis (Example: FIG. 12). The shape is made out of a biocompatible polymer (ex. PCL, PLA, PEG) in all areas with positive y values and a biocompatible ceramic (ex. Hydroxyapatite) or metal (ex. Stainless steel, field's metal) in all areas with negative y values. The ratio of the densities of the two materials should be between 6:1 and 16:1. The article can be scaled to any length, but the points in the FIG. 12 describe an object that can fit within a capsule (FIG. 13) such as a 000 capsule.

This shape has been tested against an ellipsoid and a sphere with the same volumes and similar dimension for its righting ability. The articles were tested under a high speed camera at 1000 FPS in several different liquids, including water, oil and gastric fluid, as well as on different surfaces, including plastic and porcine stomach tissue. The results (FIGS. 14-17) showed that the article had faster righting times overall, as well as faster righting times at angles close to the stable orientation. Since the article is most likely to start close to its stable orientation, this makes the article better than the other shapes.

The articles were also tested for their ability to stay righted by being placed on a tilting mixer. The mixer was set to tilt 15 degrees in each direction at 50 rpm. The article never left its stable orientation, while the sphere tilted 18 degrees from its optimal orientation and the ellipsoid tilted 31 degrees from its optimal orientation (FIGS. 18-21).

The article was also placed into a suspended full pig stomach in vitro using a plastic tube as an artificial esophagus and compared how many times it landed in the correct orientation when compared to a sphere made out of only PCL. Out of 60 trials for each of the articles done in water filled, oil filled or empty stomachs, it was found that the article having a shape as in FIG. 12 landed in the correct orientation every time while the sphere landed in the correct orientation only 25% of the time.

Figure 22:
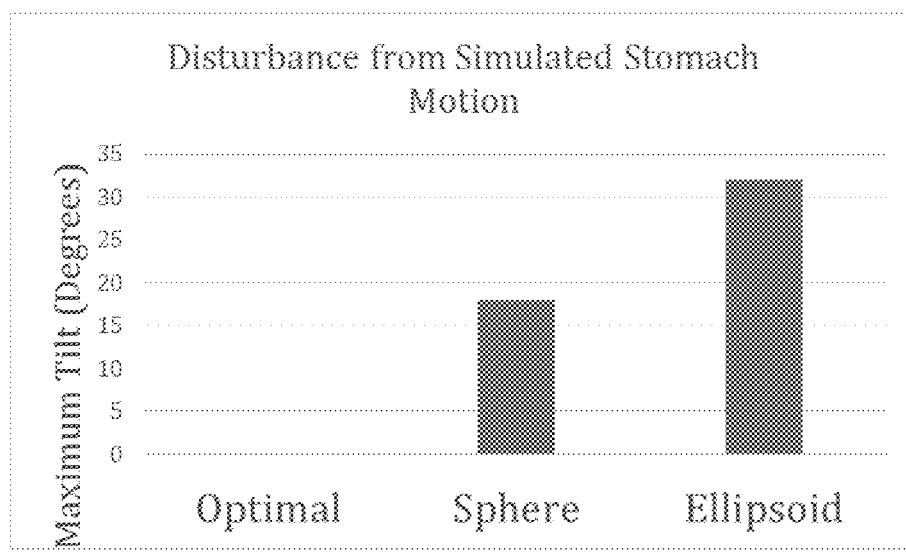
FIG. 22 is a plot of maximum tilt versus shape, according to one set of embodiments.
Figure 23:
FIG. 23 is a photograph of a maximum tilt testing apparatus, according to one set of embodiments.

Additionally, a similar experiment was performed in vivo. 6 self-righting articles and 6 articles that did not self-right but were the same shape were fed to a sedated pig via a gastric tube. The pigs were then shaken vigorously to simulate walking. After shaking the pigs, they were placed under x-ray and counted the number of articles that remained in the correct orientation. These articles were identified by placing a piece of metal inside of them (FIGS. 22-23). The self-righting articles already had a half sphere of metal on their lower half, which displayed as a full circle under x-ray when self-righted and as a waning moon when not self-righted. A circular washer was placed in the control articles and showed as a full circle when self-righted or as a warped oval when not righted. 65/66 self-righting trials showed the correct orientation after shaking, while only 7/31 control articles showed the correct orientation.

Example 3

Figure 24:
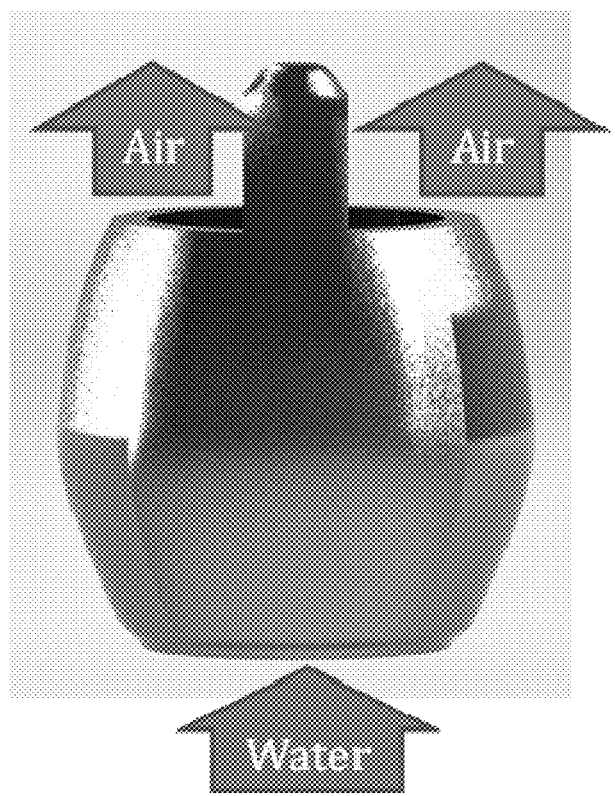
FIG. 24 is a photograph of an exemplary self-righting article comprising air/water vents, according to one set of embodiments.

An object with similar shape to that described in Example 2, but with holes, vents and slits built into the article. Such holes and slits can be used to allow fluid to enter the system or could be used to store articles within the system (FIG. 24). These slits can also be used to hollow out the article to keep the density ratios to reasonable values that can be realized using available materials. For example, by hollowing out the top section of an article, a higher density material can be used to fill in the remaining top areas; higher density materials are allowed, because the only constraints on the article are the outer shape and the center of mass. When making holes, the article should try to remain axisymmetric, or as close to axisymmetric as possible.

Such examples of these holes and slits include but are not limited to the following:

1. A cylinder with a radius less than the radius of the article that is centered at the y axis.
2. A conic section that is centered about the y axis which allows the radius to change as the radius of the system changes.

3. A vertical straight cut with a given width from the top or bottom of the system.

4. Any other sort of cut to the article which maintains the overall integrity of the system.

Example 4

An object with similar shape to that described in Examples 2 and 3, but with a drug delivery article built into the system. This article could be a drug loaded solid or hollow needle. It could be a hollow needle connected to a reservoir, or it could be a series of needles that are loaded or coated with a drug. Other drug delivery articles such as patches are possible as well.

In the example of needles, the needles could either be housed inside or outside of the system. When housed outside the system, they could be connected via an adhesive or embedded within the mold of the article. When housed inside the system, it could be housed within a hollowed out hole in the article.

The needle puncture could be passively actuated from the gravitational force of the article. In this implementation, the weight of the article could push the needles into the tissue.

Example 5

An object with similar shape to that described in Examples 2-4 but with a piece of electronics built into the system.

By adding a piece of electronics to the article in combination with the anchor, the article could be used as a gastro retentive mechanism for electronics. The sensor could have access to the tissue wall or the inside of the GI tract due to the directionality of the article. For example, a pH sensor attached to the bottom of the article would be able to read the pH of the stomach wall area or the inside stomach area depending on its placement on the system.

Example 6

Figure 25:
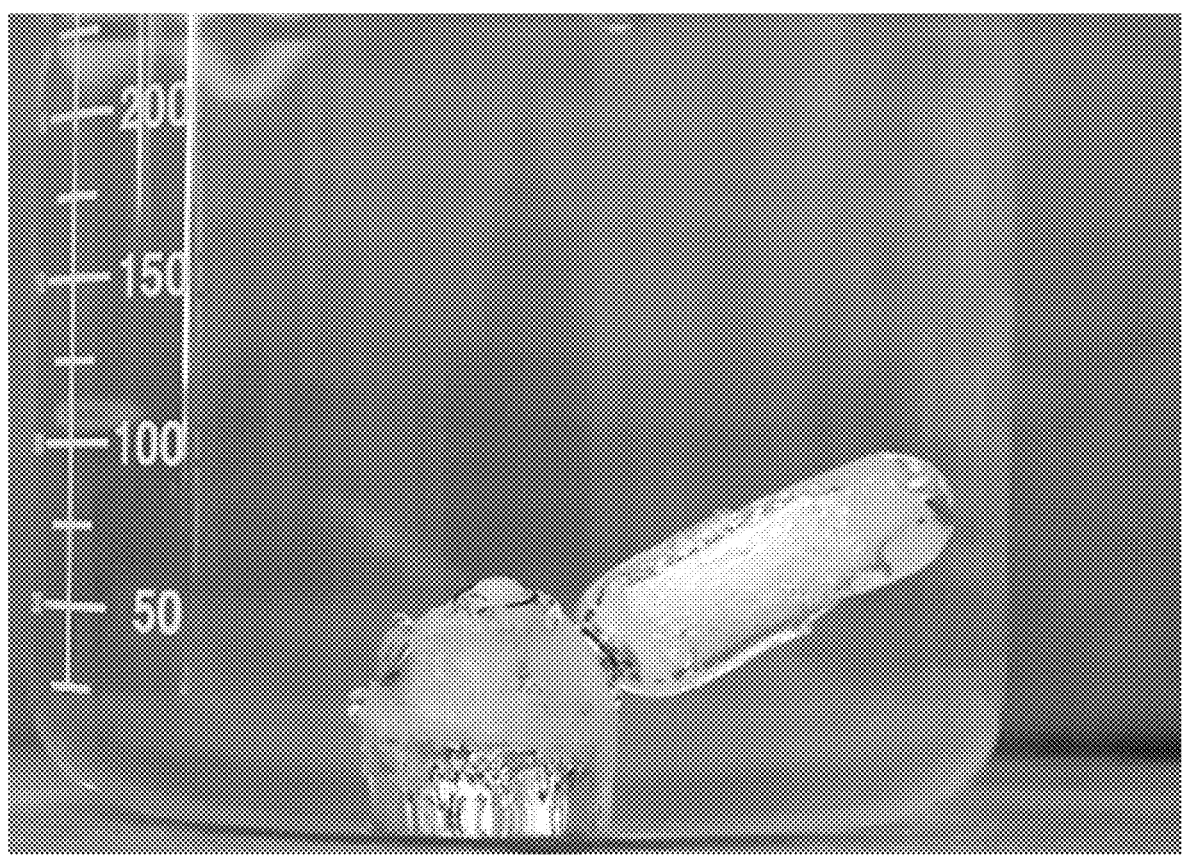
FIG. 25 is a photograph of an exemplary self-righting article comprising a magnetic portion, attached to a magnetic object, according to one set of embodiments.

An object with similar shape to that described in Examples 2-4 but with the ability to attach other articles to the system remotely (FIG. 25).

By adding an attractive and/or adhesive force to the walls of the system, a patient could be able to swallow other capsules filled with new articles or with drugs and have them aggregate together at the system. Such forces could be generated by a magnet, an adhesive, a vacuum or any number of other mechanisms.

For example, a magnet could be attached to the wall of the system as well as the wall of an electronic sensor. The patient could first swallow the self-righting system and have it anchor to the tissue wall as described in example 4. Then the patient could take a separate capsule containing an electronic sensor. The magnetic force generated between the two articles from the placed magnets would allow the two systems to attach. Because the self-righting system is anchored to the tissue wall, the electronic sensor will be able to remain in the stomach as well, even though it does not have any gastro retentive properties. This system could allow for any sort of article to become gastro retentive.

Example 7—Self-Actuating Article

Figure 27:
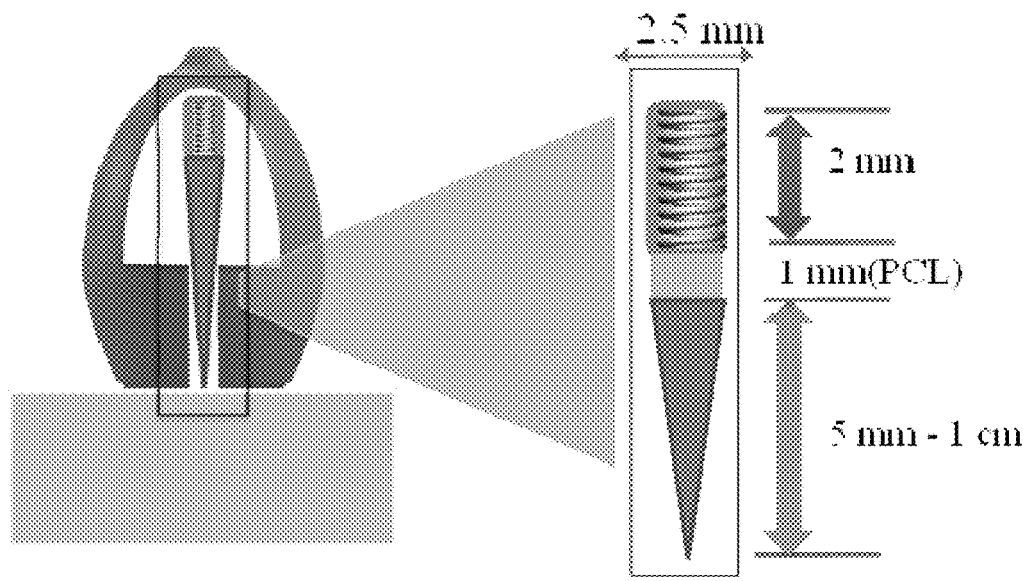
FIG. 27 is a schematic of an exemplary self-actuating article, according to one set of embodiments, a photograph of the article in vivo, and a photograph of the article as compared to an uncompressed spring, according to one set of embodiments.
Figure 27:
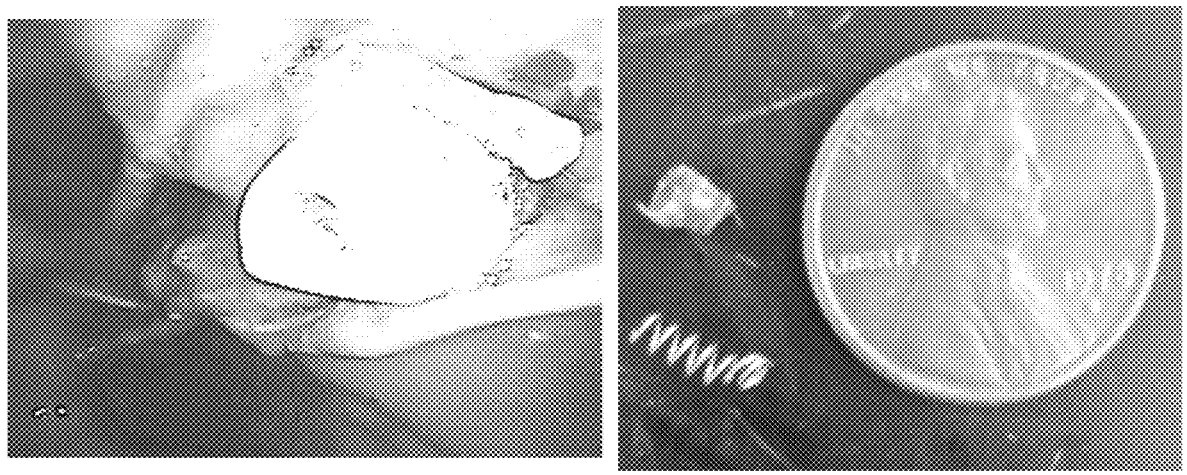

The device could be actuated actively. This could include mechanisms such as shape memory nitinol, expanding elastomers, or compressed springs. The compressed spring could be immobilized in a solid biodegradable and biocompatible polymer or a sugar (ex. Sucrose, maltose), a mechanism which has been shown to work in vivo (FIG. 27). These mechanisms could then be housed within the hollowed out sections of the article or outside the article. Ways of anchoring the device to the system article but are not limited to magnets, tying knots, and applying adhesives.

Figure 28:
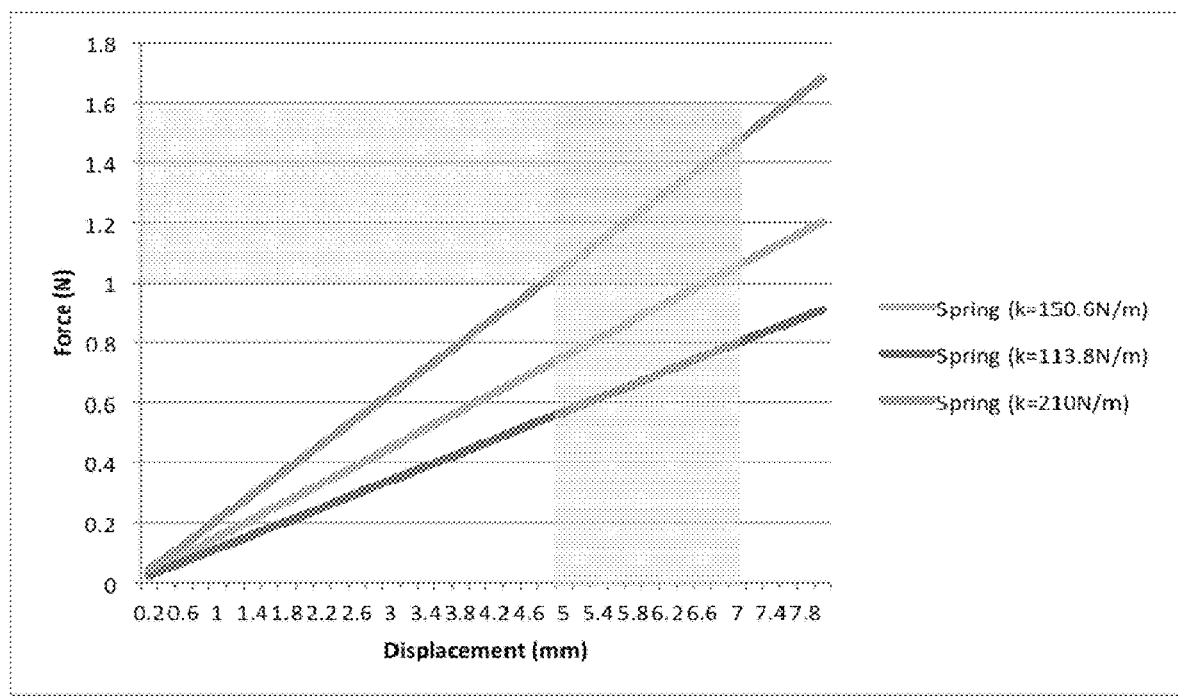
FIG. 28 is a plot of force versus displacement for various spring constants, according to one set of embodiments.

Delving further into the spring example, it may be desirable that the needle enter into the sub-mucosal layer of the GI tract in order to deliver drug, e.g., the needle should penetrate at least 1 mm into the tissue. If the needle penetrates more than 5 mm into the tissue, then the patient will risk perforation. For this reason, the spring may be compressed between 1-5 mm. Also, while the amount of force required to penetrate the GI tissue is generally low, on the order of 1-10 mN, it may take about 100 mN of force to enter into the muscular layer of the stomach in between the mucosal and sub-mucosal layer. In some cases, the spring will contain enough force when compressed that it will push on the tissue with a force of 100 mN plus a safety factor of 3×-10×. This means that the spring could, in some cases, have a spring constant of around 100-250 N/m (FIG. 28).

Additionally, the compressed spring may be encased in a material that can hold such a force. The material may also be brittle, such that e.g., the spring to break out of the material all at once. A brittle material such as (crystallized) sugar will generally crack quickly and completely once it experiences a given stress. Caramelized sucrose generally fractures under 0.1 Mpa of stress. If the compressed spring exerts 1 N of force on the sucrose coating it, then the sucrose coating may be at least 3.56 mm in diameter to contain the spring. Any more caramelized sucrose added to the coating acts could be used as a timing mechanism for the device (e.g., without wishing to be bound by theory—the thickness of the coating may be at least proportional to the time required to degrade the coating).

Figure 29:
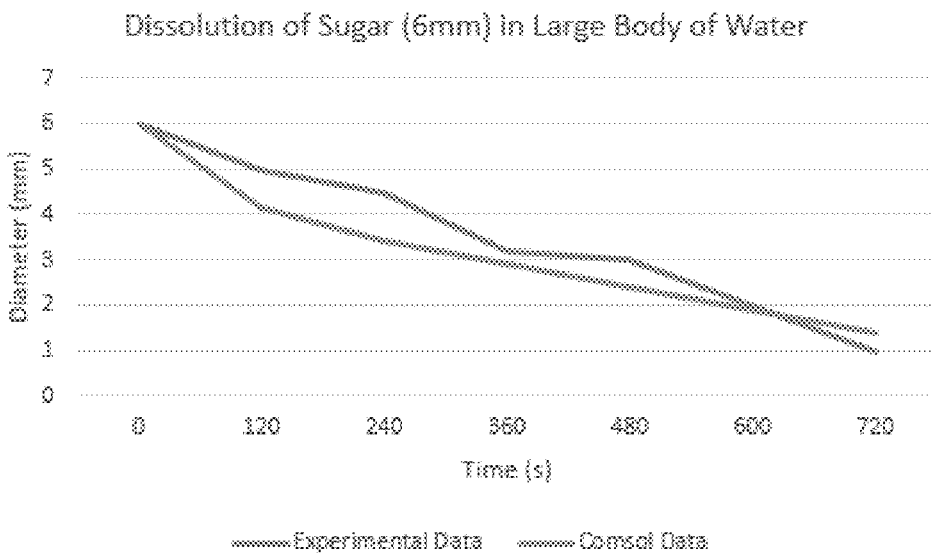
FIG. 29 is a plot of diameter versus time for sugar dissolution, according to one set of embodiments.
Figure 30:
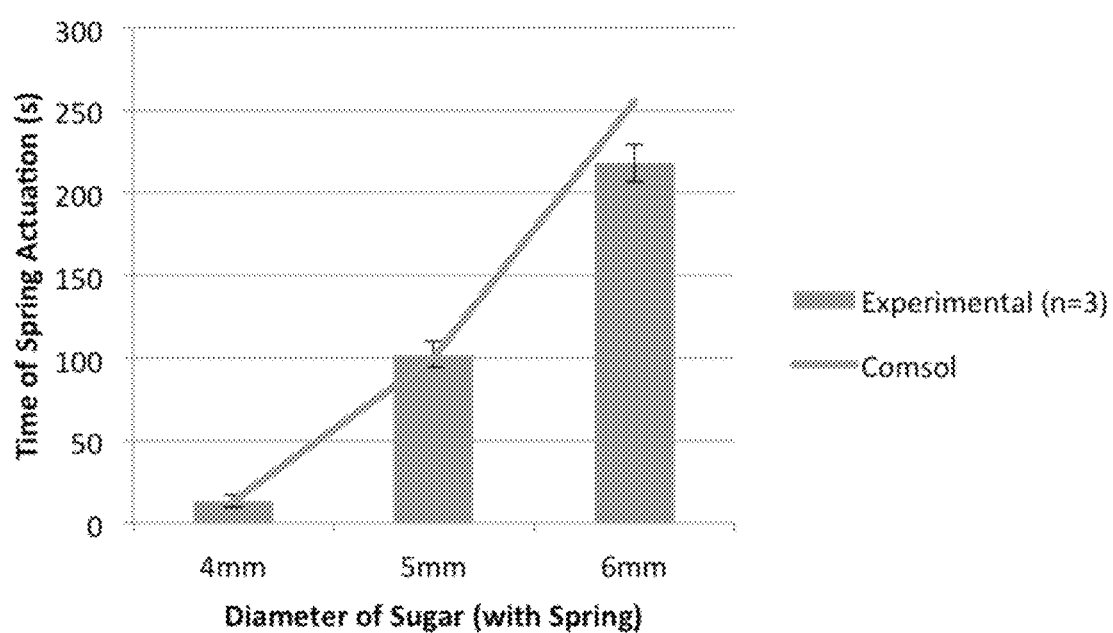
FIG. 30 is a plot of spring actuation time versus diameter, according to one set of embodiments.

Using modeling software that runs a diffusion mass transfer problem with an interface balance, it was determined that the actuation could be delayed between 1-4 minutes once the sucrose coated spring was dissolved in water by coating the spring with between 4-6 mm of sucrose. This was confirmed by experiment (FIGS. 29-30). A delay of at least 20 seconds was shown to be sufficient such that the actuation occurs in the stomach instead of in the mouth or esophagus.

In order to make sure that liquid reaches the sucrose to start this dissolution process, vents may be added to the top and bottom of the device to allow for fluid flow. These vents allow e.g., a way for the air trapped inside to escape. They may also be hydroscopic to allow for water to easily pass though.

Figure 31:
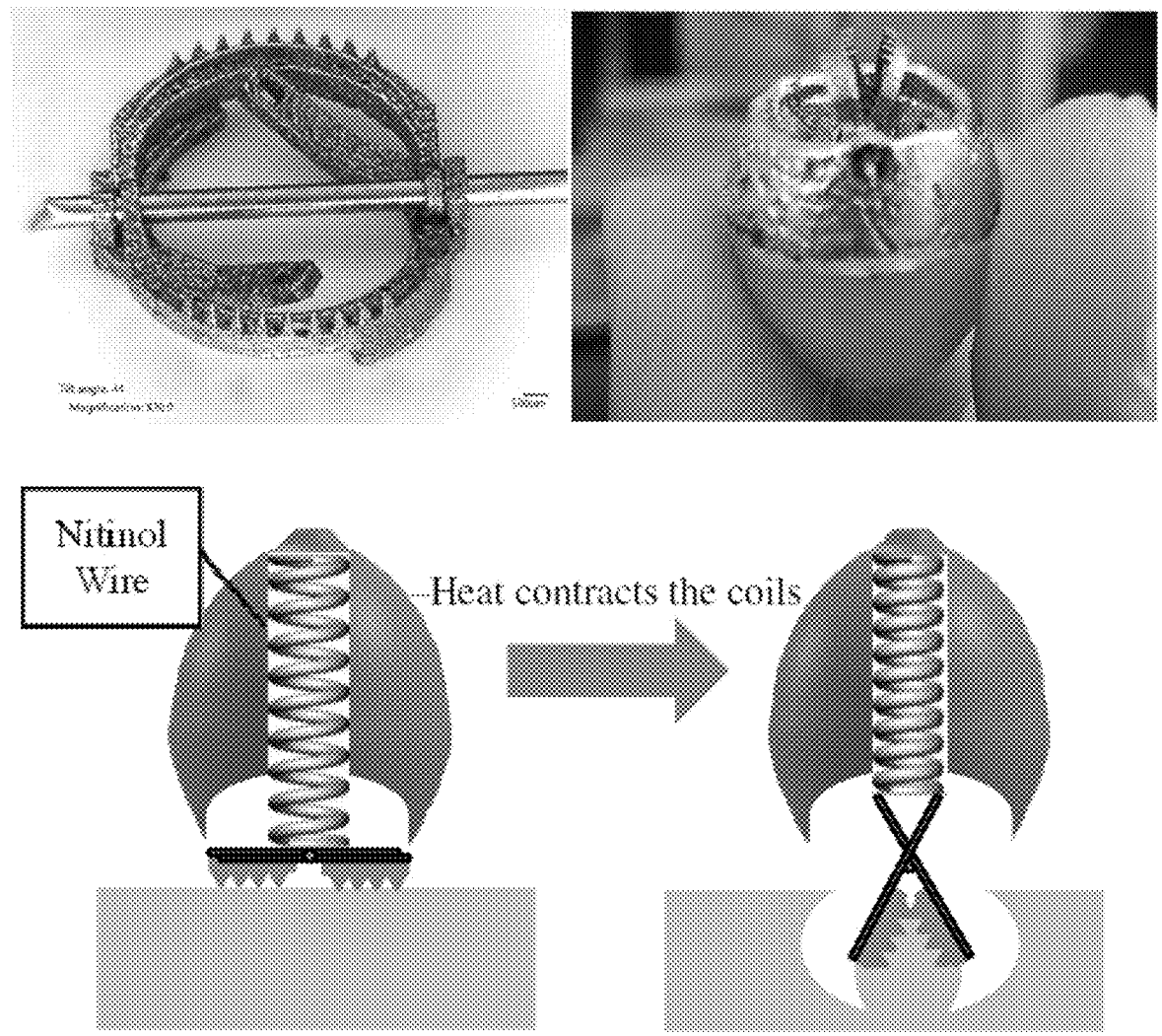
FIG. 31 is a photograph and diagram of an exemplary tissue interfacing component (e.g., biopsy punch) associated with a spring, according to one set of embodiments.

In some cases, an anchoring device will allow the system to attach itself via physical or chemical means to the tissue wall of the GI tract. Such a device could include a barbed or hooked needle, a mucoadhesive patch, a trapping and closing mechanism (FIG. 31), vacuum suction, or any number of other mechanisms. The anchoring device could be located on the bottom of the device to ensure that it is facing the tissue wall.

Figure 32:
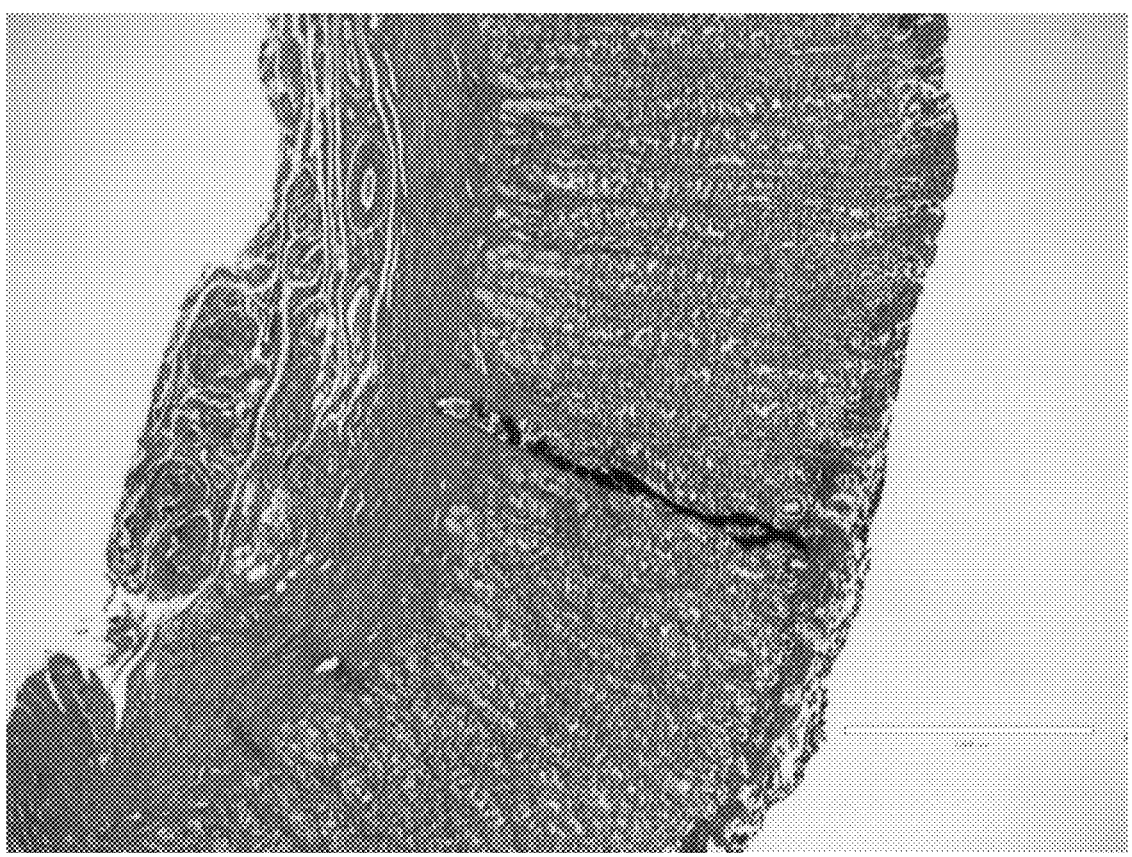
FIG. 32 is a histology of a needle inserted into tissue in vitro from a spring associated article, reaching the muscle layer of the stomach tissue, according to one set of embodiments.

If the anchoring device uses hooks, such as the hooked needle, then it could reach the muscular layer of the tissue in between the mucosal and submucosal layers. FIG. 32 shows a histology slide of a piece of stomach tissue penetrated by the device penetrating to the muscular layer of interest. This penetrate was created by using a sugar coated spring like the ones described above that was compressed 6 mm and had a spring constant of 210 N/m.

Figure 37:
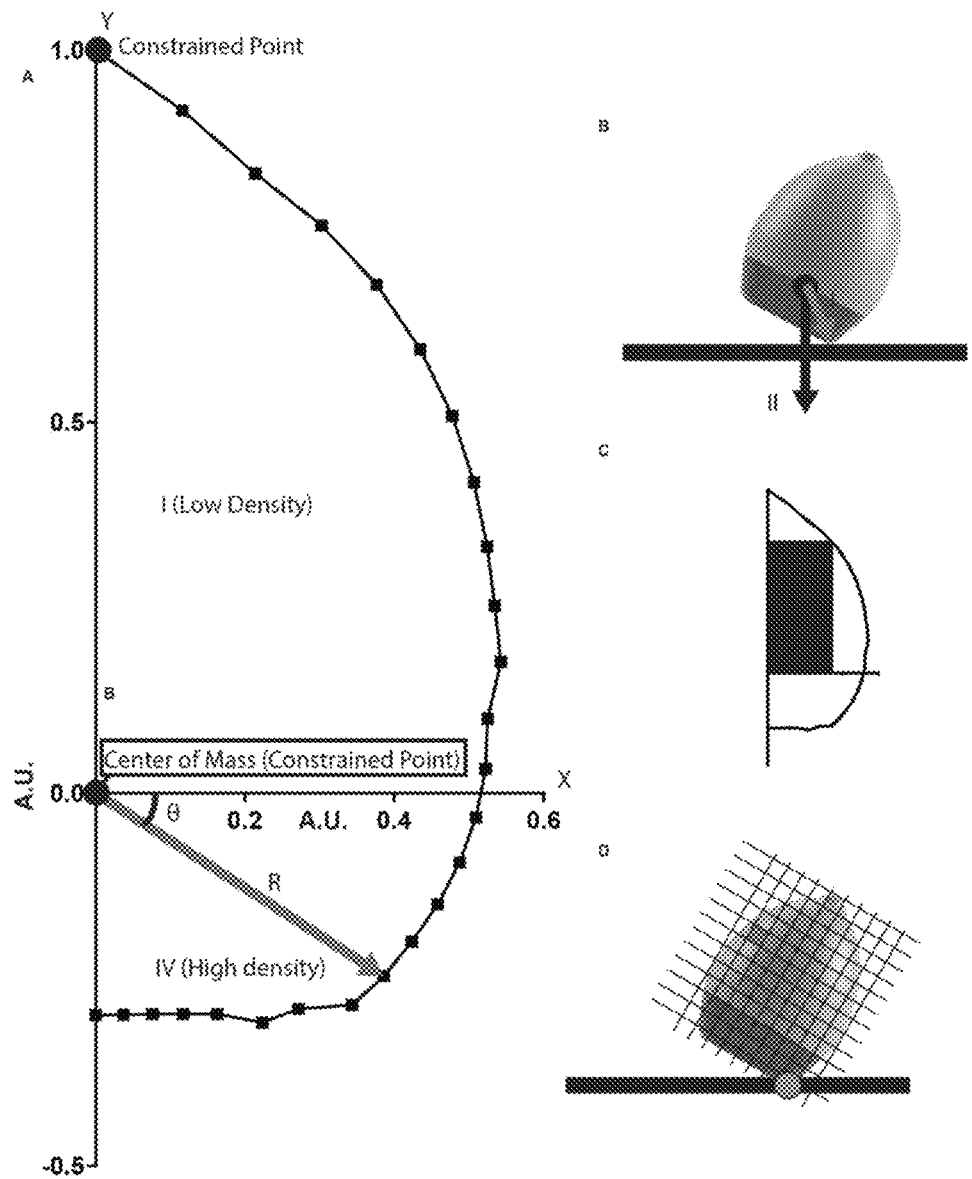
FIG. 37 shows computational results from self-orientating shape optimization for an exemplary system, according to one set of embodiments.

Computational Optimization:

The optimized shape was created by performing a two dimensional curve optimization over a 180 degree plane in quadrants I and IV and revolving the curve about the Y axis. FIG. 37 illustrates the optimized curve as well as the vectors and methods described in this section. The optimization function varied the radius of 25 different points spaced apart at equal angles along a curve drawn in polar coordinates. When reconverted into Cartesian coordinates, the space inside the revolved curve and below the X-Z plane was set to contain high density material (7.7 g/cm$^3$) while space above the X-Z plane and inside the revolved curve was set to contain low density material (1.1 g/cm$^3$). To simulate a hollow top section, a 4 mm in radius cylinder centered about the Y axis, beginning at the X-Z plane and ending at the curve boundary was removed from the top portion of the shape. The mass of the spring and the micropost were incorporated into the model. In order to define a scale for the shape the center of mass was constrained to the origin and the highest possible point to the coordinate [0,1]. The final shape was scaled to fit the size constraints. These constraints matched the requirements of an axisymmetric mono-monostatic shape, so no possible solutions were lost.

The optimization itself utilized Newton's kinematic equations to find a given shape's self-orientation time, t:

$$\Delta\theta = \omega t + \tfrac{1}{2}\alpha t^2 \quad \text{Equation (1)}$$

$$\alpha = \tau/I \quad \text{Equation (2)}$$

$$\omega = \omega_0 + \alpha t \quad \text{Equation (3)}$$

$$I = \int r^2 dM \quad \text{Equation (4)}$$

$$\tau = d \ast F \ast \sin(\theta) \quad \text{Equation (5)}$$

where angular acceleration $\alpha$, and angular velocity $\omega$, are determined based on the device's moment of inertia I, and torque $\tau$. The gravitational force F, acted as the external force in the model and was used to calculate the simulated torque applied to the lever arm d, defined as the distance between the device's center of mass and point of contact with the tissue wall.

The angular acceleration of the device at a given orientation, defined by equation 2, determines the orientation speed and varies with torque and moment of inertia. The moment of inertia was calculated along with the total weight of the device by breaking the 3D space up into a 50×50×50 array of equally sized blocks, assigning a density to each block, and performing a summation described in equation 4.

Calculating the torque on the device, required determining both the direction and magnitude of the force and distance vectors as per equation 5. The force vector was the gravitational force on the object starting from the center of mass and pointing in a direction perpendicular to the surface of contact. The distance vector was calculated as the distance between the center of mass and the pivot point of the device on the surface of contact. When determining the pivot point, the greater curvature of the device was taken into account, as areas with concave curvature do not touch the surface.

Sucrose Encapsulation Dissolution Modeling

The radius at which the sucrose encapsulation would propagate a crack was calculated using Griffith's criterion:

$$\sigma_c^2 = \frac{2\gamma E}{\pi a},$$

where $\sigma_c$ is the critical stress applied by the spring, $\gamma$ is the surface energy of the material, E is the Young's modulus of the material, and a is the surface area perpendicular to the applied stress. Because all variables in the equation remain constant aside from the surface area, the dissolution rate defines the time until the cracking event and spring release. The COMSOL models and experimental testing are based on a spring that provides 1N of force. The physical spring was created by cutting a purchased spring into the appropriate size.

COMSOL Multiphysics (Stockholm, Sweden) was used to mathematically model the dissolution of a sucrose cylinder in both still water and water that flowed at 0.02 m/s, similar to that of the human stomach (37). Fick's law was used to estimate the rate of the diffusion process at the shrinking boundary between the sucrose and the water. Diffusion coefficient of $5.2 \ast 10^{-10}$ m$^2$/s, an equilibrium concentration for sucrose in water of 6720 mol/m$^3$, and mass transfer coefficient of $7.8 \ast 10^4$ m/s (found experimentally) were used as parameters. The COMSOL model was run at starting sucrose cylinder diameters of 6 mm, 5 mm, and 4 mm, and the time it took for the cylinder to dissolve to a diameter of 1.7 mm was used to predict the actuation timing if a spring had been present in the cylinder.

To calculate the mass transfer coefficient of sucrose in water, sucrose was caramelized at 215° C. for 15 minutes in a PDMS mold with a 6 mm in diameter hole to create a cylindrical shape. The caramelized sucrose cylinder was placed in a 500 mL beaker of water at room temperature, and the diameter of the sucrose was measured every minute. The rate of dissolution was modeled and the slope of the linear fit was determined to be the mass transfer coefficient.

In order to test the dissolution of the sucrose coating on springs, sucrose encapsulated springs were placed in 500 mL beaker of water at room temperature, and the timing of the spring actuation was recorded for 4 mm, 5 mm, and 6 mm diameter sucrose spring, with three trials each.

Example 17—Distance Between Tip and Tissue

The following example demonstrates the relationship between velocity and gap size (i.e. the distance between the tip of the tissue interfacing component and the tissue engaging surface), as described herein.

Figure 36:
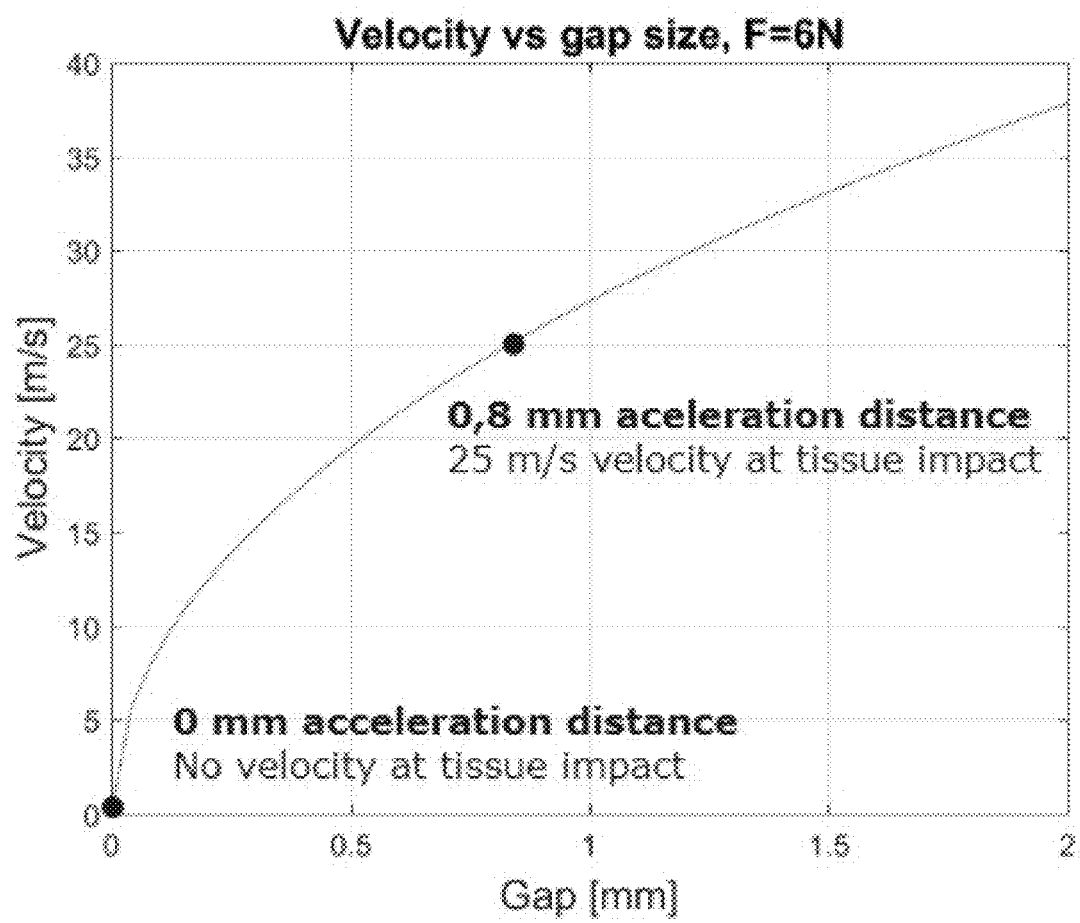
FIG. 36 is a plot of velocity versus distance between the tissue interfacing component and the tissue engaging surface (e.g., gap size), according to one set of embodiments.

Table 3 shows the relationship between starting distance from and the velocity of the tip in m/s, for various springs with different spring constants (e.g., 500 N/m, 1000 N/m, and 1500 N/m). FIG. 36 shows a plot of velocity versus gap (in mm) for a particular force (6 N).

TABLE 3

| | Velocity of TIC at impact with tissue (m/s) | | |
|---|---|---|---|
| Starting Distance from tissue engaging surface (m) | 500 N/m Spring Constant | 1000 N/m Spring Constant | 1500 N/m Spring Constant |
| 0 | 0 | 0 | 0 |
| 0.0001 | 0.707106781 | 1 | 1.224744871 |
| 0.0002 | 1.414213562 | 2 | 2.449489743 |
| 0.0003 | 2.121320344 | 3 | 3.674234614 |
| 0.001 | 7.071067812 | 10 | 12.24744871 |
| 0.0015 | 10.60660172 | 15 | 18.37117307 |
| 0.002 | 14.14213562 | 20 | 24.49489743 |
| 0.01 | 70.71067812 | 100 | 122.4744871 |
| | mass of TIC (kg) | 0.00001 | |

Example 18—Assembly Process

FIGS. 34A-34E show an exemplary process for assembling a self-righting system, as described herein.

Example 20—Delivery of a Molecule to the GI Tract Via Liquid Injection

This example demonstrates the use of a liquid injecting self-orienting millimeter-scale actuator (L-SOMA) for delivery of a liquid (e.g., comprising a therapeutic agent).

In this example, the L-SOMA generally comprises a chamber for holding the liquid formulation prior to release in the gastrointestinal tract (e.g., in the stomach such as at the stomach wall); a tissue-interfacing component (e.g., needle) based delivery mechanism of the liquid; and a system (e.g., comprising isomalt) for actuation of needle insertion and pressure mechanism.

FIGS. 39A-39D illustrate various exemplary L-SOMA components and the four states of compression while performing an injection.

Prior to injection, the liquid drug formulation is kept and protected inside the system by the means of a chamber with a volume of approximately 80 µL. This chamber comprises 3 members that together makes a fully sealed inner volume; 1) L-SOMA bottom portion, 2) An outer septum (e.g., plug) made from silicone or TPE, 3). A 2K molded plunger made from a hard polymer and a soft TPE acting as an inner septum. In some embodiments, the plunger is made entirely from chlorobutyl rubber, bromobutyl rubber or any similar rubber and/or isoprene or similar polymer. In some embodiments, an SK molded plunger is used made from a hard polymer and a chlorobutyl rubber, bromobutyl rubber or any similar rubber and/or isoprene or similar polymer.

These septums are generally capable of sealing around the injection needle as well as preventing food or liquid from passing through from the outside environment. Therefore, for example, the enzymes in the stomach would not be able to reach the drug formulation through the septum, and the formulation would not leak out of the septum.

Needle Based Delivery Mechanism

In order to deliver the liquid formulation into the tissue, a needle may be used to aid in delivery. The needle is inserted directly through the inner septum, creating a tight-fitting seal. The needle may be hollow (e.g., comprising a channel); however, the liquid formulation is not necessarily passed through the top of the needle. Instead, a hole (e.g., inlet) may be present in the side of the needle. Liquid may be configured to pass through this hole and out of the beveled end. For example, a liquid chamber (e.g., reservoir) may be placed in fluidic communication with the hole upon activation of the spring, thus facilitating the transfer of fluid from the liquid chamber into the needle.

The hole is at a height on the needle such that the hole is outside the liquid chamber prior to activation. When the device is actuated, in this example, the needle is moved e.g., 5 mm down. This movement inserts the needle approx. 4.6 mm in this example into the stomach tissue as well as moving the side hole into the liquid chamber enabling a flow path from the chamber to the tissue. The height of the needle can be adjusted, and so can the penetration stroke of the needle. Both values can be adjusted by up to 2 mm or more. The top end of the needle may be closed off and used as a connection point to an actuating spring via a needle hub. Therefore, the only way for fluid to move through the needle is from the hole in the side to the hole in the tip.

Dual Sequential Actuation Mechanism

The L-SOMA autonomously orients in the stomach after ingestion in order to align its injection mechanism with the tissue (FIGS. 40A-40E). The shape and density distribution of the device draws inspiration from the leopard tortoise, an animal with the ability to self-orient from any configuration. The device's high curvature upper portion coupled with its low center of mass ensures that it only possesses one stable orientation, defined as an angle in which the device's center of mass is at a local minimum. Additionally, the flat bottom of the L-SOMA stabilizes its preferred configuration and ensures that it does not tip over and misfire into the lumen if a patient moves about during actuation. The robust self-righting nature of the shape is described in the Examples above (e.g., when validating its ability to deliver solid dosage forms). After configuring the device to allow for liquid dosing, the L-SOMA was re-tested for self-orientation 100 times on a silicone mold of simulated stomach tissue. The L-SOMA device oriented to its preferred configuration during every experiment in under 1 second.

As soon as the L-SOMA is ingested, a hydration based actuator plug (e.g., made from isomalt) begins to dissolve. The plug holds a hub connected to the injection needle in place. Once dissolved, the plug releases the hub and a compressed spring expands to deliver the needle into the tissue. After a set distance, the hub is stopped by a tab on the housing of the device. This ensures that the needle inserts a set distance into the tissue. From experiments, it was determined that the device actuated in 4+−1 minutes after exposure to water in vitro. In vivo, the device actuated in 4+−2 minutes.

Figures 41A, 41N:
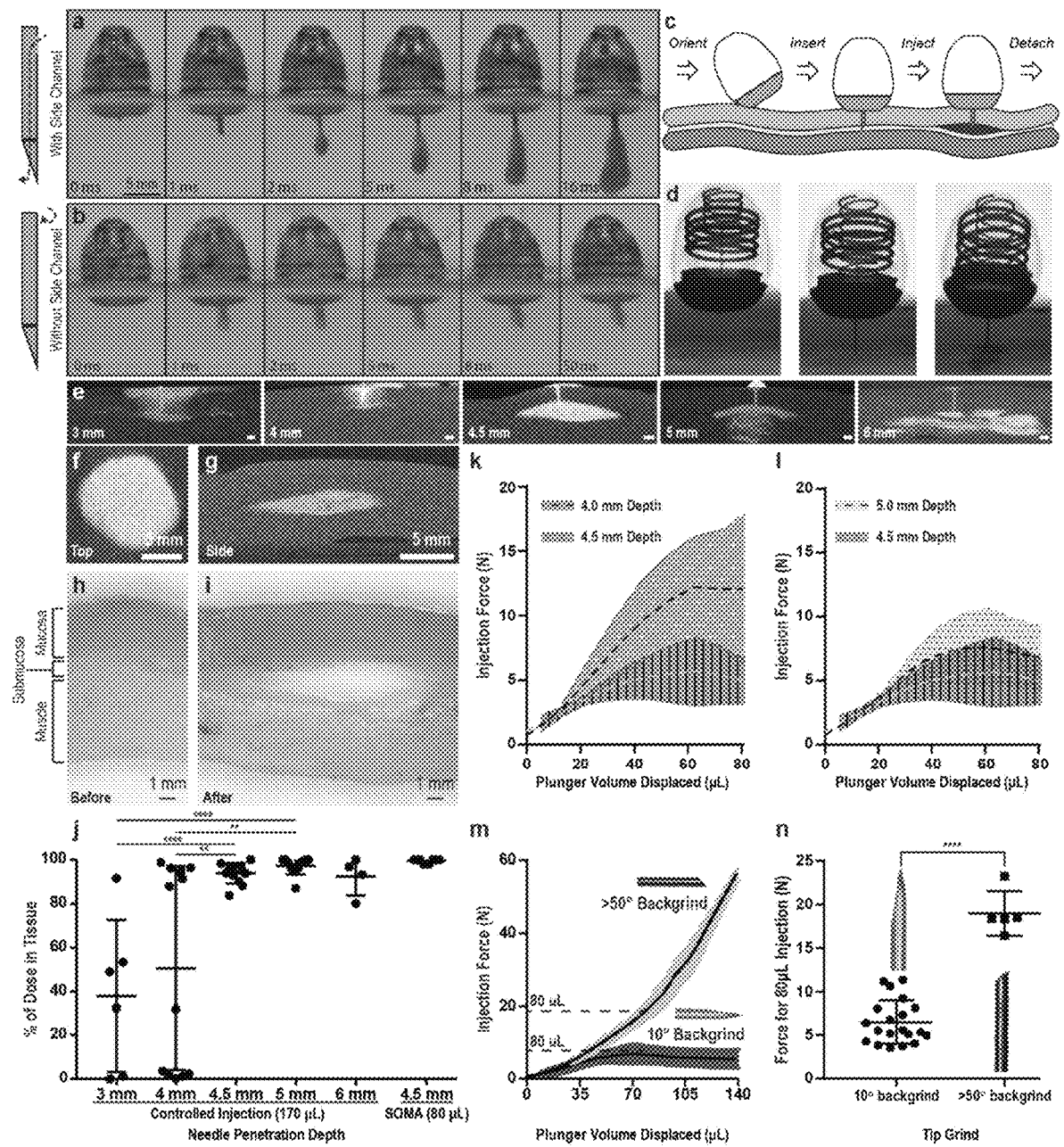
FIGS. 41A-41N show, according to one set of embodiments, (A) High speed photography at 5000 fps showing an L-SOMA with and (B) without a side hole injecting dye into 0.3% agarose gel. The side hole allows liquid to travel through the needle and out into the targeted area. (C) exemplary L-SOMA timeline in the stomach. (D) Micro-CT images of an L-SOMA actuating into Ex vivo swine stomach tissue and injecting contrast dye. (E) Controlled injections of 170 µL of contrast dye at different insertion depths into ex vivo swine stomach tissue. The average thicknesses of the tissue samples were 7.0+−1.3 mm. Insertion either 3 mm or 4 mm into the tissue allowed the needle tip to reach the stomach mucosa layer. An injection depth of 4.5 mm allowed the needle tip to reach the stomach submucosa. Insertion further into the tissue targeted either the stomach submucosa or the muscularis. (F) Top and (G) side view of an 80 µL depot of contrast dye injected by an L-SOMA capsule with a needle insertion length of 4.5 mm. (H) A microtome image of fixed swine stomach tissue before and (I) after an injection with the L-SOMA demonstrating that the depot is injected into the submucosa. (J) A plot representing the percent of contrast dye which remained in the tissue after injection. The value was calculated using the 3D reconstructions of the Micro-CT images. (K and L) The force required to inject a depot into ex vivo swine stomach tissue at a given needle insertion depth. (Error=SD; 4 mm n=11; 4.5 mm n=9; 5 mm n=18). (M and N) The force required to displace a given plunger volume while trying to inject contrast dye into ex vivo swine stomach tissue using a needle with a 10° backgrind and a backgrind of >50°. In the experiments with >50° backgrind needles, no dye entered the tissue as measured through MicroCT imaging analysis; instead the volume displacement was caused by compression of the plunger parts. (Error=SD; 10° n=20; >50° n=5). ($P<0.01$; **$P<0.0001$)

Once the device inserts the needle, the needle hub immediately actuates a second compressed spring which delivers the loaded liquid formulation. By decoupling the needle insertion from the liquid injection, the device is able to inject its entire liquid dose at an exact tissue depth instead of injecting the dose as the needle moves through the tissue. High speed photography of an initial prototype L-SOMA device with a 21 G needle actuating into 0.3% agarose gel demonstrated that all of the liquid exits through the needle tip and none of the liquid exits through the bottom membrane (FIG. 41A, FIG. 41B). This ensures that the liquid dose enters the tissue and is not expelled on top of the tissue. These experiments were repeated in ex vivo swine stomach tissue and demonstrated that the L-SOMA was able to insert a 30 G needle into the tissue and then subsequently inject contrast dye into the tissue (FIG. 41D). 29 G and 32 G needles were also successfully demonstrated.

Depth of Needle Penetration to Submucosa and Creating a Depot

In order to determine how the penetration depth of the needle affected the delivery of the liquid dose, we performed controlled injections of contrast dye to varying known depths of ex vivo swine stomach tissue and took MicroCT images of the depots created (FIG. 41E). The layers of tissue targeted by specific injection depths were confirmed by taking microtome slices of the tissue and looking for areas disturbed by dye injection (FIG. 41H and FIG. 41I). The percent of liquid that remained in the tissue after dosing was also measured using a volume calculator on the MicroCT software (FIG. 41J). The ex vivo swine stomachs measured 6.99+−1.28 mm thick at the spots of injection, and we dosed to depths of 3, 4, 4.5, 5, and 6 mm. In total during these controlled injection experiments, we delivered a total volume of 170 µL of contrast dye. This compare to a maximum dose volume of 80 µL for the L-SOMA device. It was found that for the 3 mm and 4 mm injection depths, the needles sometimes did not reach the stomach submucosa. When injected only into the mucosa, the dose of contrast dye leaked out and only a fraction of the liquid remained inside of the tissue. It was found that insertion depths of 4.5 mm or greater consistently delivered the full liquid dose to the submucosa layer and experienced no leakage. Insertion depths of 5 mm and 6 mm saw occasional injections into the muscularis layer of the stomach tissue. During injections to this tissue layer, the contrast dye generated a marbling pattern.

During these injection experiments, we measured the forces required to deliver a given dose of liquid into the tissue (FIG. 41K, FIG. 41L). It was found that delivering an 80 µL liquid dose through a needle inserted 4 mm into the tissue required 12.1±6.0 N for force, statistically significantly more force than the 5.7±2.7 N of force required to dose the same amount of liquid through a needle inserted 4.5 mm into the tissue (P=0.009). While it was found that 7.6±3.1 N force was required to inject an 80 µL liquid dose through a needle inserted 5 mm into the tissue, this was not statistically significantly more than the injection force found for a 4.5 mm needle insertion depth (P=0.12). Additionally, the 8.0±4.1 N force required when dosing into the muscularis layer of tissue at a needle insertion depth of 5 mm (n=6) was not statistically significantly different from the injection forces required for liquid dosing at this depth overall (P=0.8). This suggests that penetration into the muscular layer would not generally affect the force required to inject a liquid dose and therefore would not generally limit the delivered dose volume.

Taking into account the experimental data related to liquid dosing, it was decided to design a SOMA device which inserted its needle 4.5 mm into the tissue. This insertion depth provided a statistically significantly greater dose retention compared to 3 mm and 4 mm insertion depths. Also, by choosing a lower insertion depth than 5 mm and 6 mm, tissue disturbance was reduced and this mitigated the potential for other complications. 6 L-SOMA devices were actuated with this needle insertion depth and dosed a total of 80 µL of contrast dye per L-SOMA. During these experiments, it was observed that a depot was created in the submucosa (FIGS. 41F-41I). Additionally, during these L-SOMA injections, the entire dose was delivered into the tissue every time (FIG. 41J). Further tests in an in vivo swine stomach demonstrated that the SOMA injected dye directly into the stomach submucosa. Animals were terminated immediately after dosing these dye loaded devices and histology was obtained.

Figure 42:
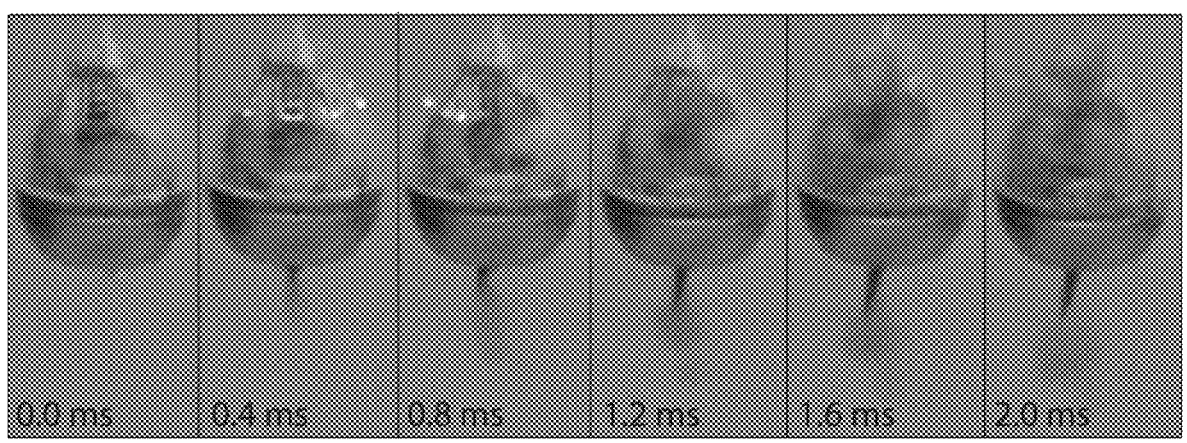
FIG. 42 shows actuation of a liquid in water by an exemplary system, according to one set of embodiments.
Figure 43:
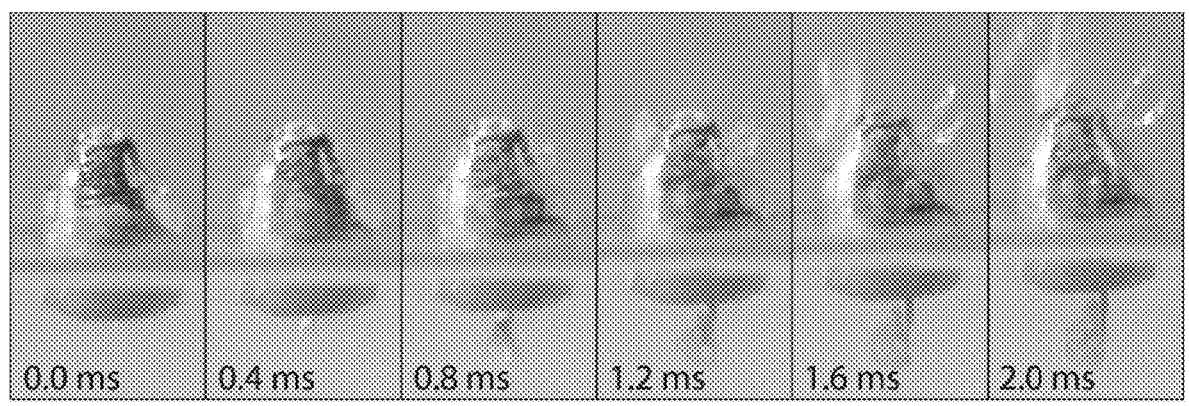
FIG. 43 shows actuation of a liquid in water by an exemplary system, according to one set of embodiments.

FIGS. 42 and 43 show exemplary actuation of L-SOMA in water. As shown in FIG. 42, dye is released from the liquid compartment into a water bath in the span of 2 milliseconds after the device is actuated. The dye leaves through the tip of the needle. As shown in FIG. 43, dye is released from the liquid compartment into a 0.35% agarose gel in the span of 2 milliseconds after the device is actuated. The dye leaves through the tip of the needle.

Figure 44:
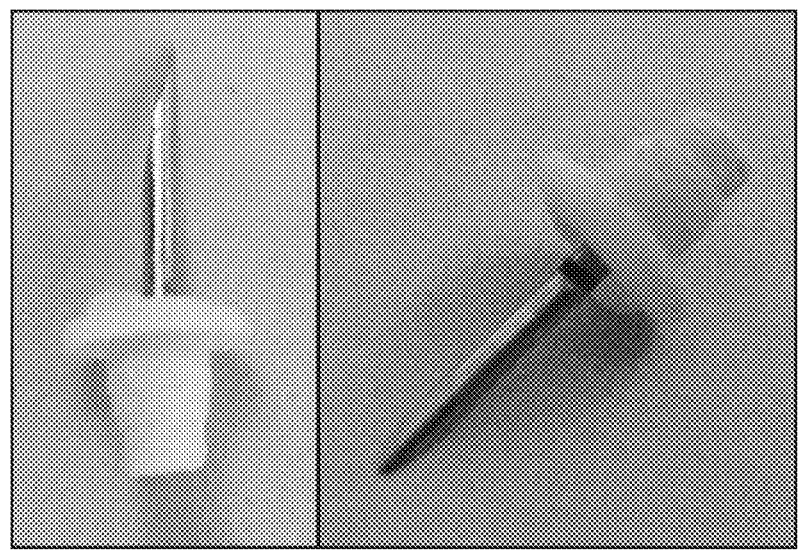
FIG. 44 shows an exemplary tissue interfacing component, according to one set of embodiments.
Figures 45A, 45B, 45C, 45D, 45E, 45F, 45G, 45H, 45I, 45J:
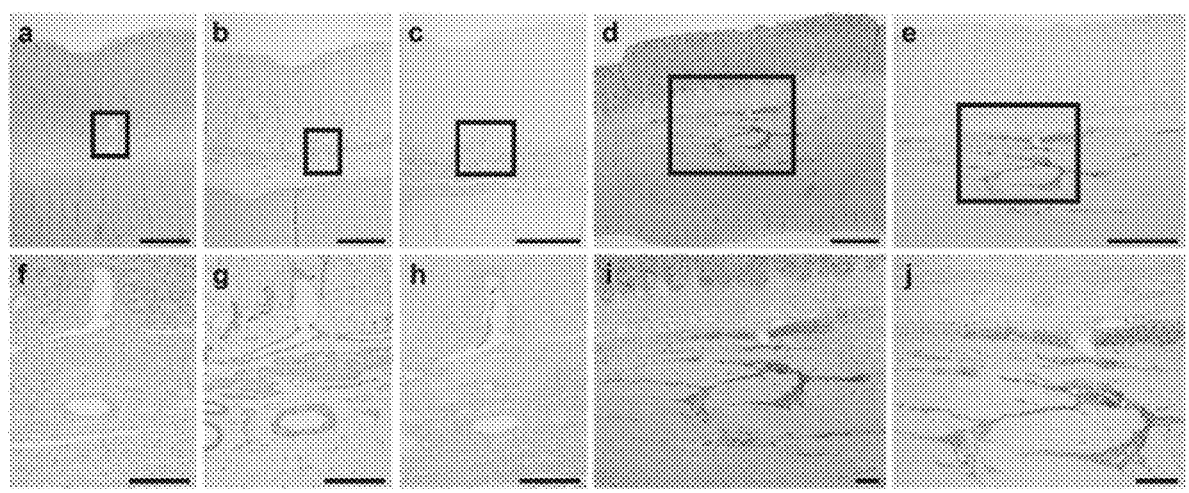
FIGS. 45A-45J show histology in swine after L-SOMA capsule administration, according to one set of embodiments.
Figures 46A, 46B, 46C:
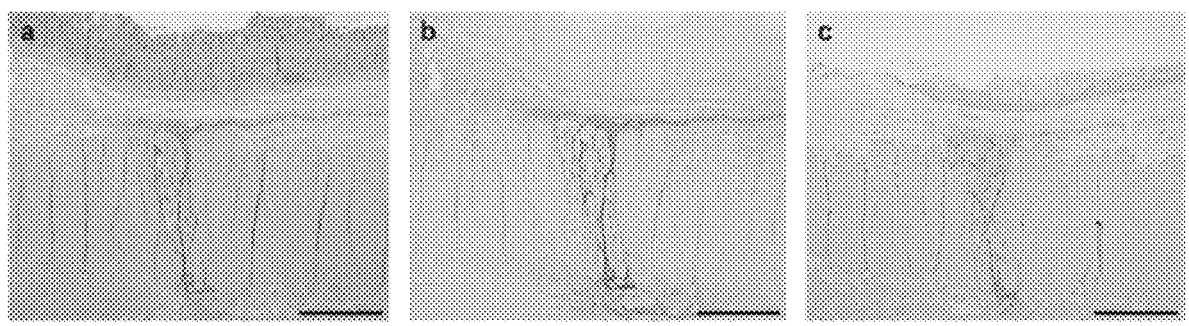
FIGS. 46A-46C show dog ex vivo histology from LSOMA injection, according to one set of embodiments. Histology of ex vivo dog stomach after an LSOMA insulin injection using a (A) hematoxylin and eosin stain, (B) an immunohistochemistry stain against insulin, (C) or an immunohistochemistry stain against smooth muscle actin. Scale bar=1 mm.

FIG. 44 shows a photograph of an exemplary needle with a hole on its side connected to the needle/spring attachment. The liquid passes through the side hole and out of the beveled end.

Use of Long Beveled Needle Tip

As the injection force was generally related to the insertion depth, needles with higher angle grinds were tested. These needles possessed an outlet hole which was smaller in the direction of needle insertion and therefore targeted an insertion depth more specifically. It was found that these needles were unable to insert any significant amount of liquid into the tissue even at forces of >50N. Although the plunger was displaced by the tensile strength tester used to measure the force, no contrast dye in the tissue after trying to deliver the dose. These forces instead were generally due to the compression of the rubber stoppers and other materials used in the dosing mechanism. From these experiments a needle with a low angle grind was chosen for the L-SOMA.

Dissolvable or Hydratable Needle

The needle that is inserted into the tissue can either be removed from the tissue and brought back into the device via a retractable mechanism, a swelling hydrogel, or it can lose its sharpness. A third spring can be used to bring the needle back from its inserted state into the device. A dissolvable needle can be used to eliminate the needle. However, because the design currently uses a needle in contact with the fluid inside of the device, tin some cases it would be desirable that it not dissolve from the outside surface. Therefore, for example, it may comprise a protective coating on the outside surface of the needle. Such a coating could be a metal such as gold or it could be a polymer such as parylene. This layer could be anywhere between 300 nm to 5 um thick. It is desirable that a dissolvable needle maintains its functionality after being inserted into the tissue. For example, it should be able to easily penetrate the tissue. In some cases it may use a relatively sharp tip. It may also be configured to pass liquid through an inside tube. Additionally, it may be configured to have a hole on the top section to allow liquid to enter. Some examples of materials that the needle could be made of include: a sugar or sugar like material such as isomalt or sucrose; a biodegradable polymer or co-polymer such as PVP, PVA, Soluplus; a hydrogel; gelatin; a starch. The needle may be configured to dissolve from the inside tube to the outside. If the needle hydrates and becomes soft, then this may also eliminate the potential for a perforation from the protruding needle. If there is a soft boundary made around the tip of the needle, then this may also prevent perforation. If the needle became floppy, such as a piece of pasta, then this may also work. If the needle broke into small pieces then this may also work. The needle could be made of a degradable metal, such that it would break up. Such metals include zinc, magnesium and iron along with others.

Work Used to Expel Fluid and Spring Force Necessary

It was found that it takes, in some embodiments, in the range of 3-10 N of force to expel the liquid quickly out of the device. However, the liquid does not necessarily need to be expelled quickly. As long as the force provided by the spring is greater than the force required to create a depot in the tissue then the liquid will eventually enter the tissue. Springs were tested with as low as 5 N of maximum force. It is therefore expected that the spring force can go down significantly from there. Higher forces would also still work.

Needles of Different Gauges Require Different Amounts of Work for Expulsion

A smaller gauge needle may use more work to push the liquid through the tube. However, any needle size will work for this device. Needles as low as 32 G and as high as 18 G were tested, but higher and lower needle gauges will work.

Hole Size and Use of Sprinkler Needles

A low angle grind produces a larger hole which is useful. Aside from the side hole which lets the liquid into the needle, it was found that the sprinkler needle did not necessarily help the efficacy of the injection, in some embodiments. This may be, in some cases, because injection into the mucosa layer itself did not produce favorable results.

Use in Different Animals

The L-SOMA can be used in humans, but it can also be used in other animals such as swine, horses, cows, etc.

Adding Electronics for Sensing or Actuation

The L-SOMA can have electronics such as wireless communication devices like NFC and Bluetooth embedded inside of the device, tethered to the device or on the outside of the device. Other electronic equipment that can be included would be batteries, wires, microcontrollers, capacitors, resistors, etc. One use of the electronics could be to send a message when the capsule has actuated. Another could be a sensor that is used to measure temperature or a molecule inside of the stomach or inside the stomach mucosa. Another could be a triggerable actuation mechanism.

In Vivo Tests

In vivo swine experiments were performed in which L-SOMA devices loaded with either an inactivated GLP-1 receptor agonist or fast acting insulin were prepared. L-SOMA dosing experiments were compared to subcutaneous dosing experiments and experiments where swine were dosed with the liquid formulation into the stomach lumen. Using an endoscope, L-SOMA devices were placed into the stomachs of swine and allowed to independently actuate. After 2 hours the devices were removed from the animal. Time 0 corresponds to the time at which the device was placed in the stomach and not the time that the device actuated. The swine dosed were partially fasted but contained a layer of gastric fluid and food approximately the same height as the L-SOMA capsule. Even with the food, the L-SOMA was able to deliver the drug load with an efficacy similar to a subcutaneous injection.

After dosing, the animals were monitored for one week. The animals maintained their normal behavior and eating patterns. No blood in the stool was observed. Additionally, animals were sacrificed for histology directly after dosing with an L-SOMA and saw no hole in the tissue from the inserted needle or evidence of a perforation. In the Examples above, it was demonstrated the ability for the SOMA device and other ingestible devices to safely pass through the GI tract intact after actuation with or without protruding needles and without causing an obstruction. Retrospective medical studies on ingested sharp objects also demonstrate the low risk of complications associated with sharp objects less than 1 cm in length. In order to address the potential complication of a protruding needle, a biodegradable injection needle made from gelatin in the L-SOMA in vitro was tested. Additionally, an L-SOMA with the ability to retract the needle into the device after injection was tested in vitro. Both devices were able to inject a liquid formulation and subsequently eliminate the sharp object in their respective manners.

The L-SOMA was designed in order to prevent or reduce the risk of GI obstruction. The volume of the device is less than the volume of an OROS capsule, an FDA approved daily dosed oral drug delivery device which does not degrade while passing through the GI tract and has obstruction rates of 1 in 29 million. Several other non-degradable capsule with metal components such as ingestible electronics have also been approved by the FDA and support a comparable environmental analysis of the L-SOMA.

Loading Different APIs and Formulations

Any liquid can be loaded into to the L-SOMA and any material can be put in solution and added to the L-SOMA. Such solutes include water, oil, and ethanol. Such drugs include insulin, glp1 receptor agonists, monoclonal antibodies, proteins, nucleic acids, lipid nanoparticles, polymer nanoparticles, small molecule drugs e.g. epinephrine etc. (such as those listed herein)

Alternative Actuation Mechanisms

The L-SOMA does not necessarily need to be propelled by a spring, although a spring may be used. L-SOMA may be actuated by a chemical reaction which produces gas, or a stored pressurized gas. L-SOMA could also be actuated by a magnet, an electromagnet, a swellable hydrogel/polymer etc.

Example 21—Delivery of Antibody, Peptide, and Small Molecules

The following example details the use and design of the L-SOMA described generally in Example 20 for delivery of molecules such as antibodies, peptides, and small molecules. Other active therapeutic agents are also possible with this exemplary article.

Oral administration provides a simple and non-invasive method for drug delivery yet generally cannot achieve the desired pharmacokinetics realized by subcutaneous and intramuscular injections. In this example, an oral auto-injector capsule capable of providing absorption kinetics and systemic bioavailability on par with parenteral administration for liquid formulations of drugs ranging in size from small molecules to monoclonal antibodies is demonstrated. To demonstrate the broad utility of this platform technology, capsules were administered to swine with clinically relevant doses of four commonly injected medications, including: adalimumab, a semaglutide-like inactivated GLP-1 analog, insulin and epinephrine.

Issues of sub-optimal kinetics and limited drug dose were addressed by developing a capsule with the ability to rapidly deliver liquid depot injections of drugs, ranging in size from small molecules to monoclonal antibodies, directly into the gastric submucosa for immediate systemic uptake after administration. Unlike a solid drug post, a liquid formulation is generally able to spread throughout the submucosa. This may provide a greater surface area for systemic uptake and at the same time allows for a greater volume of injected drug. In some cases, by targeting the stomach rather than the small intestine, the capsule may be able to deliver its payload immediately, thereby circumventing the 1-4 hour waiting time generally required for gastric emptying. The 4-6 mm thick tissue of the stomach wall also generally provides a greater safety margin for injection compared to the 0.1-2 mm thick wall of the small intestine. This exemplary capsule design utilizes a self-orienting geometry that autonomously positions the device so that its injection mechanism generally always faces towards the tissue wall. The design helps to ensure that the capsule delivers the dose directly into the tissue, circumventing enzymatic degradation that occurs in the lumen.

This exemplary liquid injecting self-orienting millimeter-scale applicator (L-SOMA), a 12 mm in diameter and 15 mm tall capsule, injects a hypodermic needle beneath the gastric mucosa and thereupon delivers up to 80 μL of liquid drug formulation into the submucosal space (FIGS. 40A-40E). By decoupling the needle insertion from the liquid injection, the device achieves delivery of its entire dose to an exact tissue depth instead of releasing the dose as the needle moves through the tissue (FIGS. 41E-41J). Two membranes seal off the dose storage area and prevent leakage as a plunger pushes the liquid through a side hole in the needle and out via the needle's tip (see FIGS. 41A-41B). These engineering designs may help ensure that the entire liquid dose enters the tissue and prevents part, or all, of the dose expelling on top of the tissue.

How the penetration depth of the needle affected the delivery of the liquid dose was determined by performing injections of contrast dye to pre-defined depths in ex vivo swine stomach tissue and recording MicroCT images of the depots created (FIGS. 41E-N and FIG. 48). The percent of liquid remaining in the tissue after dosing was measured to a given depth, and confirmed the tissue layer targeted by the injections via visualization (FIG. 41H-I). During these controlled injection experiments a volume of 170 μL of contrast dye was delivered. This compared to a maximum dose volume of 80 μL for the L-SOMA device. It was observed that for the 3 mm and 4 mm injection depths the needles performed inconsistently wherein they sometimes injected dye into the mucosa, and a large proportion leaked out of the tissue. By extending the needle insertion depth to 4.5 mm or greater, the device consistently delivered the entire liquid dose into the tissue and experienced no leakage. Insertion depths of 4.5 mm, 5 mm and 6 mm saw occasional injections into the outer muscle layer of the stomach tissue. Guided by this data, we designed an L-SOMA device with a needle insertion depth of 4.5 mm, thereby reducing the perforation risk compared to deeper injection depths while ensuring that the entire drug load is delivered into the tissue. Ex vivo experiments (FIGS. 41D-G) with L-SOMA devices (FIG. 40E) revealed that needles of these dimensions reliably targeted the submucosa and the devices delivered their entire drug payload into the tissue. This enabled drugs with a wide range of molecular weights to be delivered through the stomach lining (FIG. 1r). Histology from ex vivo experiments on swine and dog stomachs as well as histology taken from swine dosed in vivo using the L-SOMA demonstrated that the injected liquid did not leak out of the stomach mucosa or serosa, confirming that the device delivered its entire payload and that the needle did not perforate the tissue (FIGS. 45A-45J and FIGS. 46A-46C).

Figures 47A, 47N:
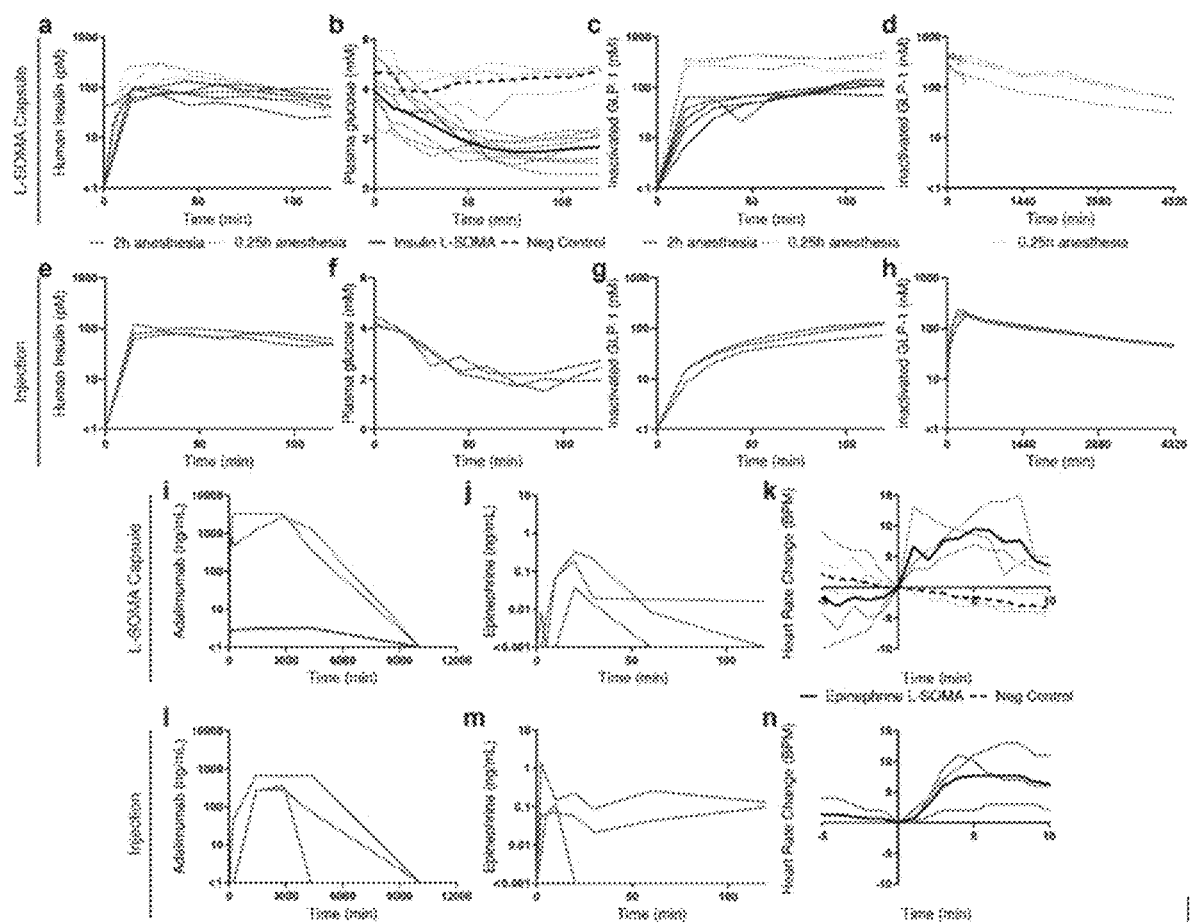
FIGS. 47A-47N show in vivo oral delivery of monoclonal antibodies, peptides, and small molecule drugs in swine, according to one set of embodiments. (A) Blood plasma human insulin and (B) glucose levels after dosing an L-SOMA capsule containing 1 mg of recombinant human insulin (n=8). The negative control for plasma glucose is the L-SOMA delivery of 4 mg inactivated GLP-1 analog (n=4 animal replicates). (C-D) Blood plasma levels of inactivated GLP-1 analog after dosing an L-SOMA containing 4 mg of inactivated GLP-1 analog. (n=9). Swine receiving anesthesia only during L-SOMA administration (0.25 h) and swine receiving anesthesia for two hours after administration are noted on the graphs. (E) Blood plasma human insulin and (F) glucose levels after subcutaneously dosing 1 mg of recombinant human insulin (n=3). (G-H) Blood plasma levels of inactivated GLP-1 analog after subcutaneously dosing 4 mg of inactivated GLP-1 analog. (n=3). (I) Blood serum levels of adalimumab after dosing an L-SOMA capsule containing 4 mg of adalimumab (n=3). (J) Blood plasma levels of epinephrine and (K) associated heart rate change after dosing an L-SOMA capsule containing 0.24 mg epinephrine (n=3). The negative control for heart rate change is an endoscopic gavage dosing containing 0.24 mg epinephrine (n=3). (L) Blood serum adalimumab levels after subcutaneous dosing of 4 mg adalimumab (n=3). (M) Blood plasma epinephrine levels and (N) associated heart rate change after intramuscular dosing of 0.24 mg of epinephrine (n=3). For the heart rate change data, time 0 corresponds to the time of device actuation or injection. For all other data, time 0 corresponds to the time of device administration. Solid black lines represent the average blood glucose or heart rate change for a given administration group. All other lines represent the dosing of a different animal or the same animal dosed at least three weeks apart.
Figure 48:
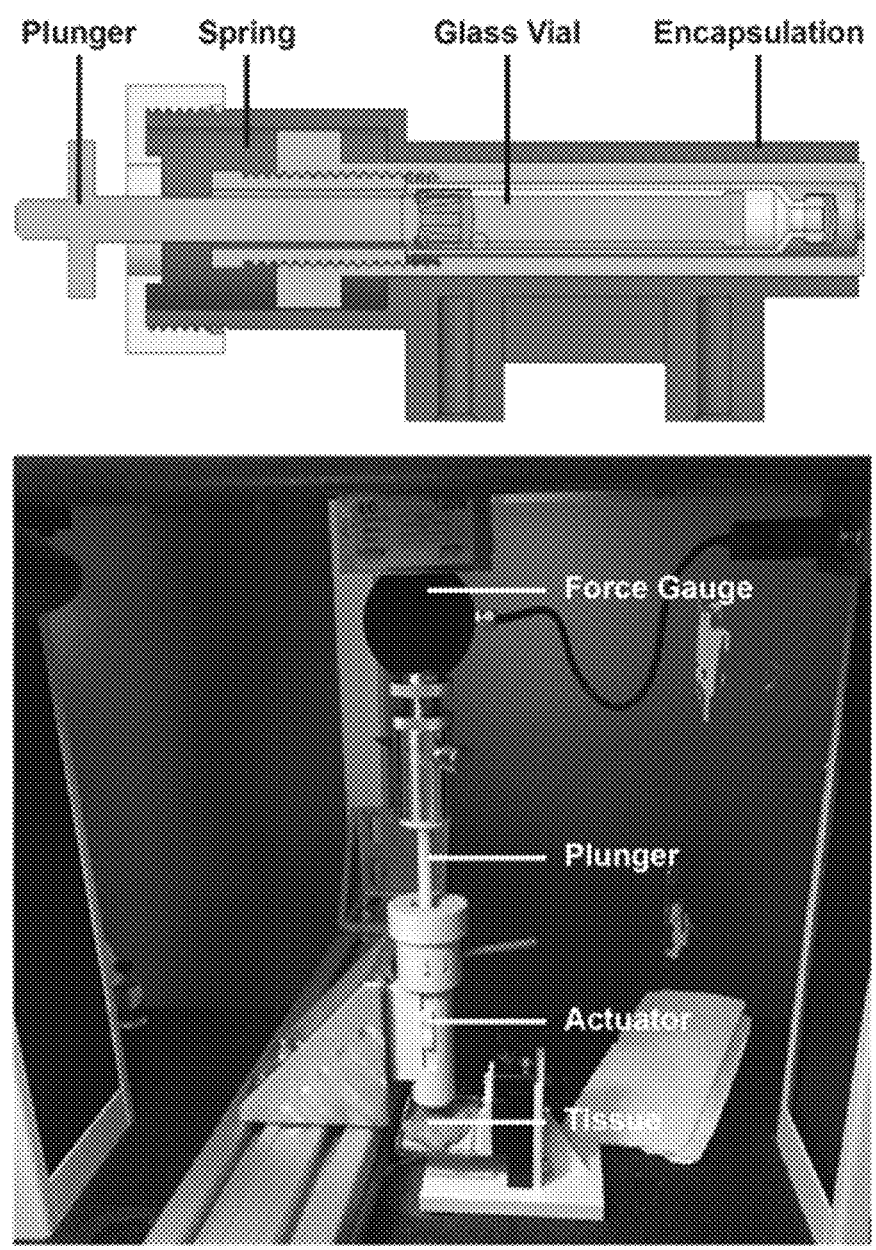
FIG. 48 shows an injection test mechanism setup, according to one set of embodiments. (Top) Computer aided design of the custom actuation mechanism used to insert a needle a controlled distance and inject an exact amount of fluid. (Bottom) Experimental setup of controlled injection studies. The texture analyzer pushes down on the plunger which causes the liquid to inject into the swine stomach tissue below.
Figure 49:
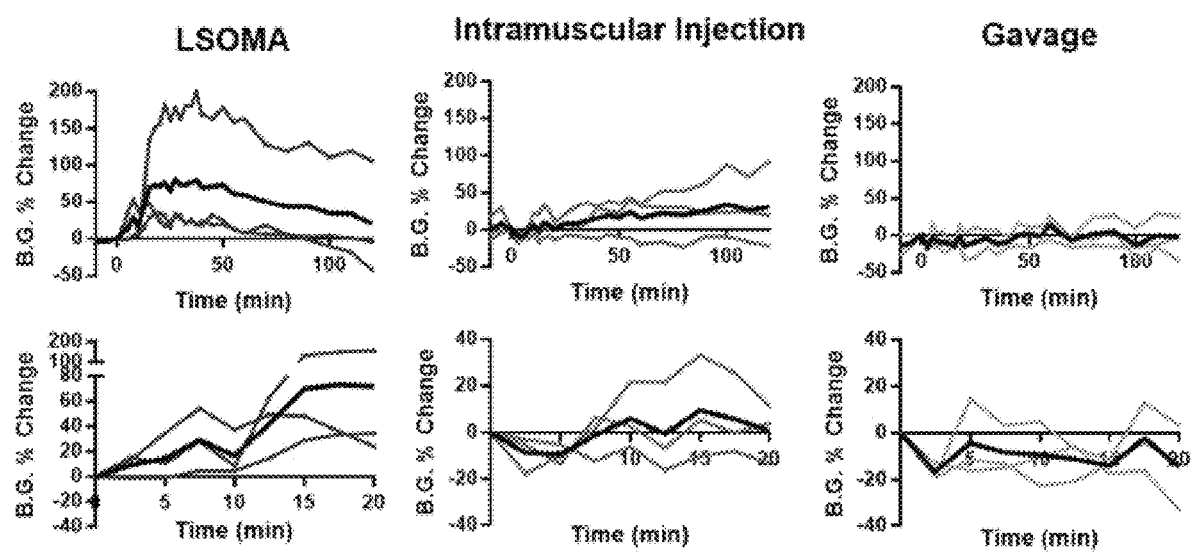
FIG. 49 shows blood glucose change in swine after 0.24 mg epinephrine injection, according to one set of embodiments. Thin lines represent individual swine profiles and bold lines represent the mean values.
Figure 50:
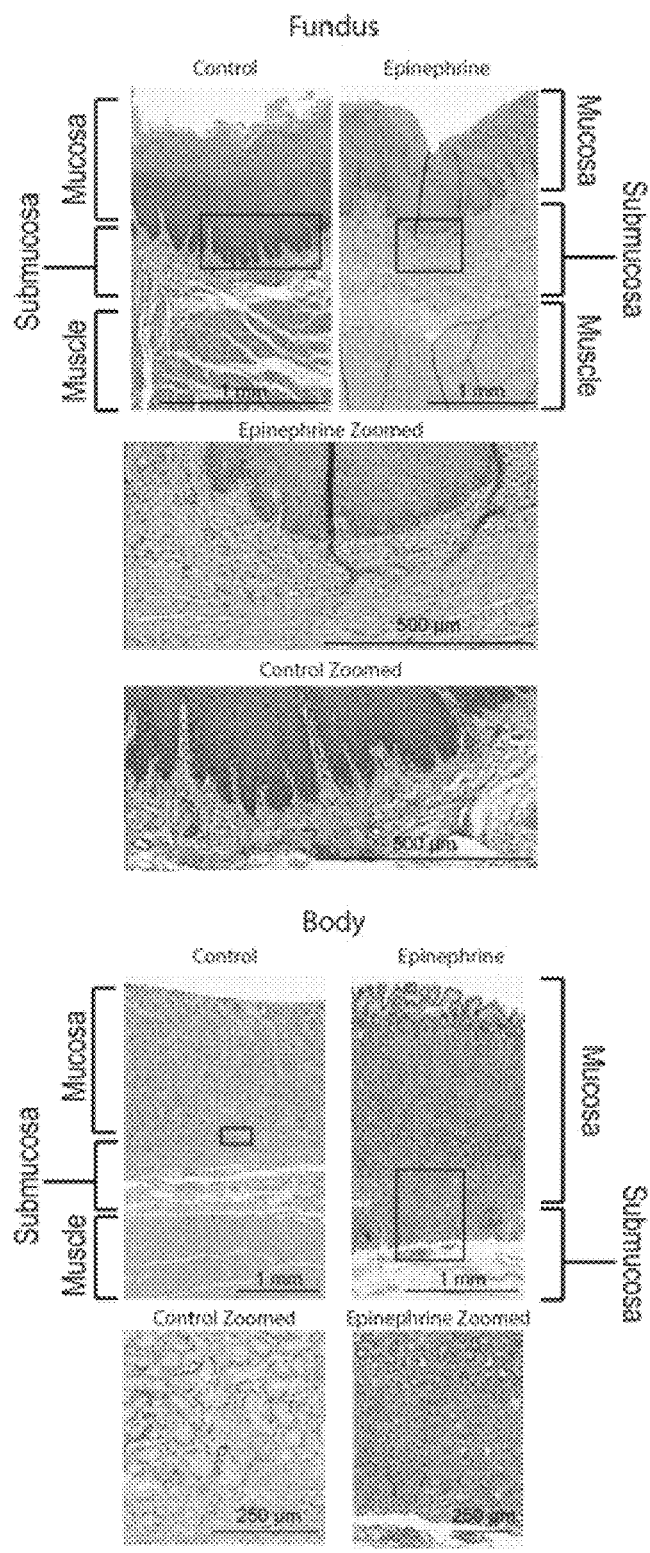
FIG. 50 shows in vivo swine histology after L-SOMA epinephrine injection, according to one set of embodiments. Hematoxylin and eosin stain histology of swine stomach after L-SOMA injection. L-SOMA devices were injected in the fundus or body of the stomachs.

In vivo swine experiments were performed in which a single L-SOMA device was dosed to each animal loaded with 1 mg of recombinant human insulin, 4 mg of a semaglutide-like inactivated GLP-1 analog, 4 mg of the monoclonal antibody adalimumab, or 0.24 mg of the small molecule epinephrine (FIGS. 47A-47N). L-SOMA dosings were compared to subcutaneous or intramuscular dosings as positive controls. Using an endoscope, we placed L-SOMA devices into the stomachs of swine and allowed them to independently actuate. After 2 hours the devices were removed from the animal. Within 15 minutes after L-SOMA administration of insulin, inactivated GLP-1, or epinephrine, plasma exposure of drug was observed. Adalimumab was observed in the serum within one hour after L-SOMA administration. Insulin dosed swine experienced immediate hypoglycemic onset (FIG. 47B, FIG. 47F), and epinephrine dosed swine experienced an abrupt rise in heart rate (FIG. 47K, FIG. 47N) and blood glucose (see FIG. 49) in both the intramuscular injection and L-SOMA experimental groups. H&E staining from the epinephrine dosed swine showed no evidence of necrosis or adverse effects elicited by the drug (see FIG. 50). Swine dosed with adalimumab or inactivated GLP-1 using either L-SOMA capsules or subcutaneous injections possessed drug in their blood plasma for at least 3 days after dosing by virtue of the drugs' extended half-lives.

Although the swine dosed were partially fasted, some swine contained a layer of gastric fluid and food in their stomachs. In these swine, the L-SOMAs were able to partially displace the food layer, insert their needles into the tissue, and still deliver the drug load. Of note, one device loaded with GLP-1 analog actuated in the stomach, but the swine showed no systemic uptake. This may, in some cases, be due to the drug formulation not reaching the gastric submucosa. All other 22 L-SOMA-dosed swine demonstrated systemic uptake.

The bioavailabilities in swine were calculated from L-SOMA dosing for insulin and GLP-1 analog and compared them to the bioavailabilities from subcutaneous administration of the same formulation and amount of drug. L-SOMA dosed recombinant human insulin demonstrated a 48±16% (SD) bioavailability over a two hour sampling period (Range=25%-81%, n=8). This compared to a 57±8% (SD) bioavailability for the swine dosed with insulin subcutaneously (Range=50.8%-66.2%, n=3). The bioavailability of L-SOMA dosed GLP-1 analog over a three day sampling period was 103±42% (SD) (Range=55%-135%, n=3) when excluding the L-SOMA which showed 0% uptake after actuation in the stomach and 78±62% when including this extra data point. This compared to a 78±4% (SD) bioavailability for subcutaneously dosed GLP-1 analog.

Figure 51:
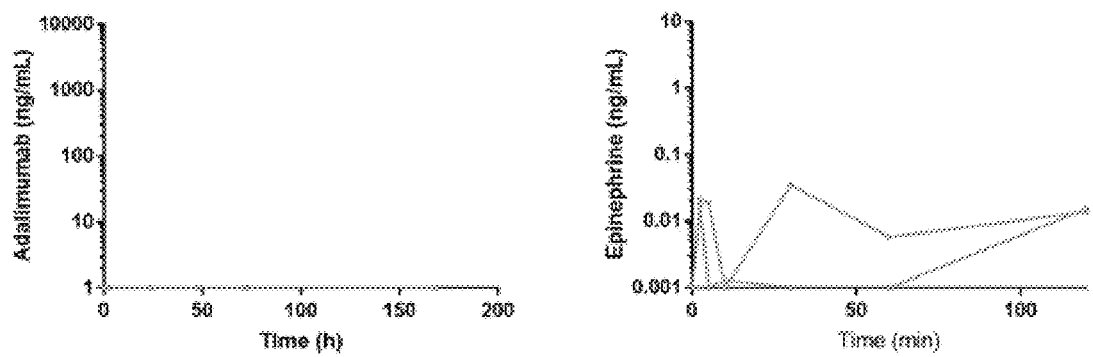
FIG. 51 shows pharmacokinetics of gavage dosed epinephrine and adalimumab, according to one set of embodiments. Dissolved adalimumab (4 mg) or epinephrine (0.24 mg) were dosed through an endoscope into the lumen of swine stomachs (n=3 animal replicates)

Insulin and GLP-1 generally have limited ability to traverse the stomach lining for systemic uptake when administered without a permeation enhancer or physical permeation enhancing device. For both epinephrine and adalimumab, endoscopic gavage experiments with an equivalent drug load to the L-SOMA were performed on swine as negative controls, and negligible uptake was observed (see FIG. 51).

After dosing, the animals were monitored for one week. The animals maintained their normal behavior and eating patterns. No blood in the stool was observed. Retrospective medical studies and experimental studies in large animal models on ingested sharp objects demonstrate the low risk of complications associated with sharp objects generally less than 1 cm in length. Furthermore, the Carr-Locke injection needle, a 25 G and 5 mm long needle, is used routinely by gastroenterologists during endoscopies in the stomach with near non-existent complication rates. In comparison, the L-SOMA uses a 32 G needle that protrudes only 4.5 mm from the device. To mitigate the issue of an exposed needle in the gastrointestinal tract, an L-SOMA was designed with the ability to retract the needle into the device after injection. This technology mitigates the risk associated with the sharp objects present in the L-SOMA system at the cost of adding additional complexity to the device (see FIG. 52). Hollow needles to further mitigate the issue of perforation during gastrointestinal transit may also be used.

Figure 53A:
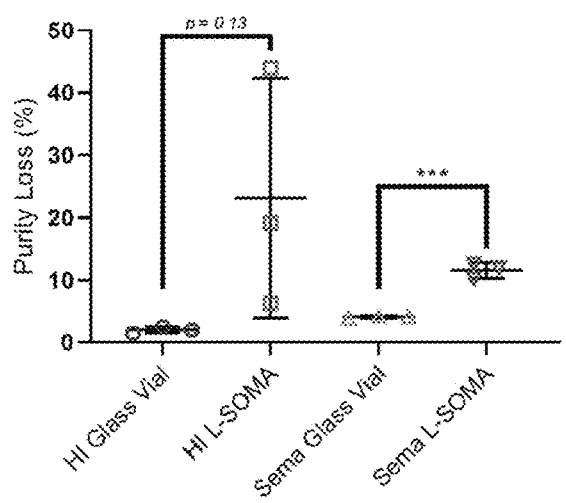
FIGS. 53A-53B show liquid formulation stability, according to one set of embodiments. Human Insulin (HI) and Semaglutide (Sema) formulations were placed inside of either an L-SOMA or a glass vial apparatus and were subjected to a 40° C. and 75% relative humidity environment for two weeks. (a) Purity loss and (b) high molecular weight protein (HMWP) formation were then measured. (Error=SD, n=3 device replicates, P<0.01, *P<0.001).
Figure 53B:
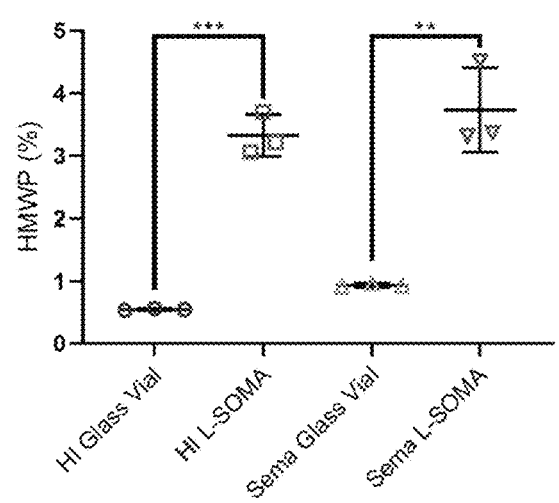

Stability studies for both human insulin and semaglutide liquid formulations were performed and demonstrated that the purity loss and high molecular weight protein formation for the formulations placed in the L-SOMA system was greater than for formulations placed in a glass vial system after undergoing two weeks in a 40° C. and 75% relative humidity environment (FIGS. 53A-53B). Additionally, the purity loss for the liquid formulation was higher than the purity loss for the solid formulation we previously reported using in the SOMA system. Optimization of the L-SOMA storage system and loaded liquid formulation will be required to ensure long term stability of the filled drug.

The L-SOMA pill's ability to dose four different drugs with a range of molecular weights, half-lives, pharmacodynamics effects and dose size requirements were demonstrated in this example. The capsule's rapid pharmacokinetic uptake within minutes after administration, loading capacity of up to 4 mg of bioavailable drug, and capacity to function with a wide span of molecules enables the compatibility of this capsule with a new set of drugs that could not previously be orally delivered. While the ability to deliver epinephrine for anaphylaxis using the L-SOMA may be hindered by throat swelling in serious cases, the capsule could still be used to deliver the drug for asthma treatment or treatment of slower onset anaphylaxis. Additionally, the use of epinephrine in the L-SOMA device demonstrates the ability to deliver small molecule drugs. Poorly soluble small molecule drugs which demonstrate low systemic uptake may also be suitable candidates for the L-SOMA system. The broad-ranging applicability of the L-SOMA means that it is generally possible to load the capsule with any liquid formulation including small molecule or macromolecule drugs; albeit reformulation and up concentration may be necessary to reach the required therapeutic dose for a given drug. Compared to the solid formulations, liquid formulations do not rely on the solid state properties of the drug such as the capacity to be compressed into needle-like shapes and therefore widen the range of molecules which can be administered via this device. The L-SOMA demonstrates the ability to load and deliver formulations containing both fast acting drugs and drugs with extended half-lives, encompassing a range of drug modalities, via an oral capsule. In doing so, it can provide a less intrusive route of administration for drugs that are otherwise limited to injectables, and thereby advantageously achieve higher compliance amongst patients and ultimately, better clinical outcomes.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, gomboc, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. A self-righting article, comprising:
    a self-actuating component comprising a spring and a support material adapted to maintain the spring in at least a partially compressed state, wherein the support material is configured for at least partial degradation in a biological fluid;
    a chamber comprising a liquid active pharmaceutical agent (or non-active to serve as contrast or cushion); and
    a tissue interfacing component operably linked to the self-actuating component, the tissue interfacing component comprising an inlet, an outlet, and a channel fluidically connected to the inlet and the outlet;
    wherein the chamber is configured to be in fluidic communication with the inlet upon activation of the self-actuating component, and
    wherein when the self-righting article is at least partially supported by the tissue of the subject, the self-righting article orients in a direction to allow the tissue interfacing component to release at least a portion of the active pharmaceutical agent into the tissue.

2. A self-righting article as in claim 1, comprising a plug associated with the tissue interfacing component, wherein the tissue interfacing component is configured to pierce the plug upon activation of the self-actuating component.

3. A self-righting article as in claim 1, wherein the tissue interfacing component is dissolvable or retractable or becomes soft after actuation/penetration.

4. A self-righting article as in claim 1, wherein the support material is configured as a plug and wherein the plug is operably linked to the tissue interfacing component.

5. A self-righting article as in claim 1, wherein the support material is configured within the self-righting article such that the biological fluid entering the self-righting article contacts a first surface to initiate the at least partial degradation of the support material.

6. A self-righting article as in claim 1, wherein the support material is selected from the group consisting of a sugar, a derivative of a sugar, sugar alcohol, maltose, isomalt, starch, calcium carbonate, zinc, sodium chloride, polymers, and combinations thereof.

7. A self-righting article as in claim 1, wherein the self-righting article comprises one or more vents configured such that the self-actuating component is in fluidic communication with an external environment.

8. A self-righting article as in claim 1, wherein the one or more vents are covered by a coating.

9. A self-righting article as in claim 1, wherein the biological fluid is gastric fluid.

10. A self-righting article as in claim 1, wherein the article comprises a component configured to retract the tissue interfacing component.

11. A self-righting article as in claim 1, wherein the article comprises a tissue interfacing component capable of piercing tissue where such components are multi-layered with an inner layer of an aqueous sensitive material.

12. A self-righting article as in claim 1, wherein the aqueous sensitive material comprises gelatin.

13. A self-righting article as in claim 1, wherein the tissue interfacing component comprises an outer layer impervious to aqueous fluid such that following triggering an inner layer of the tissue interfacing component is exposed to the fluid in the chamber, mechanically weakening at least a portion of the tissue interfacing component after passage of the fluid through the needle.

14. A self-interfacing article as in claim 1, wherein the article comprises a tissue interfacing component configured to retract upon contact with a plug of the self-righting element thereby revealing an aqueous inner layer on both sides upon piercing tissue.

15. An article suitable for ingestion into a lumen of a subject, the lumen having a lumen wall, wherein the article comprises:
    an outer shell having an exterior shape comprising a round cross-section, the outer shell defining a first axis;
    an actuation mechanism comprising a self-actuating component comprising a first spring component and a support material adapted to maintain the first spring component in at least a partially compressed state, wherein the support material is configured for at least partial degradation in a biological fluid;
    a chamber disposed within the outer shell, the chamber comprising a liquid active pharmaceutical agent; and
    a tissue interfacing component disposed relative to the outer shell and configured for transfer of liquid from the chamber to a portion of tissue of the lumen wall at a location internal to the subject,
    wherein the article is self-righting having a geometric center and a center of mass, the center of mass being offset from the geometric center in a first direction along the first axis.

16. An article as in claim 15, wherein when the article is supported by tissue of the lumen wall while being oriented such that the center of mass is offset laterally from the geometric center, the article experiences an externally applied torque due to gravity acting to orient the article with the first axis oriented along the direction of gravity such that the tissue interfacing component interacts with the tissue at the location internal to the subject, and upon at least partial degradation of the support material, the actuation mechanism acts on the liquid active pharmaceutical agent such that the tissue interfacing components releases at least a portion of the liquid active pharmaceutical agent into the tissue at the location internal to the subject.

17. An article as in claim 15, wherein the liquid active pharmaceutical agent and the chamber are constructed and arranged such that, when the article is oriented with the first axis oriented along the direction of gravity and the tissue interfacing component is interacting with the tissue, the center of mass of the liquid is disposed below said geometric center relative to the surface of the tissue.

18. An article as in claim 16, wherein the liquid active pharmaceutical agent and the chamber are constructed and arranged such that, when the article is oriented with the first axis oriented along the direction of gravity and the tissue interfacing component is interacting with the tissue, the center of mass of the liquid is disposed closer to the surface of the tissue than the geometric center of the article.

19. An article as in claim 15, wherein the chamber comprises a movable wall, wherein the movable wall is configured to expel liquid active pharmaceutical agent from the chamber.

20. An article as in claim 19, wherein the chamber comprises a cylindrical wall, and wherein the movable wall of the chamber comprises a plunger in slideable engagement with the cylindrical wall.

21. An article as in claim 19, wherein the tissue interfacing component is operably linked to the self-actuating component, the tissue interfacing component comprising an inlet, an outlet, and a channel fluidically connected to the inlet and the outlet.

22. An article as in claim 21, wherein the channel is configured to be in fluidic communication with the chamber comprising the liquid active pharmaceutical ingredient upon activation of the activation mechanism.

23. An article as in claim 19, wherein the tissue interfacing component forms or comprises an injection needle operably linked to the first spring component, wherein the first spring component is operable from a first configuration to a second configuration upon at least partial degradation of the support material, wherein the injection needle is retained within the article when the first spring component is in the first configuration, and wherein the injection needle is configured to be advanced from the article and into the lumen wall by movement of the first spring component from the first configuration to the second configuration.

24. An article as in claim 23, wherein the injection needle extends through the chamber when the first spring assumes the first configuration and/or when the first spring assumes the second configuration.

25. An article as in claim 24, wherein the injection needle comprises a tissue penetration end, a second end portion opposite the tissue penetrating end, and a side wall extending between the tissue penetrating end and the second end portion, the side wall comprising a side hole disposed such that, when the first spring component is in the second configuration, fluid communication is established between the chamber and the tissue penetration end of the injection needle.

26. An article as in claim 25, wherein, when the first spring component is in the first configuration, the side hole is positioned outside the chamber comprising the liquid active pharmaceutical agent.

27. An article as in claim 25, wherein the chamber further comprises an end wall arranged opposite the movable wall, wherein the end wall comprises a penetrable seal, and wherein, when the first spring component assumes the first configuration, the tissue penetrating end of the injection needle is embedded in the penetrable seal, and wherein, when the first spring component assumes the second configuration, the injection needle pierces the penetrable seal.

28. An article as in claim 21, wherein the actuation mechanism comprises a second spring component held releasably in a compressed state, the second spring component being configured to release from the compressed state, upon the first spring component moving from the first configuration into the second configuration, to drive the movable wall to expel liquid active pharmaceutical agent from the chamber.

29. An article as in claim 28, wherein the first spring component is arranged coaxially with the second spring component, such as radially within the second spring component, with at least partial axial overlap between the first spring component and the second spring com-ponent.

30. An article as in claim 21, wherein the actuation assembly comprises a third spring component held releasably in a compressed state, the third spring component being configured to release when all or a predefined portion of expellable liquid active pharmaceutical agent from the chamber has been expelled, the release of the third spring component causing the injection needle to retract relative to the article housing.

31. An article as in claim 30, wherein the third spring component is arranged coaxially with the first spring component, such as radially within the first spring component, with at least partial axial overlap between the third spring component and the first spring component.

32. An article as in claim 15, wherein the tissue interfacing component comprises a jet injection component and wherein the first spring component is configured to expel liquid active pharmaceutical agent through the jet injection component at a penetration velocity allowing the liquid active pharmaceutical agent to penetrate gastric submucosa of the lumen wall.

* * * * *

UNITED STATES PATENT AND TRADEMARK OFFICE
CERTIFICATE OF CORRECTION

PATENT NO. : 11,771,829 B2
APPLICATION NO. : 16/778152
DATED : October 3, 2023
INVENTOR(S) : Robert S. Langer et al.

Page 1 of 1

It is certified that error appears in the above-identified patent and that said Letters Patent is hereby corrected as shown below:

On the Title Page

Item (72), in the Inventors, Lines 7-8, "Bagsbærd (DK);" should read --Bagsværd (DK);--.

In the Claims

In Claim 16, Column 85, Lines 11-12, "tissue interfacing components releases" should read --tissue interfacing component releases--.

In Claim 29, Column 86, Line 36, "second spring com-ponent." should read --second spring component.--.

Signed and Sealed this
Twenty-eighth Day of November, 2023

Katherine Kelly Vidal
*Director of the United States Patent and Trademark Office*